(12) United States Patent
Taylor et al.

(10) Patent No.: US 11,702,704 B2
(45) Date of Patent: Jul. 18, 2023

(54) DETECTING OVARIAN CANCER

(71) Applicants: Mayo Foundation for Medical Education and Research, Rochester, MN (US); Exact Sciences Corporation, Madison, WI (US)

(72) Inventors: William R. Taylor, Lake City, MN (US); John B. Kisiel, Rochester, MN (US); Douglas W. Mahoney, Elgin, MN (US); David A. Ahlquist, Rochester, MN (US); Hatim T. Allawi, Middleton, WI (US); Michael W. Kaiser, Stoughton, WI (US)

(73) Assignees: Mayo Foundation for Medical Education and Research, Rochester, MN (US); Exact Sciences Corporation, Madison, WI (US)

( * ) Notice: Subject to any disclaimer, the term of this patent is extended or adjusted under 35 U.S.C. 154(b) by 180 days.

(21) Appl. No.: 17/085,542

(22) Filed: Oct. 30, 2020

(65) Prior Publication Data

US 2021/0130907 A1    May 6, 2021

Related U.S. Application Data

(60) Provisional application No. 63/065,081, filed on Aug. 13, 2020, provisional application No. 62/928,888, filed on Oct. 31, 2019.

(51) Int. Cl.
*C12Q 1/6886* (2018.01)
*C12Q 1/6869* (2018.01)
*C12N 15/117* (2010.01)
*G01N 33/50* (2006.01)

(52) U.S. Cl.
CPC .......... *C12Q 1/6886* (2013.01); *C12N 15/117* (2013.01); *C12Q 1/6869* (2013.01); *G01N 33/50* (2013.01); *C12Q 2521/301* (2013.01); *C12Q 2523/125* (2013.01)

(58) Field of Classification Search
CPC . C12Q 1/6886; C12Q 2523/125; G01N 33/50
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,965,188 A | 10/1990 | Mullis et al. |
| 5,011,769 A | 4/1991 | Duck et al. |
| 5,124,246 A | 6/1992 | Urdea et al. |
| 5,288,609 A | 2/1994 | Engelhardt et al. |
| 5,338,671 A | 8/1994 | Scalice et al. |
| 5,403,711 A | 4/1995 | Walder et al. |
| 5,409,818 A | 4/1995 | Davey et al. |
| 5,494,810 A | 2/1996 | Barany et al. |
| 5,508,169 A | 4/1996 | Deugau et al. |
| 5,624,802 A | 4/1997 | Urdea et al. |
| 5,639,611 A | 6/1997 | Wallace et al. |
| 5,660,988 A | 8/1997 | Duck et al. |
| 5,710,264 A | 1/1998 | Urdea et al. |
| 5,773,258 A | 6/1998 | Birch et al. |
| 5,786,146 A | 7/1998 | Herman et al. |
| 5,792,614 A | 8/1998 | Western et al. |
| 5,846,717 A | 12/1998 | Brow et al. |
| 5,849,481 A | 12/1998 | Urdea et al. |
| 5,851,770 A | 12/1998 | Babon et al. |
| 5,882,867 A | 3/1999 | Ullman et al. |
| 5,914,230 A | 6/1999 | Liu et al. |
| 5,958,692 A | 9/1999 | Cotton et al. |
| 5,965,408 A | 10/1999 | Short |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade |
| 6,063,573 A | 5/2000 | Kayyem |
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Western et al. |
| 6,150,097 A | 11/2000 | Tyagi et al. |
| 6,183,960 B1 | 2/2001 | Lizardi |
| 6,210,884 B1 | 4/2001 | Lizardi |
| 6,221,583 B1 | 4/2001 | Kayyem et al. |
| 6,235,502 B1 | 5/2001 | Weissman et al. |
| 6,248,229 B1 | 6/2001 | Meade |
| 6,251,594 B1 | 6/2001 | Gonzalgo et al. |

(Continued)

FOREIGN PATENT DOCUMENTS

| | | |
|---|---|---|
| WO | WO 95/00669 | 1/1995 |
| WO | WO 95/15373 | 6/1995 |

(Continued)

OTHER PUBLICATIONS

Calin et al. Blood. 2009. 114(23):4761-4770. (Year: 2009).*
Li et al. Chemico-Biological Interactions. 2022. 361:109967, 14 pages. (Year: 2022).*
Talukdar et al. Cancer Res. 2021. 81:2612-2624. (Year: 2021).*
Earp et al. Genomics. 2015. 106:311-321. (Year: 2015).*
He et al. Scientific Reports. 2016. 6:24706, 11 pages. (Year: 2016).*
Marinelli et al. Gynecologic Oncology. 2022. 165:568-576. (Year: 2022).*
Sundararajan et al. Scientific Reports. 2019. 9:8295, 9 pages. (Year: 2019).*

(Continued)

*Primary Examiner* — Joseph G. Dauner
(74) *Attorney, Agent, or Firm* — Casimir Jones, S.C.; Peter J. Schlueter

(57) ABSTRACT

Provided herein is technology for ovarian cancer screening and particularly, but not exclusively, to methods, compositions, and related uses for detecting the presence of ovarian cancer and sub-types of ovarian cancer (e.g., clear cell ovarian cancer, endometrioid ovarian cancer, mucinous ovarian cancer, serous ovarian cancer).

17 Claims, 24 Drawing Sheets

Specification includes a Sequence Listing.

(56) References Cited

U.S. PATENT DOCUMENTS

| | | |
|---|---|---|
| 6,265,171 B1 | 7/2001 | Herman et al. |
| 6,872,816 B1 | 3/2005 | Hall et al. |
| 7,037,650 B2 | 5/2006 | Gonzalgo et al. |
| 7,662,594 B2 | 2/2010 | Kong et al. |
| 8,361,720 B2 | 1/2013 | Oldham-Haltom et al. |
| 8,715,937 B2 | 5/2014 | Zou et al. |
| 8,808,990 B2 | 8/2014 | Lidgard et al. |
| 8,916,344 B2 | 12/2014 | Zou et al. |
| 9,000,146 B2 | 4/2015 | Bruinsma et al. |
| 9,096,893 B2 | 8/2015 | Allawi et al. |
| 9,169,511 B2 | 10/2015 | Bruinsma et al. |
| 9,212,392 B2 | 12/2015 | Allawi et al. |
| 2007/0202525 A1 | 8/2007 | Quake et al. |
| 2012/0122088 A1 | 5/2012 | Zou et al. |
| 2012/0122106 A1 | 5/2012 | Zou et al. |
| 2014/0199696 A1 | 7/2014 | Mansour et al. |
| 2019/0161806 A1 | 5/2019 | Ahlquist et al. |
| 2019/0177769 A1 | 6/2019 | Allawi et al. |

FOREIGN PATENT DOCUMENTS

| | | | |
|---|---|---|---|
| WO | WO 97/46705 | 12/1997 | |
| WO | WO 99/28498 | 6/1999 | |
| WO | WO 00/26401 | 5/2000 | |
| WO | WO 05/023091 | 3/2005 | |
| WO | WO 2005/038051 | 4/2005 | |
| WO | WO-2007067695 A2 * | 6/2007 | ......... A61K 31/7072 |
| WO | WO 2009/153667 | 12/2009 | |
| WO | WO-2009153667 A2 * | 12/2009 | ........... C12Q 1/6886 |
| WO | WO 2012/155072 | 11/2012 | |
| WO | WO 2013/070950 | 5/2013 | |
| WO | WO 2013/096661 | 6/2013 | |
| WO | WO 2013/116375 | 8/2013 | |
| WO | WO 2015/116837 | 8/2015 | |
| WO | WO 2017/075061 | 5/2017 | |
| WO | WO-2017192221 A1 * | 11/2017 | ........... C12Q 1/6806 |

OTHER PUBLICATIONS

Bakkum-Gamez et al. Journal of Clinical Oncology. 2020. 28(15 suppl):6072-6072. (Year: 2020).*

International Search Report and Written Opinion for PCT/US2020/058235, dated Mar. 22, 2021. 32 pages.

Antequera et al., High levels of de novo methylation and altered chromatin structure at CpG islands in cell lines. Cell. Aug. 10, 1990;62(3):503-14.

Ballabio et al., Screening for steroid sulfatase (STS) gene deletions by multiplex DNA amplification. Hum Genet. May 1990;84(6):571-3.

Baranay. Genetic disease detection and DNA amplification using cloned thermostable ligase. Proc. Natl. Acad. Sci USA 1991. vol. 88, 189-93.

Bustin. Absolute quantification of mRNA using real-time reverse transcription polymerase chain reaction assays. J Mol Endocrinol. Oct. 2000;25(2):169-93.

Chamberlain et al., Deletion screening of the Duchenne muscular dystrophy locus via multiplex DNA amplification. Nucleic Acids Res. Dec. 9, 1988;16(23):11141-56.

Chamberlin et al., New RNA polymerase from *Escherichia coli* infected with bacteriophage T7. Nature. Oct. 17, 1970;228(5268):227-31.

Don et al., 'Touchdown' PCR to circumvent spurious priming during gene amplification. Nucleic Acids Res. Jul. 25, 1991;19(14):4008.

Dowdy and Wearden, Statistics for Research, John Wiley & Sons, New York, 1983. TOC only. 6 pages.

Eads et al., CpG island hypermethylation in human colorectal tumors is not associated with DNA methyltransferase overexpression. Cancer Res. May 15, 1999;59(10):2302-6.

Egan. Signal Detection Theory and ROC Analysis, Academic Press, New York. 1975. TOC only. 9 pages.

Erlich (ed.), PCR Technology, Stockton Press. 1989. TOC only. 5 pages.

Feil et al., Methylation analysis on individual chromosomes: improved protocol for bisulphite genomic sequencing. Nucleic Acids Res. Feb. 25, 1994;22(4):695-6.

Frommer et al., A genomic sequencing protocol that yields a positive display of 5-methylcytosine residues in individual DNA strands. Proc Natl Acad Sci U S A. Mar. 1, 1992;89(5):1827-31.

Gardiner-Garden et al., CpG islands in vertebrate genomes.J Mol Biol. Jul. 20, 1987;196(2):261-82.

Gonzalgo et al., Rapid quantitation of methylation differences at specific sites using methylation-sensitive single nucleotide primer extension (Ms-SNuPE). Nucleic Acids Res. Jun. 15, 1997;25(12):2529-31.

Gonzalgo et al., Identification and characterization of differentially methylated regions of genomic DNA by methylation-sensitive arbitrarily primed PCR. Cancer Res. Feb. 15, 1997;57(4):594-9.

Grafstrom et al., The characteristics of DNA methylation in an in vitro DNA synthesizing system from mouse fibroblasts. Nucleic Acids Res. Apr. 25, 1985;13(8):2827-42.

Grigg et al., Sequencing 5-methylcytosine residues in genomic DNA. Bioessays. Jun. 1994;16(6):431-6.

Grigg. Sequencing 5-methylcytosine residues by the bisulphite method. DNA Seq. 1996;6(4):189-98.

Gu et al., Genome-scale DNA methylation mapping of clinical samples at single-nucleotide resolution. Nat Methods. Feb. 2010;7(2):133-6.

Gu et al., Preparation of reduced representation bisulfite sequencing libraries for genome-scale DNA methylation profiling. Nat Protoc. Apr. 2011;6(4):468-81.

Guilfoyle et al., Ligation-mediated PCR amplification of specific fragments from a class-II restriction endonuclease total digest. Nucleic Acids Res. May 1, 1997;25(9):1854-8.

Hall et al., Sensitive detection of DNA polymorphisms by the serial invasive signal amplification reaction. Proc Natl Acad Sci U S A. Jul. 18, 2000;97(15):8272-7.

Hayden et al., Multiplex-ready PCR: a new method for multiplexed SSR and SNP genotyping. BMC Genomics. Feb. 18, 2008;9:80.

Hecker et al., High and low annealing temperatures increase both specificity and yield in touchdown and stepdown PCR. Biotechniques. Mar. 1996;20(3):478-85.

Herman et al., Methylation-specific PCR: a novel PCR assay for methylation status of CpG islands. Proc Natl Acad Sci U S A. Sep. 3, 1996;93(18):9821-6.

Higuchi et al., A general method of in vitro preparation and specific mutagenesis of DNA fragments: study of protein and DNA interactions. Nucleic Acids Res. Aug. 11, 1988;16(15):7351-67.

Higuchi et al., Kinetic PCR analysis: real-time monitoring of DNA amplification reactions. Biotechnology (N Y). Sep. 1993;11(9):1026-30.

Higuchi et al., Simultaneous amplification and detection of specific DNA sequences. Biotechnology (N Y). Apr. 1992;10(4):413-7.

In re Herz, 537 F.2d 549, 551-52, 190 USPQ 461,463 (CCPA 1976) 4 pages.

Kacian et al., A replicating RNA molecule suitable for a detailed analysis of extracellular evolution and replication. Proc Natl Acad Sci U S A. Oct. 1972;69(10):3038-42.

Kalinina et al., Nanoliter scale PCR with TaqMan detection. Nucleic Acids Res. May 15, 1997;25(10):1999-2004.

Kawai et al., Comparison of DNA methylation patterns among mouse cell lines by restriction landmark genomic scanning. Mol Cell Biol. Nov. 1994;14(11):7421-7.

Kuppuswamy et al., Single nucleotide primer extension to detect genetic diseases: experimental application to hemophilia B (factor IX) and cystic fibrosis genes. Proc Natl Acad Sci U S A. Feb. 15, 1991;88(4):1143-7.

Laird. Principles and challenges of genomewide DNA methylation analysis. Nat Rev Genet. Mar. 2010;11(3):191-203.

Li et al., MethPrimer: designing primers for methylation PCRs. Bioinformatics. Nov. 2002;18(11):1427-31.

Lyamichev et al., Polymorphism identification and quantitative detection of genomic DNA by invasive cleavage of oligonucleotide probes. Nat Biotechnol. Mar. 1999;17(3):292-6.

(56) References Cited

OTHER PUBLICATIONS

Martin et al., Genomic sequencing indicates a correlation between DNA hypomethylation in the 5' region of the pS2 gene and its expression in human breast cancer cell lines. Gene. May 19, 1995;157(1-2):261-4.
Meissner et al., Genome-scale DNA methylation maps of pluripotent and differentiated cells. Nature. Aug. 7, 2008;454(7205):766-70.
Meissner et al., Reduced representation bisulfite sequencing for comparative high-resolution DNA methylation analysis. Nucleic Acids Res. Oct. 13, 2005;33(18):5868-77.
Nyce et al., Variable effects of DNA-synthesis inhibitors upon DNA methylation in mammalian cells. Nucleic Acids Res. May 27, 1986;14(10):4353-67.
Olek et al., A modified and improved method for bisulphite based cytosine methylation analysis. Nucleic Acids Res. Dec. 15, 1996;24(24):5064-6.
Olek et al., The pre-implantation ontogeny of the H19 methylation imprint. Nat Genet. Nov. 1997;17(3):275-6.
Ozols et al., Epithelial ovarian cancer. Principles and Practice of Gynecologic Oncology. Lippincott Williams & Wilkins; Philadelphia, PA, USA: 2000. pp. 981-1057.
Ramsahoye et al., Non-CpG methylation is prevalent in embryonic stem cells and may be mediated by DNA methyltransferase 3a. Proc Natl Acad Sci U S A. May 9, 2000;97(10):5237-42.
Rein et al., Identifying 5-methylcytosine and related modifications in DNA genomes. Nucleic Acids Res. May 15, 1998;26(10):2255-64.
Roux. Using mismatched primer-template pairs in touchdown PCR. Biotechniques. May 1994;16(5):812-4.
Sadri et al., Rapid analysis of DNA methylation using new restriction enzyme sites created by bisulfite modification. Nucleic Acids Res. Dec. 15, 1996;24(24):5058-9.
Salomon et al., Methylation of mouse DNA in vivo: di- and tripyrimidine sequences containing 5-methylcytosine. Biochim Biophys Acta. Apr. 15, 1970;204(2):340-51.
Schouten et al., Relative quantification of 40 nucleic acid sequences by multiplex ligation-dependent probe amplification. Nucleic Acids Res. Jun. 15, 2002;30(12):e57. 13 pages.
Singer-Sam et al., A quantitative HpaII-PCR assay to measure methylation of DNA from a small number of cells. Nucleic Acids Res. Feb. 11, 1990;18(3):687.
Singer-Sam et al., A sensitive, quantitative assay for measurement of allele-specific transcripts differing by a single nucleotide. PCR Methods Appl. Feb. 1992;1(3):160-3.
Szabo et al., Allele-specific expression and total expression levels of imprinted genes during early mouse development: implications for imprinting mechanisms. Genes Dev. Dec. 15, 1995;9(24):3097-108.
Toyota et al., Identification of differentially methylated sequences in colorectal cancer by methylated CpG island amplification. Cancer Res. May 15, 1999;59(10):2307-12.
Triglia et al., A procedure for in vitro amplification of DNA segments that lie outside the boundaries of known sequences. Nucleic Acids Res. Aug. 25, 1988;16(16):8186.
Vogelstein et al., Digital PCR. Proc Natl Acad Sci U S A. Aug. 3, 1999;96(16):9236-41.
Woodcock et al., The majority of methylated deoxycytidines in human DNA are not in the CpG dinucleotide. Biochem Biophys Res Commun. Jun. 15, 1987;145(2):888-94.
Wu et al., The ligation amplification reaction (LAR)—amplification of specific DNA sequences using sequential rounds of template-dependent ligation. Genomics. May 1989;4(4):560-9.
Xiong et al., COBRA: a sensitive and quantitative DNA methylation assay. Nucleic Acids Res. Jun. 15, 1997;25(12):2532-4.
Zeschnigk et al., Imprinted segments in the human genome: different DNA methylation patterns in the Prader-Willi/Angelman syndrome region as determined by the genomic sequencing method. Hum Mol Genet. Mar. 1997;6(3):387-95.
Zhang et al., DNA methylation analysis of chromosome 21 gene promoters at single base pair and single allele resolution. PLoS Genet. Mar. 2009;5(3):e1000438. 15 pages.
Zou et al, Highly methylated genes in colorectal neoplasia: implications for screening. Cancer Epidemiol Biomarkers Prev. Dec. 2007;16(12):2686-96.
Zou et al., Sensitive quantification of methylated markers with a novel methylation specific technology. Clin Chem 2010. 56: A199 abstract D-144. 1 page.

\* cited by examiner

FIG. 1

AGRN_8794
>hg19_dna range=chr1:968670-968849 5'pad=0 3'pad=10 strand=+
repeatMasking=none WT
GCGCCGCACCTGGGGCCCTCCCCCACCTACGCCCCGCCAGGGCGGGGCCGCGGGCGCAGACACTCGCGGGCACAC
GCACGACGACGCGCACACGCGGTCGCACGCGGCCCCCCGAGCCCCCTGCGGCGACTCCGATTCACCCCCGCGGGT
GCGGGGCGCGGACCCGCCCGGCCCAGCTCC (SEQ ID NO:284)

BST
GCGTCGTATTTGGGGTTTTTTTTTATTTACGTTTCGTTAGGGCGGGGTCGCGGGCGTAGATATTCGCGGGTATAC
GTACGACGACGCGTATACGCGGTCGTACGCGGTTTTTCGAGTTTTTTGCGGCGATTTCGATTTATTTTCGCGGGT
GCGGGGCGCGGATTCGTTCGGTTTAGTTTT (SEQ ID NO:285)

AGRN_8794_FP      GCGGTTTTTCGAGTTTTTTGCG (SEQ ID NO:137)
AGRN_8794_RP      GAACGAATCCGCGCC (SEQ ID NO:138)
AGRN_8794_Pb_A5   AGGCCACGGACG GGCGATTTCGATTTATTTTCG/3C6/ (SEQ ID NO:235)

BCAT1_6015
>hg19_dna range=chr12:25055940-25056138 5'pad=0 3'pad=10 strand=+
repeatMasking=none WT
GCGGGGCTGCAGAGAGCGGCAGTGGCACGGAGCGCGCGGCTGGAAGCGAAAGCAGGCGGTGTGGCCAAGCCCCGG
CGCACGGCCCATAGGGCGCTGGGTACCACGACCTGGGGCCGCGCGCCAGGGCCAGGCGCAGGGTACGACGCAACC
CCTCCAGCATCCCTTGGGGAGGAGCCTCCAACCGTCTCGTCCCAGTCTG (SEQ ID NO:286)

BST
GCGGGGTTGTAGAGAGCGGTAGTGGTACGGAGCGCGCGGTTGGAAGCGAAAGTAGGCGGTGTGGTTAAGTTTCGG
CGTACGGTTTATAGGGCGTTGGGTATTACGATTTGGGGTCGCGCGTTAGGGTTAGGCGTAGGGTACGACGTAATT
TTTTTAGTATTTTTTGGGGAGGAGTTTTTAATCGTTTCGTTTTAGTTTG (SEQ ID NO:287)

BCAT1_6015_FP     GCGGTGTGGTTAAGTTTCGG (SEQ ID NO:139)
BCAT1_6015_RP     CGCGACCCCAAATCGTA (SEQ ID NO:140)
BCAT1_6015_Pb_A1  CGCGCCGAGG GCGTACGGTTTATAGGGC/3C6/ (SEQ ID NO:236)

BHLHE23_8339
>hg19_dna range=chr20:61638294-61638506 5'pad=0 3'pad=0 strand=+
repeatMasking=none WT
GCGACGCGCAGGGGGCGGGCTCTACCTCCCCCTCGCCCCGCTTCGGTTTTAAGCCGCGGAGGCGCCCGGTGGGA
CCTCGCTGCTGTCCAATCAGGGGGGACCGGGTGAGCTCCTCTTCCTGGAGCCGGGCTCCACCAGCGCCGCAGGCT
CACAGGCCGGGGGTGGGGGCTCTGGACCGAGGGGCGGCGCGGGGCGGCGCGGGGCGGCGCGCG (SEQ ID
NO:288)

FIG. 1 (CONT'D)

GCGACGCGTAGGGGGCGGGTTTTATTTTTTTTTCGTTTTCGTTTCGGTTTTAAGTCGCGGAGGCGTTCGGTGGGA
TTTCGTTGTTGTTTAATTAGGGGGGATCGGGTGAGTTTTTTTTTTGGAGTCGGGTTTTATTAGCGTCGTAGGTT
TATAGGTCGGGGGTGGGGGTTTTGGATCGAGGGGCGGCGCGGGGCGGCGCGGGGCGGCGCGCG (SEQ ID
NO:289)

BHLHE23_8339_FP    CGGGTTTTATTTTTTTTTCGTTTTCGTTTC (SEQ ID NO:141)
BHLHE23_8339_RP    AACGAAATCCCACCGAACG (SEQ ID NO:142)
BHLHE23_8339_Pb_A1     CGCGCCGAGG CGGTTTTAAGTCGCGGA/3C6/ (SEQ ID NO:237)

ELMO1_9100
>hg19_dna range=chr7:37488054-37488165 5'pad=10 3'pad=2 strand=+
repeatMasking=none WT
AACTGCAGAGCGCCCCGACGCGCCCGCAGCCCTCACCCTGCCGAGCGCGGCGGCCACCCCCGCCCGAGCCGCGGC
GCCCCCAGGGAGGAAACAAAAGTGTCTCCGCGGCGCC (SEQ ID NO:290)

BST
AATTGTAGAGCGTTTCGACGCGTTCGTAGTTTTTATTTTGTCGAGCGCGGCGGTTATTTTCGTTCGAGTCGCGGC
GTTTTTAGGGAGGAAATAAAAGTGTTTTCGCGGCGTT (SEQ ID NO:291)

ELMO1_9100_FP      GTAGAGCGTTTCGACGCG (SEQ ID NO:143)
ELMO1_9100_RP      TCGAACGAAAATAACCGCCG (SEQ ID NO:144)
ELMO1_9100_Pb_A5   AGGCCACGGACG GCGCTCGACAAAATAAAAAC/3C6/ (SEQ ID NO:238)

EPS8L2
>hg19_dna range=chr11:726397-726519 5'pad=10 3'pad=3 strand=-
repeatMasking=none WT
GCCCGGGCCCCAGCTCATCCCCCGCCCCCGCTCACCGCGGGCTGAAGGCCTTGGCTTCCAGCCAGGCGCGGACCT
CGTCCGGACCCGACTCGTAGGTGAGCGGCTGGCTCACGGGCTGGCTGC (SEQ ID NO:292)

BST
GTTCGGGTTTTAGTTTATTTTTCGTTTTCGTTTATCGCGGGTTGAAGGTTTTGGTTTTTAGTTAGGCGCGGATTT
CGTTCGGATTCGATTCGTAGGTGAGCGGTTGGTTTACGGGTTGGTTGT (SEQ ID NO:293)

FIG. 1 (CONT'D)

EPS8L2_FP    GTTTTTAGTTAGGCGCGGATTTC (SEQ ID NO:145)

EPS8L2_RP    AACCCGTAAACCAACCGC (SEQ ID NO:146)

EPS8L2_Pb_A1    CGCGCCGAGG CGTTCGGATTCGATTCGT/3C6/ (SEQ ID NO:239)

---

JAM3

>hg19_dna range=chr11:133938908-133939011 5'pad=0 3'pad=0 strand=- repeatMasking=none WT
GAGCCGGAGTCGCGGTGGCCGCCTCAGCGCCATGTCGAGGGTTGCTGAGGGGCCAGCGGCAGCGCGGCGCGGCTT
GTAGTCCCCGCGCGCATGCGCCCAGCCTG (SEQ ID NO:294)

BST
Existing design
GAGTCGGAGTCGCGGTGGTCGTTTTAGCGTTATGTCGAGGGTTGTTGAGGGGTTAGCGGTAGCGCGGCGCGGTTT
GTAGTTTTCGCGCGTATGCGTTTAGTTTG (SEQ ID NO:295)

JAM3_FP     TGGTCGTTTTAGCGTTATGTCG (SEQ ID NO:147)
JAM3_RP     CGAAAACTACAAACCGCGC (SEQ ID NO:148)
JAM3_Pb_A5_LQ    AGGCCACGGACG CCGCGCTACCGCTA/3C6/ (SEQ ID NO:240)

---

KCNA3_7320

>hg19_dna range=chr1:111217250-111217357 5'pad=10 3'pad=6 strand=+ repeatMasking=none WT
AGGTGGTCCCCGGGCACCACGGTCATGTCGGGCGGCAGCTCGCGGCCTGCGGCGGGCTCCGCGTAGCCGTGGTTC
ACCAGCGTGTGGGCACCGCCGCTGCTCGCTGGG (SEQ ID NO:296)

BST
AGGTGGTTTTCGGGTATTACGGTTATGTCGGGCGGTAGTTCGCGGTTTGCGGCGGGTTTCGCGTAGTCGTGGTTT
ATTAGCGTGTGGGTATCGTCGTTGTTCGTTGGG (SEQ ID NO:297)

KCNA3_7320_FP    CGGTTATGTCGGGCGG (SEQ ID NO:149)
KCNA3_7320_RP    CAACGACGATACCCACACG (SEQ ID NO:150)
KCNA3_7320_Pb_A1    CGCGCCGAGG GCTAATAAACCACGACTACG/3C6/ (SEQ ID NO:241)

---

KCNA3_7518    Chr1:111217487-111217673

>hg19_dna range=chr1:111217481-111217679 5'pad=6 3'pad=6 strand=+ repeatMasking=none WT
CTCCCCGCCCTTTCGCCGCCTCCGCCCCCGAGCCGAGCCCACGCCTGTTGCAGCCAAAGCCGCGATGCTCTGTC
TGGGTCTGGCGCGGTCAGCCGGGCTCCCGCACGGGGACGCCTCCTCCCTCCTTCTCGCGCTCTCCGCCCCCTCCC
CTGCGGGGCGCGCGCCCGCCTCCGCGTCCCCTTAGGATTCCCGCCCACC (SEQ ID NO:298)

FIG. 1 (CONT'D)

BST
TTTTTCGTTTTTTCGTCGTTTTCGTTTTCGAGTCGAGTTTATCGTTTGTTGTAGTTAAAGTCGCGATGTTTTGTT
TGGGTTTGGCGCGGTTAGTCGGGTTTTCGTACGGGGACGTTTTTTTTTTTTTTTCGCGTTTTTCGTTTTTTTT
TTGCGGGGCGCGCGTTCGTTTTCGCGTTTTTTTAGGATTTTCGTTTATT (SEQ ID NO:299)

| KCNA3_7518_FP | TCGTTTTTTCGTCGTTTTCGTTTTC (SEQ ID NO:151) |
| KCNA3_7518_RP | CCCGTACGAAAACCCGA (SEQ ID NO:152) |
| KCNA3_7518_Pb_A5 | AGGCCACGGACG CGAGTCGAGTTTATCGTTTG/3C6/ (SEQ ID NO:242) |

MDFI_6321
>hg19_dna range=chr6:41606064-41606357 5'pad=10 3'pad=6 strand=-
repeatMasking=none WT
GATCCCCGCGCGGGGCCCGCCATGCGCGCCTGCTCCGGGCGCCCCTGCCCAGGTCCCGCTGGCTCCCGGGTGCTC
GCCTGGCGCCCCTTCCCCTCTCACTCGCTGCTTTCTCCCATTTCGGCGCCAGCTCACGCCGTTCGCCCCTTCCTT
CTTCCTTCTCTCCCTCCAGCCCCCTCGCTCCTCCCCTACTCGCCTCTCCCCTCCCCTCTTCCCTGGCCCACCCT
CTCCCCGCCCCCTCCTCGCCTTCTCAGTCGCCCCTCTGCGGGTCCCCTCCCCGCGCCGGGCTTGGCCC (SEQ
ID NO:300)

BST
GATTTTCGCGCGGGGTTCGTTATGCGCGTTTGTTTCGGGCGTTTTTGTTTAGGTTTCGTTGGTTTTCGGGTGTTC
GTTTGGCGTTTTTTTTTTTTTATTCGTTGTTTTTTTTTATTTCGGCGTTAGTTTACGTCGTTCGTTTTTTTTTT
TTTTTTTTTTTTTTTAGTTTTTTCGTTTTTTTTTATTCGTTTTTTTTTTTTTTTTTTGGTTTATTT
TTTTTCGTTTTTTTTTCGTTTTTTTAGTCGTTTTTTTGCGGGTTTTTTTTTTCGCGTCGGGTTTGGTTT (SEQ
ID NO:301)

MDFI_6321_BST plasmid sequence
GATTTTCGCGCGGGGTTCGTTATGCGCGTTTGTTTCGGGCGTTTTTGTTTAGGTTTCGTTGGTTTTCGGGTGTTC
GTTTGGCGTTTTTTTTTTTTTATTCGTTGTTTTTTTTTATTTCGGCGTTAGTTTACGTCGTTCGTTTTTTTTTT
TTTTTTTTTTTTTTTAG (SEQ ID NO:302)

| MDFI_6321_FP | GTTCGTTATGCGCGTTTGTTTC (SEQ ID NO:153) |
| MDFI_6321_RP | GAACACCCGAAAACCAACGA (SEQ ID NO:154) |
| MDFI_6321_Pb_A1 | CGCGCCGAGG CGGGCGTTTTTGTTTAGG/3C6/ (SEQ ID NO:243) |

RASSF1_8293   chr3:50378182-50378372
>hg19_dna range=chr3:50378172-50378382 5'pad=10 3'pad=10 strand=-
repeatMasking=none

FIG. 1 (CONT'D)

WT
TTTCCATTGCGCGGCTCTCCTCAGCTCCTTCCCGCCGCCCAGTCTGGATCCTGGGGGAGGCGCTGAAGTCGGGGC
CCGCCCTGTGGCCCGCCCGGCCCGCGCTTGCTAGCGCCCAAAGCCAGCGAAGCACGGGCCCAACCGGGCCATGT
CGGGGGAGCCTGAGCTCATTGAGCTGCGGGAGCTGGCACCCGCTGGGCGCGCTGGGAAGGG (SEQ ID
NO:303)

BST
TTTTTATTGCGCGGTTTTTTTTAGTTTTTTTTCGTCGTTTAGTTTGGATTTTGGGGGAGGCGTTGAAGTCGGGGT
TCGTTTTGTGGTTTCGTTCGGTTCGCGTTTGTTAGCGTTTAAAGTTAGCGAAGTACGGGTTTAATCGGGTTATGT
CGGGGGAGTTTGAGTTTATTGAGTTGCGGGAGTTGGTATTCGTTGGGCGCGTTGGGAAGGG (SEQ ID
NO:304)

RASSF1_8293_FP      GTTTTGTGGTTTCGTTCGGTTC (SEQ ID NO:155)
RASSF1_8293_RP      CCGATTAAACCCGTACTTCGC (SEQ ID NO:156)
RASSF1_8293_Pb_A5   AGGCCACGGACG CGCGTTTGTTAGCGTTTAAA/3C6/ (SEQ ID NO:244)

---

SFMBT2_2363   chr10:7451790-7452428
>hg19_dna range=chr10:7451780-7452430 5'pad=10 3'pad=2 strand=-
repeatMasking=none WT
GCCGCCCACCTTCCTCGTTTCTGCACTCATTTTAGCGACGCAGCCGCCGCTGCTACCTACCCCGCGCTCCCGCGT
CTCCTCCGCGCTGGGGTCTCCCCTTTCTTTTGGTTTGGGTGGGAGAAAAAGATGGTGAGGACGGGGAATCGGAGA
CCGGCATGGGGGTAAAAATCGTGCAGACATTCGGAATCGCTCCCTTGGAAACATTTGCCTGAGCAACTGAAATAA
AATTGGCAGTAGTAGTTTTGGAGCGTGCTCCAGCGAGGATGGTCTTTTTGTTCATTATTTTCTCTTTAAAGTAAT
ATCCTGTCACTTAGGGGCTTTCCGGTTGTCTCCTCTTATTCGACCCCCTTTCAAAATTGCTGACTTGAGCTGGTT
CTGGAGTTTATTTTTTAATATGCGTGCGTGGGTATGTGTATGTGTGTATGTTTTGCAGAAATCCGCCAAAATG
CAACTGTAGGAACTGCGAGATGTATTTATTGATTTTGACCAGGGGCGGTGGGAAGGGGCTGGAGGGAGCTGGGGG
ATCCTGGAGGGTGGGAAGTGGCTGATTCTCGGTGGCCGGACACTCATCCAGAGCCTGATCCGTACTCGTGTTTTC
TTGGAAGCGCCACAACTGCGGGGAAGGAGTCTTTAGAAACCGTGCCAGTTT (SEQ ID NO:305)

BST
GTCGTTTATTTTTTTCGTTTTTGTATTTATTTTAGCGACGTAGTCGTCGTTGTTATTTATTTCGCGTTTTCGCGT
TTTTTCGCGTTGGGGTTTTTTTTTTTTTGGTTTGGGTGGGAGAAAAAGATGGTGAGGACGGGGAATCGGAGA
TCGGTATGGGGGTAAAAATCGTGTAGATATTCGGAATCGTTTTTTTGGAAATATTTGTTTGAGTAATTGAAATAA
AATTGGTAGTAGTAGTTTTGGAGCGTGTTTTAGCGAGGATGGTTTTTTTGTTTATTATTTTTTTTTAAAGTAAT
ATTTTGTTATTTAGGGGTTTTTCGGTTGTTTTTTTTATTCGATTTTTTTTAAAATTGTTGATTTGAGTTGGTT
TTGGAGTTTATTTTTTAATATGCGTGCGTGGGTATGTGTATGTGTGTATGTTTTGTAGAAATTCGTTAAAATG
TAATTGTAGGAATTGCGAGATGTATTTATTGATTTTGATTAGGGGCGGTGGGAAGGGGTTGGAGGGAGTTGGGGG
ATTTTGGAGGGTGGGAAGTGGTTGATTTTCGGTGGTCGGATATTTATTTAGAGTTTGATTCGTATTCGTGTTTTT
TTGGAAGCGTTATAATTGCGGGGAAGGAGTTTTTAGAAATCGTGTTAGTTT (SEQ ID NO:306)

FIG. 1 (CONT'D)

SFMBT2_2363_BST plasmid sequence
GTCGTTTATTTTTTTCGTTTTTGTATTTATTTTAGCGACGTAGTCGTCGTTGTTATTTATTTCGCGTTTTCGCGT
TTTTTTCGCGTTGGGGTTT (SEQ ID NO:307)

SFMBT2_1839_BST plasmid sequence
GAAGTGGCTGATTCTCGGTGGCCGGACACTCATCCAGAGCCTGATCCGTACTCGTGTTTTCTTGGAAGCGCCACA
ACTGCGGGGAAGGAGTCTTTAGAAACCGTGCCAGTTT (SEQ ID NO:308)

SFMBT2_2363_FP    TTTCGTTTTTGTATTTATTTTAGCGACGT (SEQ ID NO:157)
SFMBT2_2363_RP    ACGCGAAAAAAACGCGAAAACG (SEQ ID NO:158)
SFMBT2_2363_Pb_A1 CGCGCCGAGG GCGAAATAAATAACAACGACGA/3C6/ (SEQ ID NO:245)

SFMBT2_1839_FP    CTGATTCTCGGTGGCCG (SEQ ID NO:309)
SFMBT2_1839_RP    GGCGCTTCCAAGAAAACACG (SEQ ID NO:310)
SFMBT2_1839_Pb_A5 AGGCCACGGACG CGAGTACGGATCAGGCT/3C6/ (SEQ ID NO:311)

SKI_2465    Chr1:2222218-2222508
>hg19_dna range=chr1:2222208-2222518 5'pad=10 3'pad=10 strand=+
repeatMasking=none WT
CCTGTAAAGCCGGGGATGGCAGGACGCATTGTCACCCCCTCCTGCCGCTCTTACGAAACACTCTTAATTGAGTCC
GATTCTTGGTGAATCAGCCTTCCAAGAACCGCGACCGCAGCATCCTGTGCCGCTTCTGTGTTCCGCATTTTTCTC
TTTCTGCAGCGTTTCCTCTCATTCTGGATGGAAAGGCCTGTTTGTCTCCCTCAATCTTTGGCGAGGGTGGCAGGC
AGCCAGGCGGCCATTACGGGCCGCGCCTCCCACCAGCCAGTCGCTGGCAGGAGCGTCCGGGGAGGGAGCAGACCC
CGTTCACCCTC (SEQ ID NO:312)

BST
TTTGTAAAGTCGGGGATGGTAGGACGTATTGTTATTTTTTTTGTCGTTTTTACGAAATATTTTTAATTGAGTTC
GATTTTTGGTGAATTAGTTTTTTAAGAATCGCGATCGTAGTATTTTGTGTCGTTTTTGTGTTTCGTATTTTTTT
TTTTTGTAGCGTTTTTTTTTATTTTGGATGGAAAGGTTTGTTTGTTTTTTTTAATTTTTGGCGAGGGTGGTAGGT
AGTTAGGCGGTTATTACGGGTCGCGTTTTTTATTAGTTAGTCGTTGGTAGGAGCGTTCGGGGAGGGAGTAGATTT
CGTTTATTTTT (SEQ ID NO:313)

SKI_2465_BST plasmid sequence
GTAGGTAGTTAGGCGGTTATTACGGGTCGCGTTTTTTATTAGTTAGTCGTTGGTAGGAGCGTTCGGGGAGGGAGT
AGATTTCGTTTATTTTT (SEQ ID NO:314)

SKI_2465_FP GTTAGGCGGTTATTACGGGTC (SEQ ID NO:159)
SKI_2465_RP GAAATCTACTCCCTCCCCGA (SEQ ID NO:160)
SKI_2465_Pb_A5    AGGCCACGGACG CGCGTTTTTTATTAGTTAGTCGTT/3C6/ (SEQ ID NO:246)

SPOCK2_7433    chr10:73847355-73847446

\>hg19_dna range=chr10:73847345-73847456 5'pad=10 3'pad=10 strand=+ repeatMasking=none WT
CCCAGAGCCCCGGTCACACTCCCGTCCCATGCTGTCCCCCTCCCGCAAAGCCCACGGTGGGAACAGAGGGCACCG
CGCGAGCCGATGCCACCCTCACTGCCGGCCCCACCCA (SEQ ID NO:315)

BST
TTTAGAGTTTCGGTTATATTTTCGTTTTATGTTGTTTTTTTTCGTAAAGTTTACGGTGGGAATAGAGGGTATCG
CGCGAGTCGATGTTATTTTTATTGTCGGTTTTATTTA (SEQ ID NO:316)

SPOCK2_7433_FP    TATGTTGTTTTTTTTCGTAAAGTTTACGGT (SEQ ID NO:161)
SPOCK2_7433_RP    CCGACAATAAAAATAACATCGACTCG (SEQ ID NO:162)
SPOCK2_7433_Pb_A1 CGCGCCGAGG GCGCGATACCCTCTATTC/3C6/ (SEQ ID NO:247)

---

VIPR2   chr7:158937203-158937476

\>hg19_dna range=chr7:158937193-158937479 5'pad=10 3'pad=3 strand=+ repeatMasking=none WT
CCTCCCAACCCGAGTCCCGCAACCCGGCGGGACCGGAGCTCAGCGCTTCACGCTCTCCGGGAGGAAGCTCCGGAC
CCCGGGCGACCCCGCTCCCTCTCCCGGACCCCGCCCGCGCTCCAGCACCCGGGAGGAAGGCGAAGACCGGCGGGA
GGAGCGCTCTTCTCGGAAGGGGAGAACCGGGTCCGAGGCGCCGTGGGGCGGGGGTCGCGGGCGCACTCACGGGGG
CGAGCAGCCAGCAGGTCAGCAGCGCGGGAGGCAGCAGCGTCCGCATCCCGAGCTCAGCGTGC (SEQ ID NO:317)

BST
TTTTTTAATTCGAGTTTCGTAATTCGGCGGGATCGGAGTTTAGCGTTTTACGTTTTTCGGGAGGAAGTTTCGGAT
TTCGGGCGATTTCGTTTTTTTTTTCGGATTTCGTTCGCGTTTTAGTATTCGGGAGGAAGGCGAAGATCGGCGGGA
GGAGCGTTTTTTTCGGAAGGGGAGAATCGGGTTCGAGGCGTCGTGGGGCGGGGGTCGCGGGCGTATTTACGGGGG
CGAGTAGTTAGTAGGTTAGTAGCGCGGGAGGTAGTAGCGTTCGTATTTCGAGTTTAGCGTGT (SEQ ID NO:318)

VIPR_FP    TCGTTCGCGTTTTAGTATTCGG (SEQ ID NO:163)
VIPR_RP    CGAAAAAAACGCTCCTCCCG (SEQ ID NO:164)
VIPR_Pb_A5 AGGCCACGGACG GCCGATCTTCGCCTT/3C6/ (SEQ ID NO:248)

---

ZMIZ1   chr10:81002589-81002797

\>hg19_dna range=chr10:81002587-81002801 5'pad=2 3'pad=4 strand=+ repeatMasking=none

FIG. 1 (CONT'D)

WT
GTCGGGTCGTGCGTTCGCTCGGCAGCGGCGTGCACCAGCACCACCCCTGCGTGCAAGTTTGAAATGTGAGCTGCC
TCCGATTCATACTCGCTCGCGCTCCCTCGCAGCGAAGTGGCTGGGCTGACGGTCTGCGCGCGCGAGTGAGTGCGG
GCGGCGGGCTGGGGGGCGGGGTGCGGACGGCGAGGCTCGCGGGGCGGGAGGGCGCGCGCGAGCC (SEQ ID
NO:319)

BST
GTCGGGTCGTGCGTTCGTTCGGTAGCGGCGTGTATTAGTATTATTTTTGCGTGTAAGTTTGAAATGTGAGTTGTT
TTCGATTTATATTCGTTCGCGTTTTTTCGTAGCGAAGTGGTTGGGTTGACGGTTTGCGCGCGCGAGTGAGTGCGG
GCGGCGGGTTGGGGGGCGGGGTGCGGACGGCGAGGTTCGCGGGGCGGGAGGGCGCGCGCGAGTT (SEQ ID
NO:320)

ZMIZ1_2684_FP      GTTCGTTCGGTAGCGGC (SEQ ID NO:165)

ZMIZ1_2684_RP      ACCACTTCGCTACGAAAAAACG (SEQ ID NO:166)

ZMIZ1_2684_Pb_A1   CGCGCCGAGG GCGAACGAATATAAATCGAAAAC/3C6/ (SEQ ID NO:249)

ZNF382      chr19:37096085-37096209

>hg19_dna range=chr19:37096075-37096214 5'pad=10 3'pad=5 strand=+
repeatMasking=none WT
TGGCAGAAGCGTAGTGCCAGCCGCAATAGGGCGGCCGTGGGTGCAAACGGAGGGGAGCGCCGGCAGCTAGCACCG
CGCGGCGACTAACGGGCCGCCCCGGAGACTCCTGGGAGCTCAGGCCCACGCGCGAGTGCGCAGGC (SEQ ID
NO:321)

BST
TGGTAGAAGCGTAGTGTTAGTCGTAATAGGGCGGTCGTGGGTGTAAACGGAGGGGAGCGTCGGTAGTTAGTATCG
CGCGGCGATTAACGGGTCGTTTCGGAGATTTTTGGGAGTTTAGGTTTACGCGCGAGTGCGTAGGT (SEQ ID
NO:322)

ZNF382_FP    TAGTCGTAATAGGGCGGTCG (SEQ ID NO:167)

ZNF382_RP    CCGAAACGACCCGTTAATCG (SEQ ID NO:168)

ZNF382_Pb_A5    AGGCCACGGACG GCCGCGCGATACTAA/3C6/ (SEQ ID NO:250)

GYPC_3753    chr2:127413592-127413887

>hg19_dna range=chr2:127413582-127413897 5'pad=10 3'pad=10 strand=+
repeatMasking=none WT
AGAAGTGGGCGGGTGTGTGTTTAAAAAAAAAAAGGGGGTGGAAACCCCACCAGCCAAGTCTGCAGAAAAAAAAT
AAATGAAGTCTGCCTATCTCCGGGCCAGAGCCCCTCCCCTCGGCCCGCGCGGGAGGAGTGTGACCCAGGTGCCGC
TTCCTCTCGCCGCCGAGGGTCAGGAGCCCGGGAGCGCGACCCTCCCCGGCCCGGCCTGGCCCGGCCTGGCCAGT
CCCCGCGGTCTCTGCCCGGGCTGACGCCCAGGAATGTGGTCGACGAGAAGCCCCAACAGCACGGCGTGGCCTCTC
AGCCTCGGTGAGTACC (SEQ ID NO:323)

FIG. 1 (CONT'D)

BST
AGAAGTGGGCGGGTGTGTGTTTAAAAAAAAAAAAGGGGGTGGAAATTTTATTAGTTAAGTTTGTAGAAAAAAAAT
AAATGAAGTTTGTTTATTTTCGGGTTAGAGTTTTTTTTTTCGGTTCGCGCGGGAGGAGTGT<u>GATTTAGGTGTCGT
TTTTTTTCGT</u>\[CGTCGAGGGTTAGGAGT\]TCGGGAGCGCGATTTTTTTTCGGTTCGGTTTGGTTCGGTTTGGTTAGT
TTTCGCGGTTTTTGTTCGGGTTGACGTTTAGGAATGTGGTCGACGAGAAGTTTTAATAGTACGGCGTGGTTTTTT
AGTTTCGGTGAGTATT (SEQ ID NO:324)

GYPC_3753_BST plasmid sequnce
GGAGTGTGATTTAGGTGTCGTTTTTTTTTCGT\[CGTCGAGGGTTAGGAGT\]TCGGGAGCGCGATTTTTTTTCGGTTCG
GT (SEQ ID NO:325)

GYPC_3753_FP       TGATTTAGGTGTCGTTTTTTTTCGTC (SEQ ID NO:169)
GYPC_3753_RP       GAAAAAAAATCGCGCTCCCG (SEQ ID NO:170)
GYPC_3753_Pb_A5    AGGCCACGGACG CGTCGAGGGTTAGGAGT/3C6/ (SEQ ID NO:251)

---

GYPC   chr2:127413898-127413988
>hg19_dna range=chr2:127413888-127413992 5'pad=10 3'pad=4 strand=+
repeatMasking=none WT
GGTGAGTACCCGCCGTGGGGAAGGGTCCTGGGGACCCACTGGAGGCCGCGGCCCGCAGCAGCCAGGGGCCGAGCC
ACGGCCACGGACGCCCTGGTGTCCCGGTCC (SEQ ID NO:326)

BST
GGTGAGTATTCGTCGTGGGGAAGGGTTTTGGGGATTTATTGGAGGTCGCGGTTCGTAGTAGTTAG\[GGGTCGAGTT
ACGGTTAC\]GGACGTTTTGGTGTTTCGGTTT (SEQ ID NO:327)

GYPC_3981_FP       ATTTATTGGAGGTCGCGGTTC (SEQ ID NO:171)
GYPC_3981_RP       CCGAAACACCAAAACGTCCG (SEQ ID NO:172)
GYPC_3981_Pb_A1    CGCGCCGAGG GTAACCGTAACTCGACCC/3C6/ (SEQ ID NO:252)

---

RFTN1   chr3:16554329-16554496
>hg19_dna range=chr3:16554319-16554502 5'pad=10 3'pad=6 strand=+
repeatMasking=none WT
GGGGACTCTCGGCACCCGCGTCCCTGTGCTTCTGGTGGTTCCGGCGCTTCCTCGGAGCGCGCGGCATGTCTGCTC
CTACACGTCCAGCACCTCTGTCCCCAGAGCAAACCCACCTCCCAGGGCACACGCAGAGGGGCAGTCAGGCACCGC
CTCCACCCTGCCCCACCCAGGCCGCGCGCACCCC (SEQ ID NO:328)

FIG. 1 (CONT'D)

BST
GGGGATTTTCGGTATTCGCGTTTTTGTGTTTTTGGTGGTTTCGGCGTTTTTTCGGAGCGCGCGGTATGTTTGTTT
TTATACGTTTAGTATTTTTGTTTTTAGAGTAAATTTATTTTTTAGGGTATACGTAGAGGGGTAGTTAGGTATCGT
TTTTATTTTGTTTTATTTAGGTCGCGCGTATTTT (SEQ ID NO:329)

RFTN1_FP_V2   GTGTTTTTGGTGGTTTCGGC (SEQ ID NO:173)
RFTN1_RP      ATACTAAACGTATAAAAACAAACATACCGC (SEQ ID NO:174)
RFTN1_Pb_A5   AGGCCACGGACG CGCGCTCCGAAAAAAC/3C6/ (SEQ ID NO:253)

---

PARP15     chr3:122296692-122296851
>hg19_dna range=chr3:122296682-122296861 5'pad=10 3'pad=10 strand=+ repeatMasking=none WT
CTCTTCCTCCCGGAGTATGGTGAGGAGCGCGGGGGACGGGTGCGGGAAGGGGACAGCAGGGCTGAGCCTGGGGCC
CGCAAGACCCAGCAGCCCGAGCGGGCGCAGAGACCCCACGCCACGCACAACCCTCTCTTCTAGGGGCGCCGACT
ACACTGACTTCCCTGTTCCGGAAGAGGGGG (SEQ ID NO:330)

BST
TTTTTTTTTTCGGAGTATGGTGAGGAGCGCGGGGGACGGGTGCGGGAAGGGGATAGTAGGGTTGAGTTTGGGGTT
CGTAAGATTTAGTAGTTCGAGCGGGCGTAGAGATTTTACGTTACGTATAATTTTTTTTTTAGGGGCGTCGATT
ATATTGATTTTTTGTTTCGGAAGAGGGGG (SEQ ID NO:331)

PARP15_6789_FP      GGTTCGTAAGATTTAGTAGTTCGAGC (SEQ ID NO:175)
PARP15_6789_RP      CGAAACAAAAAAATCAATATAATCGACGC (SEQ ID NO:176)
PARP15_6789_Pb_A1   CGCGCCGAGG CGGGCGTAGAGATTTTACG/3C6/ (SEQ ID NO:254)

---

GP5     chr3:194118822-194118924
>hg19_dna range=chr3:194118812-194118934 5'pad=10 3'pad=10 strand=+ repeatMasking=none WT
CTCTGCAGGACGCCGCGGCCCATTCCGAAGAGCAGGATGTGCGTGAGGTTGGTGGGCAGGCCTAGCGCGGAGATG
CGCGCCACGTCGCCCCCCGAGCACTGCGCGGCGTCCCGGAAGACACAC (SEQ ID NO:332)

BST
TTTTGTAGGACGTCGCGGTTTATTTCGAAGAGTAGGATGTGCGTGAGGTTGGTGGGTAGGTTTAGCGCGGAGATG
CGCGTTACGTCGTTTTTCGAGTATTGCGCGGCGTTTCGGAAGATATAT (SEQ ID NO:333)

GP5_8905_FP     TAGGACGTCGCGGTTTATTTC (SEQ ID NO:177)
GP5_8905_RP     CGCAATACTCGAAAAACGACG (SEQ ID NO:178)
GP5_8905_Pb_A5  AGGCCACGGACG GTAACGCGCATCTCCG/3C6/ (SEQ ID NO:255)

FIG. 1 (CONT'D)

GPRIN1     chr5:176023887-176023974

>hg19_dna range=chr5:176023884-176023984 5'pad=3 3'pad=10 strand=-
repeatMasking=none WT
GCCAAGGGGCGCCCGCGCCGCCGCCCGCCGCCCGTGCCGGCCCCGGCCGTTCGGGCTCGGTGCGCACCGCGCCCC
CAGATGGCGCCGCCAAGCGTCCGCCC (SEQ ID NO:334)

BST
GTTAAGGGGCGTTCGCGTCGTCGTTCGTCGTTCGTGTCGGTTTCGGTCGTTCGGGTTCGGTGCGTATCGCGTTTT
TAGATGGCGTCGTTAAGCGTTCGTTT (SEQ ID NO:335)

GPRIN1_FP    TCGCGTCGTCGTTCGT (SEQ ID NO:179)

GPRIN1_RP    GACGCCATCTAAAAACGCGA (SEQ ID NO:180)

GPRIN1_Pb_A1    CGCGCCGAGG TCGTTCGTGTCGGTTTC/3C6/ (SEQ ID NO:256)

HCG4_0331    chr6:29760284-29760410

>hg19_dna range=chr6:29760274-29760420 5'pad=10 3'pad=10 strand=+
repeatMasking=none WT
GCTTCCTCTCCGTGGGCGACGTGGACGACACGCAGTGCGTGCGGCTCGACAGCGACGCCACGAGTCCCAGGATGG
AGCCGCGGGCGCCGTGGATGGAGCAGGAGGGGCCGGAATATTGGGAAGAGGAGACAGGGACCGCCAAGGCCA
(SEQ ID NO:336)

BST
GTTTTTTTTTTCGTGGGCGACGTGGACGATACGTAGTGCGTGCGGTTCGATAGCGACGTTACGAGTTTTAGGATGG
AGTCGCGGGCGTCGTGGATGGAGTAGGAGGGGTCGGAATATTGGGAAGAGGAGATAGGGATCGTTAAGGTTA
(SEQ ID NO:337)

HCG4_0331_FP    GGCGACGTGGACGATAC (SEQ ID NO:181)

HCG4_0331_RP    CTAAAACTCGTAACGTCGCTATCG (SEQ ID NO:182

HCG4_0331_Pb_A5    AGGCCACGGACG GAACCGCACGCACTA/3C6/ (SEQ ID NO:257)

HCG4_0556    chr6:29760436-29760577

>hg19_dna range=chr6:29760426-29760578 5'pad=10 3'pad=1 strand=+
repeatMasking=none WT
CAGTTTTACCGAGTGAACCTGCGGACCCTGAGCGGCTACTACAACCAGAGTGAGGCCTGTGAGTGACACCGGCCG
GGGGCGCAGGTCACTACCCCTCCACATCCCCCACGGACCGCCCGGGTCTCCCCGAGTCTCTGGGTCCGAGATCCA
CGC (SEQ ID NO:338)

FIG. 1 (CONT'D)

BST
TAGTTTTATCGAGTGAATTTGCGGATTTTGAGCGGTTATTATAATTAGAGTGAGGTTTGTGAGTGATATCGGTCG
GGGGCGTAGGTTATTATTTTTTTATATTTTTTACGGATCGTTCGGGTTTTTTCGAGTTTTTGGGTTCGAGATTTA
CGT (SEQ ID NO:339)

HCG4_0556_FP        GGTTTGTGAGTGATATCGGTCG (SEQ ID NO:183)
HCG4_0556_RP        CGAACCCAAAAACTCGAAAAACC (SEQ ID NO:184)
HCG4_0556_Pb_A1     CGCGCCGAGG CCGAACGATCCGTAAAAAATATAA/3C6/ (SEQ ID NO:258)

---

NKX2-6_4159   chr8:23564076-23564193
>hg19_dna range=chr8:23564066-23564203 5'pad=10 3'pad=10 strand=+ repeatMasking=none WT
TGTCCTTGACCGAGAAGGGGGTGGAGGTGACGGGGCTCAGCAGCATCCCGAAGGCGGATGGGGCGGGGCCGAGGA
GGTCCGGGTGAGGAGCGGCACCCTGAACTTCCCGTCTTGTCGCTGCAGGCCCCGCAGACAGAC (SEQ ID NO:340)

BST
TGTTTTTGATCGAGAAGGGGGTGGAGGTGACGGGGTTTAGTAGTATTTCGAAGGCGGATGGGGCGGGGTCGAGGA
GGTTCGGGTGAGGAGCGGTATTTTGAATTTTTCGTTTTGTCGTTGTAGGTTTCGTAGATAGAT (SEQ ID NO:341)

NKX2-6_4159_FP    GGGTTTAGTAGTATTTCGAAGGCG (SEQ ID NO:185)
NKX2-6_4159_RP    GAAAAATTCAAAATACCGCTCCTCAC (SEQ ID NO:186)
NKX2-6_4159_Pb_A5 AGGCCACGGACG CCCGAACCTCCTCGA/3C6/ (SEQ ID NO:259)

---

C1QL3   chr10:16562562-16562645
>hg19_dna range=chr10:16562552-16562655 5'pad=10 3'pad=10 strand=- repeatMasking=none WT
ATGAAGGCTACGAGGTGCTCAAGTTCGACGACGTGGTCACCAACCTCGGAAACCACTACGACCCCACCACCGGCA
AGTTCACCTGCTCCATCCCGGGCATCTAC (SEQ ID NO:342)

BST
ATGAAGGTTACGAGGTGTTTAAGTTCGACGACGTGGTTATTAATTTCGGAAATTATTACGATTTTATTATCGGTA
AGTTTATTTGTTTTATTTCGGGTATTTAT (SEQ ID NO:343)

C1QL3_FP     GAAGGTTACGAGGTGTTTAAGTTCG (SEQ ID NO:187)
C1QL3_RP     AACAAATAAACTTACCGATAATAAAATCGTAATAATTTC (SEQ ID NO:188)
C1QL3_Pb_A1  CGCGCCGAGG GACGACGTGGTTATTAATTTCG/3C6/ (SEQ ID NO:260)

FIG. 1 (CONT'D)

FAIM2  Chr12:50297643-50297814

>hg19_dna range=chr12:50297633-50297817 5'pad=10 3'pad=3 strand=+ repeatMasking=none WT
AGCCTGCCTGCGTCTCTTCCTTCCTCCGCGTGGGTTCTAGCAACATCCACTGCAGCCGGGCCAGGCGAGCCGGCG
CGTACCATCGGCGCGGGGGGAGGAGAGGGCCGGGCCTGGGAAGATGCTGCGGAGGACGCTGCGGATTCGCGAGCC
CGGGGTAAGGCGGCGGCGCACCGCCCCCTCCCGCC (SEQ ID NO:344)

BST
AGTTTGTTTGCGTTTTTTTTTTTTTCGCGTGGGTTTTAGTAATATTTATTGTAGTCGGGTTAGGCGAGTCGGCG
CGTATTATCGGCGCGGGGGGAGGAGAGGGTCGGGTTTGGGAAGATGTTGCGGAGGACGTTGCGGATTCGCGAGTT
CGGGGTAAGGCGGCGGCGTATCGTTTTTTTTCGTT (SEQ ID NO:345)

FAIM2_FP     TTGCGGAGGACGTTGC (SEQ ID NO:189)
FAIM2_RP     GAAAAAAAACGATACGCCGCC (SEQ ID NO:190)
FAIM2_Pb_A1  CGCGCCGAGG CGGATTCGCGAGTTCG/3C6/ (SEQ ID NO:261)

LOC100131366      chr14:103655515-103655633

>hg19_dna range=chr14:103655508-103655639 5'pad=7 3'pad=6 strand=- repeatMasking=none WT
GGGGGGCGGGGCTGGGGAGAGGGTGGCCCCTGCACACTAGTCCCCTCCCCTCGACCCCGCAGCCCCGCGGCGCGT
TTCCTGAGGCGCCCCGCCACGTCCCGCGAGTCTCTGCCAAGTTCCCGCGCGGGTGC (SEQ ID NO:346)

BST
GGGGGGCGGGGTTGGGGAGAGGGTGGTTTTTGTATATTAGTTTTTTTTTTTCGATTTCGTAGTTTCGCGGCGCGT
TTTTTGAGGCGTTTTCGTTACGTTTCGCGAGTTTTTGTTAAGTTTTCGCGCGGGTGT (SEQ ID NO:347)

LOC100131366_FP     TTTCGATTTCGTAGTTTCGCGG (SEQ ID NO:191)
LOC100131366_RP     CTCGCGAAACGTAACGAAAAC (SEQ ID NO:192)
LOC100131366_Pb_A5  AGGCCACGGACG GCGCGTTTTTTGAGGC/3C6/ (SEQ ID NO:262)

NTN1    chr17:9143164-9143445

>hg19_dna range=chr17:9143154-9143455 5'pad=10 3'pad=10 strand=- repeatMasking=none WT
GGGGAGGGGCCGCCGAGGGTCCCGCCCCCCGCGCCGTGCGGCCCCGCCCCCTCCCTCCCCCCACCTGGGAAAGCC
CTCGCGGGCCAAGTCCGCGGCGGCCGGGCCAAGGCGCCCGCTCTCGCTCGGCCCCGCCCTGGCGCCCGCCCGCCC
GCCCGCCCGCTGCCTCGGCGCTAGGCCTTCTTGCACTTGCCCTTCTTCTCACGCTGCTGGAACTTGCGCAGCCGC
CGCGCCCACGTGTCCCGCCACTGGATCACCAGGCTGCTTTTATCGGCCACGATGCCGCTCTGGTCCGGAGAGTCC
TC (SEQ ID NO:348)

FIG. 1 (CONT'D)

BST
GGGGAGGGGTCGTCGAGGGTTTCGTTTTTCGCGTCGTGCGGTTTCGTTTTTTTTTTTTTTTATTTGGGAAAGTT
TTCGCGGGTTAAGTTCGCGGCGGTCGGGTTAAGG<u>CGTTCGTTTTCGTTCGGTTT</u>CGTTTTGGCGTTCGTTCGTTC
GTTCGTTCGTTGTTTCGGCGTT<u>AGGT</u>TTTTTTGTATTTGTTTTTTTTTTTACGTTGTTGGAATTTGCGTAGTCGT
CGCGTTTACGTGTTTCGTTATTGGATTATTAGGTTGTTTTTATCGGTTACGATGTCGTTTTGGTTCGGAGAGTTT
TT (SEQ ID NO:349)

NTN1_BST plasmid sequence
GTTAAGG<u>CGTTCGTTTTCGTTCGGTTT</u>CGTTTTGGCGTTCGTTCGTTCGTTCGTTCGTT<u>GTTTCGGCGTTAGGT</u>T
TTTTTGT (SEQ ID NO:350)

NTN1_FP      CGTTCGTTTTCGTTCGGTTTC (SEQ ID NO:193)
NTN1_RP      ACCTAACGCCGAAACAACG (SEQ ID NO:194)
NTN1_Pb_A1   CGCGCCGAGG CGTTTTGGCGTTCGTTC/3C6/ (SEQ ID NO:263)

---

ARL5C_1519    chr17:37321484-37321627
>hg19_dna range=chr17:37321474-37321631 5'pad=10 3'pad=4 strand=-
repeatMasking=none WT
GCCCCGGGCCTTTCAGACACTTTTCTGGAATGTGAAGGGAGGTGGGGGCTCAGCTGTCTTTTCCACCGTCCCGGA
GTGGGGCAGGTGTCGGAGCTGGGTGGGAAGCAGACGCGGTACGGTGGGCAGAGGTCCCCAGCCTGCGGGGAGCGC
TATCTCCT (SEQ ID NO:351)

BST
GTTTCGGGTTTTTTAGATATTTTTTTGGAATGTGAAGGGAGGTGGGGGTTTA<u>GTTGTTTTTTTTATCGTTTCGGA</u>
GTGGGGTAGGTGTCGGAGTTGGGTGGGAAGTAGACGCGGT<u>ACGGTGGGTAGAGG</u>TTTTTAGTTTGCGGGGAGCGT
TATTTTTT (SEQ ID NO:352)

ARL5C_1519_FP     GTTGTTTTTTTTATCGTTTCGGAGTG (SEQ ID NO:195)
ARL5C_1519_RP     CCTCTACCCACCGTACCG (SEQ ID NO:196)
ARL5C_1519_Pb_A5  AGGCCACGGACG GCGTCTACTTCCCACC/3C6/ (SEQ ID NO:264)

---

C17orf64    chr17:58498720-58498794
>hg19_dna range=chr17:58498713-58498798 5'pad=7 3'pad=4 strand=+
repeatMasking=none WT
GGGCCTCCGGGCTACCCCTACTTGAAGCCGCTATGCCCCTCTCCTGTGCCCGAGGTGGCCGCTGGGTGGCAGGGG
AGGCCCGGGCC (SEQ ID NO:353)

FIG. 1 (CONT'D)

BST
GGGTTTTCGGGTTATTTTTATTTGAAGTCGTTATGTTTTTTT<span style="border:1px solid">TTTGTGTTCGAGGTGGTC</span>GTTGGGTGGTAGGGG
<u>AGGTTCGGGTT</u> (SEQ ID NO:354)

C17orf64_8780_FP   GTTTTCGGGTTATTTTTATTTGAAGTCG (SEQ ID NO:197)

C17orf64_8780_RP   TCCCCTACCACCCAACG (SEQ ID NO:198)

C17orf64_8780_Pb_A1    CGCGCCGAGG GACCACCTCGAACACAAA/3C6/ (SEQ ID NO:265)

---

OXT    Chr20:3052753-3052884

>hg19_dna range=chr20:3052743-3052891 5'pad=10 3'pad=7 strand=+
repeatMasking=none WT
GGGCAAAGGCCGCTGCTTCGGGCCCAATATCTGCTGCGCGGAAGAGCTGGGCTGCTTCGTGGGCACCGCCGAAGC
GCTGCGCTGCCAGGAGGAGAACTACCTGCCGTCGCCCTGCCAGTCCGGCCAGAAGGCGTGCGGGAGCGGGGGCC
(SEQ ID NO:355)

BST
GGGTAAAGGTCGTTGTTTCGGGTTTAATATTTGTTGCGCGGAAGAGTTGGG<span style="border:1px solid">TTGTTTCGTGGGTATCGTC</span>GAAGC
<u>GTTGCGTTGTTAGG</u>AGGAGAATTATTTGTCGTCGTTTTGTTAGTTCGGTTAGAAGGCGTGCGGGAGCGGGGGTT
(SEQ ID NO:356)

OXT_FP     GGGTTTAATATTTGTTGCGCGG (SEQ ID NO:199)

OXT_RP     CGAAGCGTTGCGTTGTTAG (SEQ ID NO:200)

OXT_Pb_A5  AGGCCACGGACG GACGATACCCACGAAACAA/3C6/ (SEQ ID NO:266)

---

PEAR1   Chr1:156863357-156863488

>hg19_dna range=chr1:156863347-156863492 5'pad=10 3'pad=4 strand=+
repeatMasking=none TTTCCCTCCCGGGCGCCTGGATCTCCCCTCCCCCGGCTCCTGTTTCCTTGTCAAAACTTCCTGCCTTGGCGAGGG
CCCGAGTTCCCACCCCCTTCCTGCCCCCGCCCCTCGGCGCCCCTCCCGGCCCTGCGATCAGCAGCGTCCC
(SEQ ID NO:357)

BST
TTTTTTTTTCGGGCGTTTGGATTTTTTTTTTTCGGTTTTTGTTTTTTTGTTAAAATTTTTTGTTT<u>TGGCGAGGG
TTCGAGTTTTTATTTTT</u><span style="border:1px solid">TTTTTGTTTTTCGTTTTTCGGC</span>GTTTTTTTCGGTTTTGCGATTAGTAGCGTTTT
(SEQ ID NO:358)

PEAR1_FP    TTGGCGAGGGTTCGAGT (SEQ ID NO:201)

PEAR1_RP    CTAATCGCAAAACCGAAAAAAACG (SEQ ID NO:202)

PEAR1_Pb_A1 CGCGCCGAGG GCCGAAAAACGAAAAACAAAAA/3C6/ (SEQ ID NO:267)

FIG. 1 (CONT'D)

ATP10A
>hg19_dna range=chr15:26108540-26108828 5'pad=10 3'pad=10 strand=+
repeatMasking=none WT
CGGTGGCCACGGCCCCGCCCTCGTTCCGCGCCCGGACTGGGCCACGCCGGATAGCGGGAAACAAAAAAAGCCCGA
GCTGGAAACTTCAGAGAGGTTTAGTTTCGTTTCCCAGAAGCATCAGTTCGGTCCCAAAACGCTGCAAACGCGCGC
TGCCTGCAGTAGGAGAGAGGAAACCGCGAAGCGCGAGAAAAGGCGCCCCGTCCCCAAGCAGCCCGCGCGCCCTT
CCAGGGGCCAGACCTGCTCCATCCTGGACGGCGAAACGACCTCGGGAGACCCCGGTTAGGACCT (SEQ ID
NO:359)

BST
CGGTGGTTACGGTTTCGTTTTCGTTTCGCGTTCGGATTGGGTTACGTCGGATAGCGGGAAATAAAAAAAGTTCGA
GTTGGAAATTTTAGAGAGGTTTAGTTTCGTTTTTTAGAAGTATTAGTTCGGTTTTAAAACGTTGTAAACGCGCGT
TGTTTGTAGTAGGAGAGAGGAAATCGCGAAGCGCGAGAAAAGGCGTTTTCGTTTTTAAGTAGTTCGCGCGTTTTT
TTAGGGGTTAGATTTGTTTTATTTTGGACGGCGAAACGATTTCGGGAGATTTCGGTTAGGATTT (SEQ ID
NO:360)

ATP10A_FP    GAGAGGAAATCGCGAAGCG (SEQ ID NO:203)

ATP10A_RP    CCCCTAAAAAAACGCGCGA (SEQ ID NO:204)

ATP10A_Pb_A5    AGGCCACGGACG GCGAGAAAAGGCGTTTTC/3C6/ (SEQ ID NO:268)

---

CELF2 10:11207221-11207812
>hg19_dna range=chr10:11207212-11207819 5'pad=9 3'pad=7 strand=-
repeatMasking=none WT
GGGGGTGCGGGGAGGAGTCGGGAGCAGCCCCTGGAGCACAGGGGCCGCCAGCACCGGCTGCTTCCAGCCCTCCTG
CCTACCCGCCCTTCCTCCTGCAGGCTGGGGGCTCGGACAGCCCCAGTGCCCCGCGACGCCCACCTGGACGCCTGG
CGACCCCCGCCCCGCGCTCTGTACCTTTACTCTGCGGAGGGTTCTGACTCCGGTCCCGGAGGACGTTGATCTGGT
AGACGGCTCCGTAAGGCTCAAAAAGTTCTTTCAGCTCCTTTTCCGACCATGACCGGGGGATCTGTCCGACAAACA
TCTTAATGGCATCTGGGTCTGGTTGGTCTGAGTGATCCAAAGCTCCGTTCATCTTGTTGGCTGTGCCGTTACTGT
CAAAAACGGAACCGGGAGCCAGAGTTAGGGCGGCACGATGAGGGACAGGAAGAAAAAATAGTGGGGGTGGGGGAG
CGGGGAGGCGGAAGGAGGAGGAAGAAGAGCAGTGGCAAAGTGCCTAATGAGTCGTAGAAATTTGATGAACTAAAA
CAAAGCGGAGGCACCATGAGTTGCTCCTCGGCGGCGGCGAGGCTCTCACTGCGTGCTGCTGTCGAGCAGAGCCGG
GGGAGCAC (SEQ ID NO:361)

BST
GGGGGTGCGGGGAGGAGTCGGGAGTAGTTTTTGGAGTATAGGGGTCGTTAGTATCGGTTGTTTTAGTTTTTTTG
TTTATTCGTTTTTTTTTTGTAGGTTGGGGGTTCGGATAGTTTTAGTGTTTCGCGACGTTTATTTGGACGTTTGG
CGATTTTCGTTTCGCGTTTTGTATTTTTATTTTGCGGAGGGTTTTGATTTCGGTTTCGGAGGACGTTGATTTGGT
AGACGGTTTCGTAAGGTTTAAAAAGTTTTTTTAGTTTTTTTTTCGATTATGATCGGGGATTTGTTCGATAAATA
TTTTAATGGTATTTGGGTTTGGTTGGTTTGAGTGATTTAAAGTTTCGTTTATTTTGTTGGTTGTGTCGTTATTGT
TAAAAACGGAATCGGGAGTTAGAGTTAGGGCGGTACGATGAGGGATAGGAAGAAAAAATAGTGGGGGTGGGGGAG
CGGGGAGGCGGAAGGAGGAGGAAGAAGAGTAGTGGTAAAGTGTTTAATGAGTCGTAGAAATTTGATGAATTAAAA

FIG. 1 (CONT'D)

TAAAGCGGAGGTATTATGAGTTGTTTTTCGGCGGCGGCGAGGTTTTTATTGCGTGTTGTTGTCGAGTAGAGTCGG
GGGAGTAT (SEQ ID NO:362)

CELF2_BST plasmid sequence
GTTTTAGTGTTTCGCGACGTTTATTTGGACGTTTGGCGATTTTCGTTTCGCGTTTTGTATTTTTATTTTGCGGAG
GGTTTTGATTTCGGTTTCGGA (SEQ ID NO:363)

CELF2_FP      GACGTTTATTTGGACGTTTGGC (SEQ ID NO:205)
CELF2_RP      ACCGAAATCAAAACCCTCCG (SEQ ID NO:206)
CELF2_Pb_A1   CGCGCCGAGG CGATTTTCGTTTCGCGTT/3C6/ (SEQ ID NO:269)

CELF2_FP_V2   GTTTCGCGACGTTTATTTGGAC (SEQ ID NO:207)
CELF2_RP      ACCGAAATCAAAACCCTCCG (SEQ ID NO:208)
CELF2_Pb_A1_V2   CGCGCCGAGG CGTTTGGCGATTTTCGTT/3C6/ (SEQ ID NO:270)

CAPN2
>hg19_dna range=chr1:223936858-223937009 5'pad=10 3'pad=5 strand=-
repeatMasking=none
WT
GCACCCGGCGCCCGAGCTGCGAAAGGGACGCCCTTCTCCTCCCGCGCGGAACTTCAGGAGTGCGGGGCCCGAGTG
TAAACTGGACCACCGTGGGGCCGCGCGGGCCCCTGGGCATCACCACAAACTGTGCCTGTGGCCATCGTGTCAGGA
CA (SEQ ID NO:364)
BST
GTATTCGGCGTTCGAGTTGCGAAAGGGACGTTTTTTTTTTTCGCGCGGAATTTTAGGAGTGCGGGGTTCGAGTG
TAAATTGGATTATCGTGGGGTCGCGCGGGTTTTTGGGTATTATTATAAATTGTGTTTGTGGTTATCGTGTTAGGA
TA (SEQ ID NO:365)

CAPN2_Reg2_FP    GCGCGGAATTTTAGGAGTGC (SEQ ID NO:209)
CAPN2_Reg2_RP    CGCGACCCCACGATAATC (SEQ ID NO:210)
CAPN2_Reg2_Pb_A5  AGGCCACGGACG CGGGGTTCGAGTGTAAAT/3C6/ (SEQ ID NO:271)

DSCR6 21:38378492-38378858
>hg19_dna range=chr21:38378483-38378866 5'pad=9 3'pad=8 strand=+
repeatMasking=none
WT
GGAGAAGCCGGGACTCCTCACATCCCACATCCGGCAGGGGAAGCCCAGCAGGTGAGCGCAGGTCCCCCCAGTCCC
CGAGGGAGTGCGCCCGACGGAAACGCCCCTAGCCCGCGGGCCTCGCTTTCCTCTCCCGGGTTCCTGGGTCACTTC
CCGCTGTCTCCAGCCCGAGCTCGTGGCCCAATCCCTGGTACCTCCATCCTCTGGTCACCCCTTCTCTGGTGCCC

FIG. 1 (CONT'D)

CCTCCCCGACTTTTCTTTGTCCCGTCCCCACCCTTGCCCGGGCCTGCCGGACCCCCCTCCTTGACACCCGGCGCC
ACCTCCTTGAGCTTTTCTCGTCTCCTCCCCATCCCCGGCTCCCTGGTCCCCTCCCGGAACTTCTCTGGTCCCCTC
CGCTCCTCC (SEQ ID NO:366)
BST
GGAGAAGTCGGGATTTTTTATATTTTATATTCGGTAGGGGAAGTTTAGTAGGTGAGCGTAGGTTTTTTTAGTTTT
CGAGGGAGTGCGTTCGACGGAAACGTTTTTAGTTCGCGGGTTTCGTTTTTTTTTTCGGGTTTTTGGGTTATTTT
TCGTTGTTTTTAGTTCGAGTTCGTGGTTTTAATTTTTGGTATTTTTATTTTTTGGTTATTTTTTTTTTGGTGTTT
TTTTTTCGATTTTTTTTTGTTTCGTTTTTATTTTTGTTCGGGTTTGTCGGATTTTTTTTTTGATATTCGGCGTT
ATTTTTTTGAGTTTTTTTCGTTTTTTTTTTATTTTCGGTTTTTTGGTTTTTTTTCGGAATTTTTTTGGTTTTTTT
CGTTTTTTT (SEQ ID NO:367)

DSCR6_BST plasmid sequence
GTTTTTTTTAGTTTTCGAGGGAGTGCGTTCGACGGAAACGTTTTTAGTTCGCGGGTTTCGTTTTTTTTTTCGGGT
(SEQ ID NO:368)

DSCR6_FP    GTTTTCGAGGGAGTGCGTTC (SEQ ID NO:211)
DSCR6_RP    CGAAAAAAAAAAAACGAAACCCGC (SEQ ID NO:212)
DSCR6_Pb_A1 CGCGCCGAGG CGACGGAAACGTTTTTAGTTC/3C6/ (SEQ ID NO:272)

---

NR2F6 19:17346347-17346780
>hg19_dna range=chr19:17346337-17346783 5'pad=10 3'pad=3 strand=+
repeatMasking=none
WT
CAGCCATACTCGGCCGAGTCGACCTGCAGGCGGCCCAGCTTGTCCACCTGCTCCTGGAAGGCGCGCACCTGGTCC
ATGAAAGCCACGGCGCGCTCGGCGGCCATAGGCGCGGCGTGGAGGCCGGCGGCGGCCAGTAGCGGCGCCGTGTGC
AGGGGCAGCGCCGCCTGCGCCGCGTTCAGCACGAAGAGCTCGCTCCAGCTCAGGCGCAGCAGCGCCACCTGGTCG
GCCACCGGCAGCTCGGGGAAGAAGGGCGCGTGGCGCGCCCACTCCACGGTGCTGAAGAGCAGCCGCGCCGCCAGC
TCGCACACGTTGTCGATGCCCAGCACCGCGCCCGCCGCGCCGCCCCTGCGCCGAAGCGTCCGGCCGCCGCAGGG
TAGGGCTCAGCGCGCAGCAGCTGCGCGATCAGTTCGGACACCGGCTGCCCCGGGAAGAGGTCTCCGCCGCTC
(SEQ ID NO:369)
BST
TAGTTATATTCGGTCGAGTCGATTTGTAGGCGGTTTAGTTTGTTTATTTGTTTTTGGAAGGCGCGTATTTGGTTT
ATGAAAGTTACGGCGCGTTCGGCGGTTATAGGCGCGGCGTGGAGGTCGGCGGCGGTTAGTAGCGGCGTCGTGTGT
AGGGGTAGCGTCGTTTGCGTCGCGTTTAGTACGAAGAGTTCGTTTTAGTTTAGGCGTAGTAGCGTTATTTGGTCG
GTTATCGGTAGTTCGGGGAAGAAGGGCGCGTGGCGCGTTTATTTTACGGTGTTGAAGAGTAGTCGCGTCGTTAGT
TCGTATACGTTGTCGATGTTTAGTATCGCGTTCGTCGCGTCGTTTTTGCGTCGAAGCGTTCGGTCGTCGTAGGG
TAGGGTTTAGCGCGTAGTAGTTGCGCGATTAGTTCGGATATCGGTTGTTTCGGGAAGAGGTTTTCGTCGTTT
(SEQ ID NO:370)

FIG. 1 (CONT'D)

NR2F6_BST plasmid sequence
GTTTATTTTACGGTGTTGAAGAGTAGTCGCGTCGTTAGTTCGTATACGTTGTCGATGTTTAGTATCGCGTTCGTC
GCGTCGTTTTTTGCGTCGAAGCG (SEQ ID NO:371)

NR2F6_FP      GGTGTTGAAGAGTAGTCGCGT (SEQ ID NO:213)
NR2F6_RP      CGACGCAAAAAACGACGC (SEQ ID NO:214)
NR2F6_Pb_A5 AGGCCACGGACG TCGTTAGTTCGTATACGTTGTC/3C6/ (SEQ ID NO:273)

CDO1 5:115152022-115152432
>hg19_dna range=chr5:115152020-115152435 5'pad=2 3'pad=3 strand=+
repeatMasking=none
WT
GCCGGCAAAGAGCTGGTGCAGGATGCGGATCAGATCAGCCAGGGTCCGTGGCTTCAGCACTTCGGTCTGTTCCAT
CTCGTGGGGAGCTGGCTGCGCGCGCGTCTCACTGCTGGGCTGCGGTGGAGGAGCTGAGCGAGCCAAGGAGCTGGG
GGCGAGGGAGCCTAACAGCCCGCTAGACCGCTAAGCAGACACACACGCACAAACCCAGCATTAGAGTGCCGAAAC
GTAAGGATGTCGTCGCAGAGACAGCAAGAGACCCACCCCCAGGCCCCTGGCAGCGCAGTGGATCCGGGATCGCTG
GAGACGCGGTGCACACACAAATCAGGTTCAGATCTGTGGGGTTCATCCTCCCGGGCCCCTTTTAAGCGCTTGGAG
TCACTAGGAATGTACCAACGGCCCTCGGAGGGAGGACGAGG (SEQ ID NO:372)
BST
GTCGGTAAAGAGTTGGTGTAGGATGCGGATTAGATTAGTTAGGGTTCGTGGTTTTAGTATTTCGGTTTGTTTTAT
TTCGTGGGGAGTTGGTTGCGCGCGCGTTTTATTGTTGGGTTGCGGTGGAGGAGTTGAGCGAGTTAAGGAGTTGGG
GGCGAGGGAGTTTAATAGTTCGTTAGATCGTTAAGTAGATATATACGTATAAATTTAGTATTAGAGTGTCGAAAC
GTAAGGATGTCGTCGTAGAGATAGTAAGAGATTTATTTTAGGTTTTTGGTAGCGTAGTGGATTCGGGATCGTTG
GAGACGCGGTGTATATATAAATTAGGTTTAGATTTGTGGGGTTTATTTTTTCGGGTTTTTTTTAAGCGTTTGGAG
TTATTAGGAATGTATTAACGGTTTTCGGAGGGAGGACGAGG (SEQ ID NO:373)

CDO1_BST plasmid sequence
GAGTGTCGAAACGTAAGGATGTCGTCGTAGAGATAGTAAGAGATTTATTTTAGGTTTTTGGTAGCGTAGTGGAT
TCGGGATCGTTGGAGACGCGGTGTATATATAAATTAGGTTTAGA (SEQ ID NO:374)

CDO1_FP      CGAAACGTAAGGATGTCGTCG (SEQ ID NO:215)
CDO1_RP      AATTTATATATACACCGCGTCTCCAAC (SEQ ID NO:216)
CDO1_Pb_A1 CGCGCCGAGG CGATCCCGAATCCACTAC/3C6/ (SEQ ID NO:274)

DNMT3A 2:25500046-25500305
>hg19_dna range=chr2:25500041-25500307 5'pad=5 3'pad=2 strand=+
repeatMasking=none

GCACTCGCCAGCGCTTTGTTCGTGACCGGCCTTTTAAGGGCTGTCTCACCCATCTTGTCTGGCTCTGCCTCCCTG
TTTCCTTTCCGTCCTCTCTCCCACCACAGCCAGCTCCCCACTTTTTTCGCGGGGGCCCCCTCCAGCCTGTCCGGG
GCCTCCCCGTTCCCAGGCCAGGGCTTCCCCCTCCTCCCAGACCTCGTTGCTCTGCCCGGTGAGGCCCCGGGCTCC
CAGCAGGGGGCGCCTGCTCGCGATCAGGTGGCGGCCTGGGGG (SEQ ID NO:375)

BST

GTATTCGTTAGCGTTTTGTTCGTGATCGGTTTTTTAAGGGTTGTTTTATTTATTTTGTTTGGTTTTGTTTTTTTG
TTTTTTTTTCGTTTTTTTTTTTATTATAGTTAGTTTTTTATTTTTTTCGCGGGGGTTTTTTTTAGTTTGTTCGGG
GTTTTTTCGTTTTTAGGTTAGGGTTTTTTTTTTTTTAGATTTCGTTGTTTTGTTCGGTGAGGTTTCGGGTTTT
TAGTAGGGGGCGTTTGTTCGCGATTAGGTGGCGGTTTGGGGG (SEQ ID NO:376)

DNMT3A_Reg2 plasmid sequence
GATTTCGTTGTTTTGTTCGGTGAGGTTTCGGGTTTTTAGTAGGGGGCGTTTGTTCGCGATTAGGTGGCGGTTTGG
GGG (SEQ ID NO:377)

DNMT3A_Reg2_FP     TGTTTTGTTCGGTGAGGTTTCG (SEQ ID NO:217)
DNMT3A_Reg2_RP     CAAACCGCCACCTAATCGC (SEQ ID NO:218)
DNMT3A_Reg2_Pb_A5  AGGCCACGGACG CGAACAAACGCCCCC/3C6/ (SEQ ID NO:275)

SIM2 21:38076892-38077026
WT
>hg19_dna range=chr21:38076882-38077036 5'pad=10 3'pad=10 strand=+
repeatMasking=none
GAGGGGACCTGGATCCCTGAACCCCGGGGCGGAAAGGGAGCCTCCGGGCGGCTGTGGGTGCCGCGCTCCTCGGAG
CCAGCAGCTGCTGGGGCGGCGTCCGAACTCCCCAGGTCTGCGCACGGCAATGGGGGCACCGGGCCTTCTGTCTGT
CCTCA (SEQ ID NO:378)
BST
GAGGGGATTTGGATTTTTGAATTTCGGGGCGGAAAGGGAGTTTTCGGGCGGTTGTGGGTGTCGCGTTTTTCGGAG
TTAGTAGTTGTTGGGGCGGCGTTCGAATTTTTTAGGTTTGCGTACGGTAATGGGGGTATCGGGTTTTTGTTTGT
TTTTA (SEQ ID NO:379)

SIM2 prostate sequence:
GAATTCGGGTTTAGCGCGGGTTTTTCGCGGTAGTGGTCGTAGTTCGGGAAGTTCGGGGCGCGGTGTTTT
CGTGAATTC (SEQ ID NO:380)

SIM2_Reg2_FP     AAAGGGAGTTTTCGGGCG (SEQ ID NO:219)
SIM2_Reg2_RP     ACCCGATACCCCCATTACC (SEQ ID NO:220)
SIM2_Reg2_Pb_A1  CGCGCCGAGG CGTACGCAAACCTAAAAAATTC/3C6/ (SEQ ID NO:276)

FIG. 1 (CONT'D)

CMTM3
>hg19_dna range=chr16:66638172-66638351 5'pad=10 3'pad=10 strand=+
repeatMasking=none
CGGGGACAGGAGGGGTGGCCAAGAAAGTCGCAAGAAAACTCCGGCCCCAAGAAAAAGAGAGGGCATGGGTTGCG
GAGCCGACATCACGGCCGGGGTCTTTGCTGTTTAGACGCCTGGGTTCCCGGATCCCAGACACGCGCACGGGCAGG
AAGTTAGACC (SEQ ID NO:381)

CGGGGATAGGAGGGGTGGTTAAGAAAGTCGTAAGAAAATTTCGGTTTTTAAGAAAAAGAGAGGGTATGGGTTGCG
GAGTCGATATTACGGTCGGGGTTTTTGTTGTTTAGACGTTTGGGTTTTCGGATTTTAGATACGCGTACGGGTAGG
AAGTTAGATT (SEQ ID NO:382)

CMTM3_FP    GGTGGTTAAGAAAGTCGTAAGAAAATTTCG (SEQ ID NO:221)

CMTM3_RP    TCTAAACAACAAAAACCCCGACC (SEQ ID NO:222)

CMTM3_Pb_A5 AGGCCACGGACG CGTAATATCGACTCCGCAA/3C6/ (SEQ ID NO:277)

SRC
>hg19_dna range=chr20:36013121-36013303 5'pad=10 3'pad=10 strand=+
repeatMasking=none
GTTGCCTGGGTCCGCCCAGAGATGAGTCGGGACGCGCGGCCCACGTGCGGCGGAGGGGCAGCTGGGTCGCTCGGG
GAACGGGGCACCGGATGGCCCCGGTTGGGCCCGCGCCAGGATGCGCCCCTGCGCCCTCTGCTGGCGCTCTGCGGT
CACCGCAGCCCCG (SEQ ID NO:383)

GTTGTTTGGGTTCGTTTAGAGATGAGTCGGGACGCGCGGTTTACGTGCGGCGGAGGGGTAGTTGGGTCGTTCGGG
GAACGGGGTATCGGATGGTTTCGGTTGGGTTCGCGTTAGGATGCGTTTTTGCGTTTTTTGTTGGCGTTTTGCGGT
TATCGTAGTTTCG (SEQ ID NO:384)

SRC_FP      GGATGGTTTCGGTTGGGTTC (SEQ ID NO:223)

SRC_RP      GCAAAACGCCAACAAAAAACG (SEQ ID NO:224)

SRC_Pb_A5   AGGCCACGGACG CGCGTTAGGATGCGT/3C6/ (SEQ ID NO:278)

LRRC41_9559
>hg19_dna range=chr1:46769340-46769650 5'pad=0 3'pad=0 strand=-
repeatMasking=none

CGGACGAATTCTGGGGAAAGGTCGAGGGAACTAGAGCTCCCGACTATGCAAACCCTAGAGGGTAAACTGGGGGCT

AAGAGGGCCCCGTGCGTGTTTTGGCGGGCTAGGTCCTGGGCTTCAGGGCAGAGAAGAGGGCCGAGTGGATCGCCT

TGCCTTACCTCCTCAGGATCTCCGGATTCGGTAAGCATCTTTTGCTCGTCCTCCAGTCCCATGTCTGGCTACGGT

TCTAGATTCAACACGAGCAGCAACAGCGGCACCTAACCCAGTTCAGGATCAAGAAGGACTTGTAAGGGTCACTCA

GCGGAAATCCG (SEQ ID NO:385)

CGGACGAATTTTGGGGAAAGGTCGAGGGAATTAGAGTTTTCGATTATGTAAATTTTAGAGGGTAAATTGGGGGTT

AAGAGGGTTTCGTGCGTGTTTTGGCGGGTTAGGTTTTGGGTTTTAGGGTAGAGAAGAGGGTCGAGTGGATCGTTT

TGTTTTATTTTTTAGGATTTTCGGATTCGGTAAGTATTTTTGTTCGTTTTTAGTTTTATGTTTGGTTACGGT

FIG. 1 (CONT'D)

TTTAGATTTAATACGAGTAGTAATAGCGGTATTTAATTTAGTTTAGGATTAAGAAGGATTTGTAAGGGTTATTTA
GCGGAAATTCG (SEQ ID NO:386)

LRRC41 plasmid sequence
CGGACGAATTTTGGGGAAAGGTCGAGGGAATTAGAGTTTTCGATTATGTAAATTTTAGAGGGTAAATTGGGGGTT
AAGAGGGTTTCGTGCGTGTTTTGGCGGGTTAGGTTTTGGGTTTTAGGGTAGAGAAGAGGGTCGAGTGGATCGTTT
TGTT (SEQ ID NO:387)

LRRC41_9559_FP      GGTCGAGGGAATTAGAGTTTTCG (SEQ ID NO:225)
LRRC41_9559_RP      AACCTAACCCGCCAAAACAC (SEQ ID NO:226)
LRRC41_9559_Pb_A1   CGCGCCGAGG CGCACGAAACCCTCTTA/3C6/ (SEQ ID NO:279)

---

TSHZ3
>hg19_dna range=chr19:31839415-31840120 5'pad=0 3'pad=0 strand=+
repeatMasking=none
WT
CGTCCCAGAACTAAGTGCTATGCGGAGATGAGGGTGGGAGCAGCAGTACAAGGAGGGGGTGGGGGCGAGGAAACA
CAAACAGGGGAGAAGGAAACGCCAGCATCTAACATGGACTTGACAGTCATCTGACAATACCCAGACCCTGTGCGC
TCCGGGTTCCACCGCTGTGCCCAGTTTGGGCCCAAGAAATGAGGAATCAATCGTGTTAGTACTAAGGTGGCCGAG
GGGACCGGCTCGCTCACTCGTTCGCGCTCCCTGGCTCGGCGGACACCAGGCAGTCCCCGGCGGTCGGCCGCTCG
GAGGACGCGGAAGATGTCCCGGGGAACTCAGGTGACCCCGCCCGCCACCCACAGAAAGAGCCAGGCCGGGGTTGC
TTCCCATTCCCTCTGCAGCCGGAGAGCTGAGGAGGTAGGGACCTGGCGCGGCTCAGCGCGCTCCGCGAGCGGCTC
CCCAAATGGGTGCGAGAGGGAAGAGGGCAGAGCGCGGCGGGGCGTCCGGGGGGCGCCCGGTACCCGAGGCGGGCG
CACGCACCCAAACAGGAGAGCGGCGCCCGGAGTTACTCAGTGCGGGCAGAAGAGCGGGGCGAGGAGCGGGGTCGC
GCCCGCTGGAGGCGCGGGGCGAGCGGAGGAAGAGGAGGAGGAGAGCAGAAGGAAGGGGAAGCGGCTCGTACCTGC
TGCGCGCCGGGGCGCCTGCTGCTTCCTCCTC (SEQ ID NO:388)

BST
CGTTTTAGAATTAAGTGTTATGCGGAGATGAGGGTGGGAGTAGTAGTATAAGGAGGGGGTGGGGGCGAGGAAATA
TAAATAGGGGAGAAGGAAACGTTAGTATTTAATATGGATTTGATAGTTATTTGATAATATTTAGATTTTGTGCGT
TTCGGGTTTTATCGTTGTGTTTAGTTTGGGTTTAAGAAATGAGGAATTAATCGTGTTAGTATTAAGGTGGTCGAG
GGGATCGGTTCGTTTATTCGTTCGCGTTTTTTGGTTCGGCGGATATTAGGTAGTTTTCGGCGGTCGGTCGTTCG
GAGGACGCGGAAGATGTTTCGGGGAATTTAGGTGATTTCGTTCGTTATTTATAGAAAGAGTTAGGTCGGGGTTGT
TTTTTATTTTTTTTGTAGTCGGAGAGTTGAGGAGGTAGGGATTTGGCGCGGTTTAGCGCGTTTCGCGAGCGGTTT
TTTAAATGGGTGCGAGAGGGAAGAGGGTAGAGCGCGGCGGGGCGTTCGGGGGCGTTCGGTATTCGAGGCGGGCG
TACGTATTTAAATAGGAGAGCGGCGTTCGGAGTTATTTAGTGCGGGTAGAAGAGCGGGGCGAGGAGCGGGGTCGC
GTTCGTTGGAGGCGCGGGGCGAGCGGAGGAAGAGGAGGAGGAGAGTAGAAGGAAGGGGAAGCGGTTCGTATTTGT
TGCGCGTCGGGGCGTTTGTTGTTTTTTTTTT (SEQ ID NO:389)

FIG. 1 (CONT'D)

```
TSHZ3 plasmid sequence
GAATTAATCGTGTTAGTATTAAGGTGGTCGAGGGGATCGGTTCGTTTATTCGTTCGCGTTTTTTGGTTCGGCGGA
TATTAGGTAGTTTTTCGGCGGTCGGTCGTTCGGAGGACGCGGAAGATGTTTCGGGGAATTTAGGTGATTTCGTTC
GTTA (SEQ ID NO:390)

TSHZ3_FP     GGGATCGGTTCGTTTATTCGTTC (SEQ ID NO:227)

TSHZ3_RP     CCCGAAACATCTTCCGCG (SEQ ID NO:228)

TSHZ3_Pb_A5 AGGCCACGGACG CGCGTTTTTTGGTTCGG/3C6/ (SEQ ID NO:280)
```

---

```
HDGFRP3
>hg19_dna range=chr15:83875827-83875946 5'pad=0 3'pad=0 strand=+
repeatMasking=none
CGTCGGGCCTGCGGGGGCCGGACCCGCCTTCGAAAGTGGGCGGAAGGATGGCCGCCCTGGCGGAGTGCGGGCGAG
GCCGGGAGCCCTTGCCTCAGCCCCGGCCCGGTCTTCTTCGTGCCG (SEQ ID NO:391)

CGTCGGGTTTGCGGGGGTCGGATTCGTTTTCGAAAGTGGGCGGAAGGATGGTCGTTTTGGCGGAGTGCGGGCGAG
GTCGGGAGTTTTTGTTTTAGTTTCGGTTCGGTTTTTTTCGTGTCG (SEQ ID NO:392)

HDGFRP3_FP   GATTCGTTTTCGAAAGTGGGC (SEQ ID NO:229)

HDGFRP3_RP   TAAAACAAAAACTCCCGACCTCG (SEQ ID NO:230)

HDGFRP3_Pb_A1    CGCGCCGAGG CGGAAGGATGGTCGTTTT/3C6/ (SEQ ID NO:281)
```

---

```
TACC2
>hg19_dna range=chr10:123922953-123923142 5'pad=0 3'pad=0 strand=-
repeatMasking=none
CGGTGTGGTCCGAAAGGCTCTTCTCTTAAACCCCCCGGCAGCCGGCTCCTGTGTGTGACACGATGATGTCATCAT
CGCCGAGCAGCCCCAACGCCTGCATCTTCACAAAGCTCCATCGCGGGCTCCGGAAACGGGGCTGGGGGTGGGGAG
GCGAAGACCCTCCCTCTGCCCCGGCCCCTCCCGCCTCGCC (SEQ ID NO:393)

CGGTGTGGTTCGAAAGGTTTTTTTTTTAAATTTTTCGGTAGTCGGTTTTTGTGTGTGATACGATGATGTTATTAT
CGTCGAGTAGTTTTAACGTTTGTATTTTTATAAAGTTTTATCGCGGGTTTCGGAAACGGGGTTGGGGGTGGGGAG
GCGAAGATTTTTTTTTTGTTTCGGTTTTTTTCGTTCGTT (SEQ ID NO:394)

TACC2_FP     GTTTTTGTGTGTGATACGATGATGTTATTATC (SEQ ID NO:231)

TACC2_RP     GTTTCCGAAACCCGCGA (SEQ ID NO:232)

TACC2_Pb_A5 AGGCCACGGACG CGTCGAGTAGTTTTAACGTTTG/3C6/ (SEQ ID NO:282)
```

FIG. 1 (CONT'D)

LBH

```
>hg19_dna range=chr2:30453651-30453973 5'pad=0 3'pad=0 strand=+
repeatMasking=none
CGGGCGTATGTGTGTCTCCAATGGAAAAATCCTACCCAGGACGACACCACATCCTTGCTCCCACAAATAAAACCT
TCCACGGAACTCAGGGCTGCAGACCAGCCCTTCGCAAGCCAACGCGCCCCGTGGGCACTCGGTCCCCCGGCTCCG
CGTCTCTGCCACCTTCCCACCGCTTCTTCTTTAACCATGCTCTTGTTTCCCCTCGCTGATCGCAAGGCTGCGGGC
GAGGATTCCAGAGAGAGGCCTAGTATGGGGAACAAACGCTTCAGAGGGGTCCGAGGTGGGCTGGGGACAGCCAGT
GGATGGGAAGGAGGGCGCTGGCG (SEQ ID NO:395)

CGGGCGTATGTGTGTTTTTAATGGAAAAATTTTATTTAGGACGATATTATATTTTTGTTTTTATAAATAAAATTT
TTTACGGAATTTAGGGTTGTAGATTAGTTTTTCGTAAGTTAACGCGTTTCGTGGGTATTCGGTTTTTCGGTTTCG
CGTTTTTGTTATTTTTTATCGTTTTTTTTTAATTATGTTTTTGTTTTTTTTCGTTGATCGTAAGGTTGCGGGC
GAGGATTTTAGAGAGAGGTTTAGTATGGGGAATAAACGTTTTAGAGGGGTTCGAGGTGGGTTGGGGATAGTTAGT
GGATGGGAAGGAGGGCGTTGGCG (SEQ ID NO:396)
```

LBH plasmid sequence

```
TACGGAATTTAGGGTTGTAGATTAGTTTTTCGTAAGTTAACGCGTTTCGTGGGTATTCGGTTTTTCGGTTTCGCG
TTTTTGTTATTTTTTATCGTTTTTTTTTAATTATGTTTTTGTTTTTTTTCGTTGATCGTAAGGTTGCGGGCGA
GGATTTTAGAGAGAGGTTTAGTATGGG (SEQ ID NO:397)

LBH_FP      TAGTTTTTCGTAAGTTAACGCGTTTC (SEQ ID NO:233)
LBH_RP      CCCGCAACCTTACGATCAAC (SEQ ID NO:234)
LBH_Pb_A1   CGCGCCGAGG CGTGGGTATTCGGTTTTTC/3C6/ (SEQ ID NO:283)
```

DETECTING OVARIAN CANCER

CROSS-REFERENCE TO RELATED APPLICATIONS

This application claims the priority benefit of U.S. Provisional Application No. 62/928,888, filed Oct. 31, 2019 and U.S. Provisional Application No. 63/065,081, filed Aug. 13, 2020, which are incorporated herein by reference in their entireties.

SEQUENCE LISTING

The text of the computer readable sequence listing filed Oct. 30, 2020, titled "38034-203_ST25", created Oct. 30, 2020, having a file size of 64,000 bytes, is hereby incorporated by reference in its entirety.

FIELD OF INVENTION

Provided herein is technology for ovarian cancer screening and particularly, but not exclusively, to methods, compositions, and related uses for detecting the presence of ovarian cancer and sub-types of ovarian cancer (e.g., clear cell ovarian cancer, endometrioid ovarian cancer, mucinous ovarian cancer, serous ovarian cancer).

BACKGROUND

Ovarian cancer is among the most lethal gynecologic malignancies in developed countries. In the United States, approximately 23,000 women are diagnosed with the disease and almost 14,000 women die from it each year. There are three main types of ovarian cancer: epithelial, germ cell, and sex cord stromal. About 90% of ovarian cancers start in the epithelium tissue, which is the lining on the outside of the ovary. This type of ovarian cancer is divided into serous, mucinous, endometrioid, clear cell, transitional and undifferentiated types. The risk of epithelial ovarian cancer increases with age, especially after the age of 50. Germ cell tumors account for about 5% of ovarian cancers. They begin in the egg-producing cells. This type of ovarian cancer can occur in women of any age, but about 80% are found in women under the age of 30. The main subtypes are teratoma, dysgerminoma, endodermal sinus tumor and choriocarcinoma. Sex cord stromal tumors, about 5% of ovarian cancers, grow in the connective tissue that holds the ovary together and makes estrogen and progesterone. Most are found in older women.

Despite progress in cancer therapy, ovarian cancer mortality has remained virtually unchanged over the past two decades. Given the steep survival gradient relative to the stage at which the disease is diagnosed, early detection remains the most important factor in improving long-term survival of ovarian cancer patients.

Improved methods for detecting ovarian cancer and various subtypes of ovarian cancer (e.g., clear cell ovarian cancer, endometrioid ovarian cancer, mucinous ovarian cancer, and serous ovarian cancer) are needed.

The present invention addresses these needs.

SUMMARY

As noted, ovarian cancer (OC) is the foremost cause of gynecological cancer death and is overall one of the most frequent causes of fatal malignancy in women (see, Ozor R. F., et al., Epithelial ovarian cancer. In: Hoskin W. J., Perez C. A., Young R. C., editors. Principles and Practice of Gynecologic Oncology. Lippincott Williams & Wilkins; Philadelphia, Pa., USA: 2000. pp. 981-1057). The symptoms are often nonspecific, hampering early detection, so the majority of patients present with advanced-stage disease.

Recently, the characteristics of several subtypes of OC have been elucidated by the findings from histopathological, molecular, and genetic studies. The main histotypes are epithelial in origin and include serous ovarian cancer (serous OC), Clear Cell Carcinoma (clear cell OC), Endometrioid Carcinoma (endometrioid OC), and Mucinous Carcinoma (mucinous OC). Serous OC is the most malignant form of ovarian cancer and accounts for up to 70% of all ovarian cancer cases. Clear cell OC is the second most common histotype accounting for about 10-13% of women diagnosed with ovarian cancer. Endometrioid OC is the third most common histotype of ovarian cancer and like clear cell carcinoma is believed to arise from endometriosis. Mucinous OC account for 4% of ovarian carcinomas and are commonly diagnosed at a low stage.

To lessen the heavy toll of OC and its various subtypes (e.g., clear cell OC, serous OC, endometrioid OC, mucinous OC), effective screening approaches are urgently needed. There is an imperative for innovation that will deliver accurate, affordable, and safe screening tools for the pre-symptomatic detection of earliest stage cancer and advanced precancer.

The present invention addresses such needs. Indeed, the present invention provides novel methylated DNA markers that discriminate cases of OC and its various subtypes (e.g., clear cell OC, serous OC, endometrioid OC, mucinous OC).

Methylated DNA has been studied as a potential class of biomarkers in the tissues of most tumor types. In many instances, DNA methyltransferases add a methyl group to DNA at cytosine-phosphate-guanine (CpG) island sites as an epigenetic control of gene expression. In a biologically attractive mechanism, acquired methylation events in promoter regions of tumor suppressor genes are thought to silence expression, thus contributing to oncogenesis. DNA methylation may be a more chemically and biologically stable diagnostic tool than RNA or protein expression (Laird (2010) Nat Rev Genet 11: 191-203). Furthermore, in other cancers like sporadic colon cancer, methylation markers offer excellent specificity and are more broadly informative and sensitive than are individual DNA mutations (Zou et al (2007) Cancer Epidemiol Biomarkers Prev 16: 2686-96).

Analysis of CpG islands has yielded important findings when applied to animal models and human cell lines. For example, Zhang and colleagues found that amplicons from different parts of the same CpG island may have different levels of methylation (Zhang et al. (2009) PLoS Genet 5: e1000438). Further, methylation levels were distributed bi-modally between highly methylated and unmethylated sequences, further supporting the binary switch-like pattern of DNA methyltransferase activity (Zhang et al. (2009) PLoS Genet 5: e1000438). Analysis of murine tissues in vivo and cell lines in vitro demonstrated that only about 0.3% of high CpG density promoters (HCP, defined as having >7% CpG sequence within a 300 base pair region) were methylated, whereas areas of low CpG density (LCP, defined as having <5% CpG sequence within a 300 base pair region) tended to be frequently methylated in a dynamic tissue-specific pattern (Meissner et al. (2008) Nature 454: 766-70). HCPs include promoters for ubiquitous housekeeping genes and highly regulated developmental genes. Among the HCP sites methylated at >50% were several established markers such as Wnt 2, NDRG2, SFRP2, and BMP3 (Meissner et al. (2008) Nature 454: 766-70).

Epigenetic methylation of DNA at cytosine-phosphate-guanine (CpG) island sites by DNA methyltransferases has been studied as a potential class of biomarkers in the tissues of most tumor types. In a biologically attractive mechanism, acquired methylation events in promotor regions of tumor suppressor genes are thought to silence expression, contributing to oncogenesis. DNA methylation may be a more chemically and biologically stable diagnostic tool than RNA or protein expression. Furthermore, in other cancers like sporadic colon cancer, aberrant methylation markers are more broadly informative and sensitive than are individual DNA mutations and offer excellent specificity.

Several methods are available to search for novel methylation markers. While microarray based interrogation of CpG methylation is a reasonable, high-throughput approach, this strategy is biased towards known regions of interest, mainly established tumor suppressor promotors. Alternative methods for genome-wide analysis of DNA methylation have been developed in the last decade. There are three basic approaches. The first employs digestion of DNA by restriction enzymes which recognize specific methylated sites, followed by several possible analytic techniques which provide methylation data limited to the enzyme recognition site or the primers used to amplify the DNA in quantification steps (such as methylation-specific PCR; MSP). A second approach enriches methylated fractions of genomic DNA using anti-bodies directed to methyl-cytosine or other methylation-specific binding domains followed by microarray analysis or sequencing to map the fragment to a reference genome. This approach does not provide single nucleotide resolution of all methylated sites within the fragment. A third approach begins with bisulfate treatment of the DNA to convert all unmethylated cytosines to uracil, followed by restriction enzyme digestion and complete sequencing of all fragments after coupling to an adapter ligand. The choice of restriction enzymes can enrich the fragments for CpG dense regions, reducing the number of redundant sequences which may map to multiple gene positions during analysis.

RRBS yields CpG methylation status data at single nucleotide resolution of 80-90% of all CpG islands and a majority of tumor suppressor promoters at medium to high read coverage. In cancer case—control studies, analysis of these reads results in the identification of differentially methylated regions (DMRs). In previous RRBS analysis of pancreatic cancer specimens, hundreds of DMRs were uncovered, many of which had never been associated with carcinogenesis and many of which were unannotated. Further validation studies on independent tissue samples sets confirmed marker CpGs which were 100% sensitive and specific in terms of performance.

Provided herein is technology for OC and various OC subtypes (e.g., clear cell OC, endometrioid OC, mucinous OC, serous OC) screening and particularly, but not exclusively, to methods, compositions, and related uses for detecting the presence of OC and various OC subtypes (e.g., clear cell OC, endometrioid OC, mucinous OC, serous OC).

Indeed, as described in Examples I and II, experiments conducted during the course for identifying embodiments for the present invention identified a novel set of differentially methylated regions (DMRs) for discriminating 1) cancer of the ovary derived DNA from non-neoplastic control DNA, 2) DNA derived from clear cell OC tissue from non-neoplastic control DNA, 3) DNA derived from endometrioid OC tissue from non-neoplastic control DNA, 4) DNA derived from mucinous OC tissue from non-neoplastic control DNA, and 5) DNA derived from serous OC tissue from non-neoplastic control DNA.

Such experiments list and describe 560 novel DNA methylation markers distinguishing OC tissue from benign tissue (see, Tables 1A, 1B, 3, 4A, 6A, and 8A; Examples I and II), clear cell OC tissue from benign tissue (see, Tables 1A, 1B, 2A, 4B, 5B, 6A, 8B; Examples I and II), endometrioid OC tissue from benign tissue (see, Tables 1A, 1B, 2B, 4C, 5C, 6A, and 8C; Examples I and II), mucinous OC tissue from benign tissue (see, Tables 1A, 1B, 2C, 4D, 5D, 6A, and 8D; Examples I and II), serous OC tissue from benign tissue (see, Tables 1A, 1B, 2D, 4E, 5A, 6A, and 8E; Examples I and II), and detecting OC (e.g., OC, clear cell OC, endometrioid OC, mucinous OC, serous OC) within a blood sample (see, Table 9; Example III).

From these 560 novel DNA methylation markers, further experiments identified the following markers and/or panels of markers capable of distinguishing ovarian cancer tissue from benign tissue:

AGRN_A, ATP10A_A, ATP10A_B, ATP10A_C, ATP10A_D, BCAT1, CCND2_D, CMTM3_A, ELMO1_A, ELMO1_B, ELMO1_C, EMX1, EPS8L2_A, EPS8L2_B, EPS8L2_C, EPS8L2_D, FAIM2_A, FLJ40208_A, GPRIN1_, INA_A, ITGA4_B, KCNA3_A, KCNA3_C, LBH, LIME1_A, LIME1_B, LOC646278, LRRC4, LRRC41_A, MAX.chr1.110626771-110626832, MAX.chr1.147790358-147790381, MAX.chr1.161591532-161591608, MAX.chr15.28351937-28352173, MAX.chr15.28352203-28352671, MAX.chr15.29131258-29131734, MAX.chr4.8859995-8860062, MAX.chr5.42952182-42952292, MDFI, NCOR2, NKX2-6, OPLAH_A, PARP15, PDE10A, PPP1R16B, RASSF1_B, SEPTIN9, SKI, SLC12A8, SRC_A, SSBP4_B, ST8SIA1, TACC2_A, TSHZ3, UBTF, VIM, VIPR2_A, ZBED4, ZMIZ1_A, ZMIZ1_B, ZMIZ1_C, ZNF382_A, ZNF469_B, ATP6V1B1_A, BZRAP1, GDF6, IFFO1_A, IFFO1_B, KCNAB2, LIMD2, MAML3_B, MAX.chr14.102172350-102172770, MAX.chr16.85482307-85482494, MAX.chr17.76254728-76254841, MAX.chr5.42993898-42994179, and RASAL3 (see, Tables 1A, 1B, 6A; Example I);

MAX.chr16.85482307-85482494, GDF6, IFFO_A, MAX.chr5.42993898-42994179, MAX.chr17.76254728-76254841, MAX.chr14.102172350-102172770, RASAL3, BZRAP1, and LIMD2 (see, Table 3; Example I);

PALLD, PRDM14, MAX.chr1.147790358-147790381, BCAT1, MAML3_A, SKI, DNMT3A_A, and C2CD4D (see, Table 4A; Example I); and BCAT1_6015, SKI, SIM2_B, DNMT3A_A, CDO1_A, and DSCR6 (see, Table 8A; Example II).

From these 560 novel DNA methylation markers, further experiments identified the following markers and/or panels of markers for detecting ovarian cancer (e.g., OC, clear cell OC, endometrioid OC, mucinous OC, serous OC) in blood samples (e.g., plasma samples, whole blood samples, leukocytes samples, serum samples):

GPRIN1 (e.g., GPRIN1_A, GPRIN1_B), CDO1 (e.g., CDO1_A, CDO1_B), SRC (e.g., SRC_A, SRC_B), SIM2 (e.g., SIM2_A, SIM2_B), AGRN (e.g., AGRN_A, AGRN_B, AGRN_C, AGRN_8794), FAIM2 (e.g., FAIM2_A, FAIM2_B), CELF2 (e.g., CELF2_A, CELF2_B), DSCR6, GYPC (e.g., GYPC_A, GYPC_B,

GYPC_C), CAPN2 (e.g., CAPN2_A, CAPN2_B), and BCAT1 (see, Table 9; Example III); and ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GPS, DSCR6, SKI, SIM2_A, AGRN_8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333 (see, Table 10, Example III).

From these 560 novel DNA methylation markers, further experiments identified the following markers and/or panels of markers for detecting ovarian cancer (e.g., OC, clear cell OC, endometrioid OC, mucinous OC, serous OC) in blood samples (e.g., plasma samples, whole blood samples, leukocyte samples, serum samples) in combination with increased levels of cancer antigen 125 (CA-125) in the blood sample:

CA-125 and ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GPS, DSCR6, SKI, and SIM2_A (see, Tables 11, 12 and 13, Example III).

From these 560 novel DNA methylation markers, further experiments identified the following markers and/or panels of markers capable of distinguishing clear cell OC tissue from ovarian tissue:

TACC2_A, LRRC41_A, EPS8L2, LBH, LIME1_B, MDFI, FAIM2_A, GYPC_A, AGRN_B, and ZBED4 (see, Table 2A; Example I);

MT1A_A, CELF2_A, KCNA3_A, MDFI, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, MAX.chr14.105512178-105512224, EPS8L2_E, SKI, GPRIN1_A, MAX.chr8.142215938-142216298, CDO1_A, DNMT3A_A, SIM2_A, SKI, MT1A_B, GYPC_A, BCL2L11, PISD, and C2CD4D (see, Table 4B; Example I);

NCOR2, MT1A_B, CELF2_A, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, SKI, GPRIN1_A, CDO1_A, SIM2_A, IFFO1_A, MT1A_B, GYPC_A, BCL2L11, GDF6, and C2CD4D (see, Table 5B; Example I); and AGRN_8794, BHLHE23_8339, EPS8L2_F, RASSF1_8293, MDFI_6321, SKI, GYPC_C, NKX2-6_4159, LOC100131366, FAIM2_B, GPRIN1_B, LRRC41_B, TACC2_B, LBH, SIM2_B, CDO1_A, and DSCR6 (see, Table 8B; Example II).

From these 560 novel DNA methylation markers, further experiments identified the following markers and/or panels of markers capable of distinguishing endometrioid OC tissue from benign tissue:

PARP15, GPRIN1_A, GYPC1_A, F1134208, MAX.chr1.147790358-147790381, FAIM2_A, SH2B3, KCNQ5, IRF4, and BCAT1 (see, Table 2B; Example I);

NCOR2, CELF2_A, PALLD, PRDM14, MAX.chr1.147790358-147790381, BCAT1, MAX.chr11.14926602-14926671, MAML3_A, SKI, GPRIN1_A, SKI, BCL2L11, and C2CD4D (see, Table 4C; Example I);

NCOR2, PALLD, PRDM14, MAX.chr1.147790358-147790381, MAX.chr11.14926602-14926671, DSCR6, GPRIN1_A, CDO1_A, SIM2_A, IFFO1_A, and C2CD4D (see, Table 5C; Example I); and BCAT1_6015, EPS8L2_F, SKI, NKX2-6_4159, C1QL3_B, GPRIN1_B, PARP15, OXT_C, SIM2_B, DNMT3A_A, and CELF2_A (see, Table 8C; Example II).

From these 560 novel DNA methylation markers, further experiments identified the following markers and/or panels of markers capable of distinguishing mucinous OC tissue from benign tissue:

CMTM3_A, ATP10A_C, TSHZ3, ZMIZ1_B, ATP10A_B, ELMO1_B, TACC2_A, LRRC4, VIM, and ZNF382_A (see, Table 2C; Example I);

NCOR2, MT1A_A, KCNA3_A, ZMIZ1_C, TACC2_A, MAX.chr1.147790358-147790381, BCAT1, AGRN_B, SKI, SLC12A8, ZMIZ1_B, BCL2L11, and GATA2 (see, Table 4D; Example I);

NCOR2, PALLD, TACC2_A, BCAT1, AGRN_B, SKI, SLC12A8, ZMIZ1_B, and BCL2L11 (see, Table 5D; Example I); and BCAT1_6015, ELMO1_9100, KCNA3_7518, KCNA3_7320, MDFI_6321, SKI, VIPR_B, ZNF382_B, ATP10A_E, CMTM3_B, ZMIZ1_D, SRC_B, HDGFRP3, TACC2_B, TSHZ3, LBH, DNMT3A_A (see, Table 8D; Example II).

From these 560 novel DNA methylation markers, further experiments identified the following markers and/or panels of markers capable of distinguishing serous OC tissue from benign tissue:

MAX.chr1.147790358-147790381, MAML3, NR2F6, DNMT3A_A, SKI, SOBP, UBTF, AGRN_C, MAX.chr12.30975740-30975780, and CAPN2_A (see, Table 2D; Example I);

PALLD, PRDM14, MAX.chr1.147790358-147790381, CAPN2_A, MAX.chr6.10382190-10382225, SKI, NR2F6, IFFO1_A, MT1A_B, IFFO1_B, GDF6, and C2CD4D (see, Table 4E; Example I);

NCOR2, MAX.chr1.147790358-147790381, MAX.chr6.10382190-10382225, IFFO1_A, GDF6, and C2CD4D (see, Table 5A; Example I); and SKI, PEAR1_B, CAPN2_B, SIM2_B, DNMT3A_A, CDO1_A, and NR2F6 (see, Table 8E; Example II).

As described herein, the technology provides a number of methylated DNA markers and subsets thereof (e.g., sets of 2, 3, 4, 5, 6, 7, or 8 markers) with high discrimination for ovarian cancer overall and various types of ovarian cancer (e.g., clear cell OC, endometrioid OC, mucinous OC, serous OC). Experiments applied a selection filter to candidate markers to identify markers that provide a high signal to noise ratio and a low background level to provide high specificity for purposes of ovarian cancer screening or diagnosis.

In some embodiments, the technology is related to assessing the presence of and methylation state of one or more of the markers identified herein in a biological sample (e.g., ovarian tissue, plasma sample). These markers comprise one or more differentially methylated regions (DMR) as discussed herein, e.g., as provided in Tables 1A and 6A. Methylation state is assessed in embodiments of the technology. As such, the technology provided herein is not restricted in the method by which a gene's methylation state is measured. For example, in some embodiments the methylation state is measured by a genome scanning method. For example, one method involves restriction landmark genomic scanning (Kawai et al. (1994)*Mol. Cell. Biol.* 14: 7421-7427) and another example involves methylation-sensitive arbitrarily primed PCR (Gonzalgo et al. (1997) *Cancer Res.* 57: 594-599). In some embodiments, changes in methylation patterns at specific CpG sites are monitored by digestion of genomic DNA with methylation-sensitive restriction enzymes followed by Southern analysis of the regions of interest (digestion-Southern method). In some embodiments, analyzing changes in methylation patterns involves a PCR-based process that involves digestion of genomic DNA with methylation-sensitive restriction enzymes or methylation-dependent restriction enzymes prior to PCR amplification (Singer-Sam et al. (1990) *Nucl. Acids Res.* 18: 687). In addition, other techniques have been reported that utilize bisulfate treatment of DNA as a starting point for methylation analysis. These include methylation-specific PCR (MSP) (Herman et al. (1992) *Proc. Natl. Acad. Sci. USA* 93: 9821-9826) and restriction enzyme digestion of PCR products amplified from bisulfite-converted DNA (Sadri and Hornsby (1996) *Nucl. Acids Res.* 24: 5058-5059; and Xiong and Laird (1997) *Nucl. Acids Res.* 25: 2532-2534). PCR techniques have been developed for detection of gene mutations (Kuppuswamy et al. (1991) *Proc. Natl. Acad. Sci. USA* 88: 1143-1147) and quantification of allelic-specific expression (Szabo and Mann (1995) *Genes Dev.* 9: 3097-3108; and Singer-Sam et al. (1992) *PCR Methods Appl.* 1: 160-163). Such techniques use internal primers, which anneal to a PCR-generated template and terminate immediately 5' of the single nucleotide to be assayed. Methods using a "quantitative Ms-SNuPE assay" as described in U.S. Pat. No. 7,037,650 are used in some embodiments.

Upon evaluating a methylation state, the methylation state is often expressed as the fraction or percentage of individual strands of DNA that is methylated at a particular site (e.g., at a single nucleotide, at a particular region or locus, at a longer sequence of interest, e.g., up to a ~100-bp, 200-bp, 500-bp, 1000-bp subsequence of a DNA or longer) relative to the total population of DNA in the sample comprising that particular site. Traditionally, the amount of the unmethylated nucleic acid is determined by PCR using calibrators. Then, a known amount of DNA is bisulfite treated and the resulting methylation-specific sequence is determined using either a real-time PCR or other exponential amplification, e.g., a QuARTS assay (e.g., as provided by U.S. Pat. No. 8,361,720; and U.S. Pat. Appl. Pub. Nos. 2012/0122088 and 2012/0122106, incorporated herein by reference).

For example, in some embodiments, methods comprise generating a standard curve for the unmethylated target by using external standards. The standard curve is constructed from at least two points and relates the real-time Ct value for unmethylated DNA to known quantitative standards. Then, a second standard curve for the methylated target is constructed from at least two points and external standards. This second standard curve relates the Ct for methylated DNA to known quantitative standards. Next, the test sample Ct values are determined for the methylated and unmethylated populations and the genomic equivalents of DNA are calculated from the standard curves produced by the first two steps. The percentage of methylation at the site of interest is calculated from the amount of methylated DNAs relative to the total amount of DNAs in the population, e.g., (number of methylated DNAs)/(the number of methylated DNAs+number of unmethylated DNAs)×100.

Also provided herein are compositions and kits for practicing the methods. For example, in some embodiments, reagents (e.g., primers, probes) specific for one or more markers are provided alone or in sets (e.g., sets of primers pairs for amplifying a plurality of markers). Additional reagents for conducting a detection assay may also be provided (e.g., enzymes, buffers, positive and negative controls for conducting QuARTS, PCR, sequencing, bisulfite, or other assays). In some embodiments, the kits contain a reagent capable of modifying DNA in a methylation-specific manner (e.g., a methylation-sensitive restriction enzyme, a methylation-dependent restriction enzyme, and a bisulfite reagent). In some embodiments, the kits containing one or more reagent necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

In some embodiments, the technology described herein is associated with a programmable machine designed to perform a sequence of arithmetic or logical operations as provided by the methods described herein. For example, some embodiments of the technology are associated with (e.g., implemented in) computer software and/or computer hardware. In one aspect, the technology relates to a computer comprising a form of memory, an element for performing arithmetic and logical operations, and a processing element (e.g., a microprocessor) for executing a series of instructions (e.g., a method as provided herein) to read, manipulate, and store data. In some embodiments, a microprocessor is part of a system for determining a methylation state (e.g., of one or more DMR, e.g., DMR 1-560 as provided in Tables 1A and 6A); comparing methylation states (e.g., of one or more DMR, e.g., DMR 1-560 as provided in Tables 1A and 6A); generating standard curves; determining a Ct value; calculating a fraction, frequency, or percentage of methylation (e.g., of one or more DMR, e.g., DMR 1-560 as provided in Tables 1A and 6A); identifying a CpG island; determining a specificity and/or sensitivity of an assay or marker; calculating an ROC curve and an associated AUC; sequence analysis; all as described herein or is known in the art.

In some embodiments, a microprocessor or computer uses methylation state data in an algorithm to predict a site of a cancer.

In some embodiments, a software or hardware component receives the results of multiple assays and determines a single value result to report to a user that indicates a cancer risk based on the results of the multiple assays (e.g., determining the methylation state of multiple DMR, e.g., as provided in Tables 1A and 6A). Related embodiments calculate a risk factor based on a mathematical combination (e.g., a weighted combination, a linear combination) of the results from multiple assays, e.g., determining the methylation states of multiple markers (such as multiple DMR, e.g., as provided in Tables 1A and 6A). In some embodiments, the methylation state of a DMR defines a dimension and may have values in a multidimensional space and the coordinate defined by the methylation states of multiple DMR is a result, e.g., to report to a user, e.g., related to a cancer risk.

Some embodiments comprise a storage medium and memory components. Memory components (e.g., volatile and/or nonvolatile memory) find use in storing instructions (e.g., an embodiment of a process as provided herein) and/or data (e.g., a work piece such as methylation measurements, sequences, and statistical descriptions associated therewith). Some embodiments relate to systems also comprising one or more of a CPU, a graphics card, and a user interface (e.g., comprising an output device such as display and an input device such as a keyboard).

Programmable machines associated with the technology comprise conventional extant technologies and technologies in development or yet to be developed (e.g., a quantum computer, a chemical computer, a DNA computer, an optical computer, a spintronics based computer, etc.).

In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship.

In some embodiments, data are stored on a computer-readable storage medium such as a hard disk, flash memory, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

For example, some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, Calif. and Motorola Corporation of Schaumburg, Ill. Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C #, Visual Basic, Java, Python, Perl, and JavaScript.

Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows, Linux, UNIX, Mac OS X, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device.

All such components, computers, and systems described herein as associated with the technology may be logical or virtual.

Accordingly, provided herein is technology related to a method of screening for ovarian cancer and/or various forms of ovarian cancer (e.g., clear cell OC, endometrioid OC, mucinous OC, serous OC) in a sample obtained from a subject, the method comprising assaying a methylation state of a marker in a sample obtained from a subject (e.g., ovarian tissue) (e.g., plasma sample) and identifying the subject as having OC and/or a specific form of OC (e.g., clear cell OC, endometrioid OC, mucinous OC, serous OC) when the methylation state of the marker is different than a methylation state of the marker assayed in a subject that does not have such cancer, wherein the marker comprises a base in a differentially methylated region (DMR) selected from a group consisting of DMR 1-560 as provided in Tables 1A and 6A.

In some embodiments wherein the sample obtained from the subject is ovarian tissue and the methylation state of one or more of the following markers is different than a methylation state of the one or more markers assayed in a subject that does not have ovarian cancer indicates the subject has ovarian cancer: AGRN_A, ATP10A_A, ATP10A_B, ATP10A_C, ATP10A_D, BCAT1, CCND2_D, CMTM3_A, ELMO1_A, ELMO1_B, ELMO1_C, EMX1, EPS8L2_A, EPS8L2_B, EPS8L2_C, EPS8L2_D, FAIM2_A, FLJ34208_A, GPRIN1, GYPC_A, INA_A, ITGA4_B, KCNA3_A, KCNA3_C, LBH, LIME1_A, LIME1_B, LOC646278, LRRC4, LRRC41_A, MAX.chr1.110626771-110626832, MAX.chr1.147790358-147790381, MAX.chr1.161591532-161591608, MAX.chr15.28351937-28352173, MAX.chr15.28352203-28352671, MAX.chr15.29131258-29131734, MAX.chr4.8859995-8860062, MAX.chr5.42952182-42952292, MDFI, NCOR2, NKX2-6, OPLAH_A, PARP15, PDE10A, PPP1R16B, RASSF1_B, SEPTIN9, SKI, SLC12A8, SRC_A, SSBP4_B, ST8SIA1, TACC2_A, TSHZ3, UBTF, VIM, VIPR2_A, ZBED4, ZMIZ1_A, ZMIZ1_B, ZMIZ1_C, ZNF382_A, ZNF469_B, ATP6V1B1_A, BZRAP1, GDF6, IFFO1_A, IFFO1_B, KCNAB2, LIMD2, MAML3_B, MAX.chr14.102172350-102172770, MAX.chr16.85482307-85482494, MAX.chr17.76254728-76254841, MAX.chr5.42993898-42994179, and RASAL3 (see, Tables 1A, 1B, 6A; Example I).

In some embodiments wherein the sample obtained from the subject is ovarian tissue and the methylation state of one or more of the following markers is different than a methylation state of the one or more markers assayed in a subject that does not have ovarian cancer indicates the subject has ovarian cancer: MAX.chr16.85482307-85482494, GDF6, IFFO_A, MAX.chr5.42993898-42994179, MAX.chr17.76254728-76254841, MAX.chr14.102172350-102172770, RASAL3, BZRAP1, and LIMD2 (see, Table 3; Example I).

In some embodiments wherein the sample obtained from the subject is ovarian tissue and the methylation state of one or more of the following markers is different than a methylation state of the one or more markers assayed in a subject that does not have ovarian cancer indicates the subject has ovarian cancer: PALLD, PRDM14, MAX.chr1.147790358-147790381, BCAT1, MAML3_A, SKI, DNMT3A_A, and C2CD4D (see, Table 4A; Example I).

In some embodiments wherein the sample obtained from the subject is ovarian tissue and the methylation state of one or more of the following markers is different than a methylation state of the one or more markers assayed in a subject that does not have ovarian cancer indicates the subject has ovarian cancer: BCAT1_6015, SKI, SIM2_B, DNMT3A_A, CDO1_A, and DSCR6 (see, Table 8A; Example II).

In some embodiments wherein the sample obtained from the subject is ovarian tissue and the methylation state of one or more of the following markers is different than a methylation state of the one or more markers assayed in a subject that does not have ovarian cancer indicates the subject has clear cell ovarian cancer: TACC2_A, LRRC41_A, EPS8L2, LBH, LIME1_B, MDFI, FAIM2_A, GYPC_A, AGRN_B, and ZBED4 (see, Table 2A; Example I).

In some embodiments wherein the sample obtained from the subject is ovarian tissue and the methylation state of one or more of the following markers is different than a methylation state of the one or more markers assayed in a subject that does not have ovarian cancer indicates the subject has clear cell ovarian cancer: MT1A_A, CELF2_A, KCNA3_A, MDFI, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, MAX.chr14.105512178-105512224, EPS8L2_E, SKI, GPRIN1_A, MAX.chr8.142215938-142216298, CDO1_A, DNMT3A_A, SIM2_A, SKI, MT1A_B, GYPC_A, BCL2L11, PISD, and C2CD4D (see, Table 4B; Example I).

In some embodiments wherein the sample obtained from the subject is ovarian tissue and the methylation state of one or more of the following markers is different than a methylation state of the one or more markers assayed in a subject that does not have ovarian cancer indicates the subject has clear cell ovarian cancer: NCOR2, MT1A_B, CELF2_A, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, SKI, GPRIN1_A, CDO1_A, SIM2_A, IFFO1_A, MT1A_B, GYPC_A, BCL2L11, GDF6, and C2CD4D (see, Table 5B; Example I).

In some embodiments wherein the sample obtained from the subject is ovarian tissue and the methylation state of one or more of the following markers is different than a methylation state of the one or more markers assayed in a subject that does not have ovarian cancer indicates the subject has clear cell ovarian cancer: AGRN_8794, BHLHE23_8339, EPS8L2_F, RASSF1_8293, MDFI_6321, SKI, GYPC_C, NKX2-6_4159, LOC100131366, FAIM2_B, GPRIN1_B, LRRC41_B, TACC2_B, LBH, SIM2_B, CDO1_A, and DSCR6 (see, Table 8B; Example II).

In some embodiments wherein the sample obtained from the subject is ovarian tissue and the methylation state of one or more of the following markers is different than a methylation state of the one or more markers assayed in a subject that does not have ovarian cancer indicates the subject has endometrioid ovarian cancer: PARP15, GPRIN1_A, GYPC1_A, F1134208, MAX.chr1.147790358-147790381, FAIM2_A, SH2B3, KCNQ5, IRF4, and BCAT1 (see, Table 2B; Example I).

In some embodiments wherein the sample obtained from the subject is ovarian tissue and the methylation state of one or more of the following markers is different than a methylation state of the one or more markers assayed in a subject that does not have ovarian cancer indicates the subject has endometrioid ovarian cancer: NCOR2, CELF2_A, PALLD, PRDM14, MAX.chr1.147790358-147790381, BCAT1, MAX.chr11.14926602-14926671, MAML3_A, SKI, GPRIN1_A, SKI, BCL2L11, and C2CD4D (see, Table 4C; Example I).

In some embodiments wherein the sample obtained from the subject is ovarian tissue and the methylation state of one or more of the following markers is different than a methylation state of the one or more markers assayed in a subject that does not have ovarian cancer indicates the subject has endometrioid ovarian cancer: NCOR2, PALLD, PRDM14, MAX.chr1.147790358-147790381, MAX.chr11.14926602-14926671, DSCR6, GPRIN1_A, CDO1_A, SIM2_A, IFFO1_A, and C2CD4D (see, Table 5C; Example I).

In some embodiments wherein the sample obtained from the subject is ovarian tissue and the methylation state of one or more of the following markers is different than a methylation state of the one or more markers assayed in a subject that does not have ovarian cancer indicates the subject has endometrioid ovarian cancer: BCAT1_6015, EPS8L2_F, SKI, NKX2-6_4159, C1QL3_B, GPRIN1_B, PARP15, OXT_C, SIM2_B, DNMT3A_A, and CELF2_A (see, Table 8C; Example II).

In some embodiments wherein the sample obtained from the subject is ovarian tissue and the methylation state of one or more of the following markers is different than a methylation state of the one or more markers assayed in a subject that does not have ovarian cancer indicates the subject has mucinous ovarian cancer: CMTM3_A, ATP10A_C, TSHZ3, ZMIZ1_B, ATP10A_B, ELMO1_B, TACC2_A, LRRC4, VIM, and ZNF382_A (see, Table 2C; Example I).

In some embodiments wherein the sample obtained from the subject is ovarian tissue and the methylation state of one or more of the following markers is different than a methylation state of the one or more markers assayed in a subject that does not have ovarian cancer indicates the subject has mucinous ovarian cancer: NCOR2, MT1A_A, KCNA3_A, ZMIZ1_C, TACC2_A, MAX.chr1.147790358-147790381, BCAT1, AGRN_B, SKI, SLC12A8, ZMIZ1_B, BCL2L11, and GATA2 (see, Table 4D; Example I).

In some embodiments wherein the sample obtained from the subject is ovarian tissue and the methylation state of one or more of the following markers is different than a methylation state of the one or more markers assayed in a subject that does not have ovarian cancer indicates the subject has mucinous ovarian cancer: NCOR2, PALLD, TACC2_A, BCAT1, AGRN_B, SKI, SLC12A8, ZMIZ1_B, and BCL2L11 (see, Table 5D; Example I).

In some embodiments wherein the sample obtained from the subject is ovarian tissue and the methylation state of one or more of the following markers is different than a methylation state of the one or more markers assayed in a subject that does not have ovarian cancer indicates the subject has mucinous ovarian cancer: BCAT1_6015, ELMO1_9100, KCNA3_7518, KCNA3_7320, MDFI_6321, SKI, VIPR_B, ZNF382_B, ATP10A_E, CMTM3_B, ZMIZ1_D, SRC_B, HDGFRP3, TACC2_B, TSHZ3, LBH, DNMT3A_A (see, Table 8D; Example II).

In some embodiments wherein the sample obtained from the subject is ovarian tissue and the methylation state of one or more of the following markers is different than a methylation state of the one or more markers assayed in a subject that does not have ovarian cancer indicates the subject has serous ovarian cancer: MAX.chr1.147790358-147790381, MAML3, NR2F6, DNMT3A_A, SKI, SOBP, UBTF, AGRN_C, MAX.chr12.30975740-30975780, and CAPN2_A (see, Table 2D; Example I).

In some embodiments wherein the sample obtained from the subject is ovarian tissue and the methylation state of one or more of the following markers is different than a methylation state of the one or more markers assayed in a subject that does not have ovarian cancer indicates the subject has serous ovarian cancer: PALLD, PRDM14, MAX.chr1.147790358-147790381, CAPN2_A, MAX.chr6.10382190-10382225, SKI, NR2F6, IFFO1_A, MT1A_B, IFFO1_B, GDF6, and C2CD4D (see, Table 4E; Example I).

In some embodiments wherein the sample obtained from the subject is ovarian tissue and the methylation state of one or more of the following markers is different than a methylation state of the one or more markers assayed in a subject that does not have ovarian cancer indicates the subject has serous ovarian cancer: NCOR2, MAX.chr1.147790358-147790381, MAX.chr6.10382190-10382225, IFFO1_A, GDF6, and C2CD4D (see, Table 5A; Example I).

In some embodiments wherein the sample obtained from the subject is ovarian tissue and the methylation state of one or more of the following markers is different than a methylation state of the one or more markers assayed in a subject that does not have ovarian cancer indicates the subject has serous ovarian cancer: SKI, PEAR1_B, CAPN2_B, SIM2_B, DNMT3A_A, CDO1_A, and NR2F6 (see, Table 8E; Example II).

In some embodiments wherein the sample obtained from the subject is a blood sample (e.g., plasma sample, whole blood sample, leukocyte sample, serum sample) and the methylation state of one or more of the following markers is different than a methylation state of the one or more markers assayed in a subject that does not have OC indicates the subject has OC: GPRIN1 (e.g., GPRIN1_A, GPRIN1_B), CDO1 (e.g., CDO1_A, CDO1_B), SRC (e.g., SRC_A, SRC_B), SIM2 (e.g., SIM2_A, SIM2_B), AGRN (e.g., AGRN_A, AGRN_B, AGRN_C, AGRN_8794), FAIM2 (e.g., FAIM2_A, FAIM2_B), CELF2 (e.g., CELF2_A, CELF2_B), DSCR6, GYPC (e.g., GYPC_A, GYPC_B, GYPC_C), CAPN2 (e.g., CAPN2_A, CAPN2_B), and BCAT1 (see, Table 9; Example III).

In some embodiments wherein the sample obtained from the subject is a blood sample (e.g., plasma sample, whole blood sample, leukocyte sample, serum sample) and the methylation state of one or more of the following markers is different than a methylation state of the one or more markers assayed in a subject that does not have OC indicates the subject has OC: ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GPS, DSCR6, SKI, SIM2_A, AGRN_8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333 (see, Table 10, Example III).

In some embodiments wherein the sample obtained from the subject is a blood sample (e.g., plasma sample, whole blood sample, leukocyte sample, serum sample) and 1) increased levels of CA-125 are detected, and 2) the methylation state of one or more of the following markers is different than a methylation state of the one or more markers assayed in a subject that does not have OC indicates the subject has OC: ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GPS, DSCR6, SKI, and SIM2_A (see, Table 11-13, Example III).

The technology is related to identifying and discriminating ovarian cancer and/or various forms of ovarian cancer (e.g., clear cell OC, endometrioid OC, mucinous OC, serous OC). Some embodiments provide methods comprising assaying a plurality of markers, e.g., comprising assaying 1, 2, 3, 2 to 11 to 100 or 120 or 375 or 560 markers (e.g., 1-4, 1-6, 1-7, 1-8, 1-9, 1-10, 1-11, 1-12, 1-13, 1-14, 1-15, 1-16, 1-17, 1-18, 1-19, 1-20, 1-25, 1-50, 1-75, 1-100, 1-200, 1-300, 1-400, 1-500, 1-560) (e.g., 2-4, 2-6, 2-7, 2-8, 2-9, 2-10, 2-11, 2-12, 2-13, 2-14, 2-15, 2-16, 2-17, 2-18, 2-19, 2-20, 2-25, 2-50, 2-75, 2-100, 2-200, 2-300, 2-400, 2-500, 2-560) (e.g., 3-4, 3-6, 3-7, 3-8, 3-9, 3-10, 3-11, 3-12, 3-13, 3-14, 3-15, 3-16, 3-17, 3-18, 3-19, 3-20, 3-25, 3-50, 3-75, 3-100, 3-200, 3-300, 3-400, 3-500, 3-560) (e.g., 4-5, 4-6, 4-7, 4-8, 4-9, 4-10, 4-11, 4-12, 4-13, 4-14, 4-15, 4-16, 4-17, 4-18, 4-19, 4-20, 4-25, 4-50, 4-75, 4-100, 4-200, 4-300, 4-400, 4-500, 4-560) (e.g., 5-6, 5-7, 5-8, 5-9, 5-10, 5-11, 5-12, 5-13, 5-14, 5-15, 5-16, 5-17, 5-18, 5-19, 5-20, 5-25, 5-50, 5-75, 5-100, 5-200, 5-300, 5-400, 5-500, 5-560).

The technology is not limited in the methylation state assessed. In some embodiments assessing the methylation state of the marker in the sample comprises determining the methylation state of one base. In some embodiments, assaying the methylation state of the marker in the sample comprises determining the extent of methylation at a plurality of bases. Moreover, in some embodiments the methylation state of the marker comprises an increased methylation of the marker relative to a normal methylation state of the marker. In some embodiments, the methylation state of the marker comprises a decreased methylation of the marker relative to a normal methylation state of the marker. In some embodiments the methylation state of the marker comprises a different pattern of methylation of the marker relative to a normal methylation state of the marker.

Furthermore, in some embodiments the marker is a region of 100 or fewer bases, the marker is a region of 500 or fewer bases, the marker is a region of 1000 or fewer bases, the marker is a region of 5000 or fewer bases, or, in some embodiments, the marker is one base. In some embodiments the marker is in a high CpG density promoter.

The technology is not limited by sample type. For example, in some embodiments the sample is a stool sample, a tissue sample (e.g., ovarian tissue sample), a blood sample (e.g., plasma, serum, whole blood), an excretion, or a urine sample.

Furthermore, the technology is not limited in the method used to determine methylation state. In some embodiments the assaying comprises using methylation specific polymerase chain reaction, nucleic acid sequencing, mass spectrometry, methylation specific nuclease, mass-based separation, or target capture. In some embodiments, the assaying comprises use of a methylation specific oligonucleotide. In some embodiments, the technology uses massively parallel sequencing (e.g., next-generation sequencing) to determine methylation state, e.g., sequencing-by-synthesis, real-time (e.g., single-molecule) sequencing, bead emulsion sequencing, nanopore sequencing, etc.

The technology provides reagents for detecting a DMR, e.g., in some embodiments are provided a set of oligonucleotides comprising the sequences provided by SEQ ID NO: 1-283 (see, Tables 1C and 6B). In some embodiments are provided an oligonucleotide comprising a sequence complementary to a chromosomal region having a base in a DMR, e.g., an oligonucleotide sensitive to methylation state of a DMR.

The technology provides various panels of markers use for identifying ovarian cancer, e.g., in some embodiments the marker comprises a chromosomal region having an annotation that is AGRN_A, ATP10A_A, ATP10A_B, ATP10A_C, ATP10A_D, BCAT1, CCND2_D, CMTM3_A, ELMO1_A, ELMO1_B, ELMO1_C, EMX1, EPS8L2_A, EPS8L2_B, EPS8L2_C, EPS8L2_D, FAIM2_A, FLJ34208_A, GPRIN1, GYPC_A, INA_A, ITGA4_B, KCNA3_A, KCNA3_C, LBH, LIME1_A, LIME1_B, LOC646278, LRRC4, LRRC41_A, MAX.chr1.110626771-110626832, MAX.chr1.147790358-147790381, MAX.chr1.161591532-161591608, MAX.chr15.28351937-28352173, MAX.chr15.28352203-28352671, MAX.chr15.29131258-29131734, MAX.chr4.8859995-8860062, MAX.chr5.42952182-42952292, MDFI, NCOR2, NKX2-6, OPLAH_A, PARP15, PDE10A, PPP1R16B, RASSF1_B, SEPTIN9, SKI, SLC12A8, SRC_A, SSBP4_B, ST8SIA1, TACC2_A, TSHZ3, UBTF, VIM, VIPR2_A, ZBED4, ZMIZ1_A, ZMIZ1_B, ZMIZ1_C, ZNF382_A, ZNF469_B, ATP6V1B1_A, BZRAP1, GDF6, IFFO1_A, IFFO1_B, KCNAB2, LIMD2, MAML3_B, MAX.chr14.102172350-102172770, MAX.chr16.85482307-85482494, MAX.chr17.76254728-76254841, MAX.chr5.42993898-42994179, and RASAL3 (see, Tables 1A, 1B, 6A, 6B; Example I).

The technology provides various panels of markers use for identifying ovarian cancer, e.g., in some embodiments the marker comprises a chromosomal region having an annotation that is MAX.chr16.85482307-85482494, GDF6, IFFO_A, MAX.chr5.42993898-42994179, MAX.chr17.76254728-76254841, MAX.chr14.102172350-102172770, RASAL3, BZRAP1, and LIMD2 (see, Table 3; Example I).

The technology provides various panels of markers use for identifying ovarian cancer, e.g., in some embodiments the marker comprises a chromosomal region having an annotation that is PALLD, PRDM14, MAX.chr1.147790358-147790381, BCAT1, MAML3_A, SKI, DNMT3A_A, and C2CD4D (see, Table 4A; Example I).

The technology provides various panels of markers use for identifying ovarian cancer, e.g., in some embodiments the marker comprises a chromosomal region having an annotation that is BCAT1_6015, SKI, SIM2_B, DNMT3A_A, CDO1_A, and DSCR6 (see, Table 8A; Example II).

The technology provides various panels of markers use for identifying clear cell ovarian cancer, e.g., in some embodiments the marker comprises a chromosomal region having an annotation that is TACC2_A, LRRC41_A, EPS8L2, LBH, LIME1_B, MDFI, FAIM2_A, GYPC_A, AGRN_B, and ZBED4 (see, Table 2A; Example I).

The technology provides various panels of markers use for identifying clear cell ovarian cancer, e.g., in some embodiments the marker comprises a chromosomal region having an annotation that is MT1A_A, CELF2_A, KCNA3_A, MDFI, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, MAX.chr14.105512178-105512224, EPS8L2_E, SKI, GPRIN1_A, MAX.chr8.142215938-142216298, CDO1_A, DNMT3A_A, SIM2_A, SKI, MT1A_B, GYPC_A, BCL2L11, PISD, and C2CD4D (see, Table 4B; Example I).

The technology provides various panels of markers use for identifying clear cell ovarian cancer, e.g., in some embodiments the marker comprises a chromosomal region having an annotation that is NCOR2, MT1A_B, CELF2_A, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, SKI, GPRIN1_A, CDO1_A, SIM2_A, IFFO1_A, MT1A_B, GYPC_A, BCL2L11, GDF6, and C2CD4D (see, Table 5B; Example I).

The technology provides various panels of markers use for identifying clear cell ovarian cancer, e.g., in some embodiments the marker comprises a chromosomal region having an annotation that is AGRN_8794, BHLHE23_8339, EPS8L2_F, RASSF1_8293, MDFI_6321, SKI, GYPC_C, NKX2-6_4159, LOC100131366, FAIM2_B, GPRIN1_B, LRRC41_B, TACC2_B, LBH, SIM2_B, CDO1_A, and DSCR6 (see, Table 8B; Example II).

The technology provides various panels of markers use for identifying endometrioid ovarian cancer, e.g., in some embodiments the marker comprises a chromosomal region having an annotation that is PARP15, GPRIN1_A, GYPC1_A, F1134208, MAX.chr1.147790358-147790381, FAIM2_A, SH2B3, KCNQ5, IRF4, and BCAT1 (see, Table 2B; Example I).

The technology provides various panels of markers use for identifying endometrioid ovarian cancer, e.g., in some embodiments the marker comprises a chromosomal region having an annotation that is NCOR2, CELF2_A, PALLD, PRDM14, MAX.chr1.147790358-147790381, BCAT1, MAX.chr11.14926602-14926671, MAML3_A, SKI, GPRIN1_A, SKI, BCL2L11, and C2CD4D (see, Table 4C; Example I).

The technology provides various panels of markers use for identifying endometrioid ovarian cancer, e.g., in some embodiments the marker comprises a chromosomal region having an annotation that is NCOR2, PALLD, PRDM14, MAX.chr1.147790358-147790381, MAX.chr11.14926602-

14926671, DSCR6, GPRIN1_A, CDO1_A, SIM2_A, IFFO1_A, and C2CD4D (see, Table 5C; Example I).

The technology provides various panels of markers use for identifying endometrioid ovarian cancer, e.g., in some embodiments the marker comprises a chromosomal region having an annotation that is BCAT1_6015, EPS8L2_F, SKI, NKX2-6_4159, C1QL3_B, GPRIN1_B, PARP15, OXT_C, SIM2_B, DNMT3A_A, and CELF2_A (see, Table 8C; Example II).

The technology provides various panels of markers use for identifying mucinous ovarian cancer, e.g., in some embodiments the marker comprises a chromosomal region having an annotation that is CMTM3_A, ATP10A_C, TSHZ3, ZMIZ1_B, ATP10A_B, ELMO1_B, TACC2_A, LRRC4, VIM, and ZNF382_A (see, Table 2C; Example I).

The technology provides various panels of markers use for identifying mucinous ovarian cancer, e.g., in some embodiments the marker comprises a chromosomal region having an annotation that is NCOR2, MT1A_A, KCNA3_A, ZMIZ1_C, TACC2_A, MAX.chr1.147790358-147790381, BCAT1, AGRN_B, SKI, SLC12A8, ZMIZ1_B, BCL2L11, and GATA2 (see, Table 4D; Example I).

The technology provides various panels of markers use for identifying mucinous ovarian cancer, e.g., in some embodiments the marker comprises a chromosomal region having an annotation that is NCOR2, PALLD, TACC2_A, BCAT1, AGRN_B, SKI, SLC12A8, ZMIZ1_B, and BCL2L11 (see, Table 5D; Example I).

The technology provides various panels of markers use for identifying mucinous ovarian cancer, e.g., in some embodiments the marker comprises a chromosomal region having an annotation that is BCAT1_6015, ELMO1_9100, KCNA3_7518, KCNA3_7320, MDFI_6321, SKI, VIPR_B, ZNF382_B, ATP10A_E, CMTM3_B, ZMIZ1_D, SRC_B, HDGFRP3, TACC2_B, TSHZ3, LBH, DNMT3A_A (see, Table 8D; Example II).

The technology provides various panels of markers use for identifying serous ovarian cancer, e.g., in some embodiments the marker comprises a chromosomal region having an annotation that is MAX.chr1.147790358-147790381, MAML3, NR2F6, DNMT3A_A, SKI, SOBP, UBTF, AGRN_C, MAX.chr12.30975740-30975780, and CAPN2_A (see, Table 2D; Example I).

The technology provides various panels of markers use for identifying serous ovarian cancer, e.g., in some embodiments the marker comprises a chromosomal region having an annotation that is PALLD, PRDM14, MAX.chr1.147790358-147790381, CAPN2_A, MAX.chr6.10382190-10382225, SKI, NR2F6, IFFO1_A, MT1A_B, IFFO1_B, GDF6, and C2CD4D (see, Table 4E; Example I).

The technology provides various panels of markers use for identifying serous ovarian cancer, e.g., in some embodiments the marker comprises a chromosomal region having an annotation that is NCOR2, MAX.chr1.147790358-147790381, MAX.chr6.10382190-10382225, IFFO1_A, GDF6, and C2CD4D (see, Table 5A; Example I).

The technology provides various panels of markers use for identifying serous ovarian cancer, e.g., in some embodiments the marker comprises a chromosomal region having an annotation that is SKI, PEAR1_B, CAPN2_B, SIM2_B, DNMT3A_A, CDO1_A, and NR2F6 (see, Table 8E; Example II).

The technology provides various panels of markers use for identifying ovarian cancer, e.g., in some embodiments the marker comprises a chromosomal region having an annotation that is GPRIN1 (e.g., GPRIN1_A, GPRIN1_B), CDO1 (e.g., CDO1_A, CDO1_B), SRC (e.g., SRC_A, SRC_B), SIM2 (e.g., SIM2_A, SIM2_B), AGRN (e.g., AGRN_A, AGRN_B, AGRN_C, AGRN_8794), FAIM2 (e.g., FAIM2_A, FAIM2_B), CELF2 (e.g., CELF2_A, CELF2_B), DSCR6, GYPC (e.g., GYPC_A, GYPC_B, GYPC_C), CAPN2 (e.g., CAPN2_A, CAPN2_B), and BCAT1 (see, Table 9; Example III).

The technology provides various panels of markers use for identifying ovarian cancer, e.g., in some embodiments the marker comprises a chromosomal region having an annotation that is ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GPS, DSCR6, SKI, SIM2_A, AGRN_8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333 (see, Table 10, Example III).

The technology provides various panels of markers use for identifying ovarian cancer, e.g., in some embodiments the marker comprises a chromosomal region having an annotation that is ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GPS, DSCR6, SKI, SIM2_A, AGRN_8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333 (see, Table 10, Example III).

Kit embodiments are provided, e.g., a kit comprising a reagent capable of modifying DNA in a methylation-specific manner (e.g., a methylation-sensitive restriction enzyme, a methylation-dependent restriction enzyme, and a bisulfite reagent); and a control nucleic acid comprising a sequence from a DMR selected from a group consisting of DMR 1-560 (from Tables 1A and 6A) and having a methylation state associated with a subject who does not have ovarian cancer or a subtype of OC (e.g., clear cell OC, endometrioid OC, mucinous OC, serous OC). In some embodiments, kits comprise a bisulfite reagent and an oligonucleotide as described herein. In some embodiments, kits comprise a reagent capable of modifying DNA in a methylation-specific manner (e.g., a methylation-sensitive restriction enzyme, a methylation-dependent restriction enzyme, and a bisulfite reagent); and a control nucleic acid comprising a sequence from a DMR selected from a group consisting of DMR 1-560 (from Tables 1A and 6A) and having a methylation state associated with a subject who has ovarian cancer or a subtype of ovarian cancer (e.g., clear cell OC, endometrioid OC, mucinous OC, serous OC). Some kit embodiments comprise a sample collector for obtaining a sample from a subject (e.g., a stool sample; ovarian tissue sample; plasma sample, serum sample, whole blood sample); a reagent capable of modifying DNA in a methylation-specific manner (e.g., a methylation-sensitive restriction enzyme, a methylation-dependent restriction enzyme, and a bisulfite reagent); and an oligonucleotide as described herein.

The technology is related to embodiments of compositions (e.g., reaction mixtures). In some embodiments are provided a composition comprising a nucleic acid comprising a DMR and a reagent capable of modifying DNA in a methylation-specific manner (e.g., a methylation-sensitive restriction enzyme, a methylation-dependent restriction enzyme, and a bisulfite reagent). Some embodiments provide a composition comprising a nucleic acid comprising a DMR and an oligonucleotide as described herein. Some embodiments provide a composition comprising a nucleic acid comprising a DMR and a methylation-sensitive restriction enzyme. Some embodiments provide a composition comprising a nucleic acid comprising a DMR and a polymerase.

Additional related method embodiments are provided for screening for ovarian cancer and/or various forms of ovarian cancer (e.g., clear cell OC, endometrioid OC, mucinous OC, serous OC) in a sample obtained from a subject (e.g., ovarian tissue sample; plasma sample; stool sample), e.g., a method comprising determining a methylation state of a marker in the sample comprising a base in a DMR that is one or more of DMR 1-506 (from Tables 1A and 6A); comparing the methylation state of the marker from the subject sample to a methylation state of the marker from a normal control sample from a subject who does not have ovarian cancer (e.g., ovarian cancer and/or a form of ovarian cancer: clear cell OC, endometrioid OC, mucinous OC, serous OC); and determining a confidence interval and/or a p value of the difference in the methylation state of the subject sample and the normal control sample. In some embodiments, the confidence interval is 90%, 95%, 97.5%, 98%, 99%, 99.5%, 99.9% or 99.99% and the p value is 0.1, 0.05, 0.025, 0.02, 0.01, 0.005, 0.001, or 0.0001. Some embodiments of methods provide steps of reacting a nucleic acid comprising a DMR with a reagent capable of modifying nucleic acid in a methylation-specific manner (e.g., a methylation-sensitive restriction enzyme, a methylation-dependent restriction enzyme, and a bisulfate reagent) to produce, for example, nucleic acid modified in a methylation-specific manner; sequencing the nucleic acid modified in a methylation-specific manner to provide a nucleotide sequence of the nucleic acid modified in a methylation-specific manner; comparing the nucleotide sequence of the nucleic acid modified in a methylation-specific manner with a nucleotide sequence of a nucleic acid comprising the DMR from a subject who does not have ovarian cancer and/or a form of ovarian cancer to identify differences in the two sequences; and identifying the subject as having ovarian cancer and/or a form of ovarian cancer (e.g., clear cell OC, endometrioid OC, mucinous OC, serous OC) when a difference is present.

Systems for screening for ovarian cancer in a sample obtained from a subject are provided by the technology. Exemplary embodiments of systems include, e.g., a system for screening for ovarian cancer and/or types of ovarian cancer (e.g., clear cell OC, endometrioid OC, mucinous OC, serous OC) in a sample obtained from a subject (e.g., ovarian tissue sample; plasma sample; stool sample), the system comprising an analysis component configured to determine the methylation state of a sample, a software component configured to compare the methylation state of the sample with a control sample or a reference sample methylation state recorded in a database, and an alert component configured to alert a user of a ovarian-cancer-associated methylation state. An alert is determined in some embodiments by a software component that receives the results from multiple assays (e.g., determining the methylation states of multiple markers, e.g., DMR, e.g., as provided in Tables 1A and 6A) and calculating a value or result to report based on the multiple results. Some embodiments provide a database of weighted parameters associated with each DMR provided herein for use in calculating a value or result and/or an alert to report to a user (e.g., such as a physician, nurse, clinician, etc.). In some embodiments all results from multiple assays are reported and in some embodiments one or more results are used to provide a score, value, or result based on a composite of one or more results from multiple assays that is indicative of a cancer risk in a subject.

In some embodiments of systems, a sample comprises a nucleic acid comprising a DMR. In some embodiments the system further comprises a component for isolating a nucleic acid, a component for collecting a sample such as a component for collecting a stool sample. In some embodiments, the system comprises nucleic acid sequences comprising a DMR. In some embodiments the database comprises nucleic acid sequences from subjects who do not have ovarian cancer and/or specific types of ovarian cancer (e.g., clear cell OC, endometrioid OC, mucinous OC, serous OC). Also provided are nucleic acids, e.g., a set of nucleic acids, each nucleic acid having a sequence comprising a DMR. In some embodiments the set of nucleic acids wherein each nucleic acid has a sequence from a subject who does not have ovarian cancer and/or specific types of ovarian cancer. Related system embodiments comprise a set of nucleic acids as described and a database of nucleic acid sequences associated with the set of nucleic acids. Some embodiments further comprise a reagent capable of modifying DNA in a methylation-specific manner (e.g., a methylation-sensitive restriction enzyme, a methylation-dependent restriction enzyme, and a bisulfate reagent). And, some embodiments further comprise a nucleic acid sequencer.

In certain embodiments, methods for characterizing a sample (e.g., ovarian tissue sample; plasma sample; whole blood sample; serum sample; stool sample) from a human patient are provided. For example, in some embodiments such embodiments comprise obtaining DNA from a sample of a human patient; assaying a methylation state of a DNA methylation marker comprising a base in a differentially methylated region (DMR) selected from a group consisting of DMR 1-560 from Tables 1A and 6A; and comparing the assayed methylation state of the one or more DNA methylation markers with methylation level references for the one or more DNA methylation markers for human patients not having ovarian cancer and/or specific types of ovarian cancer (e.g., clear cell OC, endometrioid OC, mucinous OC, serous OC).

Such methods are not limited to a particular type of sample from a human patient. In some embodiments, the sample is a ovarian tissue sample. In some embodiments, the sample is a plasma sample. In some embodiments, the sample is a stool sample, a tissue sample, an ovarian tissue sample, a blood sample (e.g., plasma sample, whole blood sample, serum sample), or a urine sample.

In some embodiments, such methods comprise assaying a plurality of DNA methylation markers (e.g., 1-4, 1-6, 1-7, 1-8, 1-9, 1-10, 1-11, 1-12, 1-13, 1-14, 1-15, 1-16, 1-17, 1-18, 1-19, 1-20, 1-25, 1-50, 1-75, 1-100, 1-200, 1-300, 1-400, 1-500, 1-560) (e.g., 2-4, 2-6, 2-7, 2-8, 2-9, 2-10, 2-11, 2-12, 2-13, 2-14, 2-15, 2-16, 2-17, 2-18, 2-19, 2-20, 2-25, 2-50, 2-75, 2-100, 2-200, 2-300, 2-400, 2-500, 2-560) (e.g., 3-4, 3-6, 3-7, 3-8, 3-9, 3-10, 3-11, 3-12, 3-13, 3-14, 3-15, 3-16, 3-17, 3-18, 3-19, 3-20, 3-25, 3-50, 3-75, 3-100, 3-200, 3-300, 3-400, 3-500, 3-560) (e.g., 4-5, 4-6, 4-7, 4-8, 4-9, 4-10, 4-11, 4-12, 4-13, 4-14, 4-15, 4-16, 4-17, 4-18, 4-19, 4-20, 4-25, 4-50, 4-75, 4-100, 4-200, 4-300, 4-400, 4-500, 4-560) (e.g., 5-6, 5-7, 5-8, 5-9, 5-10, 5-11, 5-12, 5-13, 5-14, 5-15, 5-16, 5-17, 5-18, 5-19, 5-20, 5-25, 5-50, 5-75, 5-100, 5-200, 5-300, 5-400, 5-500, 5-560). In some embodiments, such methods comprise assaying 2 to 11 DNA methylation markers. In some embodiments, such methods comprise assaying 12 to 120 DNA methylation markers. In some embodiments, such methods comprise assaying 2 to 375 DNA methylation markers. In some embodiments, such methods comprise assaying the methylation state of the one or more DNA methylation markers in the sample comprises determining the methylation state of one base. In some embodiments, such methods comprise assaying the methylation state of the one or more DNA methylation markers in the sample comprises determining the extent of methylation at a plurality of bases. In some embodiments, such methods comprise assaying a methylation state of a forward strand or assaying a methylation state of a reverse strand.

In some embodiments, the DNA methylation marker is a region of 100 or fewer bases. In some embodiments, the DNA methylation marker is a region of 500 or fewer bases. In some embodiments, the DNA methylation marker is a region of 1000 or fewer bases. In some embodiments, the DNA methylation marker is a region of 5000 or fewer bases. In some embodiments, the DNA methylation marker is one base. In some embodiments, the DNA methylation marker is in a high CpG density promoter.

In some embodiments, the assaying comprises using methylation specific polymerase chain reaction, nucleic acid sequencing, mass spectrometry, methylation specific nuclease, mass-based separation, or target capture.

In some embodiments, the assaying comprises use of a methylation specific oligonucleotide. In some embodiments, the methylation specific oligonucleotide is selected from the group consisting of SEQ ID NO: 1-283 (Tables 1C, 6B).

In some embodiments, a chromosomal region having an annotation selected from the group consisting of AGRN_A, ATP10A_A, ATP10A_B, ATP10A_C, ATP10A_D, BCAT1, CCND2_D, CMTM3_A, ELMO1_A, ELMO1_B, ELMO1_C, EMX1, EPS8L2_A, EPS8L2_B, EPS8L2_C, EPS8L2_D, FAIM2_A, FLJ34208_A, GPRIN1, GYPC_A, INA_A, ITGA4_B, KCNA3_A, KCNA3_C, LBH, LIME1_A, LIME1_B, LOC646278, LRRC4, LRRC41_A, MAX.chr1.110626771-110626832, MAX.chr1.147790358-147790381, MAX.chr1.161591532-161591608, MAX.chr15.28351937-28352173, MAX.chr15.28352203-28352671, MAX.chr15.29131258-29131734, MAX.chr4.8859995-8860062, MAX.chr5.42952182-42952292, MDFI, NCOR2, NKX2-6, OPLAH_A, PARP15, PDE10A, PPP1R16B, RASSF1_B, SEPTIN9, SKI, SLC12A8, SRC_A, SSBP4_B, ST8SIA1, TACC2_A, TSHZ3, UBTF, VIM, VIPR2_A, ZBED4, ZMIZ1_A, ZMIZ1_B, ZMIZ1_C, ZNF382_A, ZNF469_B, ATP6V1B1_A, BZRAP1, GDF6, IFFO1_A, IFFO1_B, KCNAB2, LIMD2, MAML3_B, MAX.chr14.102172350-102172770, MAX.chr16.85482307-85482494, MAX.chr17.76254728-76254841, MAX.chr5.42993898-42994179, and RASAL3 (see, Tables 1A, 1B, 6A, 6B; Example I) comprises the DNA methylation marker.

In some embodiments, a chromosomal region having an annotation selected from the group consisting of MAX.chr16.85482307-85482494, GDF6, IFFO_A, MAX.chr5.42993898-42994179, MAX.chr17.76254728-76254841, MAX.chr14.102172350-102172770, RASAL3, BZRAP1, and LIMD2 (see, Table 3; Example I) comprises the DNA methylation marker.

In some embodiments, a chromosomal region having an annotation selected from the group consisting of PALLD, PRDM14, MAX.chr1.147790358-147790381, BCAT1, MAML3_A, SKI, DNMT3A_A, and C2CD4D (see, Table 4A; Example I) comprises the DNA methylation marker.

In some embodiments, a chromosomal region having an annotation selected from the group consisting of BCAT1_6015, SKI, SIM2_B, DNMT3A_A, CDO1_A, and DSCR6 (see, Table 8A; Example II) comprises the DNA methylation marker.

In some embodiments, a chromosomal region having an annotation selected from the group consisting of TACC2_A, LRRC41_A, EPS8L2, LBH, LIME1_B, MDFI, FAIM2_A, GYPC_A, AGRN_B, and ZBED4 (see, Table 2A; Example I) comprises the DNA methylation marker.

In some embodiments, a chromosomal region having an annotation selected from the group consisting of MT1A_A, CELF2_A, KCNA3_A, MDFI, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, MAX.chr14.105512178-105512224, EPS8L2_E, SKI, GPRIN1_A, MAX.chr8.142215938-142216298, CDO1_A, DNMT3A_A, SIM2_A, SKI, MT1A_B, GYPC_A, BCL2L11, PISD, and C2CD4D (see, Table 4B; Example I) comprises the DNA methylation marker.

In some embodiments, a chromosomal region having an annotation selected from the group consisting of NCOR2, MT1A_B, CELF2_A, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, SKI, GPRIN1_A, CDO1_A, SIM2_A, IFFO1_A, MT1A_B, GYPC_A, BCL2L11, GDF6, and C2CD4D (see, Table 5B; Example I) comprises the DNA methylation marker.

In some embodiments, a chromosomal region having an annotation selected from the group consisting of AGRN_8794, BHLHE23_8339, EPS8L2_F, RASSF1_8293, MDFI_6321, SKI, GYPC_C, NKX2-6_4159, LOC100131366, FAIM2_B, GPRIN1_B, LRRC41_B, TACC2_B, LBH, SIM2_B, CDO1_A, and DSCR6 (see, Table 8B; Example II) comprises the DNA methylation marker.

In some embodiments, a chromosomal region having an annotation selected from the group consisting of PARP15, GPRIN1_A, GYPC1_A, F1134208, MAX.chr1.147790358-147790381, FAIM2_A, SH2B3, KCNQ5, IRF4, and BCAT1 (see, Table 2B; Example I) comprises the DNA methylation marker.

In some embodiments, a chromosomal region having an annotation selected from the group consisting of NCOR2, CELF2_A, PALLD, PRDM14, MAX.chr1.147790358-147790381, BCAT1, MAX.chr11.14926602-14926671, MAML3_A, SKI, GPRIN1_A, SKI, BCL2L11, and C2CD4D (see, Table 4C; Example I) comprises the DNA methylation marker.

In some embodiments, a chromosomal region having an annotation selected from the group consisting of NCOR2, PALLD, PRDM14, MAX.chr1.147790358-147790381, MAX.chr11.14926602-14926671, DSCR6, GPRIN1_A, CDO1_A, SIM2_A, IFFO1_A, and C2CD4D (see, Table 5C; Example I) comprises the DNA methylation marker.

In some embodiments, a chromosomal region having an annotation selected from the group consisting of BCAT1_6015, EPS8L2_F, SKI, NKX2-6_4159, C1QL3_B, GPRIN1_B, PARP15, OXT_C, SIM2_B, DNMT3A_A, and CELF2_A (see, Table 8C; Example II) comprises the DNA methylation marker.

In some embodiments, a chromosomal region having an annotation selected from the group consisting of CMTM3_A, ATP10A_C, TSHZ3, ZMIZ1_B, ATP10A_B, ELMO1_B, TACC2_A, LRRC4, VIM, and ZNF382_A (see, Table 2C; Example I) comprises the DNA methylation marker.

In some embodiments, a chromosomal region having an annotation selected from the group consisting of NCOR2, MT1A_A, KCNA3_A, ZMIZ1_C, TACC2_A, MAX.chr1.147790358-147790381, BCAT1, AGRN_B, SKI, SLC12A8, ZMIZ1_B, BCL2L11, and GATA2 (see, Table 4D; Example I) comprises the DNA methylation marker.

In some embodiments, a chromosomal region having an annotation selected from the group consisting of NCOR2, PALLD, TACC2_A, BCAT1, AGRN_B, SKI, SLC12A8, ZMIZ1_B, and BCL2L11 (see, Table 5D; Example I) comprises the DNA methylation marker.

In some embodiments, a chromosomal region having an annotation selected from the group consisting of BCAT1_6015, ELMO1_9100, KCNA3_7518, KCNA3_7320, MDFI_6321, SKI, VIPR_B, ZNF382_B, ATP10A_E, CMTM3_B, ZMIZ1_D, SRC_B, HDGFRP3, TACC2_B, TSHZ3, LBH, DNMT3A_A (see, Table 8D; Example II) comprises the DNA methylation marker.

In some embodiments, a chromosomal region having an annotation selected from the group consisting of MAX.chr1.147790358-147790381, MAML3, NR2F6, DNMT3A_A, SKI, SOBP, UBTF, AGRN_C, MAX.chr12.30975740-30975780, and CAPN2_A (see, Table 2D; Example I) comprises the DNA methylation marker.

In some embodiments, a chromosomal region having an annotation selected from the group consisting of PALLD, PRDM14, MAX.chr1.147790358-147790381, CAPN2_A, MAX.chr6.10382190-10382225, SKI, NR2F6, IFFO1_A, MT1A_B, IFFO1_B, GDF6, and C2CD4D (see, Table 4E; Example I) comprises the DNA methylation marker.

In some embodiments, a chromosomal region having an annotation selected from the group consisting of NCOR2, MAX.chr1.147790358-147790381, MAX.chr6.10382190-10382225, IFFO1_A, GDF6, and C2CD4D (see, Table 5A; Example I) comprises the DNA methylation marker.

In some embodiments, a chromosomal region having an annotation selected from the group consisting of SKI, PEAR1_B, CAPN2_B, SIM2_B, DNMT3A_A, CDO1_A, and NR2F6 (see, Table 8E; Example II) comprises the DNA methylation marker.

In some embodiments, a chromosomal region having an annotation selected from the group consisting of GPRIN1 (e.g., GPRIN1_A, GPRIN1_B), CDO1 (e.g., CDO1_A, CDO1_B), SRC (e.g., SRC_A, SRC_B), SIM2 (e.g., SIM2_A, SIM2_B), AGRN (e.g., AGRN_A, AGRN_B, AGRN_C, AGRN_8794), FAIM2 (e.g., FAIM2_A, FAIM2_B), CELF2 (e.g., CELF2_A, CELF2_B), DSCR6, GYPC (e.g., GYPC_A, GYPC_B, GYPC_C), CAPN2 (e.g., CAPN2_A, CAPN2_B), and BCAT1 (see, Table 9; Example III) comprises the DNA methylation marker.

In some embodiments, a chromosomal region having an annotation selected from the group consisting of ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GPS, DSCR6, SKI, SIM2_A, AGRN_8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333 (see, Table 10, Example III) comprises the DNA methylation marker. In some embodiments, such methods comprise determining the methylation state of two DNA methylation markers. In some embodiments, such methods comprise determining the methylation state of a pair of DNA methylation markers provided in Tables 1A and/or 6A.

In certain embodiments, the technology provides methods for characterizing a sample (e.g., ovarian tissue sample; plasma sample; whole blood sample; serum sample; stool sample) obtained from a human patient. In some embodiments, such methods comprise determining a methylation state of a DNA methylation marker in the sample comprising a base in a DMR selected from a group consisting of DMR 1-560 from Tables 1A and 6A; comparing the methylation state of the DNA methylation marker from the patient sample to a methylation state of the DNA methylation marker from a normal control sample from a human subject who does not have a ovarian cancer and/or a specific form of ovarian cancer (e.g., clear cell OC, endometrioid OC, mucinous OC, serous OC); and determining a confidence interval and/or a p value of the difference in the methylation state of the human patient and the normal control sample. In some embodiments, the confidence interval is 90%, 95%, 97.5%, 98%, 99%, 99.5%, 99.9% or 99.99% and the p value is 0.1, 0.05, 0.025, 0.02, 0.01, 0.005, 0.001, or 0.0001.

In certain embodiments, the technology provides methods for characterizing a sample obtained from a human subject (e.g., ovarian tissue sample; plasma sample; whole blood sample; serum sample; stool sample), the method comprising reacting a nucleic acid comprising a DMR with a reagent capable of modifying DNA in a methylation-specific manner (e.g., a methylation-sensitive restriction enzyme, a methylation-dependent restriction enzyme, and a bisulfate reagent) to produce nucleic acid modified in a methylation-specific manner; sequencing the nucleic acid modified in a methylation-specific manner to provide a nucleotide sequence of the nucleic acid modified in a methylation-specific manner; comparing the nucleotide sequence of the nucleic acid modified in a methylation-specific manner with a nucleotide sequence of a nucleic acid comprising the DMR from a subject who does not have ovarian cancer to identify differences in the two sequences.

In certain embodiments, the technology provides systems for characterizing a sample obtained from a human subject (e.g., ovarian tissue sample; plasma sample; stool sample), the system comprising an analysis component configured to determine the methylation state of a sample, a software component configured to compare the methylation state of the sample with a control sample or a reference sample methylation state recorded in a database, and an alert component configured to determine a single value based on a combination of methylation states and alert a user of a ovarian cancer-associated methylation state. In some embodiments, the sample comprises a nucleic acid comprising a DMR.

In some embodiments, such systems further comprise a component for isolating a nucleic acid. In some embodiments, such systems further comprise a component for collecting a sample.

In some embodiments, the sample is a stool sample, a tissue sample, a ovarian tissue sample, a blood sample (e.g., plasma sample, whole blood sample, serum sample), or a urine sample.

In some embodiments, the database comprises nucleic acid sequences comprising a DMR. In some embodiments, the database comprises nucleic acid sequences from subjects who do not have a ovarian cancer.

Additional embodiments will be apparent to persons skilled in the relevant art based on the teachings contained herein.

BRIEF DESCRIPTION OF THE DRAWINGS

FIG. 1: Marker chromosomal regions used for various methylated DNA markers recited in Table 1A and 6A and related primer and probe information. Shown are naturally occurring sequences (WT) and bisulfite-modified sequences (BST) from PCR target regions.

DEFINITIONS

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The transitional phrase "consisting essentially of" as used in claims in the present application limits the scope of a claim to the specified materials or steps "and those that do not materially affect the basic and novel characteristic(s)" of the claimed invention, as discussed in In re Herz, 537 F.2d 549, 551-52, 190 USPQ 461, 463 (CCPR 1976). For example, a composition "consisting essentially of" recited elements may contain an unrecited contaminant at a level such that, though present, the contaminant does not alter the function of the recited composition as compared to a pure composition, i.e., a composition "consisting of" the recited components.

As used herein, a "nucleic acid" or "nucleic acid molecule" generally refers to any ribonucleic acid or deoxyribonucleic acid, which may be unmodified or modified DNA or RNA. "Nucleic acids" include, without limitation, single- and double-stranded nucleic acids. As used herein, the term "nucleic acid" also includes DNA as described above that contains one or more modified bases. Thus, DNA with a backbone modified for stability or for other reasons is a "nucleic acid". The term "nucleic acid" as it is used herein embraces such chemically, enzymatically, or metabolically modified forms of nucleic acids, as well as the chemical forms of DNA characteristic of viruses and cells, including for example, simple and complex cells.

The terms "oligonucleotide" or "polynucleotide" or "nucleotide" or "nucleic acid" refer to a molecule having two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. Typical deoxyribonucleotides for DNA are thymine, adenine, cytosine, and guanine. Typical ribonucleotides for RNA are uracil, adenine, cytosine, and guanine.

As used herein, the terms "locus" or "region" of a nucleic acid refer to a subregion of a nucleic acid, e.g., a gene on a chromosome, a single nucleotide, a CpG island, etc.

The terms "complementary" and "complementarity" refer to nucleotides (e.g., 1 nucleotide) or polynucleotides (e.g., a sequence of nucleotides) related by the base-pairing rules. For example, the sequence 5'-A-G-T-3' is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands effects the efficiency and strength of hybridization between nucleic acid strands. This is of particular importance in amplification reactions and in detection methods that depend upon binding between nucleic acids.

The term "gene" refers to a nucleic acid (e.g., DNA or RNA) sequence that comprises coding sequences necessary for the production of an RNA, or of a polypeptide or its precursor. A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends, e.g., for a distance of about 1 kb on either end, such that the gene corresponds to the length of the full-length mRNA (e.g., comprising coding, regulatory, structural and other sequences). The sequences that are located 5' of the coding region and that are present on the mRNA are referred to as 5' non-translated or untranslated sequences. The sequences that are located 3' or downstream of the coding region and that are present on the mRNA are referred to as 3' non-translated or 3' untranslated sequences. The term "gene" encompasses both cDNA and genomic forms of a gene. In some organisms (e.g., eukaryotes), a genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' ends of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage, and polyadenylation.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by the hand of a person in the laboratory is naturally-occurring. A wild-type gene is often that gene or allele that is most frequently observed in a population and is thus arbitrarily designated the "normal" or "wild-type" form of the gene. In contrast, the term "modified" or "mutant" when made in reference to a gene or to a gene product refers, respectively, to a gene or to a gene product that displays modifications in sequence and/or functional properties (e.g., altered characteristics) when compared to the wild-type gene or gene product. It is noted that naturally-occurring mutants can be isolated; these are identified by the fact that they have altered characteristics when compared to the wild-type gene or gene product.

The term "allele" refers to a variation of a gene; the variations include but are not limited to variants and mutants, polymorphic loci, and single nucleotide polymorphic loci, frameshift, and splice mutations. An allele may occur naturally in a population or it might arise during the lifetime of any particular individual of the population.

Thus, the terms "variant" and "mutant" when used in reference to a nucleotide sequence refer to a nucleic acid sequence that differs by one or more nucleotides from another, usually related, nucleotide acid sequence. A "variation" is a difference between two different nucleotide sequences; typically, one sequence is a reference sequence.

"Amplification" is a special case of nucleic acid replication involving template specificity. It is to be contrasted with non-specific template replication (e.g., replication that is template-dependent but not dependent on a specific template). Template specificity is here distinguished from fidelity of replication (e.g., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specific PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q-beta replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al, Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics 4:560). Finally, thermostable template-dependant DNA polymerases (e.g., Taq and Pfu DNA polymerases), by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985, 557, 5,994,069, 6,001,567, 6,090,543, and 6,872,816; Lyamichev et al., Nat. Biotech., 17:292 (1999), Hall et al., PNAS, USA, 97:8272 (2000), and U.S. Pat. No. 9,096,893, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Baranay Proc. Natl. Acad. Sci USA 88, 189-93 (1991)); and sandwich hybridization methods (e.g., U.S. Pat. No. 5,288, 609, herein incorporated by reference in its entirety).

The term "amplifiable nucleic acid" refers to a nucleic acid that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as, e.g., a nucleic acid fragment from a restriction digest, or produced synthetically, that is capable of acting as a point of initiation of synthesis when placed under conditions in which synthesis of a primer extension product that is complementary to a nucleic acid template strand is induced, (e.g., in the presence of nucleotides and an inducing agent such as a DNA polymerase, and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," as used herein refers to a nucleic acid sought to be sorted out from other nucleic acids, e.g., by probe binding, amplification, isolation, capture, etc. For example, when used in reference to the polymerase chain reaction, "target" refers to the region of nucleic acid bounded by the primers used for polymerase chain reaction, while when used in an assay in which target DNA is not amplified, e.g., in some embodiments of an invasive cleavage assay, a target comprises the site at which a probe and invasive oligonucleotides (e.g., INVADER oligonucleotide) bind to form an invasive cleavage structure, such that the presence of the target nucleic acid can be detected. A "segment" is defined as a region of nucleic acid within the target sequence.

As used herein, "methylation" refers to cytosine methylation at positions C5 or N4 of cytosine, the N6 position of adenine, or other types of nucleic acid methylation. In vitro amplified DNA is usually unmethylated because typical in vitro DNA amplification methods do not retain the methylation pattern of the amplification template. However, "unmethylated DNA" or "methylated DNA" can also refer to amplified DNA whose original template was unmethylated or methylated, respectively.

Accordingly, as used herein a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA.

As used herein, a "methylated nucleic acid molecule" refers to a nucleic acid molecule that contains one or more methylated nucleotides.

As used herein, a "methylation state", "methylation profile", and "methylation status" of a nucleic acid molecule refers to the presence of absence of one or more methylated nucleotide bases in the nucleic acid molecule. For example, a nucleic acid molecule containing a methylated cytosine is considered methylated (e.g., the methylation state of the nucleic acid molecule is methylated). A nucleic acid molecule that does not contain any methylated nucleotides is considered unmethylated.

The methylation state of a particular nucleic acid sequence (e.g., a gene marker or DNA region as described herein) can indicate the methylation state of every base in the sequence or can indicate the methylation state of a subset of the bases (e.g., of one or more cytosines) within the sequence, or can indicate information regarding regional methylation density within the sequence with or without providing precise information of the locations within the sequence the methylation occurs.

The methylation state of a nucleotide locus in a nucleic acid molecule refers to the presence or absence of a methylated nucleotide at a particular locus in the nucleic acid molecule. For example, the methylation state of a cytosine at the 7th nucleotide in a nucleic acid molecule is methylated when the nucleotide present at the 7th nucleotide in the nucleic acid molecule is 5-methylcytosine. Similarly, the methylation state of a cytosine at the 7th nucleotide in a nucleic acid molecule is unmethylated when the nucleotide present at the 7th nucleotide in the nucleic acid molecule is cytosine (and not 5-methylcytosine).

The methylation status can optionally be represented or indicated by a "methylation value" (e.g., representing a methylation frequency, fraction, ratio, percent, etc.) A methylation value can be generated, for example, by quantifying the amount of intact nucleic acid present following restriction digestion with a methylation dependent restriction enzyme or by comparing amplification profiles after bisulfate reaction or by comparing sequences of bisulfate-treated and untreated nucleic acids. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, "methylation frequency" or "methylation percent (%)" refer to the number of instances in which a molecule or locus is methylated relative to the number of instances the molecule or locus is unmethylated.

As such, the methylation state describes the state of methylation of a nucleic acid (e.g., a genomic sequence). In addition, the methylation state refers to the characteristics of a nucleic acid segment at a particular genomic locus relevant to methylation. Such characteristics include, but are not limited to, whether any of the cytosine (C) residues within this DNA sequence are methylated, the location of methylated C residue(s), the frequency or percentage of methylated C throughout any particular region of a nucleic acid, and allelic differences in methylation due to, e.g., difference in the origin of the alleles. The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence. Additionally, the term "methylation pattern" as used herein refers to the collective sites of methylated and unmethylated nucleotides over a region of a nucleic acid. Two nucleic acids may have the same or similar methylation frequency or methylation percent but have different methylation patterns when the number of methylated and unmethylated nucleotides are the same or similar throughout the region but the locations of methylated and unmethylated nucleotides are different. Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" refers to a difference in the level or pattern of nucleic acid methylation in a cancer positive sample as compared with the level or pattern of nucleic acid methylation in a cancer negative sample. It may also refer to the difference in levels or patterns between patients that have recurrence of cancer after surgery versus patients who not have recurrence. Differential methylation and specific levels or patterns of DNA methylation are prognostic and predictive biomarkers, e.g., once the correct cut-off or predictive characteristics have been defined.

Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals or a collection of nucleic acids. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

As used herein a "nucleotide locus" refers to the location of a nucleotide in a nucleic acid molecule. A nucleotide locus of a methylated nucleotide refers to the location of a methylated nucleotide in a nucleic acid molecule.

Typically, methylation of human DNA occurs on a dinucleotide sequence including an adjacent guanine and cytosine where the cytosine is located 5' of the guanine (also termed CpG dinucleotide sequences). Most cytosines within the CpG dinucleotides are methylated in the human genome, however some remain unmethylated in specific CpG dinucleotide rich genomic regions, known as CpG islands (see, e.g, Antequera et al. (1990) *Cell* 62: 503-514).

As used herein, a "CpG island" refers to a G:C-rich region of genomic DNA containing an increased number of CpG dinucleotides relative to total genomic DNA. A CpG island can be at least 100, 200, or more base pairs in length, where the G:C content of the region is at least 50% and the ratio of observed CpG frequency over expected frequency is 0.6; in some instances, a CpG island can be at least 500 base pairs in length, where the G:C content of the region is at least 55%) and the ratio of observed CpG frequency over expected frequency is 0.65. The observed CpG frequency over expected frequency can be calculated according to the method provided in Gardiner-Garden et al (1987) *J. Mol. Biol.* 196: 261-281. For example, the observed CpG frequency over expected frequency can be calculated according to the formula $R=(A \times B)/(C \times D)$, where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence. Methylation state is typically determined in CpG islands, e.g., at promoter regions. It will be appreciated though that other sequences in the human genome are prone to DNA methylation such as CpA and CpT (see Ramsahoye (2000) Proc. Natl. Acad. Sci. USA 97: 5237-5242; Salmon and Kaye (1970) Biochim. Biophys. Acta. 204: 340-351; Grafstrom (1985) Nucleic Acids Res. 13: 2827-2842; Nyce (1986) Nucleic Acids Res. 14: 4353-4367; Woodcock (1987) Biochem. Biophys. Res. Commun. 145: 888-894).

As used herein, a "methylation-specific reagent" refers to a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such methods can be applied in a manner in which unmethylated nucleotides (e.g., each unmethylated cytosine) is modified to a different nucleotide. For example, in some embodiments, such a reagent can deaminate unmethylated cytosine nucleotides to produce deoxy uracil residues. Examples of such reagents include, but are not limited to, a methylation-sensitive restriction enzyme, a methylation-dependent restriction enzyme, and a bisulfite reagent.

A change in the nucleic acid nucleotide sequence by a methylation-specific reagent can also result in a nucleic acid molecule in which each methylated nucleotide is modified to a different nucleotide.

The term "methylation assay" refers to any assay for determining the methylation state of one or more CpG dinucleotide sequences within a sequence of a nucleic acid.

The term "MS AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al. (1997) *Cancer Research* 57: 594-599.

The term "MethyLight™" refers to the art-recognized fluorescence-based real-time PCR technique described by Eads et al. (1999) *Cancer Res.* 59: 2302-2306.

The term "HeavyMethyl™" refers to an assay wherein methylation specific blocking probes (also referred to herein as blockers) covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo & Jones (1997) *Nucleic Acids Res.* 25: 2529-2531.

The term "MSP" (Methylation-specific PCR) refers to the art-recognized methylation assay described by Herman et al. (1996) *Proc. Natl. Acad. Sci. USA* 93: 9821-9826, and by U.S. Pat. No. 5,786,146.

The term "COBRA™" (Combined Bisulfite Restriction Analysis) refers to the art-recognized methylation assay described by Xiong & Laird (1997) *Nucleic Acids Res.* 25: 2532-2534.

The term "MCA" (Methylated CpG Island Amplification) refers to the methylation assay described by Toyota et al. (1999) *Cancer Res.* 59: 2307-12, and in WO 00/26401A1.

As used herein, a "selected nucleotide" refers to one nucleotide of the four typically occurring nucleotides in a nucleic acid molecule (C, G, T, and A for DNA and C, G, U, and A for RNA), and can include methylated derivatives of the typically occurring nucleotides (e.g., when C is the selected nucleotide, both methylated and unmethylated C are included within the meaning of a selected nucleotide), whereas a methylated selected nucleotide refers specifically to a methylated typically occurring nucleotide and an unmethylated selected nucleotides refers specifically to an unmethylated typically occurring nucleotide.

The term "methylation-specific restriction enzyme" refers to a restriction enzyme that selectively digests a nucleic acid dependent on the methylation state of its recognition site. In the case of a restriction enzyme that specifically cuts if the recognition site is not methylated or is hemi-methylated (a methylation-sensitive enzyme), the cut will not take place (or will take place with a significantly reduced efficiency) if the recognition site is methylated on one or both strands. In the case of a restriction enzyme that specifically cuts only if the recognition site is methylated (a methylation-dependent enzyme), the cut will not take place (or will take place with a significantly reduced efficiency) if the recognition site is not methylated. Preferred are methylation-specific restriction enzymes, the recognition sequence of which contains a CG dinucleotide (for instance a recognition sequence such as CGCG or CCCGGG). Further preferred for some embodiments are restriction enzymes that do not cut if the cytosine in this dinucleotide is methylated at the carbon atom C5.

As used herein, a "different nucleotide" refers to a nucleotide that is chemically different from a selected nucleotide, typically such that the different nucleotide has Watson-Crick base-pairing properties that differ from the selected nucleotide, whereby the typically occurring nucleotide that is complementary to the selected nucleotide is not the same as the typically occurring nucleotide that is complementary to the different nucleotide. For example, when C is the selected nucleotide, U or T can be the different nucleotide, which is exemplified by the complementarity of C to G and the complementarity of U or T to A. As used herein, a nucleotide that is complementary to the selected nucleotide or that is complementary to the different nucleotide refers to a nucleotide that base-pairs, under high stringency conditions, with the selected nucleotide or different nucleotide with higher affinity than the complementary nucleotide's base-paring with three of the four typically occurring nucleotides. An example of complementarity is Watson-Crick base pairing in DNA (e.g., A-T and C-G) and RNA (e.g., A-U and C-G). Thus, for example, G base-pairs, under high stringency conditions, with higher affinity to C than G base-pairs to G, A, or T and, therefore, when C is the selected nucleotide, G is a nucleotide complementary to the selected nucleotide.

As used herein, the "sensitivity" of a given marker (or set of markers used together) refers to the percentage of samples that report a DNA methylation value above a threshold value that distinguishes between neoplastic and non-neoplastic samples. In some embodiments, a positive is defined as a histology-confirmed neoplasia that reports a DNA methylation value above a threshold value (e.g., the range associated with disease), and a false negative is defined as a histology-confirmed neoplasia that reports a DNA methylation value below the threshold value (e.g., the range associated with no disease). The value of sensitivity, therefore, reflects the probability that a DNA methylation measurement for a given marker obtained from a known diseased sample will be in the range of disease-associated measurements. As defined here, the clinical relevance of the calculated sensitivity value represents an estimation of the probability that a given marker would detect the presence of a clinical condition when applied to a subject with that condition.

As used herein, the "specificity" of a given marker (or set of markers used together) refers to the percentage of non-neoplastic samples that report a DNA methylation value below a threshold value that distinguishes between neoplastic and non-neoplastic samples. In some embodiments, a negative is defined as a histology-confirmed non-neoplastic sample that reports a DNA methylation value below the threshold value (e.g., the range associated with no disease) and a false positive is defined as a histology-confirmed non-neoplastic sample that reports a DNA methylation value above the threshold value (e.g., the range associated with disease). The value of specificity, therefore, reflects the probability that a DNA methylation measurement for a given marker obtained from a known non-neoplastic sample will be in the range of non-disease associated measurements. As defined here, the clinical relevance of the calculated specificity value represents an estimation of the probability that a given marker would detect the absence of a clinical condition when applied to a patient without that condition.

The term "AUC" as used herein is an abbreviation for the "area under a curve". In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better; the optimum is 1; a random test would have a ROC curve lying on the diagonal with an area of 0.5; for reference: J. P. Egan. (1975) *Signal Detection Theory and ROC Analysis*, Academic Press, New York).

The term "neoplasm" as used herein refers to any new and abnormal growth of tissue. Thus, a neoplasm can be a premalignant neoplasm or a malignant neoplasm.

The term "neoplasm-specific marker," as used herein, refers to any biological material or element that can be used to indicate the presence of a neoplasm. Examples of biological materials include, without limitation, nucleic acids, polypeptides, carbohydrates, fatty acids, cellular components (e.g., cell membranes and mitochondria), and whole cells. In some instances, markers are particular nucleic acid regions (e.g., genes, intragenic regions, specific loci, etc.). Regions of nucleic acid that are markers may be referred to, e.g., as "marker genes," "marker regions," "marker sequences," "marker loci," etc.

As used herein, the term "adenoma" refers to a benign tumor of glandular origin. Although these growths are benign, over time they may progress to become malignant.

The term "pre-cancerous" or "pre-neoplastic" and equivalents thereof refer to any cellular proliferative disorder that is undergoing malignant transformation.

A "site" of a neoplasm, adenoma, cancer, etc. is the tissue, organ, cell type, anatomical area, body part, etc. in a subject's body where the neoplasm, adenoma, cancer, etc. is located.

As used herein, a "diagnostic" test application includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition. For example, a diagnostic can be used for detecting the presence or likelihood of a subject contracting a neoplasm or the likelihood that such a subject will respond favorably to a compound (e.g., a pharmaceutical, e.g., a drug) or other treatment.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded), but may contain both the sense and anti-sense strands (i.e., the oligonucleotide may be double-stranded). An isolated nucleic acid may, after isolation from its natural or typical environment, by be combined with other nucleic acids or molecules. For example, an isolated nucleic acid may be present in a host cell in which into which it has been placed, e.g., for heterologous expression.

The term "purified" refers to molecules, either nucleic acid or amino acid sequences that are removed from their natural environment, isolated, or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the terms "purified" or "to purify" also refer to the removal of contaminants from a sample. The removal of contaminating proteins results in an increase in the percent of polypeptide or nucleic acid of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution containing salts (e.g., NaCl), detergents (e.g., SDS), and other components (e.g., Denhardt's solution, dry milk, salmon sperm DNA, etc.).

The term "sample" is used in its broadest sense. In one sense it can refer to an animal cell or tissue. In another sense, it refers to a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

As used herein, a "remote sample" as used in some contexts relates to a sample indirectly collected from a site that is not the cell, tissue, or organ source of the sample. For instance, when sample material originating from the pancreas is assessed in a stool sample (e.g., not from a sample taken directly from an ovary), the sample is a remote sample.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human. Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; pinnipeds; and horses. Thus, also provided is the diagnosis and treatment of livestock, including, but not limited to, domesticated swine, ruminants, ungulates, horses (including race horses), and the like. The presently-disclosed subject matter further includes a system for diagnosing a lung cancer in a subject. The system can be provided, for example, as a commercial kit that can be used to screen for a risk of lung cancer or diagnose a lung cancer in a subject from whom a biological sample has been collected. An exemplary system provided in accordance with the present technology includes assessing the methylation state of a marker described herein.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As used herein, the term "ovarian cancer" refers to any cancerous growth arising from the ovary, which includes, but is not limited to, traditionally diagnosed ovarian, fallopian tube and primary peritoneal cancers. In some embodiments, ovarian cancer is a type of cancer that forms in tissues of the ovary. In other embodiments, ovarian cancer is either ovarian epithelial carcinomas (cancer that begins in the cells on the surface of the ovary) or malignant germ cell tumors (cancer that begins in egg cells).

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, percentage methylation, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

DETAILED DESCRIPTION

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

Provided herein is technology for ovarian cancer screening and particularly, but not exclusively, to methods, compositions, and related uses for detecting the presence of ovarian cancer and/or specific forms of ovarian cancer (e.g., clear cell OC, endometrioid OC, mucinous OC, serous OC). As the technology is described herein, the section headings used are for organizational purposes only and are not to be construed as limiting the subject matter in any way.

Indeed, as described in Examples I, II, and III, experiments conducted during the course for identifying embodiments for the present invention identified a novel set of 560 differentially methylated regions (DMRs) for discriminating cancer of the ovarian derived DNA from non-neoplastic control DNA. From these 560 novel DNA methylation markers, further experiments identified markers capable of distinguishing different types of ovarian cancer from normal tissue and from plasma samples. For example, separate sets of DMRs were identified capable of distinguishing 1) clear cell ovarian cancer tissue from normal tissue, 2) endometrioid ovarian cancer tissue from normal tissue, 3) mucinous ovarian cancer tissue from normal tissue, 4) serous ovarian cancer tissue from normal tissue, and 5) ovarian cancer in blood samples.

Although the disclosure herein refers to certain illustrated embodiments, it is to be understood that these embodiments are presented by way of example and not by way of limitation.

In particular aspects, the present technology provides compositions and methods for identifying, determining, and/or classifying a cancer such as ovarian cancer and/or a sub-type of ovarian cancer (e.g., clear cell OC, endometrioid OC, mucinous OC, serous OC). The methods comprise determining the methylation status of at least one methylation marker in a biological sample isolated from a subject (e.g., stool sample, ovarian tissue sample, plasma sample), wherein a change in the methylation state of the marker is indicative of the presence, class, or site of ovarian cancer and/or a sub-type thereof. Particular embodiments relate to markers comprising a differentially methylated region (DMR, e.g., DMR 1-560, see Tables 1A and 6A) that are used for diagnosis (e.g., screening) of ovarian cancer and various types of ovarian cancer (e.g., clear cell OC, endometrioid OC, mucinous OC, serous OC).

In addition to embodiments wherein the methylation analysis of at least one marker, a region of a marker, or a base of a marker comprising a DMR (e.g., DMR, e.g., DMR 1-560) provided herein and listed in Tables 1A and 6A is analyzed, the technology also provides panels of markers comprising at least one marker, region of a marker, or base of a marker comprising a DMR with utility for the detection of cancers, in particular ovarian cancer.

Some embodiments of the technology are based upon the analysis of the CpG methylation status of at least one marker, region of a marker, or base of a marker comprising a DMR.

In some embodiments, the present technology provides for the use of a reagent that modifies DNA in a methylation-specific manner (e.g., a methylation-sensitive restriction enzyme, a methylation-dependent restriction enzyme, and a bisulfite reagent) in combination with one or more methylation assays to determine the methylation status of CpG dinucleotide sequences within at least one marker comprising a DMR (e.g., DMR 1-560, see Tables 1A and 6A). Genomic CpG dinucleotides can be methylated or unmethylated (alternatively known as up- and down-methylated respectively). However, the methods of the present invention are suitable for the analysis of biological samples of a heterogeneous nature, e.g., a low concentration of tumor cells, or biological materials therefrom, within a background of a remote sample (e.g., blood, organ effluent, or stool). Accordingly, when analyzing the methylation status of a CpG position within such a sample one may use a quantitative assay for determining the level (e.g., percent, fraction, ratio, proportion, or degree) of methylation at a particular CpG position.

According to the present technology, determination of the methylation status of CpG dinucleotide sequences in markers comprising a DMR has utility both in the diagnosis and characterization of cancers such as ovarian cancer.

Combinations of Markers

In some embodiments, the technology relates to assessing the methylation state of combinations of markers comprising a DMR from Tables 1A and 6A (e.g., DMR Nos. 1-560). In some embodiments, assessing the methylation state of more than one marker increases the specificity and/or sensitivity of a screen or diagnostic for identifying a neoplasm in a subject (e.g., ovarian cancer).

Various cancers are predicted by various combinations of markers, e.g., as identified by statistical techniques related to specificity and sensitivity of prediction. The technology provides methods for identifying predictive combinations and validated predictive combinations for some cancers.

Methods for Assaying Methylation State

In certain embodiments, methods for analyzing a nucleic acid for the presence of 5-methylcytosine involves treatment of DNA with a reagent that modifies DNA in a methylation-specific manner. Examples of such reagents include, but are not limited to, a methylation-sensitive restriction enzyme, a methylation-dependent restriction enzyme, and a bisulfite reagent.

A frequently used method for analyzing a nucleic acid for the presence of 5-methylcytosine is based upon the bisulfite method described by Frommer, et al. for the detection of 5-methylcytosines in DNA (Frommer et al. (1992) Proc. Natl. Acad. Sci. USA 89: 1827-31 explicitly incorporated herein by reference in its entirety for all purposes) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uracil is desulfonated under alkaline conditions to form uracil. Detection is possible because uracil base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994) 16: 431-36; Grigg G, DNA Seq. (1996) 6: 189-98), methylation-specific PCR (MSP) as is disclosed, e.g., in U.S. Pat. No. 5,786,146, or using an assay comprising sequence-specific probe cleavage, e.g., a QuARTS flap endonuclease assay (see, e.g., Zou et al. (2010) "Sensitive quantification of methylated markers with a novel methylation specific technology" Clin Chem 56: A199; and in U.S. Pat. Nos. 8,361, 720; 8,715,937; 8,916,344; and 9,212,392.

Some conventional technologies are related to methods comprising enclosing the DNA to be analyzed in an agarose matrix, thereby preventing the diffusion and renaturation of the DNA (bisulfite only reacts with single-stranded DNA), and replacing precipitation and purification steps with a fast dialysis (Olek A, et al. (1996) "A modified and improved method for bisulfite based cytosine methylation analysis" Nucleic Acids Res. 24: 5064-6). It is thus possible to analyze individual cells for methylation status, illustrating the utility and sensitivity of the method. An overview of conventional methods for detecting 5-methylcytosine is provided by Rein, T., et al. (1998) Nucleic Acids Res. 26: 2255.

The bisulfite technique typically involves amplifying short, specific fragments of a known nucleic acid subsequent to a bisulfite treatment, then either assaying the product by sequencing (Olek & Walter (1997) Nat. Genet. 17: 275-6) or a primer extension reaction (Gonzalgo & Jones (1997) Nucleic Acids Res. 25: 2529-31; WO 95/00669; U.S. Pat. No. 6,251,594) to analyze individual cytosine positions. Some methods use enzymatic digestion (Xiong & Laird (1997) Nucleic Acids Res. 25: 2532-4). Detection by hybridization has also been described in the art (Olek et al., WO 99/28498). Additionally, use of the bisulfite technique for methylation detection with respect to individual genes has been described (Grigg & Clark (1994) Bioessays 16: 431-6; Zeschnigk et al. (1997) Hum Mol Genet. 6: 387-95; Feil et al. (1994) Nucleic Acids Res. 22: 695; Martin et al. (1995) Gene 157: 261-4; WO 9746705; WO 9515373).

Various methylation assay procedures can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-specific restriction enzymes, e.g., methylation-sensitive or methylation-dependent enzymes.

For example, genomic sequencing has been simplified for analysis of methylation patterns and 5-methylcytosine distributions by using bisulfite treatment (Frommer et al. (1992) Proc. Natl. Acad. Sci. USA 89: 1827-1831). Additionally, restriction enzyme digestion of PCR products amplified from bisulfite-converted DNA finds use in assessing methylation state, e.g., as described by Sadri & Hornsby (1997) Nucl. Acids Res. 24: 5058-5059 or as embodied in the method known as COBRA™ (Combined Bisulfite Restriction Analysis) (Xiong & Laird (1997) Nucleic Acids Res. 25: 2532-2534).

COBRA™ analysis is a quantitative methylation assay useful for determining DNA methylation levels at specific loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific loci (e.g., specific genes, markers, DMR, regions of genes, regions of markers, bisulfite treated DNA sequence, CpG island, etc.); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components. Assays such as "MethyLight™" (a fluorescence-based real-time PCR technique) (Eads et al., Cancer Res. 59:2302-2306, 1999), Ms-SNuPE™ (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No. 5,786,146), and methylated CpG island amplification ("MCA"; Toyota et al., Cancer Res. 59:2307-12, 1999) are used alone or in combination with one or more of these methods.

The "HeavyMethyl™" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific loci (e.g., specific genes, markers, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase. MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, regions of genes, regions of markers, bisulfite treated DNA sequence, CpG island, etc.); optimized PCR buffers and deoxynucleotides, and specific probes.

The MethyLight™ assay is a high-throughput quantitative methylation assay that utilizes fluorescence-based real-time PCR (e.g., TaqMan®) that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The MethyLight™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HeavyMethyl™ and MSP techniques) or with oligonucleotides covering potential methylation sites.

The MethyLight™ process is used with any suitable probe (e.g. a "TaqMan®" probe, a Lightcycler® probe, etc.) For example, in some applications double-stranded genomic DNA is treated with sodium bisulfite and subjected to one of two sets of PCR reactions using TaqMan® probes, e.g., with MSP primers and/or HeavyMethyl blocker oligonucleotides and a TaqMan® probe. The TaqMan® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific loci (e.g., specific genes, markers, regions of genes, regions of markers, bisulfite treated DNA sequence, CpG island, etc.); TaqMan® or Lightcycler® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (a fluorescence-based version of the HeavyMethyl™ and MSP techniques) or with oligonucleotides covering potential methylation sites.

The QM™ process can be used with any suitable probe, e.g., "TaqMan®" probes, Lightcycler® probes, in the amplification process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to:

PCR primers for specific loci (e.g., specific genes, markers, regions of genes, regions of markers, bisulfite treated DNA sequence, CpG island, etc.); TaqMan® or Lightcycler® probes; optimized PCR buffers and deoxynucleotides; and Taq polymerase.

The Ms-SNuPE™ technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site of interest. Small amounts of DNA can be analyzed (e.g., microdissected pathology sections) and it avoids utilization of restriction enzymes for determining the methylation status at CpG sites.

Typical reagents (e.g., as might be found in a typical Ms-SNuPE™-based kit) for Ms-SNuPE™ analysis may include, but are not limited to: PCR primers for specific loci (e.g., specific genes, markers, regions of genes, regions of markers, bisulfite treated DNA sequence, CpG island, etc.); optimized PCR buffers and deoxynucleotides; gel extraction kit; positive control primers; Ms-SNuPE™ primers for specific loci; reaction buffer (for the Ms-SNuPE reaction); and labeled nucleotides. Additionally, bisulfite conversion reagents may include: DNA denaturation buffer; sulfonation buffer; DNA recovery reagents or kit (e.g., precipitation, ultrafiltration, affinity column); desulfonation buffer; and DNA recovery components.

Reduced Representation Bisulfite Sequencing (RRBS) begins with bisulfite treatment of nucleic acid to convert all unmethylated cytosines to uracil, followed by restriction enzyme digestion (e.g., by an enzyme that recognizes a site including a CG sequence such as MspI) and complete sequencing of fragments after coupling to an adapter ligand. The choice of restriction enzyme enriches the fragments for CpG dense regions, reducing the number of redundant sequences that may map to multiple gene positions during analysis. As such, RRBS reduces the complexity of the nucleic acid sample by selecting a subset (e.g., by size selection using preparative gel electrophoresis) of restriction fragments for sequencing. As opposed to whole-genome bisulfite sequencing, every fragment produced by the restriction enzyme digestion contains DNA methylation information for at least one CpG dinucleotide. As such, RRBS enriches the sample for promoters, CpG islands, and other genomic features with a high frequency of restriction enzyme cut sites in these regions and thus provides an assay to assess the methylation state of one or more genomic loci.

A typical protocol for RRBS comprises the steps of digesting a nucleic acid sample with a restriction enzyme such as MspI, filling in overhangs and A-tailing, ligating adaptors, bisulfite conversion, and PCR. See, e.g., et al. (2005) "Genome-scale DNA methylation mapping of clinical samples at single-nucleotide resolution" *Nat Methods* 7: 133-6; Meissner et al. (2005) "Reduced representation bisulfite sequencing for comparative high-resolution DNA methylation analysis" *Nucleic Acids Res.* 33: 5868-77.

In some embodiments, a quantitative allele-specific real-time target and signal amplification (QUARTS) assay is used to evaluate methylation state. Three reactions sequentially occur in each QUARTS assay, including amplification (reaction 1) and target probe cleavage (reaction 2) in the primary reaction; and FRET cleavage and fluorescent signal generation (reaction 3) in the secondary reaction. When target nucleic acid is amplified with specific primers, a specific detection probe with a flap sequence loosely binds to the amplicon. The presence of the specific invasive oligonucleotide at the target binding site causes a 5' nuclease, e.g., a FEN-1 endonuclease, to release the flap sequence by cutting between the detection probe and the flap sequence. The flap sequence is complementary to a non-hairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. QuARTS can detect multiple targets in a single reaction well by using FRET cassettes with different dyes. See, e.g., in Zou et al. (2010) "Sensitive quantification of methylated markers with a novel methylation specific technology" *Clin Chem* 56: A199), and U.S. Pat. Nos. 8,361,720; 8,715,937; 8,916,344; and 9,212,392, each of which is incorporated herein by reference for all purposes.

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715 and WO 2013/116375, each of which is incorporated by reference in its entirety). In some embodiments, bisulfite treatment is conducted in the presence of denaturing solvents such as but not limited to n-alkyleneglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxybenzone acid and derivates thereof, e.g., Gallic acid (see: PCT/EP2004/011715, which is incorporated by reference in its entirety). In certain preferred embodiments, the bisulfite reaction comprises treatment with ammonium hydrogen sulfite, e.g., as described in WO 2013/116375.

In some embodiments, fragments of the treated DNA are amplified using sets of primer oligonucleotides according to the present invention (e.g., see Tables 1C and 6B) and an amplification enzyme. The amplification of several DNA segments can be carried out simultaneously in one and the same reaction vessel. Typically, the amplification is carried out using a polymerase chain reaction (PCR). Amplicons are typically 100 to 2000 base pairs in length.

In another embodiment of the method, the methylation status of CpG positions within or near a marker comprising a DMR (e.g., DMR 1-560, Tables 1A and 6A) may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primer pairs contain at least one primer that hybridizes to a bisulfite treated CpG dinucleotide. Therefore, the sequence of said primers comprises at least one CpG dinucleotide. MSP primers specific for non-methylated DNA contain a "T" at the position of the C position in the CpG.

The fragments obtained by means of the amplification can carry a directly or indirectly detectable label. In some embodiments, the labels are fluorescent labels, radionuclides, or detachable molecule fragments having a typical mass that can be detected in a mass spectrometer. Where said labels are mass labels, some embodiments provide that the labeled amplicons have a single positive or negative net charge, allowing for better delectability in the mass spectrometer. The detection may be carried out and visualized by means of, e.g., matrix assisted laser desorption/ionization mass spectrometry (MALDI) or using electron spray mass spectrometry (ESI).

Methods for isolating DNA suitable for these assay technologies are known in the art. In particular, some embodiments comprise isolation of nucleic acids as described in U.S. patent application Ser. No. 13/470,251 ("Isolation of Nucleic Acids"), incorporated herein by reference in its entirety.

In some embodiments, the markers described herein find use in QUARTS assays performed on stool samples. In some embodiments, methods for producing DNA samples and, in particular, to methods for producing DNA samples that comprise highly purified, low-abundance nucleic acids in a small volume (e.g., less than 100, less than 60 microliters) and that are substantially and/or effectively free of substances that inhibit assays used to test the DNA samples (e.g., PCR, INVADER, QuARTS assays, etc.) are provided. Such DNA samples find use in diagnostic assays that qualitatively detect the presence of, or quantitatively measure the activity, expression, or amount of, a gene, a gene variant (e.g., an allele), or a gene modification (e.g., methylation) present in a sample taken from a patient. For example, some cancers are correlated with the presence of particular mutant alleles or particular methylation states, and thus detecting and/or quantifying such mutant alleles or methylation states has predictive value in the diagnosis and treatment of cancer. Many valuable genetic markers are present in extremely low amounts in samples and many of the events that produce such markers are rare. Consequently, even sensitive detection methods such as PCR require a large amount of DNA to provide enough of a low-abundance target to meet or supersede the detection threshold of the assay. Moreover, the presence of even low amounts of inhibitory substances compromise the accuracy and precision of these assays directed to detecting such low amounts of a target. Accordingly, provided herein are methods providing the requisite management of volume and concentration to produce such DNA samples.

In some embodiments, the sample comprises blood, serum, leukocytes, plasma, or saliva. In some embodiments, the subject is human. Such samples can be obtained by any number of means known in the art, such as will be apparent to the skilled person. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens. The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Nos. 8,808,990 and 9,169,511, and in WO 2012/155072, or by a related method.

The analysis of markers can be carried out separately or simultaneously with additional markers within one test sample. For example, several markers can be combined into one test for efficient processing of multiple samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events. The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

It is contemplated that embodiments of the technology are provided in the form of a kit. The kits comprise embodiments of the compositions, devices, apparatuses, etc. described herein, and instructions for use of the kit. Such instructions describe appropriate methods for preparing an analyte from a sample, e.g., for collecting a sample and preparing a nucleic acid from the sample. Individual components of the kit are packaged in appropriate containers and packaging (e.g., vials, boxes, blister packs, ampules, jars, bottles, tubes, and the like) and the components are packaged together in an appropriate container (e.g., a box or boxes) for convenient storage, shipping, and/or use by the user of the kit. It is understood that liquid components (e.g., a buffer) may be provided in a lyophilized form to be reconstituted by the user. Kits may include a control or reference for assessing, validating, and/or assuring the performance of the kit. For example, a kit for assaying the amount of a nucleic acid present in a sample may include a control comprising a known concentration of the same or another nucleic acid for comparison and, in some embodiments, a detection reagent (e.g., a primer) specific for the control nucleic acid. The kits are appropriate for use in a clinical setting and, in some embodiments, for use in a user's home. The components of a kit, in some embodiments, provide the functionalities of a system for preparing a nucleic acid solution from a sample. In some embodiments, certain components of the system are provided by the user.

Methods

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker comprising a DMR (e.g., DMR 1-560 e.g., as provided in Tables 1A and 6A) and
2) detecting ovarian cancer, clear cell OC, endometrioid OC, mucinous OC, or serous OC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of AGRN_A, ATP10A_A, ATP10A_B, ATP10A_C, ATP10A_D, BCAT1, CCND2_D, CMTM3_A, ELMO1_A, ELMO1_B, ELMO1_C, EMX1, EPS8L2_A, EPS8L2_B, EPS8L2_C, EPS8L2_D, FAIM2_A, FLJ34208_A, GPRIN1, GYPC_A, INA_A, ITGA4_B, KCNA3_A, KCNA3_C, LBH, LIME1_A, LIME1_B, LOC646278, LRRC4, LRRC41_A, MAX.chr1.110626771-110626832, MAX.chr1.147790358-147790381, MAX.chr1.161591532-161591608, MAX.chr15.28351937-28352173, MAX.chr15.28352203-28352671, MAX.chr15.29131258-29131734, MAX.chr4.8859995-8860062, MAX.chr5.42952182-42952292, MDFI, NCOR2, NKX2-6, OPLAH_A, PARP15, PDE10A, PPP1R16B, RASSF1_B, SEPTIN9, SKI, SLC12A8, SRC_A, SSBP4_B, ST8SIA1, TACC2_A, TSHZ3, UBTF, VIM, VIPR2_A, ZBED4, ZMIZ1_A, ZMIZ1_B, ZMIZ1_C, ZNF382_A, ZNF469_B, ATP6V1B1_A, BZRAP1, GDF6, IFFO1_A, IFFO1_B, KCNAB2, LIMD2, MAML3_B, MAX.chr14.102172350-102172770, MAX.chr16.85482307-85482494, MAX.chr17.76254728-76254841, MAX.chr5.42993898-42994179, and RASAL3, and 2) detecting ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of GPRIN1 (e.g., GPRIN1_A, GPRIN1_B), CDO1 (e.g., CDO1_A, CDO1_B), SRC (e.g., SRC_A, SRC_B), SIM2 (e.g., SIM2_A, SIM2_B), AGRN (e.g., AGRN_A, AGRN_B, AGRN_C, AGRN_8794), FAIM2 (e.g., FAIM2_A, FAIM2_B), CELF2 (e.g., CELF2_A, CELF2_B), DSCR6, GYPC (e.g., GYPC_A, GYPC_B, GYPC_C), CAPN2 (e.g., CAPN2_A, CAPN2_B), and BCAT1, and 2) detecting ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GPS, DSCR6, SKI, SIM2_A, AGRN_8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333, and 2) detecting ovarian cancer (e.g., afforded with a sensitivity of greater than or equal to 80% and a specificity of greater than or equal to 80%).

In some embodiments of the technology, methods are provided that comprise the following steps:

1) measuring the levels of CA-125 within a blood sample (e.g., plasma sample, whole blood sample, leukocyte sample, serum sample) obtained from the subject;

2) contacting a nucleic acid (e.g., genomic DNA, e.g., isolated from a blood sample (e.g., plasma sample, whole blood sample, leukocyte sample, serum sample) obtained from the subject with at least one reagent or series of reagents that distinguishes between methylated and non-methylated CpG dinucleotides within at least one marker selected from a chromosomal region having an annotation selected from the group consisting of ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GPS, DSCR6, SKI, and SIM2_A, and 3) detecting ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of MAX.chr16.85482307-85482494, GDF6, IFFO_A, MAX.chr5.42993898-42994179, MAX.chr17.76254728-76254841, MAX.chr14.102172350-102172770, RASAL3, BZRAP1, and LIMD2, and 2) detecting ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of PALLD, PRDM14, MAX.chr1.147790358-147790381, BCAT1, MAML3_A, SKI, DNMT3A_A, and C2CD4D, and 2) detecting ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of TACC2_A, LRRC41_A, EPS8L2, LBH, LIME1_B, MDFI, FAIM2_A, GYPC_A, AGRN_B, and ZBED4, and 2) detecting clear cell ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of MT1A_A, CELF2_A, KCNA3_A, MDFI, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, MAX.chr14.105512178-105512224, EPS8L2_E, SKI, GPRIN1_A, MAX.chr8.142215938-142216298, CDO1_A, DNMT3A_A, SIM2_A, SKI, MT1A_B, GYPC_A, BCL2L11, PISD, and C2CD4D, and 2) detecting clear cell ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of NCOR2, MT1A_B, CELF2_A, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, SKI, GPRIN1_A, CDO1_A, SIM2_A, IFFO1_A, MT1A_B, GYPC_A, BCL2L11, GDF6, and C2CD4D, and 2) detecting clear cell ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of AGRN_8794, BHLHE23_8339, EPS8L2_F, RASSF1_8293, MDFI_6321, SKI, GYPC_C, NKX2-6_4159, LOC100131366, FAIM2_B, GPRIN1_B, LRRC41_B, TACC2_B, LBH, SIM2_B, CDO1_A, and DSCR6, and 2) detecting clear cell ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of PARP15, GPRIN1_A, GYPC1_A, F1134208, MAX.chr1.147790358-147790381, FAIM2_A, SH2B3, KCNQ5, IRF4, and BCAT1, and 2) detecting endometrioid ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of NCOR2, CELF2_A, PALLD, PRDM14, MAX.chr1.147790358-147790381, BCAT1, MAX.chr11.14926602-14926671, MAML3_A, SKI, GPRIN1_A, SKI, BCL2L11, and C2CD4D, and 2) detecting endometrioid ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of NCOR2, PALLD, PRDM14, MAX.chr1.147790358-147790381, MAX.chr11.14926602-14926671, DSCR6, GPRIN1_A, CDO1_A, SIM2_A, IFFO1_A, and C2CD4D, and 2) detecting endometrioid ovarian cancer (e.g., afforded with a sensitivity of greater than or equal to 80% and a specificity of greater than or equal to 80%).

In some embodiments of the technology, methods are provided that comprise the following steps:
1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of BCAT1_6015, EPS8L2_F, SKI, NKX2-6_4159, C1QL3_B, GPRIN1_B, PARP15, OXT_C, SIM2_B, DNMT3A_A, and CELF2_A, and
2) detecting endometrioid ovarian cancer (e.g., afforded with a sensitivity of greater than or equal to 80% and a specificity of greater than or equal to 80%).

In some embodiments of the technology, methods are provided that comprise the following steps:
1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of CMTM3_A, ATP10A_C, TSHZ3, ZMIZ1_B, ATP10A_B, ELMO1_B, TACC2_A, LRRC4, VIM, and ZNF382_A, and
2) detecting mucinous ovarian cancer (e.g., afforded with a sensitivity of greater than or equal to 80% and a specificity of greater than or equal to 80%).

In some embodiments of the technology, methods are provided that comprise the following steps:
1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of NCOR2, MT1A_A, KCNA3_A, ZMIZ1_C, TACC2_A, MAX.chr1.147790358-147790381, BCAT1, AGRN_B, SKI, SLC12A8, ZMIZ1_B, BCL2L11, and GATA2, and
2) detecting mucinous ovarian cancer (e.g., afforded with a sensitivity of greater than or equal to 80% and a specificity of greater than or equal to 80%).

In some embodiments of the technology, methods are provided that comprise the following steps:
1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of NCOR2, PALLD, TACC2_A, BCAT1, AGRN_B, SKI, SLC12A8, ZMIZ1_B, and BCL2L11, and
2) detecting mucinous ovarian cancer (e.g., afforded with a sensitivity of greater than or equal to 80% and a specificity of greater than or equal to 80%).

In some embodiments of the technology, methods are provided that comprise the following steps:
1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of BCAT1_6015, ELMO1_9100, KCNA3_7518, KCNA3_7320, MDFI_6321, SKI, VIPR_B, ZNF382_B, ATP10A_E, CMTM3_B, ZMIZ1_D, SRC_B, HDGFRP3, TACC2_B, TSHZ3, LBH, DNMT3A_A, and
2) detecting mucinous ovarian cancer (e.g., afforded with a sensitivity of greater than or equal to 80% and a specificity of greater than or equal to 80%).

In some embodiments of the technology, methods are provided that comprise the following steps:
1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of MAX.chr1.147790358-147790381, MAML3, NR2F6, DNMT3A_A, SKI, SOBP, UBTF, AGRN_C, MAX.chr12.30975740-30975780, and CAPN2_A, and
2) detecting serous ovarian cancer (e.g., afforded with a sensitivity of greater than or equal to 80% and a specificity of greater than or equal to 80%).

In some embodiments of the technology, methods are provided that comprise the following steps:
1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of PALLD, PRDM14, MAX.chr1.147790358-147790381, CAPN2_A, MAX.chr6.10382190-10382225, SKI, NR2F6, IFFO1_A, MT1A_B, IFFO1_B, GDF6, and C2CD4D, and
2) detecting serous ovarian cancer (e.g., afforded with a sensitivity of greater than or equal to 80% and a specificity of greater than or equal to 80%).

In some embodiments of the technology, methods are provided that comprise the following steps:
1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of NCOR2, MAX.chr1.147790358-147790381, MAX.chr6.10382190-10382225, IFFO1_A, GDF6, and C2CD4D, and
2) detecting serous ovarian cancer (e.g., afforded with a sensitivity of greater than or equal to 80% and a specificity of greater than or equal to 80%).

In some embodiments of the technology, methods are provided that comprise the following steps:
1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of SKI, PEAR1_B, CAPN2_B, SIM2_B, DNMT3A_A, CDO1_A, and NR2F6, and 2) detecting serous ovarian cancer (e.g., afforded with a sensitivity of greater than or equal to 80% and a specificity of greater than or equal to 80%).

In some embodiments of the technology, methods are provided that comprise the following steps:

1) measuring a methylation level for one or more genes in a biological sample of a human individual through treating genomic DNA in the biological sample with a reagent that modifies DNA in a methylation-specific manner (e.g., wherein the reagent is a bisulfate reagent, a methylation-sensitive restriction enzyme, or a methylation-dependent restriction enzyme), wherein the one or more genes is selected from one of the following groups:

AGRN_A, ATP10A_A, ATP10A_B, ATP10A_C, ATP10A_D, BCAT1, CCND2_D, CMTM3_A, ELMO1_A, ELMO1_B, ELMO1_C, EMX1, EPS8L2_A, EPS8L2_B, EPS8L2_C, EPS8L2_D, FAIM2_A, FLJ34208_A, GPRIN1, GYPC_A, INA_A, ITGA4_B, KCNA3_A, KCNA3_C, LBH, LIME1_A, LIME1_B, LOC646278, LRRC4, LRRC41_A, MAX.chr1.110626771-110626832, MAX.chr1.147790358-147790381, MAX.chr1.161591532-161591608, MAX.chr15.28351937-28352173, MAX.chr15.28352203-28352671, MAX.chr15.29131258-29131734, MAX.chr4.8859995-8860062, MAX.chr5.42952182-42952292, MDFI, NCOR2, NKX2-6, OPLAH_A, PARP15, PDE10A, PPP1R16B, RASSF1_B, SEPTIN9, SKI, SLC12A8, SRC_A, SSBP4_B, ST8SIA1, TACC2_A, TSHZ3, UBTF, VIM, VIPR2_A, ZBED4, ZMIZ1_A, ZMIZ1_B, ZMIZ1_C, ZNF382_A, ZNF469_B, ATP6V1B1_A, BZRAP1, GDF6, IFFO1_A, IFFO1_B, KCNAB2, LIMD2, MAML3_B, MAX.chr14.102172350-102172770, MAX.chr16.85482307-85482494, MAX.chr17.76254728-76254841, MAX.chr5.42993898-42994179, and RASAL3 (see, Tables 1A, 1B, 6A, 6B; Example I);

MAX.chr16.85482307-85482494, GDF6, IFFO_A, MAX.chr5.42993898-42994179, MAX.chr17.76254728-76254841, MAX.chr14.102172350-102172770, RASAL3, BZRAP1, and LIMD2 (see, Table 3; Example I);

PALLD, PRDM14, MAX.chr1.147790358-147790381, BCAT1, MAML3_A, SKI, DNMT3A_A, and C2CD4D (see, Table 4A; Example I); and BCAT1_6015, SKI, SIM2_B, DNMT3A_A, CDO1_A, and DSCR6 (see, Table 8A; Example II);

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring a methylation level for one or more genes in a biological sample (e.g., blood sample, plasma sample) of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from GPRIN1 (e.g., GPRIN1_A, GPRIN1_B), CDO1 (e.g., CDO1_A, CDO1_B), SRC (e.g., SRC_A, SRC_B), SIM2 (e.g., SIM2_A, SIM2_B), AGRN (e.g., AGRN_A, AGRN_B, AGRN_C, AGRN_8794), FAIM2 (e.g., FAIM2_A, FAIM2_B), CELF2 (e.g., CELF2_A, CELF2_B), DSCR6, GYPC (e.g., GYPC_A, GYPC_B, GYPC_C), CAPN2 (e.g., CAPN2_A, CAPN2_B), and BCAT1;

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring a methylation level for one or more genes in a biological sample (e.g., blood sample, plasma sample) of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GPS, DSCR6, SKI, SIM2_A, AGRN_8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333;

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring the levels of CA-125 within a blood sample (e.g., plasma sample, whole blood sample, leukocyte sample, serum sample) obtained from a human individual;

2) measuring a methylation level for one or more genes in a blood sample (e.g., plasma sample, whole blood sample, leukocyte sample, serum sample) of a human individual through treating genomic DNA in the biological sample with a reagent that modifies DNA in a methylation-specific manner (e.g., wherein the reagent is a bisulfate reagent, a methylation-sensitive restriction enzyme, or a methylation-dependent restriction enzyme), wherein the one or more genes is selected from ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GPS, DSCR6, SKI, and SIM2_A;

3) amplifying the treated genomic DNA using a set of primers for the selected one or more genes; and 4) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring an amount of at least one methylated marker gene in DNA from the sample, wherein the one or more genes is selected from one of the following groups:

AGRN_A, ATP10A_A, ATP10A_B, ATP10A_C, ATP10A_D, BCAT1, CCND2_D, CMTM3_A, ELMO1_A, ELMO1_B, ELMO1_C, EMX1, EPS8L2_A, EPS8L2_B, EPS8L2_C, EPS8L2_D, FAIM2_A, FLJ34208_A, GPRIN1, GYPC_A, INA_A, ITGA4_B, KCNA3_A, KCNA3_C, LBH, LIME1_A, LIME1_B, LOC646278, LRRC4, LRRC41_A, MAX.chr1.110626771-110626832, MAX.chr1.147790358-147790381, MAX.chr1.161591532-161591608, MAX.chr15.28351937-28352173, MAX.chr15.28352203-28352671, MAX.chr15.29131258-29131734, MAX.chr4.8859995-8860062, MAX.chr5.42952182-42952292, MDFI, NCOR2, NKX2-6, OPLAH_A, PARP15, PDE10A, PPP1R16B, RASSF1_B, SEPTIN9, SKI, SLC12A8, SRC_A, SSBP4_B, ST8SIA1, TACC2_A, TSHZ3, UBTF, VIM, VIPR2_A, ZBED4, ZMIZ1_A, ZMIZ1_B, ZMIZ1_C, ZNF382_A, ZNF469_B, ATP6V1B1_A, BZRAP1, GDF6, IFFO1_A, IFFO1_B, KCNAB2, LIMD2, MAML3_B, MAX.chr14.102172350-102172770, MAX.chr16.85482307-85482494, MAX.chr17.76254728-76254841, MAX.chr5.42993898-42994179, and RASAL3 (see, Tables 1A, 1B, 6A, 6B; Example I);

MAX.chr16.85482307-85482494, GDF6, IFFO_A, MAX.chr5.42993898-42994179, MAX.chr17.76254728-76254841, MAX.chr14.102172350-102172770, RASAL3, BZRAP1, and LIMD2 (see, Table 3; Example I);

GPRIN1 (e.g., GPRIN1_A, GPRIN1_B), CDO1 (e.g., CDO1_A, CDO1_B), SRC (e.g., SRC_A, SRC_B), SIM2 (e.g., SIM2_A, SIM2_B), AGRN (e.g., AGRN_A, AGRN_B, AGRN_C, AGRN_8794), FAIM2 (e.g., FAIM2_A, FAIM2_B), CELF2 (e.g., CELF2_A, CELF2_B), DSCR6, GYPC (e.g., GYPC_A, GYPC_B, GYPC_C), CAPN2 (e.g., CAPN2_A, CAPN2_B), and BCAT1 (see, Table 9; Example III);

ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GPS, DSCR6, SKI, SIM2_A, AGRN_8794, BCAT1_6015, KCNA3_7518, KCNA3_7320, LOC10013136, GYPC, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333 (see, Table 10, Example III);

PALLD, PRDM14, MAX.chr1.147790358-147790381, BCAT1, MAML3_A, SKI, DNMT3A_A, and C2CD4D (see, Table 4A; Example I); and BCAT1_6015, SKI, SIM2_B, DNMT3A_A, CDO1_A, and DSCR6 (see, Table 8A; Example II);

2) measuring the amount of at least one reference marker in the DNA; and 3) calculating a value for the amount of the at least one methylated marker gene measured in the DNA as a percentage of the amount of the reference marker gene measured in the DNA, wherein the value indicates the amount of the at least one methylated marker DNA measured in the sample.

In some embodiments of the technology, methods are provided that comprise the following steps:

1) measuring a methylation level of a CpG site for one or more genes in a biological sample of a human individual through treating genomic DNA in the biological sample with bisulfite a reagent capable of modifying DNA in a methylation-specific manner (e.g., a methylation-sensitive restriction enzyme, a methylation-dependent restriction enzyme, and a bisulfite reagent);

2) amplifying the modified genomic DNA using a set of primers for the selected one or more genes; and 3) determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR;

wherein the one or more genes is selected from one of the following groups:

AGRN_A, ATP10A_A, ATP10A_B, ATP10A_C, ATP10A_D, BCAT1, CCND2_D, CMTM3_A, ELMO1_A, ELMO1_B, ELMO1_C, EMX1, EPS8L2_A, EPS8L2_B, EPS8L2_C, EPS8L2_D, FAIM2_A, FLJ34208_A, GPRIN1, GYPC_A, INA_A, ITGA4_B, KCNA3_A, KCNA3_C, LBH, LIME1_A, LIME1_B, LOC646278, LRRC4, LRRC41_A, MAX.chr1.110626771-110626832, MAX.chr1.147790358-147790381, MAX.chr1.161591532-161591608, MAX.chr15.28351937-28352173, MAX.chr15.28352203-28352671, MAX.chr15.29131258-29131734, MAX.chr4.8859995-8860062, MAX.chr5.42952182-42952292, MDFI, NCOR2, NKX2-6, OPLAH_A, PARP15, PDE10A, PPP1R16B, RASSF1_B, SEPTIN9, SKI, SLC12A8, SRC_A, SSBP4_B, ST8SIA1, TACC2_A, TSHZ3, UBTF, VIM, VIPR2_A, ZBED4, ZMIZ1_A, ZMIZ1_B, ZMIZ1_C, ZNF382_A, ZNF469_B, ATP6V1B1_A, BZRAP1, GDF6, IFFO1_A, IFFO1_B, KCNAB2, LIMD2, MAML3_B, MAX.chr14.102172350-102172770, MAX.chr16.85482307-85482494, MAX.chr17.76254728-76254841, MAX.chr5.42993898-42994179, and RASAL3 (see, Tables 1A, 1B, 6A, 6B; Example I);

GPRIN1 (e.g., GPRIN1_A, GPRIN1_B), CDO1 (e.g., CDO1_A, CDO1_B), SRC (e.g., SRC_A, SRC_B), SIM2 (e.g., SIM2_A, SIM2_B), AGRN (e.g., AGRN_A, AGRN_B, AGRN_C, AGRN_8794), FAIM2 (e.g., FAIM2_A, FAIM2_B), CELF2 (e.g., CELF2_A, CELF2_B), DSCR6, GYPC (e.g., GYPC_A, GYPC_B, GYPC_C), CAPN2 (e.g., CAPN2_A, CAPN2_B), and BCAT1 (see, Table 9; Example III);

ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GPS, DSCR6, SKI, SIM2_A, AGRN_8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333 (see, Table 10, Example III);

MAX.chr16.85482307-85482494, GDF6, IFFO_A, MAX.chr5.42993898-42994179, MAX.chr17.76254728-76254841, MAX.chr14.102172350-102172770, RASAL3, BZRAP1, and LIMD2 (see, Table 3; Example I);

PALLD, PRDM14, MAX.chr1.147790358-147790381, BCAT1, MAML3_A, SKI, DNMT3A_A, and C2CD4D (see, Table 4A; Example I); and BCAT1_6015, SKI, SIM2_B, DNMT3A_A, CDO1_A, and DSCR6 (see, Table 8A; Example II).

In some embodiments of the technology, methods are provided that comprise the following steps:

1) measuring a methylation level for one or more genes in a biological sample of a human individual through treating genomic DNA in the biological sample with a reagent that modifies DNA in a methylation-specific manner (e.g., wherein the reagent is a bisulfate reagent, a methylation-sensitive restriction enzyme, or a methylation-dependent restriction enzyme), wherein the one or more genes is selected from one of the following groups:

TACC2_A, LRRC41_A, EPS8L2, LBH, LIME1_B, MDFI, FAIM2_A, GYPC_A, AGRN_B, and ZBED4 (see, Table 2A; Example I);

MT1A_A, CELF2_A, KCNA3_A, MDFI, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, MAX.chr14.105512178-105512224, EPS8L2_E, SKI, GPRIN1_A, MAX.chr8.142215938-142216298, CDO1_A, DNMT3A_A, SIM2_A, SKI, MT1A_B, GYPC_A, BCL2L11, PISD, and C2CD4D (see, Table 4B; Example I);

NCOR2, MT1A_B, CELF2_A, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, SKI, GPRIN1_A, CDO1_A, SIM2_A, IFFO1_A, MT1A_B, GYPC_A, BCL2L11, GDF6, and C2CD4D (see, Table 5B; Example I); and AGRN_8794, BHLHE23_8339, EPS8L2_F, RASSF1_8293, MDFI_6321, SKI, GYPC_C, NKX2-6_4159, LOC100131366, FAIM2_B, GPRIN1_B, LRRC41_B, TACC2_B, LBH, SIM2_B, CDO1_A, and DSCR6 (see, Table 8B; Example II);

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring an amount of at least one methylated marker gene in DNA from the sample, wherein the one or more genes is selected from one of the following groups:

TACC2_A, LRRC41_A, EPS8L2, LBH, LIME1_B, MDFI, FAIM2_A, GYPC_A, AGRN_B, and ZBED4 (see, Table 2A; Example I);

MT1A_A, CELF2_A, KCNA3_A, MDFI, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, MAX.chr14.105512178-105512224, EPS8L2_E, SKI, GPRIN1_A, MAX.chr8.142215938-142216298, CDO1_A, DNMT3A_A, SIM2_A, SKI, MT1A_B, GYPC_A, BCL2L11, PISD, and C2CD4D (see, Table 4B; Example I);

NCOR2, MT1A_B, CELF2_A, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, SKI, GPRIN1_A, CDO1_A, SIM2_A, IFFO1_A, MT1A_B, GYPC_A, BCL2L11, GDF6, and C2CD4D (see, Table 5B; Example I); and AGRN_8794, BHLHE23_8339, EPS8L2_F, RASSF1_8293, MDFI_6321, SKI, GYPC_C, NKX2-6_4159, LOC100131366, FAIM2_B, GPRIN1_B, LRRC41_B, TACC2_B, LBH, SIM2_B, CDO1_A, and DSCR6 (see, Table 8B; Example II);

2) measuring the amount of at least one reference marker in the DNA; and 3) calculating a value for the amount of the at least one methylated marker gene measured in the DNA as a percentage of the amount of the reference marker gene measured in the DNA, wherein the value indicates the amount of the at least one methylated marker DNA measured in the sample.

In some embodiments of the technology, methods are provided that comprise the following steps:

1) measuring a methylation level of a CpG site for one or more genes in a biological sample of a human individual through treating genomic DNA in the biological sample with bisulfite a reagent capable of modifying DNA in a methylation-specific manner (e.g., a methylation-sensitive restriction enzyme, a methylation-dependent restriction enzyme, and a bisulfite reagent);

2) amplifying the modified genomic DNA using a set of primers for the selected one or more genes; and 3) determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR;

wherein the one or more genes is selected from one of the following groups:

TACC2_A, LRRC41_A, EPS8L2, LBH, LIME1_B, MDFI, FAIM2_A, GYPC_A, AGRN_B, and ZBED4 (see, Table 2A; Example I);

MT1A_A, CELF2_A, KCNA3_A, MDFI, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, MAX.chr14.105512178-105512224, EPS8L2_E, SKI, GPRIN1_A, MAX.chr8.142215938-142216298, CDO1_A, DNMT3A_A, SIM2_A, SKI, MT1A_B, GYPC_A, BCL2L11, PISD, and C2CD4D (see, Table 4B; Example I);

NCOR2, MT1A_B, CELF2_A, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, SKI, GPRIN1_A, CDO1_A, SIM2_A, IFFO1_A, MT1A_B, GYPC_A, BCL2L11, GDF6, and C2CD4D (see, Table 5B; Example I); and AGRN_8794, BHLHE23_8339, EPS8L2_F, RASSF1_8293, MDFI_6321, SKI, GYPC_C, NKX2-6_4159, LOC100131366, FAIM2_B, GPRIN1_B, LRRC41_B, TACC2_B, LBH, SIM2_B, CDO1_A, and DSCR6 (see, Table 8B; Example II).

In some embodiments of the technology, methods are provided that comprise the following steps:

1) measuring a methylation level for one or more genes in a biological sample of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from one of the following groups:

PARP15, GPRIN1_A, GYPC1_A, F1134208, MAX.chr1.147790358-147790381, FAIM2_A, SH2B3, KCNQ5, IRF4, and BCAT1 (see, Table 2B; Example I);

NCOR2, CELF2_A, PALLD, PRDM14, MAX.chr1.147790358-147790381, BCAT1, MAX.chr11.14926602-14926671, MAML3_A, SKI, GPRIN1_A, SKI, BCL2L11, and C2CD4D (see, Table 4C; Example I);

NCOR2, PALLD, PRDM14, MAX.chr1.147790358-147790381, MAX.chr11.14926602-14926671, DSCR6, GPRIN1_A, CDO1_A, SIM2_A, IFFO1_A, and C2CD4D (see, Table 5C; Example I); and BCAT1_6015, EPS8L2_F, SKI, NKX2-6_4159, C1QL3_B, GPRIN1_B, PARP15, OXT_C, SIM2_B, DNMT3A_A, and CELF2_A (see, Table 8C; Example II);

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring an amount of at least one methylated marker gene in DNA from the sample, wherein the one or more genes is selected from one of the following groups:

PARP15, GPRIN1_A, GYPC1_A, F1134208, MAX.chr1.147790358-147790381, FAIM2_A, SH2B3, KCNQ5, IRF4, and BCAT1 (see, Table 2B; Example I);

NCOR2, CELF2_A, PALLD, PRDM14, MAX.chr1.147790358-147790381, BCAT1, MAX.chr11.14926602-14926671, MAML3_A, SKI, GPRIN1_A, SKI, BCL2L11, and C2CD4D (see, Table 4C; Example I);

NCOR2, PALLD, PRDM14, MAX.chr1.147790358-147790381, MAX.chr11.14926602-14926671, DSCR6, GPRIN1_A, CDO1_A, SIM2_A, IFFO1_A, and C2CD4D (see, Table 5C; Example I); and BCAT1_6015, EPS8L2_F, SKI, NKX2-6_4159, C1QL3_B, GPRIN1_B, PARP15, OXT_C, SIM2_B, DNMT3A_A, and CELF2_A (see, Table 8C; Example II);

2) measuring the amount of at least one reference marker in the DNA; and 3) calculating a value for the amount of the at least one methylated marker gene measured in the DNA as a percentage of the amount of the reference marker gene measured in the DNA, wherein the value indicates the amount of the at least one methylated marker DNA measured in the sample.

In some embodiments of the technology, methods are provided that comprise the following steps:

1) measuring a methylation level of a CpG site for one or more genes in a biological sample of a human individual through treating genomic DNA in the biological sample with bisulfite a reagent capable of modifying DNA in a methylation-specific manner (e.g., a methylation-sensitive restriction enzyme, a methylation-dependent restriction enzyme, and a bisulfite reagent);

2) amplifying the modified genomic DNA using a set of primers for the selected one or more genes; and 3) determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR;

wherein the one or more genes is selected from one of the following groups:

PARP15, GPRIN1_A, GYPC1_A, F1134208, MAX.chr1.147790358-147790381, FAIM2_A, SH2B3, KCNQ5, IRF4, and BCAT1 (see, Table 2B; Example I);

NCOR2, CELF2_A, PALLD, PRDM14, MAX.chr1.147790358-147790381, BCAT1, MAX.chr11.14926602-14926671, MAML3_A, SKI, GPRIN1_A, SKI, BCL2L11, and C2CD4D (see, Table 4C; Example I);

NCOR2, PALLD, PRDM14, MAX.chr1.147790358-147790381, MAX.chr11.14926602-14926671, DSCR6, GPRIN1_A, CDO1_A, SIM2_A, IFFO1_A, and C2CD4D (see, Table 5C; Example I); and BCAT1_6015, EPS8L2_F, SKI, NKX2-6_4159, C1QL3_B, GPRIN1_B, PARP15, OXT_C, SIM2_B, DNMT3A_A, and CELF2_A (see, Table 8C; Example II).

In some embodiments of the technology, methods are provided that comprise the following steps:

1) measuring a methylation level for one or more genes in a biological sample of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from one of the following groups:

CMTM3_A, ATP10A_C, TSHZ3, ZMIZ1_B, ATP10A_B, ELMO1_B, TACC2_A, LRRC4, VIM, and ZNF382_A (see, Table 2C; Example I);

NCOR2, MT1A_A, KCNA3_A, ZMIZ1_C, TACC2_A, MAX.chr1.147790358-147790381, BCAT1, AGRN_B, SKI, SLC12A8, ZMIZ1_B, BCL2L11, and GATA2 (see, Table 4D; Example I);

NCOR2, PALLD, TACC2_A, BCAT1, AGRN_B, SKI, SLC12A8, ZMIZ1_B, and BCL2L11 (see, Table 5D; Example I); and BCAT1_6015, ELMO1_9100, KCNA3_7518, KCNA3_7320, MDFI_6321, SKI, VIPR_B, ZNF382_B, ATP10A_E, CMTM3_B, ZMIZ1_D, SRC_B, HDGFRP3, TACC2_B, TSHZ3, LBH, DNMT3A_A (see, Table 8D; Example II);

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring an amount of at least one methylated marker gene in DNA from the sample, wherein the one or more genes is selected from one of the following groups:

CMTM3_A, ATP10A_C, TSHZ3, ZMIZ1_B, ATP10A_B, ELMO1_B, TACC2_A, LRRC4, VIM, and ZNF382_A (see, Table 2C; Example I);

NCOR2, MT1A_A, KCNA3_A, ZMIZ1_C, TACC2_A, MAX.chr1.147790358-147790381, BCAT1, AGRN_B, SKI, SLC12A8, ZMIZ1_B, BCL2L11, and GATA2 (see, Table 4D; Example I);

NCOR2, PALLD, TACC2_A, BCAT1, AGRN_B, SKI, SLC12A8, ZMIZ1_B, and BCL2L11 (see, Table 5D; Example I); and BCAT1_6015, ELMO1_9100, KCNA3_7518, KCNA3_7320, MDFI_6321, SKI, VIPR_B, ZNF382_B, ATP10A_E, CMTM3_B, ZMIZ1_D, SRC_B, HDGFRP3, TACC2_B, TSHZ3, LBH, DNMT3A_A (see, Table 8D; Example II);

2) measuring the amount of at least one reference marker in the DNA; and 3) calculating a value for the amount of the at least one methylated marker gene measured in the DNA as a percentage of the amount of the reference marker gene measured in the DNA, wherein the value indicates the amount of the at least one methylated marker DNA measured in the sample.

In some embodiments of the technology, methods are provided that comprise the following steps:

1) measuring a methylation level of a CpG site for one or more genes in a biological sample of a human individual through treating genomic DNA in the biological sample with bisulfite a reagent capable of modifying DNA in a methylation-specific manner (e.g., a methylation-sensitive restriction enzyme, a methylation-dependent restriction enzyme, and a bisulfite reagent);

2) amplifying the modified genomic DNA using a set of primers for the selected one or more genes; and 3) determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR;

wherein the one or more genes is selected from one of the following groups:

CMTM3_A, ATP10A_C, TSHZ3, ZMIZ1_B, ATP10A_B, ELMO1_B, TACC2_A, LRRC4, VIM, and ZNF382_A (see, Table 2C; Example I);

NCOR2, MT1A_A, KCNA3_A, ZMIZ1_C, TACC2_A, MAX.chr1.147790358-147790381, BCAT1, AGRN_B, SKI, SLC12A8, ZMIZ1_B, BCL2L11, and GATA2 (see, Table 4D; Example I);

NCOR2, PALLD, TACC2_A, BCAT1, AGRN_B, SKI, SLC12A8, ZMIZ1_B, and BCL2L11 (see, Table 5D; Example I); and BCAT1_6015, ELMO1_9100, KCNA3_7518, KCNA3_7320, MDFI_6321, SKI, VIPR_B, ZNF382_B, ATP10A_E, CMTM3_B, ZMIZ1_D, SRC_B, HDGFRP3, TACC2_B, TSHZ3, LBH, DNMT3A_A (see, Table 8D; Example II).

In some embodiments of the technology, methods are provided that comprise the following steps:

1) measuring a methylation level for one or more genes in a biological sample of a human individual through treating genomic DNA in the biological sample with a reagent that modifies DNA in a methylation-specific manner (e.g., wherein the reagent is a bisulfate reagent, a methylation-sensitive restriction enzyme, or a methylation-dependent restriction enzyme), wherein the one or more genes is selected from one of the following groups:

MAX.chr1.147790358-147790381, MAML3, NR2F6, DNMT3A_A, SKI, SOBP, UBTF, AGRN_C, MAX.chr12.30975740-30975780, and CAPN2_A (see, Table 2D; Example I);

PALLD, PRDM14, MAX.chr1.147790358-147790381, CAPN2_A, MAX.chr6.10382190-10382225, SKI, NR2F6, IFFO1_A, MT1A_B, IFFO1_B, GDF6, and C2CD4D (see, Table 4E; Example I);

NCOR2, MAX.chr1.147790358-147790381, MAX.chr6.10382190-10382225, IFFO1_A, GDF6, and C2CD4D (see, Table 5A; Example I); and SKI, PEAR1_B, CAPN2_B, SIM2_B, DNMT3A_A, CDO1_A, and NR2F6 (see, Table 8E; Example II);

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring an amount of at least one methylated marker gene in DNA from the sample, wherein the one or more genes is selected from one of the following groups:

MAX.chr1.147790358-147790381, MAML3, NR2F6, DNMT3A_A, SKI, SOBP, UBTF, AGRN_C, MAX.chr12.30975740-30975780, and CAPN2_A (see, Table 2D; Example I);

PALLD, PRDM14, MAX.chr1.147790358-147790381, CAPN2_A, MAX.chr6.10382190-10382225, SKI, NR2F6, IFFO1_A, MT1A_B, IFFO1_B, GDF6, and C2CD4D (see, Table 4E; Example I);

NCOR2, MAX.chr1.147790358-147790381, MAX.chr6.10382190-10382225, IFFO1_A, GDF6, and C2CD4D (see, Table 5A; Example I); and SKI, PEAR1_B, CAPN2_B, SIM2_B, DNMT3A_A, CDO1_A, and NR2F6 (see, Table 8E; Example II);

2) measuring the amount of at least one reference marker in the DNA; and 3) calculating a value for the amount of the at least one methylated marker gene measured in the DNA as a percentage of the amount of the reference marker gene measured in the DNA, wherein the value indicates the amount of the at least one methylated marker DNA measured in the sample.

In some embodiments of the technology, methods are provided that comprise the following steps:

1) measuring a methylation level of a CpG site for one or more genes in a biological sample of a human individual through treating genomic DNA in the biological sample with bisulfite a reagent capable of modifying DNA in a methylation-specific manner (e.g., a methylation-sensitive restriction enzyme, a methylation-dependent restriction enzyme, and a bisulfite reagent);

2) amplifying the modified genomic DNA using a set of primers for the selected one or more genes; and 3) determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR;

wherein the one or more genes is selected from one of the following groups:

MAX.chr1.147790358-147790381, MAML3, NR2F6, DNMT3A_A, SKI, SOBP, UBTF, AGRN_C, MAX.chr12.30975740-30975780, and CAPN2_A (see, Table 2D; Example I);

PALLD, PRDM14, MAX.chr1.147790358-147790381, CAPN2_A, MAX.chr6.10382190-10382225, SKI, NR2F6, IFFO1_A, MT1A_B, IFFO1_B, GDF6, and C2CD4D (see, Table 4E; Example I);

NCOR2, MAX.chr1.147790358-147790381, MAX.chr6.10382190-10382225, IFFO1_A, GDF6, and C2CD4D (see, Table 5A; Example I); and SKI, PEAR1_B, CAPN2_B, SIM2_B, DNMT3A_A, CDO1_A, and NR2F6 (see, Table 8E; Example II).

Within any of such methods, determining the methylation level for any of such markers is accomplished with the primers recited in Tables 1C or 6B.

Preferably, the sensitivity for such methods is from about 70% to about 100%, or from about 80% to about 90%, or from about 80% to about 85%. Preferably, the specificity is from about 70% to about 100%, or from about 80% to about 90%, or from about 80% to about 85%.

Genomic DNA may be isolated by any means, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction, or binding of the DNA to a solid phase support. The choice of method will be affected by several factors including time, expense, and required quantity of DNA. All clinical sample types comprising neoplastic matter or pre-neoplastic matter are suitable for use in the present method, e.g., cell lines, histological slides, biopsies, paraffin-embedded tissue, body fluids, stool, ovarian tissue, colonic effluent, urine, blood plasma, blood serum, whole blood, isolated blood cells, cells isolated from the blood, and combinations thereof.

The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Appl. Ser. No. 61/485,386 or by a related method.

The genomic DNA sample is then treated with at least one reagent, or series of reagents, that distinguishes between methylated and non-methylated CpG dinucleotides within at least one marker comprising a DMR (e.g., DMR 1-560, e.g., as provided by Tables 1A and 6A).

In some embodiments, the reagent converts cytosine bases which are unmethylated at the 5'-position to uracil, thymine, or another base which is dissimilar to cytosine in terms of hybridization behavior. However in some embodiments, the reagent may be a methylation sensitive restriction enzyme.

In some embodiments, the genomic DNA sample is treated in such a manner that cytosine bases that are unmethylated at the 5' position are converted to uracil, thymine, or another base that is dissimilar to cytosine in terms of hybridization behavior. In some embodiments, this treatment is carried out with bisulfate (hydrogen sulfite, disulfite) followed by alkaline hydrolysis.

The treated nucleic acid is then analyzed to determine the methylation state of the target gene sequences (at least one gene, genomic sequence, or nucleotide from a marker comprising a DMR, e.g., at least one DMR chosen from DMR 1-560, e.g., as provided in Tables 1A and 6A). The method of analysis may be selected from those known in the art, including those listed herein, e.g., QuARTS and MSP as described herein.

Aberrant methylation, more specifically hypermethylation of a marker comprising a DMR (e.g., DMR 1-560, e.g., as provided by Tables 1A and 6A) is associated with an ovarian cancer.

The technology relates to the analysis of any sample associated with an ovarian cancer. For example, in some embodiments the sample comprises a tissue and/or biological fluid obtained from a patient. In some embodiments, the sample comprises a secretion. In some embodiments, the sample comprises blood, serum, plasma, gastric secretions, pancreatic juice, a gastrointestinal biopsy sample, microdissected cells from an ovarian tissue biopsy, and/or cells recovered from stool. In some embodiments, the sample comprises ovarian tissue. In some embodiments, the subject is human. The sample may include cells, secretions, or tissues from the ovary, breast, liver, bile ducts, pancreas, stomach, colon, rectum, esophagus, small intestine, appendix, duodenum, polyps, gall bladder, anus, and/or peritoneum. In some embodiments, the sample comprises cellular fluid, ascites, urine, feces, pancreatic fluid, fluid obtained during endoscopy, blood, mucus, or saliva. In some embodiments, the sample is a stool sample.

Such samples can be obtained by any number of means known in the art, such as will be apparent to the skilled person. For instance, urine and fecal samples are easily attainable, while blood, ascites, serum, or pancreatic fluid samples can be obtained parenterally by using a needle and syringe, for instance. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens In some embodiments, the technology relates to a method for treating a patient (e.g., a patient with ovarian cancer) (e.g., a patient with one or more of clear cell OC, endometrioid OC, mucinous OC, serous OC), the method comprising determining the methylation state of one or more DMR as provided herein and administering a treatment to the patient based on the results of determining the methylation state. The treatment may be administration of a pharmaceutical compound, a vaccine, performing a surgery, imaging the patient, performing another test. Preferably, said use is in a method of clinical screening, a method of prognosis assessment, a method of monitoring the results of therapy, a method to identify patients most likely to respond to a particular therapeutic treatment, a method of imaging a patient or subject, and a method for drug screening and development.

In some embodiments of the technology, a method for diagnosing an ovarian cancer in a subject is provided. The terms "diagnosing" and "diagnosis" as used herein refer to methods by which the skilled artisan can estimate and even determine whether or not a subject is suffering from a given disease or condition or may develop a given disease or condition in the future. The skilled artisan often makes a diagnosis on the basis of one or more diagnostic indicators, such as for example a biomarker (e.g., a DMR as disclosed herein), the methylation state of which is indicative of the presence, severity, or absence of the condition.

Along with diagnosis, clinical cancer prognosis relates to determining the aggressiveness of the cancer and the likelihood of tumor recurrence to plan the most effective therapy. If a more accurate prognosis can be made or even a potential risk for developing the cancer can be assessed, appropriate therapy, and in some instances less severe therapy for the patient can be chosen. Assessment (e.g., determining methylation state) of cancer biomarkers is useful to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of determining a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the diagnostic biomarkers (e.g., DMR) disclosed herein. Further, in some embodiments of the presently disclosed subject matter, multiple determination of the biomarkers over time can be made to facilitate diagnosis and/or prognosis. A temporal change in the biomarker can be used to predict a clinical outcome, monitor the progression of ovarian cancer, and/or monitor the efficacy of appropriate therapies directed against the cancer. In such an embodiment for example, one might expect to see a change in the methylation state of one or more biomarkers (e.g., DMR) disclosed herein (and potentially one or more additional biomarker(s), if monitored) in a biological sample over time during the course of an effective therapy.

The presently disclosed subject matter further provides in some embodiments a method for determining whether to initiate or continue prophylaxis or treatment of a cancer in a subject. In some embodiments, the method comprises providing a series of biological samples over a time period from the subject; analyzing the series of biological samples to determine a methylation state of at least one biomarker disclosed herein in each of the biological samples; and comparing any measurable change in the methylation states of one or more of the biomarkers in each of the biological samples. Any changes in the methylation states of biomarkers over the time period can be used to predict risk of developing cancer, predict clinical outcome, determine whether to initiate or continue the prophylaxis or therapy of the cancer, and whether a current therapy is effectively treating the cancer. For example, a first time point can be selected prior to initiation of a treatment and a second time point can be selected at some time after initiation of the treatment. Methylation states can be measured in each of the samples taken from different time points and qualitative and/or quantitative differences noted. A change in the methylation states of the biomarker levels from the different samples can be correlated with ovarian cancer risk, prognosis, determining treatment efficacy, and/or progression of the cancer in the subject.

In preferred embodiments, the methods and compositions of the invention are for treatment or diagnosis of disease at an early stage, for example, before symptoms of the disease appear. In some embodiments, the methods and compositions of the invention are for treatment or diagnosis of disease at a clinical stage.

As noted, in some embodiments, multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of cancer, or a given prognosis. Likewise, a decrease in the marker from the initial time to the second time can be indicative of a particular type or severity of cancer, or a given prognosis. Furthermore, the degree of change of one or more markers can be related to the severity of the cancer and future adverse events. The skilled artisan will understand that, while in certain embodiments comparative measurements can be made of the same biomarker at multiple time points, one can also measure a given biomarker at one time point, and a second biomarker at a second time point, and a comparison of these markers can provide diagnostic information.

As used herein, the phrase "determining the prognosis" refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the methylation state of a biomarker (e.g., a DMR). Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., having a normal methylation state of one or more DMR), the chance of a given outcome (e.g., suffering from an ovarian cancer) may be very low.

In some embodiments, a statistical analysis associates a prognostic indicator with a predisposition to an adverse outcome. For example, in some embodiments, a methylation state different from that in a normal control sample obtained from a patient who does not have a cancer can signal that a subject is more likely to suffer from a cancer than subjects with a level that is more similar to the methylation state in the control sample, as determined by a level of statistical significance. Additionally, a change in methylation state from a baseline (e.g., "normal") level can be reflective of subject prognosis, and the degree of change in methylation state can be related to the severity of adverse events. Statistical significance is often determined by comparing two or more populations and determining a confidence interval and/or a p value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the methylation state of a prognostic or diagnostic biomarker disclosed herein (e.g., a DMR) can be established, and the degree of change in the methylation state of the biomarker in a biological sample is simply compared to the threshold degree of change in the methylation state. A preferred threshold change in the methylation state for biomarkers provided herein is about 5%, about 10%, about 15%, about 20%, about 25%, about 30%, about 50%, about 75%, about 100%, and about 150%. In yet other embodiments, a "nomogram" can be established, by which a methylation state of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present methylation states of a biomarker as a function of assay units, e.g., fluorescent signal intensity, if a fluorescent label is used. Using samples taken from multiple donors, standard curves can be provided for control methylation states of the one or more biomarkers in normal tissue, as well as for "at-risk" levels of the one or more biomarkers in tissue taken from donors with metaplasia or from donors with an ovarian cancer. In certain embodiments of the method, a subject is identified as having metaplasia upon identifying an aberrant methylation state of one or more DMR provided herein in a biological sample obtained from the subject. In other embodiments of the method, the detection of an aberrant methylation state of one or more of such biomarkers in a biological sample obtained from the subject results in the subject being identified as having cancer.

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

In some embodiments, the subject is diagnosed as having an ovarian cancer if, when compared to a control methylation state, there is a measurable difference in the methylation state of at least one biomarker in the sample. Conversely, when no change in methylation state is identified in the biological sample, the subject can be identified as not having ovarian cancer, not being at risk for the cancer, or as having a low risk of the cancer. In this regard, subjects having the cancer or risk thereof can be differentiated from subjects having low to substantially no cancer or risk thereof. Those subjects having a risk of developing an ovarian cancer can be placed on a more intensive and/or regular screening schedule, including endoscopic surveillance. On the other hand, those subjects having low to substantially no risk may avoid being subjected to additional testing for ovarian cancer (e.g., invasive procedure), until such time as a future screening, for example, a screening conducted in accordance with the present technology, indicates that a risk of ovarian cancer has appeared in those subjects.

As mentioned above, depending on the embodiment of the method of the present technology, detecting a change in methylation state of the one or more biomarkers can be a qualitative determination or it can be a quantitative determination. As such, the step of diagnosing a subject as having, or at risk of developing, an ovarian cancer indicates that certain threshold measurements are made, e.g., the methylation state of the one or more biomarkers in the biological sample varies from a predetermined control methylation state. In some embodiments of the method, the control methylation state is any detectable methylation state of the biomarker. In other embodiments of the method where a control sample is tested concurrently with the biological sample, the predetermined methylation state is the methylation state in the control sample. In other embodiments of the method, the predetermined methylation state is based upon and/or identified by a standard curve. In other embodiments of the method, the predetermined methylation state is a specifically state or range of state. As such, the predetermined methylation state can be chosen, within acceptable limits that will be apparent to those skilled in the art, based in part on the embodiment of the method being practiced and the desired specificity, etc.

Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the diagnosis and treatment of livestock, including, but not limited to, domesticated swine, ruminants, ungulates, horses (including race horses), and the like.

The presently-disclosed subject matter further includes a system for diagnosing an ovarian cancer and/or a specific form of ovarian cancer (e.g., clear cell OC, endometrioid OC, mucinous OC, serous OC) in a subject. The system can be provided, for example, as a commercial kit that can be used to screen for a risk of ovarian cancer or diagnose an ovarian cancer in a subject from whom a biological sample has been collected. An exemplary system provided in accordance with the present technology includes assessing the methylation state of a DMR as provided in Tables 1A and 6A.

EXAMPLES

Example I

Tissue and blood was obtained from Mayo Clinic biospecimen repositories with institutional IRB oversight. Samples were chosen with strict adherence to subject research authorization and inclusion/exclusion criteria. Cancer sub-types included 1) serous OC, 2) clear cell OC, 3) mucinous OC, and 4) endometrioid OC. Controls included non-neoplastic fallopian tissue and whole blood derived leukocytes. Tissues were macro-dissected and histology reviewed by an expert gynecological pathologist. Samples were age matched, randomized, and blinded. Sample DNA from 77 frozen tissues (18 serous OC, 15 clear cell OC, 6 mucinous OC, 18 endometrioid OC, 6 benign fallopian tube, 14 benign fallopian tube brushings) and 19 buffy coats from cancer-free females was purified using the QIAamp DNA Tissue Mini kit and QIAamp DNA Blood Mini kit (Qiagen, Valencia Calif.), respectively. DNA was re-purified with AMPure XP beads (Beckman-Coulter, Brea Calif.) and quantified by PicoGreen (Thermo-Fisher, Waltham Mass.). DNA integrity was assessed using qPCR. 4 ovarian cancer cell lines were also sequenced (TOV21G, SKOV3, OVCAR3, CAOV3).

RRBS sequencing libraries were prepared following the Meissner protocol (Gu et al. Nature Protocols 2011 April; 6(4):468-81) with modifications. Samples were combined in a 4-plex format and sequenced by the Mayo Genomics Facility on the Illumina HiSeq 2500 instrument (Illumina, San Diego Calif.). Reads were processed by Illumina pipeline modules for image analysis and base calling. Secondary analysis was performed using SAAP-RRBS, a Mayo developed bioinformatics suite. Briefly, reads were cleaned-up using Trim-Galore and aligned to the GRCh37/hg19 reference genome build with BSMAP. Methylation ratios were determined by calculating C/(C+T) or conversely, G/(G+A) for reads mapping to reverse strand, for CpGs with coverage ≥10× and base quality score ≥20.

Individual CpGs were ranked by hypermethylation ratio, namely the number of methylated cytosines at a given locus over the total cytosine count at that site. For cases, the ratios were required to be ≥0.20 (20%); for tissue controls, ≤0.05 (5%); for buffy coat controls, ≤0.01 (1%). CpGs which did not meet these criteria were discarded. Subsequently, candidate CpGs were binned by genomic location into DMRs (differentially methylated regions) ranging from approximately 60-200 bp with a minimum cut-off of 5 CpGs per region. DMRs with excessively high CpG density (>30%) were excluded to avoid GC-related amplification problems in the validation phase. For each candidate region, a 2-D matrix was created which compared individual CpGs in a sample to sample fashion for both cases and controls. Overall OC vs all benign ovarian tissue and/or no-cancer buffy coat was analyzed, as well as subtype comparisons. These CpG matrices were then compared back to the reference sequence to assess whether genomically contiguous methylation sites had been discarded during the initial filtering. From this subset of regions, final selections required coordinated and contiguous hypermethylation (in cases) of individual CpGs across the DMR sequence on a per sample level. Conversely, control samples had to have at least 10-fold less methylation than cases and the CpG pattern had to be more random and less coordinated. At least 10% of cancer samples within a subtype cohort were required to have at least a 50% hypermethylation ratio for every CpG site within the DMR.

In a separate analysis, a proprietary DMR identification pipeline and regression package was utilized to derive DMRs based on average methylation values of the CpG. The difference in average methylation percentage was compared between OC cases, tissue controls and buffy coat controls; a tiled reading frame within 100 base pairs of each mapped CpG was used to identify DMRs where control methylation was <5%; DMRs were only analyzed if the total depth of coverage was 10 reads per subject on average and the variance across subgroups was >0. Assuming a biologically relevant increase in the odds ratio of >3× and a coverage depth of 10 reads, ≥18 samples per group were required to achieve 80% power with a two-sided test at a significance level of 5% and assuming binomial variance inflation factor of 1.

Following regression, DMRs were ranked by p-value, area under the receiver operating characteristic curve (AUC) and fold-change difference between cases and all controls. No adjustments for false discovery were made during this phase as independent validation was planned a priori.

A proprietary methodology of sample preparation, sequencing, analyses pipelines, and filters was utilized to identify and narrow differentially methylated regions (DMRs) to those which would pinpoint these gynecological cancers and excel in a clinical testing environment. From the tissue-to-tissue analysis, 471 hypermethylated ovarian cancer (OC) DMRs were identified (Table 1A and 1B). They included OC specific regions, OC subtype specific regions, as well as those regions that targeted a more universal cancer spectrum. The top subtype ranked DMRs are listed in Tables 2A, 2B, 2C, and 2D. The tissue to leukocyte (buffy coat) analysis yielded 55 hypermethylated ovarian tissue DMRs with less than 1% noise in WBCs (DMRs 472-525 shown in Tables 1A and 1B). The top overall buffy DMRs are listed in Table 3. From the tissue and buffy marker groups, 68 candidates were chosen for an initial pilot. Methylation-specific PCR assays were developed and tested on two rounds of tissue samples; those that were sequenced (frozen) and larger independent cohorts (FFPE). Short amplicon primers (<150 bp) were designed to target the most discriminant CpGs with in a DMR and tested on controls to ensure that fully methylated fragments amplified robustly and in a linear fashion; that unmethylated and/or unconverted fragments did not amplify. The 136 primer sequences are listed in Table 1C. Ultimately, 54 assays were taken forward (14 assays failed QC and were dropped).

The results from stage one validation were analyzed logistically to determine AUC and fold change. From previous work it was recognized that the epigenetics of cancer subtypes within an organ differ and that the best panels are derived from combinations of subtype markers. The analyses for the tissue and buffy coat controls were run separately. Results are highlighted in Tables 4A, 4B, 4C, 4D and 4E. A number of assays were 100% discriminant in OC from buffy coat samples and approaching 100% in the OC vs benign fallopian tube comparison.

These results provided a rich source of highly performing candidates to take into independent sample testing. Of the original 54 assays, 33 were selected. Most fell within the AUC range of 0.90-1.00, but others were included which had extremely high FC numbers (very little background) and/or those which exhibited complementarity with other methylated DNA markers (MDMS). All assays demonstrated high analytical performance—linearity, efficiency, sequence specificity (assessed using melt curve analysis), and strong amplification.

In round 2 validation, as in the previous step, the entire sample and marker set was run in one batch. ~10 ng of FFPE-derived sample DNA was run per marker—350 total. OC subtype vs normal tissue and buffy coat results for individual MDMs are listed in Table 5A, 5B, 5C, and 5D. Multiple MDMs showed marked methylation fold changes vs controls (10 to >1000) across all OC histologies.

The data was plotted in a heat matrix format, which allows one to visualize complementarity. A cross-validated 2-MDM panel was derived from rPART modeling: (C2CD4D, NCOR2) discriminated overall OC from benign fallopian tissue with 99% sensitivity and 97% specificity. Subtype rPART and random forest modeling yielded perfect discrimination in all histologies (AUC=1).

Whole methylome sequencing, stringent filtering criteria, and biological validation yielded outstanding candidate MDMs for ovarian cancer. Some MDMs discriminate all OC histologies from controls with comparably high sensitivity, while others accurately distinguish among histologies. Given high discrimination and ease of assay, such MDMs merit further exploration for clinical application as early detection markers.

Table 1A provides DMR information including chromosome number, gene annotation, and DMR start/stop position for such markers. Table 1B provides p-value, area under the receiver operating characteristic curve (AUC) and fold-change difference between OC cases and all controls. Table 1C provides the primer sequence information for various markers provided in Tables 1A and 1B.

TABLE 1A

| DMR No. | Gene Annotation | Chromosome No. | DMR Start-End Positions |
|---|---|---|---|
| 1 | A1BG | 19 | 58858941-58858983 |
| 2 | ABLIM3 | 5 | 148521010-148521347 |
| 3 | ADAM8 | 10 | 135090085-135090491 |
| 4 | ADRB1 | 10 | 115803122-115803270 |
| 5 | AEBP1 | 7 | 44143993-44144057 |
| 6 | AGRN_A | 1 | 968398-968861 |
| 7 | AGRN_B | 1 | 969237-969426 |
| 8 | AGRN_C | 1 | 975860-976046 |
| 9 | AJAP1 | 1 | 4715931-4716109 |
| 10 | AMIGO3 | 3 | 49756614-49757016 |
| 11 | ANKLE1 | 19 | 17392948-17393075 |
| 12 | ANKRD29 | 18 | 21199479-21199692 |
| 13 | ANO8 | 19 | 17439360-17439541 |
| 14 | ANPEP | 15 | 90358365-90358451 |
| 15 | ARHGEF1 | 19 | 42386936-42386997 |
| 16 | ARL10 | 5 | 175792149-175792960 |
| 17 | ARL5C | 17 | 37321417-37321631 |
| 18 | ATP10A_A | 15 | 26107757-26107986 |
| 19 | ATP10A_B | 15 | 26107990-26108203 |
| 20 | ATP10A_C | 15 | 26108433-26108524 |
| 21 | ATP10A_D | 15 | 26108550-26108818 |
| 22 | ATP2A3_A | 17 | 3867152-3867216 |
| 23 | ATP2A3_B | 17 | 3867435-3867536 |
| 24 | BCAN | 1 | 156611761-156611950 |
| 25 | BCAT1 | 12 | 25055793-25056189 |
| 26 | BCL11B_A | 14 | 99736361-99736463 |
| 27 | BCL11B_B | 14 | 99736933-99737063 |
| 28 | BCL11B_C | 14 | 99737497-99737609 |
| 29 | BEND4 | 4 | 42153526-42153625 |
| 30 | BEST4 | 1 | 45249967-45250240 |
| 31 | BHLHE23_A | 20 | 61638021-61638117 |
| 32 | BHLHE23_B | 20 | 61638192-61638565 |
| 33 | BOLA1 | 1 | 149871496-149871610 |
| 34 | C12orf42 | 12 | 103889256-103889370 |
| 35 | C14orf184 | 14 | 92040736-92040870 |
| 36 | C14orf38_A | 14 | 60043243-60043329 |
| 37 | C14orf38_B | 14 | 60043455-60043565 |
| 38 | C17orf107 | 17 | 4802571-4802889 |
| 39 | C17orf46 | 17 | 43339216-43339594 |
| 40 | C17orf64_A | 17 | 58498720-58498794 |
| 41 | C17orf64_B | 17 | 58499005-58499095 |
| 42 | C19orf35_A | 19 | 2282272-2282493 |
| 43 | C19orf35_B | 19 | 2282568-2282640 |
| 44 | C1orf200 | 1 | 9712789-9712900 |
| 45 | C1QL3_A | 10 | 16563117-16563891 |
| 46 | C3orf72 | 3 | 138663788-138663885 |
| 47 | C6orf147 | 6 | 74019480-74019585 |
| 48 | CACNA1G | 17 | 48639699-48639734 |
| 49 | CACNA2D4 | 12 | 1906505-1906559 |
| 50 | CAPN2_A | 1 | 223936868-223937004 |
| 51 | CARD11 | 7 | 3083446-3083541 |
| 52 | CCND2_A | 12 | 4381398-4381485 |
| 53 | CCND2_B | 12 | 4381789-4381895 |
| 54 | CCND2_C | 12 | 4381964-4382142 |

TABLE 1A-continued

| DMR No. | Gene Annotation | Chromosome No. | DMR Start-End Positions |
|---|---|---|---|
| 55 | CCND2_D | 12 | 4383820-4384113 |
| 56 | CD151 | 11 | 830191-830499 |
| 57 | CD38 | 4 | 15780224-15780290 |
| 58 | CD70 | 19 | 6590980-6591072 |
| 59 | CD8A_A | 2 | 87017985-87018012 |
| 60 | CD8A_B | 2 | 87018067-87018126 |
| 61 | CDO1_A | 5 | 115152022-115152432 |
| 62 | CDO1_B | 5 | 115152466-115152505 |
| 63 | CELF2_A | 10 | 11207221-11207812 |
| 64 | CELF2_B | 10 | 11207796-11207938 |
| 65 | CLIC6 | 21 | 36041908-36042182 |
| 66 | CMTM3_A | 16 | 66638182-66638341 |
| 67 | CNR1_A | 6 | 88876927-88877128 |
| 68 | CNR1_B | 6 | 88877220-88877275 |
| 69 | CNRIP1 | 2 | 68546519-68546627 |
| 70 | COL14A1 | 8 | 121137165-121137326 |
| 71 | CPT1A | 11 | 68610548-68610744 |
| 72 | CSDAP1 | 16 | 31580718-31580899 |
| 73 | CYP11A1 | 15 | 74658391-74658453 |
| 74 | CYTH2 | 19 | 48984042-48984183 |
| 75 | DAB2IP | 9 | 124462035-124462178 |
| 76 | DDN | 12 | 49391147-49391271 |
| 77 | DGKZ | 11 | 46389264-46389321 |
| 78 | DIDO1 | 20 | 61560520-61560934 |
| 79 | DLG4 | 17 | 7108434-7108738 |
| 80 | DLL4 | 15 | 41218265-41218582 |
| 81 | DNMT3A_A | 2 | 25500046-25500305 |
| 82 | DOCK2_A | 5 | 169064274-169064312 |
| 83 | DOCK2_B | 5 | 169064321-169064452 |
| 84 | DSCR6 | 21 | 38378492-38378858 |
| 85 | ELAVL3 | 19 | 11593130-11593200 |
| 86 | ELMO1_A | 7 | 37487417-37487633 |
| 87 | ELMO1_B | 7 | 37487695-37488671 |
| 88 | ELMO1_C | 7 | 37488818-37488882 |
| 89 | EMB | 5 | 49736794-49737178 |
| 90 | EMX1 | 2 | 73147710-73147772 |
| 91 | ENO3 | 17 | 4853764-4853800 |
| 92 | EPS8L2_A | 11 | 725829-725907 |
| 93 | EPS8L2_B | 11 | 726000-726061 |
| 94 | EPS8L2_C | 11 | 726066-726121 |
| 95 | EPS8L2_D | 11 | 726129-726188 |
| 96 | EPS8L2_E | 11 | 726202-726557 |
| 97 | ESPN | 1 | 6508635-6508742 |
| 98 | EVI5L | 19 | 7927507-7927609 |
| 99 | FAIM2_A | 12 | 50297610-50297988 |
| 100 | FAM69B | 9 | 139606494-139606544 |
| 101 | FEV | 2 | 219849187-219849229 |
| 102 | FLJ22536 | 6 | 21666391-21666587 |
| 103 | FLJ34208_A | 3 | 194208242-194208346 |
| 104 | FLJ34208_B | 3 | 194208392-194208424 |
| 105 | FLJ42875 | 1 | 2987463-2987488 |
| 106 | FLJ45983_A | 10 | 8097087-8097163 |
| 107 | FLJ45983_B | 10 | 8097491-8097541 |
| 108 | FOXE1 | 9 | 100616468-100616545 |
| 109 | FZD2 | 17 | 42635471-42635540 |
| 110 | GAPDHS | 19 | 36025078-36025197 |
| 111 | GATA2 | 3 | 128209003-128209339 |
| 112 | GBGT1 | 9 | 136038933-136039446 |
| 113 | GDF7 | 2 | 20866066-20866362 |
| 114 | GFI1_A | 1 | 92948353-92948494 |
| 115 | GFI1_B | 1 | 92948564-92948643 |
| 116 | GJA4 | 1 | 35258460-35258657 |
| 117 | GOLGA8A_A | 15 | 34728868-34729108 |
| 118 | GOLGA8A_B | 15 | 34729569-34729627 |
| 119 | GP5 | 3 | 194118822-194118924 |
| 120 | GPR144 | 9 | 127212625-127212653 |
| 121 | GPRIN1_A | 5 | 176023883-176024195 |
| 122 | GSX1 | 13 | 28363905-28363973 |
| 123 | GYPC_A | 2 | 127413591-127413988 |
| 124 | GYPC_B | 2 | 127414040-127414189 |
| 125 | HAAO | 2 | 43019960-43020076 |
| 126 | HCG4P6_A | 6 | 29894629-29894706 |
| 127 | HCG4P6_B | 6 | 29894728-29895060 |
| 128 | HDGFRP3 | 15 | 83875827-83875946 |
| 129 | HIC1_A | 17 | 1958916-1959035 |
| 130 | HIC1_B | 17 | 1959271-1959370 |
| 131 | HIST1H2BE | 6 | 26184228-26184336 |

TABLE 1A-continued

| DMR No. | Gene Annotation | Chromosome No. | DMR Start-End Positions |
|---|---|---|---|
| 132 | HIST1H3G | 6 | 26273744-26273884 |
| 133 | HMX3 | 10 | 124895638-124895782 |
| 134 | HOPX | 4 | 57522384-57522421 |
| 135 | HOXA6 | 7 | 27191540-27191631 |
| 136 | HOXA7 | 7 | 27196032-27196120 |
| 137 | HOXB3 | 17 | 46655280-46655642 |
| 138 | HPDL | 1 | 45792729-45792887 |
| 139 | HPSE2 | 10 | 100994002-100994115 |
| 140 | HRH2 | 5 | 175085230-175085493 |
| 141 | ICAM4 | 19 | 10398100-10398242 |
| 142 | IGFBP7 | 4 | 57976729-57976874 |
| 143 | IKZF1 | 7 | 50343339-50343420 |
| 144 | IL17C_A | 16 | 88701004-88701036 |
| 145 | IL17C_B | 16 | 88701240-88701422 |
| 146 | INA_A | 10 | 105036646-105036836 |
| 147 | IRAK2 | 3 | 10206783-10206832 |
| 148 | IRF4_A | 6 | 391420-391465 |
| 149 | IRF4_B | 6 | 391489-391525 |
| 150 | IRF4_C | 6 | 391630-391913 |
| 151 | IRF4_D | 6 | 393508-393550 |
| 152 | IRF4_E | 6 | 393636-393700 |
| 153 | ITGA4_A | 2 | 182321830-182322222 |
| 154 | ITGA4_B | 2 | 182322260-182322569 |
| 155 | ITGA5 | 12 | 54812397-54812487 |
| 156 | ITGB2 | 21 | 46352783-46352834 |
| 157 | ITPKB_A | 1 | 226924944-226925001 |
| 158 | ITPRIPL1 | 2 | 96991110-96991303 |
| 159 | JAK3_A | 19 | 17958411-17958512 |
| 160 | JAM3_A | 11 | 133938954-133939134 |
| 161 | JSRP1 | 19 | 2253171-2253346 |
| 162 | KCNA1_A | 12 | 5018819-5019101 |
| 163 | KCNA1_B | 12 | 5019343-5019751 |
| 164 | KCNA3_A | 1 | 111217012-111217118 |
| 165 | KCNA3_B | 1 | 111217162-111217358 |
| 166 | KCNA3_C | 1 | 111217478-111217843 |
| 167 | KCNA3_D | 1 | 111217621-111217793 |
| 168 | KCNK12 | 2 | 47748450-47748743 |
| 169 | KCNK4 | 11 | 64059938-64059994 |
| 170 | KCNK9_A | 8 | 140715067-140715136 |
| 171 | KCNK9_B | 8 | 140715169-140715272 |
| 172 | KCNK9_C | 8 | 140715402-140715463 |
| 173 | KCNQ5_A | 6 | 73331057-73331808 |
| 174 | KCNQ5_B | 6 | 73331977-73332327 |
| 175 | KCNQ5_C | 6 | 73332569-73332850 |
| 176 | KCTD15 | 19 | 34288332-34288538 |
| 177 | KIAA1383 | 1 | 232941174-232941363 |
| 178 | KL | 13 | 33591064-33591101 |
| 179 | KLF16 | 19 | 1857112-1857272 |
| 180 | KLHL21 | 1 | 6663497-6663739 |
| 181 | LAPTM4B | 8 | 98788068-98788302 |
| 182 | LBH | 2 | 30453651-30453973 |
| 183 | LCNL1 | 9 | 139880005-139880043 |
| 184 | LIME1_A | 20 | 62369116-62369184 |
| 185 | LIME1_B | 20 | 62369366-62369505 |
| 186 | LIMK1 | 7 | 73509063-73509133 |
| 187 | LMX1B | 9 | 129377593-129377885 |
| 188 | LOC100132891 | 8 | 72756370-72756468 |
| 189 | LOC151174 | 2 | 239140297-239140360 |
| 190 | LOC339674 | 22 | 42353684-42353820 |
| 191 | LOC440461 | 17 | 66195680-66195779 |
| 192 | LOC646278 | 15 | 29077327-29077630 |
| 193 | LOC648809 | 15 | 84748786-84749007 |
| 194 | LPHN1 | 19 | 14260451-14260665 |
| 195 | LRRC10B | 11 | 61277048-61277085 |
| 196 | LRRC32 | 11 | 76382075-76382101 |
| 197 | LRRC4 | 7 | 127671885-127672583 |
| 198 | LRRC41_A | 1 | 46767372-46769064 |
| 199 | LRRC41_B | 1 | 46769340-46769650 |
| 200 | LRRC8D | 1 | 90309263-90309378 |
| 201 | LTB | 6 | 31548580-31548608 |
| 202 | LTK | 15 | 41805316-41805441 |
| 203 | LY75 | 2 | 160760789-160760845 |
| 204 | MAML3_A | 4 | 140656481-140656692 |
| 205 | MAX.chr1.110626771-110626832 | 1 | 110626771-110626832 |
| 206 | MAX.chr1.147775386-147775483 | 1 | 147775386-147775483 |
| 207 | MAX.chr1.147790358-147790381 | 1 | 147790250-147790489 |
| 208 | MAX.chr1.148598377-148598471 | 1 | 148598377-148598471 |

TABLE 1A-continued

| DMR No. | Gene Annotation | Chromosome No. | DMR Start-End Positions |
|---|---|---|---|
| 209 | MAX.chr1.161591532-161591608 | 1 | 161591532-161591608 |
| 210 | MAX.chr1.21917279-21917313 | 1 | 21917279-21917313 |
| 211 | MAX.chr1.2472236-2472504 | 1 | 2472236-2472504 |
| 212 | MAX.chr1.2472508-2472586 | 1 | 2472508-2472586 |
| 213 | MAX.chr1.32237654-32237674 | 1 | 32237654-32237674 |
| 214 | MAX.chr1.32238032-32238105 | 1 | 32238032-32238105 |
| 215 | MAX.chr1.32238359-32238419 | 1 | 32238359-32238419 |
| 216 | MAX.chr1.32410292-32410428 | 1 | 32410292-32410428 |
| 217 | MAX.chr1.46632623-46632858 | 1 | 46632623-46632858 |
| 218 | MAX.chr1.48058986-48059074 | 1 | 48058986-48059074 |
| 219 | MAX.chr1.98510937-98511077 | 1 | 98510937-98511077 |
| 220 | MAX.chr1.98511049-98511077 | 1 | 98511049-98511077 |
| 221 | MAX.chr1.98519485-98519592 | 1 | 98519485-98519592 |
| 222 | MAX.chr10.22541609-22541719 | 10 | 22541609-22541719 |
| 223 | MAX.chr10.22541684-22541719 | 10 | 22541684-22541719 |
| 224 | MAX.chr10.22541986-22542037 | 10 | 22541986-22542037 |
| 225 | MAX.chr10.22765282-22765351 | 10 | 22765282-22765351 |
| 226 | MAX.chr11.14926602-14926671 | 11 | 14926602-14926671 |
| 227 | MAX.chr11.14926840-14926955 | 11 | 14926840-14926955 |
| 228 | MAX.chr11.45376949-45377082 | 11 | 45376949-45377082 |
| 229 | MAX.chr11.45376949-45377204 | 11 | 45376949-45377204 |
| 230 | MAX.chr11.57250516-57250847 | 11 | 57250516-57250847 |
| 231 | MAX.chr12.29302564-29302695 | 12 | 29302564-29302695 |
| 232 | MAX.chr12.30975740-30975780 | 12 | 30975740-30975780 |
| 233 | MAX.chr12.4273826-4274239 | 12 | 4273826-4274239 |
| 234 | MAX.chr14.100784600-100784781 | 14 | 100784600-100784781 |
| 235 | MAX.chr14.103557836-103558188 | 14 | 103557836-103558188 |
| 236 | MAX.chr14.105512178-105512224 | 14 | 105512131-105512271 |
| 237 | MAX.chr14.60386315-60386417 | 14 | 60386315-60386417 |
| 238 | MAX.chr14.97685168-97685437 | 14 | 97685168-97685437 |
| 239 | MAX.chr14.97685552-97685839 | 14 | 97685552-97685839 |
| 240 | MAX.chr15.28351937-28352173 | 15 | 28351937-28352173 |
| 241 | MAX.chr15.28352203-28352671 | 15 | 28352203-28352671 |
| 242 | MAX.chr15.29131258-29131734 | 15 | 29131258-29131734 |
| 243 | MAX.chr15.31685160-31685245 | 15 | 31685160-31685245 |
| 244 | MAX.chr15.65186050-65186150 | 15 | 65186050-65186150 |
| 245 | MAX.chr15.74891008-74891138 | 15 | 74891008-74891138 |
| 246 | MAX.chr15.75471061-75471202 | 15 | 75471061-75471202 |
| 247 | MAX.chr16.50875166-50875262 | 16 | 50875166-50875262 |
| 248 | MAX.chr16.50875166-50875301 | 16 | 50875166-50875301 |
| 249 | MAX.chr17.37366022-37366321 | 17 | 37366022-37366321 |
| 250 | MAX.chr19.2273768-2273823 | 19 | 2273768-2273823 |
| 251 | MAX.chr19.30716607-30716756 | 19 | 30716607-30716756 |
| 252 | MAX.chr19.37288390-37288811 | 19 | 37288390-37288811 |
| 253 | MAX.chr19.42444222-42444334 | 19 | 42444222-42444334 |
| 254 | MAX.chr19.55962661-55962773 | 19 | 55962661-55962773 |
| 255 | MAX.chr19.5828277-5828498 | 19 | 5828277-5828498 |
| 256 | MAX.chr2.118981858-118981934 | 2 | 118981858-118981934 |
| 257 | MAX.chr2.118982007-118982089 | 2 | 118982007-118982089 |
| 258 | MAX.chr2.119067767-119068112 | 2 | 119067767-119068112 |
| 259 | MAX.chr2.127783351-127783403 | 2 | 127783351-127783403 |
| 260 | MAX.chr2.175191004-175191127 | 2 | 175191004-175191127 |
| 261 | MAX.chr2.241855537-241855585 | 2 | 241855537-241855585 |
| 262 | MAX.chr2.25438959-25439001 | 2 | 25438959-25439001 |
| 263 | MAX.chr2.25439173-25439276 | 2 | 25439173-25439276 |
| 264 | MAX.chr2.66653544-66653582 | 2 | 66653544-66653582 |
| 265 | MAX.chr2.66653881-66653935 | 2 | 66653881-66653935 |
| 266 | MAX.chr2.97193155-97193524 | 2 | 97193155-97193524 |
| 267 | MAX.chr2.97193478-97193562 | 2 | 97193478-97193562 |
| 268 | MAX.chr20.30175888-30175927 | 20 | 30175888-30175927 |
| 269 | MAX.chr20.3073377-3073486 | 20 | 3073377-3073486 |
| 270 | MAX.chr20.49308029-49308083 | 20 | 49308029-49308083 |
| 271 | MAX.chr3.107148795-107148869 | 3 | 107148795-107148869 |
| 272 | MAX.chr3.128274281-128274519 | 3 | 128274281-128274519 |
| 273 | MAX.chr3.138679378-138679414 | 3 | 138679378-138679414 |
| 274 | MAX.chr3.18485437-18485723 | 3 | 18485437-18485723 |
| 275 | MAX.chr3.186490624-186490778 | 3 | 186490624-186490778 |
| 276 | MAX.chr3.69591053-69591097 | 3 | 69591053-69591097 |
| 277 | MAX.chr4.174430671-174430719 | 4 | 174430671-174430719 |
| 278 | MAX.chr4.174430751-174430776 | 4 | 174430751-174430776 |
| 279 | MAX.chr4.41869404-41869433 | 4 | 41869404-41869433 |
| 280 | MAX.chr4.8859707-8859944 | 4 | 8859707-8859944 |
| 281 | MAX.chr4.8859995-8860062 | 4 | 8859995-8860062 |
| 282 | MAX.chr4.8860076-8860122 | 4 | 8860076-8860122 |
| 283 | MAX.chr5.178957539-178957851 | 5 | 178957539-178957851 |
| 284 | MAX.chr5.2038771-2038990 | 5 | 2038771-2038990 |
| 285 | MAX.chr5.42951482-42951568 | 5 | 42951482-42951568 |

TABLE 1A-continued

| DMR No. | Gene Annotation | Chromosome No. | DMR Start-End Positions |
|---|---|---|---|
| 286 | MAX.chr5.42952182-42952292 | 5 | 42952182-42952292 |
| 287 | MAX.chr6.10382190-10382225 | 6 | 10382154-10382261 |
| 288 | MAX.chr6.108440553-108440720 | 6 | 108440553-108440720 |
| 289 | MAX.chr6.157557273-157557374 | 6 | 157557273-157557374 |
| 290 | MAX.chr6.28175549-28175579 | 6 | 28175549-28175579 |
| 291 | MAX.chr6.42738979-42739055 | 6 | 42738979-42739055 |
| 292 | MAX.chr7.127744282-127744490 | 7 | 127744282-127744490 |
| 293 | MAX.chr7.142494643-142495353 | 7 | 142494643-142495353 |
| 294 | MAX.chr7.1706293-1706418 | 7 | 1706293-1706418 |
| 295 | MAX.chr7.99595234-99595474 | 7 | 99595234-99595474 |
| 296 | MAX.chr8.124173231-124173268 | 8 | 124173231-124173268 |
| 297 | MAX.chr8.142215938-142216298 | 8 | 142215938-142216298 |
| 298 | MAX.chr8.145103855-145103943 | 8 | 145103855-145103943 |
| 299 | MAX.chr8.145104058-145104455 | 8 | 145104058-145104455 |
| 300 | MAX.chr8.145105537-145105891 | 8 | 145105537-145105891 |
| 301 | MAX.chr8.145105977-145106067 | 8 | 145105977-145106067 |
| 302 | MAX.chr8.6658405-6658443 | 8 | 6658405-6658443 |
| 303 | MAX.chr8.688047-688103 | 8 | 688047-688103 |
| 304 | MAX.chr9.113594-113689 | 9 | 113594-113689 |
| 305 | MAX.chr9.129485515-129485818 | 9 | 129485515-129485818 |
| 306 | MDFI | 6 | 41605839-41606346 |
| 307 | MFSD2B | 2 | 24233083-24233209 |
| 308 | MGC16275 | 17 | 72210023-72210198 |
| 309 | MPZ | 1 | 161275472-161275996 |
| 310 | MSX2 | 5 | 174152507-174152713 |
| 311 | MT1A_A | 16 | 56669159-56669211 |
| 312 | MT1A_B | 16 | 56669458-56669636 |
| 313 | MYO15B_A | 17 | 73584228-73584557 |
| 314 | MYO15B_B | 17 | 73584560-73584600 |
| 315 | MYO15B_C | 17 | 73585026-73585115 |
| 316 | MYOZ3 | 5 | 150051282-150051406 |
| 317 | NBPF3 | 1 | 21767084-21767293 |
| 318 | NCOR2 | 12 | 124941831-124942044 |
| 319 | NEFL | 8 | 24814074-24814163 |
| 320 | NFATC1 | 18 | 77159828-77159857 |
| 321 | NFATC4 | 14 | 24837473-24838153 |
| 322 | NFIC_A | 19 | 3358520-3358591 |
| 323 | NFIC_B | 19 | 3360968-3361330 |
| 324 | NFIC_C | 19 | 3435098-3435351 |
| 325 | NFIX | 19 | 13124203-13124307 |
| 326 | NID2 | 14 | 52535746-52536302 |
| 327 | NKX2-3 | 10 | 101290864-101290938 |
| 328 | NKX2-6 | 8 | 23564076-23564181 |
| 329 | NR2F6 | 19 | 17346347-17346780 |
| 330 | NRTN | 19 | 5828107-5828231 |
| 331 | NTN1 | 17 | 9143253-9143499 |
| 332 | NTRK3_A | 15 | 88799927-88799988 |
| 333 | NTRK3_B | 15 | 88800193-88800380 |
| 334 | OBSCN | 1 | 228463593-228463779 |
| 335 | OLIG1 | 21 | 34443688-34443868 |
| 336 | OLIG2 | 21 | 34399771-34399916 |
| 337 | OPLAH_A | 8 | 145106349-145106488 |
| 338 | OPLAH_B | 8 | 145106672-145106921 |
| 339 | OPRL1 | 20 | 62711578-62711704 |
| 340 | OSR2 | 8 | 99954516-99954637 |
| 341 | OXT_A | 20 | 3052709-3052813 |
| 342 | OXT_B | 20 | 3052884-3052977 |
| 343 | PALLD | 4 | 169799211-169799372 |
| 344 | PALM3 | 19 | 14168328-14168446 |
| 345 | PARP15 | 3 | 122296692-122296851 |
| 346 | PAX6 | 11 | 31825838-31825879 |
| 347 | PDE6B | 4 | 657799-658022 |
| 348 | PDE10A | 6 | 166076546-166077074 |
| 349 | PDX1 | 13 | 28498334-28498404 |
| 350 | PEAR1_A | 1 | 156863509-156863554 |
| 351 | PIF1 | 15 | 65116269-65116639 |
| 352 | PIP5KL1 | 9 | 130689558-130689627 |
| 353 | PISD | 22 | 32026204-32026773 |
| 354 | PLEKHA6 | 1 | 204328789-204328989 |
| 355 | PLEKHO1 | 1 | 150123028-150123073 |
| 356 | PLXNC1 | 12 | 94543384-94543621 |
| 357 | PNMAL2 | 19 | 46996713-46996787 |
| 358 | PPFIA4_A | 1 | 203044930-203045036 |
| 359 | PPP1R16B | 20 | 37435478-37435773 |
| 360 | PRDM14 | 8 | 70981925-70982133 |
| 361 | PRKAG2 | 7 | 151480148-151480267 |
| 362 | PRKAR1B_A | 7 | 641712-641771 |

TABLE 1A-continued

| DMR No. | Gene Annotation | Chromosome No. | DMR Start-End Positions |
|---|---|---|---|
| 363 | PRKCB_A | 16 | 23847557-23847586 |
| 364 | PRKCB_B | 16 | 23847659-23847699 |
| 365 | PRKCB_C | 16 | 23847825-23847924 |
| 366 | PRKCB_D | 16 | 23847935-23848025 |
| 367 | PROCA1 | 17 | 27038756-27038861 |
| 368 | PROKR2 | 20 | 5297178-5297272 |
| 369 | PTGDR | 14 | 52735279-52735395 |
| 370 | PTP4A3_A | 8 | 142427934-142428065 |
| 371 | PTP4A3_B | 8 | 142428209-142428278 |
| 372 | PTPRS | 19 | 5338930-5339005 |
| 373 | PTPRU | 1 | 29586282-29586672 |
| 374 | PYCARD | 16 | 31213961-31214287 |
| 375 | RAI1_A | 17 | 17626939-17627256 |
| 376 | RAI1_B | 17 | 17627449-17627542 |
| 377 | RASGEF1A | 10 | 43697946-43698226 |
| 378 | RASSF1_A | 3 | 50378163-50378232 |
| 379 | RASSF1_B | 3 | 50378242-50378506 |
| 380 | RBFOX3 | 17 | 77216036-77216108 |
| 381 | RET | 10 | 43600358-43600417 |
| 382 | RFTN1_A | 3 | 16554307-16554544 |
| 383 | RILPL2 | 12 | 123920605-123920783 |
| 384 | RNF220 | 1 | 44873859-44874011 |
| 385 | RTN4RL2 | 11 | 57244133-57244310 |
| 386 | RUNX3 | 1 | 25256939-25256984 |
| 387 | SALL3 | 18 | 76739367-76739410 |
| 388 | SCGB3A1 | 5 | 180017894-180018010 |
| 389 | SEPTIN9 | 17 | 75447349-75448208 |
| 390 | SFMBT2_A | 10 | 7450245-7450492 |
| 391 | SFMBT2_B | 10 | 7451000-7451219 |
| 392 | SFMBT2_C | 10 | 7451122-7451185 |
| 393 | SH2B3 | 12 | 111844616-111844676 |
| 394 | SH3PXD2A | 10 | 105452732-105452854 |
| 395 | SHH_A | 7 | 155596622-155596834 |
| 396 | SHH_B | 7 | 155597896-155598039 |
| 397 | SIM2_A | 21 | 38076892-38077026 |
| 398 | SKI | 1 | 2222218-2222508 |
| 399 | SLC12A8 | 3 | 124860558-124861019 |
| 400 | SLC25A47 | 14 | 100784600-100784767 |
| 401 | SLC4A11 | 20 | 3218820-3218937 |
| 402 | SLC5A5_A | 19 | 17983502-17983586 |
| 403 | SLC5A5_B | 19 | 17983598-17983715 |
| 404 | SLC8A3 | 14 | 70654428-70654774 |
| 405 | SLFN12L | 17 | 33814255-33814301 |
| 406 | SMTN | 22 | 31480775-31481518 |
| 407 | SOBP_A | 6 | 107956180-107956211 |
| 408 | SP9 | 2 | 175202051-175202128 |
| 409 | SPATA18 | 4 | 52917781-52918182 |
| 410 | SPDYA | 2 | 29033199-29033781 |
| 411 | SPEF1 | 20 | 3758385-3758848 |
| 412 | SPOCK2_A | 10 | 73847053-73847086 |
| 413 | SPOCK2_B | 10 | 73847235-73847539 |
| 414 | SPON2_A | 4 | 1165210-1165299 |
| 415 | SPON2_B | 4 | 1165343-1165543 |
| 416 | SRC_A | 20 | 36013131-36013293 |
| 417 | SSBP4_A | 19 | 18539898-18539951 |
| 418 | SSBP4_B | 19 | 18540000-18540094 |
| 419 | SSBP4_C | 19 | 18540229-18540318 |
| 420 | ST8SIA1 | 12 | 22487798-22487868 |
| 421 | STX16 | 20 | 57225361-57225498 |
| 422 | TACC1 | 8 | 38645352-38645822 |
| 423 | TACC2_A | 10 | 123922953-123923142 |
| 424 | TBKBP1 | 17 | 45772630-45772754 |
| 425 | TBX20 | 7 | 35293783-35293840 |
| 426 | TCF3 | 19 | 1651228-1651464 |
| 427 | TEAD3 | 6 | 35465820-35465933 |
| 428 | TET2 | 4 | 106067300-106067367 |
| 429 | TGFB1 | 19 | 41860019-41860100 |
| 430 | TJP2 | 9 | 71788680-71789619 |
| 431 | TMC4 | 19 | 54668457-54668534 |
| 432 | TMC6 | 17 | 76123694-76123758 |
| 433 | TMEFF2 | 2 | 193059694-193059802 |
| 434 | TMEM101 | 17 | 42092155-42092451 |
| 435 | TMEM106A | 17 | 41364038-41364262 |
| 436 | TNFRSF10C | 8 | 22960622-22960682 |
| 437 | TNFRSF8 | 1 | 12123499-12123582 |
| 438 | TRIM15 | 6 | 30139641-30139719 |
| 439 | TRIM71 | 3 | 32859445-32859594 |

TABLE 1A-continued

| DMR No. | Gene Annotation | Chromosome No. | DMR Start-End Positions |
|---|---|---|---|
| 440 | TRIM9__A | 14 | 51561036-51561087 |
| 441 | TRIM9__B | 14 | 51561136-51561442 |
| 442 | TRPV2 | 17 | 16319144-16319187 |
| 443 | TSC22D4 | 7 | 100075240-100075445 |
| 444 | TSHZ3 | 19 | 31839415-31840120 |
| 445 | TSPY26P | 20 | 30777758-30778400 |
| 446 | TXNRD1 | 12 | 104609676-104609867 |
| 447 | UBTF | 17 | 42287818-42288018 |
| 448 | ULBP1 | 6 | 150286136-150286230 |
| 449 | UST | 6 | 149069280-149069352 |
| 450 | VASP | 19 | 46012679-46012761 |
| 451 | VILL | 3 | 38035507-38035975 |
| 452 | VIM | 10 | 17271136-17272017 |
| 453 | VIPR2__A | 7 | 158937338-158937701 |
| 454 | WNT7B | 22 | 46367055-46367110 |
| 455 | XKR6 | 8 | 11059151-11059333 |
| 456 | XYLT1 | 16 | 17563754-17564236 |
| 457 | ZBED4 | 22 | 50243124-50243470 |
| 458 | ZEB2__A | 2 | 145273503-145273611 |
| 459 | ZEB2__B | 2 | 145273632-145273799 |
| 460 | ZFP3 | 17 | 4981325-4981972 |
| 461 | ZMIZ1__A | 10 | 81001957-81002169 |
| 462 | ZMIZ1__B | 10 | 81002179-81002856 |
| 463 | ZMIZ1__C | 10 | 81002774-81003124 |
| 464 | ZNF132 | 19 | 58951346-58951858 |
| 465 | ZNF382__A | 19 | 37095829-37096330 |
| 466 | ZNF469__A | 16 | 88496936-88497068 |
| 467 | ZNF469__B | 16 | 88497173-88497294 |
| 468 | ZNF703 | 8 | 37554309-37554811 |
| 469 | ZNF781 | 19 | 38182950-38183200 |
| 470 | ZSCAN12 | 6 | 28367509-28367628 |
| 471 | ZSCAN23 | 6 | 28411060-28411316 |
| 472 | ATP6V1B1__A | 2 | 71192303-71192387 |
| 473 | ATP6V1B1__B | 2 | 71192391-71192453 |
| 474 | BANK1 | 4 | 102712067-102712226 |
| 475 | BCL2L11 | 2 | 111876417-111876495 |
| 476 | BZRAP1 | 17 | 56405949-56406457 |
| 477 | C17orf64__C | 17 | 58498720-58499190 |
| 478 | C19orf35__C | 19 | 2282230-2282493 |
| 479 | C2CD4D | 1 | 151810778-151810945 |
| 480 | CCDC88C | 14 | 91790479-91790734 |
| 481 | TRIM9__C | 14 | 51560749-51561240 |
| 482 | CORO1A | 16 | 30195584-30195646 |
| 483 | DNMT3A__B | 2 | 25499898-25500026 |
| 484 | DNMT3A__C | 2 | 25500061-25500236 |
| 485 | FAM189B | 1 | 155220306-155220461 |
| 486 | FCHO1 | 19 | 17862130-17862551 |
| 487 | FXYD5 | 19 | 35646113-35646632 |
| 488 | GDF6 | 8 | 97157560-97158030 |
| 489 | GMDS | 6 | 1624813-1624862 |
| 490 | IFFO1__A | 12 | 6664906-6665023 |
| 491 | IFFO1__B | 12 | 6665135-6665425 |
| 492 | INA__B | 10 | 105036559-105036778 |
| 493 | ITPKB__B | 1 | 226862888-226863048 |
| 494 | ITPKB__C | 1 | 226924740-226924976 |
| 495 | JAK3__B | 19 | 17958411-17958961 |
| 496 | KANK3 | 19 | 8407580-8407717 |
| 497 | KCNAB2 | 1 | 6053564-6053753 |
| 498 | LIMD2 | 17 | 61778317-61778400 |
| 499 | MAML3__B | 4 | 140656559-140656624 |
| 500 | MAX.chr1.9689803-9690241 | 1 | 9689803-9690241 |
| 501 | MAX.chr10.101300125-101300155 | 10 | 101300125-101300155 |
| 502 | MAX.chr11.14926756-14927227 | 11 | 14926756-14927227 |
| 503 | MAX.chr12.30975740-30975961 | 12 | 30975740-30975961 |
| 504 | MAX.chr14.102172350-102172770 | 14 | 102172350-102172770 |
| 505 | MAX.chr16.85482307-85482494 | 16 | 85482307-85482494 |
| 506 | MAX.chr17.76254728-76254841 | 17 | 76254728-76254841 |
| 507 | MAX.chr20.56008090-56008227 | 20 | 56008090-56008227 |
| 508 | MAX.chr4.174430662-174430790 | 4 | 174430662-174430790 |
| 509 | MAX.chr5.42993898-42994179 | 5 | 42993898-42994179 |
| 510 | MAX.chr6.1379890-1379965 | 6 | 1379890-1379965 |
| 511 | MAX.chr7.2569526-2569650 | 7 | 2569526-2569650 |
| 512 | MAX.chr8.124173112-124173541 | 8 | 124173112-124173541 |
| 513 | PPFIA4__B | 1 | 203044753-203044863 |
| 514 | PPFIA4__C | 1 | 203044899-203044961 |
| 515 | PRKAR1B__B | 7 | 641251-641544 |
| 516 | PRKAR1B__C | 7 | 641566-641742 |

TABLE 1A-continued

| DMR No. | Gene Annotation | Chromosome No. | DMR Start-End Positions |
|---|---|---|---|
| 517 | PTGER4_A | 5 | 40681137-40681372 |
| 518 | PTGER4_B | 5 | 40681717-40682193 |
| 519 | PTPRCAP | 11 | 67204667-67204747 |
| 520 | RASAL3 | 19 | 15574876-15575148 |
| 521 | RASSF1_C | 3 | 50378163-50378750 |
| 522 | RUNX1 | 21 | 36398973-36399247 |
| 523 | SLC29A4 | 7 | 5336631-5336744 |
| 524 | SLC35D3 | 6 | 137244314-137244409 |
| 525 | SOBP_B | 6 | 107956152-107956211 |

TABLE 1B

| DMR No. | Gene Annotation | Area Under Curve | Fold-Change | p-value |
|---|---|---|---|---|
| 1 | A1BG | 0.6544 | 8.881 | 0.0006461 |
| 2 | ABLIM3 | 0.7567 | 14.96 | 0.000006848 |
| 3 | ADAM8 | 0.75 | 22.84 | 0.003361 |
| 4 | ADRB1 | 0.6933 | 10.87 | 0.002295 |
| 5 | AEBP1 | 0.8933 | 42.27 | 0.0002977 |
| 6 | AGRN_A | 0.99 | 80 | 0.006998 |
| 7 | AGRN_B | 0.7986 | 11.38 | 0.0006022 |
| 8 | AGRN_C | 0.8903 | 19.04 | 0.002814 |
| 9 | AJAP1 | 0.8382 | 21.54 | 0.000009943 |
| 10 | AMIGO3 | 0.9567 | 28.8 | 7.815E−08 |
| 11 | ANKLE1 | 0.7118 | 7.758 | 0.006422 |
| 12 | ANKRD29 | 0.7233 | 13.1 | 0.005132 |
| 13 | ANO8 | 0.7683 | 7.53 | 0.004867 |
| 14 | ANPEP | 0.6853 | 5.584 | 0.0001538 |
| 15 | ARHGEF1 | 0.7267 | 18.41 | 0.009129 |
| 16 | ARL10 | 0.94 | 28.12 | 0.00002384 |
| 17 | ARL5C | 0.7528 | 27.61 | 0.0001708 |
| 18 | ATP10A_A | 1 | 30.73 | 6.249E−09 |
| 19 | ATP10A_B | 1 | 245.4 | 1.1E−09 |
| 20 | ATP10A_C | 1 | 341.2 | 0.00007308 |
| 21 | ATP10A_D | 1 | 34.16 | 1.608E−11 |
| 22 | ATP2A3_A | 0.8583 | 14.21 | 0.00000201 |
| 23 | ATP2A3_B | 0.6867 | 17.2 | 0.003838 |
| 24 | BCAN | 0.9583 | 13.08 | 0.000001579 |
| 25 | BCAT1 | 1 | 79.37 | 5.014E−12 |
| 26 | BCL11B_A | 0.9867 | 6.934 | 6.682E−07 |
| 27 | BCL11B_B | 0.9833 | 57.45 | 0.0001541 |
| 28 | BCL11B_C | 0.8283 | 10.78 | 0.00004186 |
| 29 | BEND4 | 0.7941 | 7.411 | 0.0001528 |
| 30 | BEST4 | 0.66 | 24.18 | 0.0003696 |
| 31 | BHLHE23_A | 0.97 | 28.06 | 0.000001769 |
| 32 | BHLHE23_B | 0.9533 | 28.66 | 8.302E−07 |
| 33 | BOLA1 | 0.8133 | 5.7 | 0.00739 |
| 34 | C12orf42 | 0.6912 | 7.798 | 0.003686 |
| 35 | C14orf184 | 0.8567 | 46.56 | 0.001492 |
| 36 | C14orf38_A | 0.7333 | 8.048 | 0.000008448 |
| 37 | C14orf38_B | 0.6824 | 10.58 | 0.002335 |
| 38 | C17orf107 | 0.9206 | 19.7 | 0.0035 |
| 39 | C17orf46 | 0.8806 | 93.94 | 0.00008659 |
| 40 | C17orf64_A | 0.7456 | 19.39 | 0.000006859 |
| 41 | C17orf64_B | 0.8556 | 15.67 | 0.000002679 |
| 42 | C19orf35_A | 0.7485 | 8.741 | 0.0003768 |
| 43 | C19orf35_B | 0.8826 | 14.91 | 0.00001519 |
| 44 | C1orf200 | 0.9533 | 12.6 | 3.491E−07 |
| 45 | C1QL3_A | 0.8133 | 19.06 | 0.0001654 |
| 46 | C3orf72 | 0.6833 | 8.511 | 0.0001902 |
| 47 | C6orf147 | 0.6596 | 3.923 | 0.002154 |
| 48 | CACNA1G | 0.8267 | 18.84 | 0.0004358 |
| 49 | CACNA2D4 | 0.8867 | 19.07 | 0.0001017 |
| 50 | CAPN2_A | 0.8806 | 49.97 | 0.004007 |
| 51 | CARD11 | 0.9015 | 28.11 | 0.001149 |
| 52 | CCND2_A | 0.8765 | 12.62 | 0.00004201 |
| 53 | CCND2_B | 0.8033 | 6.981 | 0.0004369 |
| 54 | CCND2_C | 0.9853 | 28.97 | 0.00005149 |
| 55 | CCND2_D | 0.9967 | 38.38 | 0.0001518 |
| 56 | CD151 | 0.6853 | 16.18 | 0.007558 |
| 57 | CD38 | 0.7309 | 5.398 | 0.0001178 |
| 58 | CD70 | 0.7118 | 9.494 | 0.0001615 |
| 59 | CD8A_A | 0.8183 | 5.041 | 0.0002965 |

TABLE 1B-continued

| DMR No. | Gene Annotation | Area Under Curve | Fold-Change | p-value |
|---|---|---|---|---|
| 60 | CD8A_B | 0.6867 | 4.417 | 0.003114 |
| 61 | CDO1_A | 0.9167 | 27.11 | 0.000002148 |
| 62 | CDO1_B | 0.8987 | 12.31 | 2.355E-07 |
| 63 | CELF2_A | 0.9706 | 55.52 | 0.000000824 |
| 64 | CELF2_B | 0.9235 | 69.19 | 0.000000867 |
| 65 | CLIC6 | 0.88 | 37.52 | 0.00001932 |
| 66 | CMTM3_A | 1 | 379.6 | 0.000004797 |
| 67 | CNR1_A | 0.8333 | 11.08 | 0.0002641 |
| 68 | CNR1_B | 0.8986 | 6.632 | 2.378E-08 |
| 68 | CNR1_B | 0.965 | 47.74 | 0.008 |
| 69 | CNRIP1 | 0.7083 | 8.175 | 0.004742 |
| 70 | COL14A1 | 0.7194 | 7.588 | 0.00346 |
| 71 | CPT1A | 0.6985 | 5.504 | 0.0004104 |
| 72 | CSDAP1 | 0.8564 | 8.104 | 0.000002696 |
| 73 | CYP11A1 | 0.785 | 174.8 | 0.006516 |
| 74 | CYTH2 | 0.7147 | 11.12 | 0.001887 |
| 75 | DAB2IP | 0.7633 | 8.707 | 0.0005873 |
| 76 | DDN | 0.8361 | 13.65 | 0.00001727 |
| 77 | DGKZ | 0.8147 | 8.819 | 0.00001577 |
| 78 | DIDO1 | 0.9033 | 19.96 | 0.001844 |
| 79 | DLG4 | 0.685 | 10.81 | 0.0004877 |
| 80 | DLL4 | 0.7767 | 6.585 | 0.005444 |
| 81 | DNMT3A_A | 0.9333 | 29.9 | 0.0003524 |
| 82 | DOCK2_A | 0.6765 | 4.147 | 0.001841 |
| 83 | DOCK2_B | 0.6794 | 7.295 | 0.00009245 |
| 84 | DSCR6 | 0.9241 | 24.78 | 0.000005174 |
| 85 | ELAVL3 | 0.74 | 11.23 | 0.00009692 |
| 86 | ELMO1_A | 1 | 132.1 | 2.564E-08 |
| 87 | ELMO1_B | 1 | 203.7 | 0.0000838 |
| 88 | ELMO1_C | 1 | 59.3 | 7.298E-07 |
| 89 | EMB | 0.93 | 35.78 | 0.0003639 |
| 90 | EMX1 | 1 | 20.6 | 3.807E-09 |
| 91 | ENO3 | 0.8683 | 16.03 | 0.000003145 |
| 92 | EPS8L2_A | 1 | 57.73 | 9.647E-12 |
| 93 | EPS8L2_B | 1 | 68.16 | 0.000006863 |
| 94 | EPS8L2_C | 1 | 160.2 | 0.000005736 |
| 95 | EPS8L2_D | 1 | 52.76 | 0.00009573 |
| 96 | EPS8L2_E | 0.9567 | 102.7 | 9.648E-07 |
| 97 | ESPN | 0.6132 | 6.202 | 0.00143 |
| 98 | EVI5L | 0.8933 | 11.73 | 0.0004139 |
| 99 | FAIM2_A | 1 | 47 | 2.702E-09 |
| 100 | FAM69B | 0.7471 | 27.75 | 0.005765 |
| 101 | FEV | 0.7368 | 10.38 | 0.0007329 |
| 102 | FLJ22536 | 0.8833 | 15.99 | 0.002614 |
| 103 | FLJ34208_A | 0.9912 | 28 | 3.514E-08 |
| 104 | FLJ34208_B | 0.8806 | 18.98 | 0.00001492 |
| 105 | FLJ42875 | 0.7838 | 6.465 | 0.003577 |
| 106 | FLJ45983_A | 0.7812 | 8.717 | 0.00002707 |
| 107 | FLJ45983_B | 0.8699 | 10.64 | 0.000005396 |
| 108 | FOXE1 | 0.7639 | 6.357 | 0.00338 |
| 109 | FZD2 | 0.7083 | 99.24 | 0.009477 |
| 110 | GAPDHS | 0.7667 | 29.01 | 0.003253 |
| 111 | GATA2 | 0.9833 | 6.062 | 2.356E-08 |
| 112 | GBGT1 | 0.8567 | 28.95 | 0.0005991 |
| 113 | GDF7 | 0.8433 | 34.55 | 0.00002293 |
| 114 | GFI1_A | 0.8147 | 4.787 | 6.398E-07 |
| 115 | GFI1_B | 0.9367 | 13.76 | 0.000001453 |
| 116 | GJA4 | 0.8067 | 51.6 | 0.002206 |
| 117 | GOLGA8A_A | 0.67 | 7.573 | 0.0004803 |
| 118 | GOLGA8A_B | 0.6853 | 8.917 | 0.003308 |
| 119 | GP5 | 0.8941 | 13.92 | 0.000009619 |
| 120 | GPR144 | 0.8 | 21.8 | 0.001782 |
| 121 | GPRIN1_A | 1 | 56.59 | 1.866E-07 |
| 122 | GSX1 | 0.6926 | 4.784 | 0.002045 |
| 123 | GYPC_A | 1 | 46.94 | 1.207E-08 |
| 124 | GYPC_B | 0.9598 | 25.93 | 0.000000743 |
| 125 | HAAO | 0.6875 | 14.23 | 0.00987 |
| 126 | HCG4P6_A | 0.8559 | 19.03 | 0.00004768 |
| 127 | HCG4P6_B | 0.8643 | 53.23 | 0.00001682 |
| 128 | HDGFRP3 | 0.9083 | 264.6 | 0.005772 |
| 129 | HIC1_A | 0.82 | 15.78 | 0.008269 |
| 130 | HIC1_B | 0.84 | 8.745 | 0.009024 |
| 131 | HIST1H2BE | 0.7583 | 20.23 | 0.0003459 |
| 132 | HIST1H3G | 0.7559 | 8.885 | 0.0008868 |
| 133 | HMX3 | 0.7765 | 5.382 | 0.001231 |
| 134 | HOPX | 0.8279 | 6.978 | 0.0002184 |
| 135 | HOXA6 | 0.8745 | 8.803 | 0.00222 |

TABLE 1B-continued

| DMR No. | Gene Annotation | Area Under Curve | Fold-Change | p-value |
|---|---|---|---|---|
| 136 | HOXA7 | 0.7235 | 7.266 | 0.0001254 |
| 137 | HOXB3 | 0.8792 | 255.3 | 0.0009786 |
| 138 | HPDL | 0.7867 | 7.105 | 0.00005945 |
| 139 | HPSE2 | 0.67 | 9.805 | 0.005669 |
| 140 | HRH2 | 0.9333 | 11.87 | 5.858E-10 |
| 141 | ICAM4 | 0.8625 | 7.528 | 0.00002389 |
| 142 | IGFBP7 | 0.7639 | 16.19 | 0.002099 |
| 143 | IKZF1 | 0.7735 | 6.009 | 0.007191 |
| 144 | IL17C_A | 0.6574 | 10.14 | 0.006494 |
| 145 | IL17C_B | 0.7647 | 42.2 | 0.009096 |
| 146 | INA_A | 0.9933 | 11.07 | 0.000002026 |
| 147 | IRAK2 | 0.6632 | 16.61 | 0.00237 |
| 148 | IRF4_A | 0.8309 | 27.17 | 0.00009321 |
| 149 | IRF4_B | 0.9765 | 36.51 | 9.513E-07 |
| 150 | IRF4_C | 0.9824 | 25.5 | 0.000017 |
| 151 | IRF4_D | 0.7324 | 9.383 | 0.008479 |
| 152 | IRF4_E | 0.7456 | 8.068 | 0.002086 |
| 153 | ITGA4_A | 0.95 | 23.1 | 0.000003344 |
| 154 | ITGA4_B | 0.9917 | 17.91 | 0.000001087 |
| 155 | ITGA5 | 0.8375 | 9.488 | 0.00007725 |
| 156 | ITGB2 | 0.7306 | 4.286 | 0.001626 |
| 157 | ITPKB_A | 0.7167 | 15.83 | 0.002895 |
| 158 | ITPRIPL1 | 0.6567 | 8.02 | 0.004609 |
| 159 | JAK3_A | 0.8441 | 37.73 | 0.00007119 |
| 160 | JAM3_A | 0.8117 | 9.335 | 0.00002176 |
| 161 | JSRP1 | 0.8533 | 30 | 0.0000128 |
| 162 | KCNA1_A | 0.8456 | 18.55 | 0.00002068 |
| 163 | KCNA1_B | 0.9222 | 27.8 | 0.00001255 |
| 164 | KCNA3_A | 1 | 11.77 | 0.000000026 |
| 165 | KCNA3_B | 0.975 | 14.21 | 4.593E-08 |
| 166 | KCNA3_C | 1 | 27.74 | 0.000000133 |
| 167 | KCNA3_D | 0.6778 | 14.56 | 0.002861 |
| 168 | KCNK12 | 0.8233 | 13.36 | 0.0001527 |
| 169 | KCNK4 | 0.8412 | 10.95 | 0.001631 |
| 170 | KCNK9_A | 0.6967 | 9.458 | 0.0009651 |
| 171 | KCNK9_B | 0.6833 | 11.69 | 0.008939 |
| 172 | KCNK9_C | 0.7833 | 13.34 | 0.00008646 |
| 173 | KCNQ5_A | 0.9206 | 36.2 | 0.0002181 |
| 174 | KCNQ5_B | 0.8278 | 29.53 | 0.002382 |
| 175 | KCNQ5_C | 0.9853 | 25.67 | 0.0002584 |
| 176 | KCTD15 | 0.93 | 75.32 | 0.005265 |
| 177 | KIAA1383 | 0.6639 | 13.01 | 0.0003342 |
| 178 | KL | 0.7471 | 5.618 | 0.00007553 |
| 179 | KLF16 | 0.8867 | 43.9 | 0.0002147 |
| 180 | KLHL21 | 0.7042 | 14.21 | 0.000305 |
| 181 | LAPTM4B | 0.6667 | 93190000 | 0.9955 |
| 182 | LBH | 1 | 158.1 | 0.0000823 |
| 183 | LCNL1 | 0.8204 | 13.69 | 0.0005437 |
| 184 | LIME1_A | 0.99 | 53.73 | 1.862E-08 |
| 185 | LIME1_B | 1 | 80.14 | 8.084E-07 |
| 186 | LIMK1 | 0.9118 | 13.08 | 0.00005383 |
| 187 | LMX1B | 0.8667 | 17.28 | 0.0004894 |
| 188 | LOC100132891 | 0.7319 | 7.814 | 0.001522 |
| 189 | LOC151174 | 0.7324 | 10.59 | 0.00003981 |
| 190 | LOC339674 | 0.7029 | 12.95 | 0.00007156 |
| 191 | LOC440461 | 0.6633 | 10.07 | 0.005412 |
| 192 | LOC646278 | 1 | 13.65 | 3.871E-08 |
| 193 | LOC648809 | 0.6633 | 8.992 | 0.0002679 |
| 194 | LPHN1 | 0.8982 | 18.43 | 0.00004102 |
| 195 | LRRC10B | 0.8 | 5.359 | 0.000004834 |
| 196 | LRRC32 | 0.7412 | 11.54 | 0.0002366 |
| 197 | LRRC4 | 1 | 177.2 | 0.0002576 |
| 198 | LRRC41_A | 1 | 189.9 | 0.000006696 |
| 199 | LRRC41_B | 0.9233 | 331.1 | 0.00001455 |
| 200 | LRRC8D | 0.67 | 3.422 | 0.006004 |
| 201 | LTB | 0.8132 | 3.637 | 0.000402 |
| 202 | LTK | 0.8033 | 8.959 | 0.00003262 |
| 203 | LY75 | 0.7556 | 7.301 | 0.002031 |
| 204 | MAML3_A | 0.9583 | 14.34 | 5.424E-08 |
| 205 | MAX.chr1.110626771-110626832 | 1 | 36.78 | 1.847E-07 |
| 206 | MAX.chr1.147775386-147775483 | 0.7286 | 39.08 | 0.001102 |
| 207 | MAX.chr1.147790358-147790381 | 0.9917 | 21.51 | 5.145E-07 |
| 208 | MAX.chr1.148598377-148598471 | 0.6559 | 8.982 | 0.008606 |
| 209 | MAX.chr1.161591532-161591608 | 1 | 17.5 | 1.128E-07 |
| 210 | MAX.chr1.21917279-21917313 | 0.8778 | 9.553 | 0.00001685 |
| 211 | MAX.chr1.2472236-2472504 | 0.92 | 18.64 | 0.0004799 |
| 212 | MAX.chr1.2472508-2472586 | 0.8267 | 26.72 | 0.002689 |

TABLE 1B-continued

| DMR No. | Gene Annotation | Area Under Curve | Fold-Change | p-value |
|---|---|---|---|---|
| 213 | MAX.chr1.32237654-32237674 | 0.7542 | 7.453 | 0.0004997 |
| 214 | MAX.chr1.32238032-32238105 | 0.7778 | 16.66 | 0.0007896 |
| 215 | MAX.chr1.32238359-32238419 | 0.7056 | 9.275 | 0.004603 |
| 216 | MAX.chr1.32410292-32410428 | 0.7118 | 10.9 | 0.009478 |
| 217 | MAX.chr1.46632623-46632858 | 0.8533 | 34.46 | 0.00004827 |
| 218 | MAX.chr1.48058986-48059074 | 0.9 | 12.01 | 2.751E−08 |
| 219 | MAX.chr1.98510937-98511077 | 0.8412 | 11.62 | 0.00001779 |
| 220 | MAX.chr1.98511049-98511077 | 0.6833 | 17.37 | 0.002974 |
| 221 | MAX.chr1.98519485-98519592 | 0.6517 | 28.32 | 0.001259 |
| 222 | MAX.chr10.22541609-22541719 | 0.675 | 8.215 | 0.00122 |
| 223 | MAX.chr10.22541684-22541719 | 0.7083 | 4.839 | 0.004316 |
| 224 | MAX.chr10.22541986-22542037 | 0.91 | 12.16 | 5.242E−07 |
| 225 | MAX.chr10.22765282-22765351 | 0.84 | 14.52 | 0.0001487 |
| 226 | MAX.chr11.14926602-14926671 | 0.8467 | 12.76 | 0.000004841 |
| 227 | MAX.chr11.14926840-14926955 | 0.97 | 16.98 | 9.164E−09 |
| 228 | MAX.chr11.45376949-45377082 | 0.9517 | 115.3 | 0.000004361 |
| 229 | MAX.chr11.45376949-45377204 | 0.9221 | 46.27 | 0.0003883 |
| 230 | MAX.chr11.57250516-57250847 | 0.9333 | 80.85 | 0.000003486 |
| 231 | MAX.chr12.29302564-29302695 | 0.7338 | 10.06 | 0.0000429 |
| 232 | MAX.chr12.30975740-30975780 | 0.8861 | 13.36 | 2.012E−07 |
| 233 | MAX.chr12.4273826-4274239 | 0.8647 | 69 | 0.0002053 |
| 234 | MAX.chr14.100784600-100784781 | 0.7847 | 31.75 | 0.0008823 |
| 235 | MAX.chr14.103557836-103558188 | 0.73 | 45.31 | 0.002456 |
| 236 | MAX.chr14.105512178-105512224 | 0.9367 | 7.222 | 0.00002564 |
| 237 | MAX.chr14.60386315-60386417 | 0.8817 | 35.08 | 0.00287 |
| 238 | MAX.chr14.97685168-97685437 | 0.85 | 12.5 | 0.00002023 |
| 239 | MAX.chr14.97685552-97685839 | 0.8786 | 14.81 | 3.795E−08 |
| 240 | MAX.chr15.28351937-28352173 | 0.9917 | 147.2 | 0.0002627 |
| 241 | MAX.chr15.28352203-28352671 | 1 | 67.39 | 0.00005411 |
| 242 | MAX.chr15.29131258-29131734 | 1 | 86.77 | 0.000000195 |
| 243 | MAX.chr15.31685160-31685245 | 0.7407 | 21.19 | 0.005291 |
| 244 | MAX.chr15.65186050-65186150 | 0.8853 | 10.04 | 0.00008134 |
| 245 | MAX.chr15.74891008-74891138 | 0.7267 | 10.41 | 0.006328 |
| 246 | MAX.chr15.75471061-75471202 | 0.8929 | 21.23 | 0.001064 |
| 247 | MAX.chr16.50875166-50875262 | 0.7059 | 7.995 | 0.0008048 |
| 248 | MAX.chr16.50875166-50875301 | 0.765 | 5.509 | 0.00009394 |
| 249 | MAX.chr17.37366022-37366321 | 0.84 | 61.52 | 0.00969 |
| 250 | MAX.chr19.2273768-2273823 | 0.6931 | 9.226 | 0.0002203 |
| 251 | MAX.chr19.30716607-30716756 | 0.9324 | 30.77 | 0.001229 |
| 252 | MAX.chr19.37288390-37288811 | 0.7971 | 68.63 | 0.007985 |
| 253 | MAX.chr19.42444222-42444334 | 0.8767 | 19.68 | 0.0007796 |
| 254 | MAX.chr19.55962661-55962773 | 0.8633 | 13.64 | 0.002362 |
| 255 | MAX.chr19.5828277-5828498 | 0.6412 | 53.01 | 0.0001286 |
| 256 | MAX.chr2.118981858-118981934 | 0.8467 | 9.919 | 0.0002715 |
| 257 | MAX.chr2.118982007-118982089 | 0.89 | 12.5 | 0.000007672 |
| 258 | MAX.chr2.119067767-119068112 | 0.9267 | 9.924 | 2.498E−07 |
| 259 | MAX.chr2.127783351-127783403 | 0.6853 | 16.1 | 0.006544 |
| 260 | MAX.chr2.175191004-175191127 | 0.68 | 5.084 | 0.002279 |
| 261 | MAX.chr2.241855537-241855585 | 0.8319 | 5.466 | 0.00001195 |
| 262 | MAX.chr2.25438959-25439001 | 0.7361 | 8.401 | 0.0003554 |
| 263 | MAX.chr2.25439173-25439276 | 0.655 | 15.85 | 0.006701 |
| 264 | MAX.chr2.66653544-66653582 | 0.8724 | 16.31 | 0.0003529 |
| 265 | MAX.chr2.66653881-66653935 | 0.9062 | 16.45 | 0.00002628 |
| 266 | MAX.chr2.97193155-97193524 | 0.6764 | 11.81 | 0.009997 |
| 267 | MAX.chr2.97193478-97193562 | 0.8819 | 15.24 | 0.0000772 |
| 268 | MAX.chr20.30175888-30175927 | 0.9333 | 13.48 | 0.000008072 |
| 269 | MAX.chr20.3073377-3073486 | 0.7567 | 5.665 | 0.0006037 |
| 270 | MAX.chr20.49308029-49308083 | 0.8719 | 20.88 | 0.0003897 |
| 271 | MAX.chr3.107148795-107148869 | 0.7569 | 46.05 | 0.004906 |
| 272 | MAX.chr3.128274281-128274519 | 0.9133 | 16.16 | 0.000007595 |
| 273 | MAX.chr3.138679378-138679414 | 0.8667 | 29.07 | 0.000004821 |
| 274 | MAX.chr3.18485437-18485723 | 0.8533 | 20.2 | 0.0001419 |
| 275 | MAX.chr3.186490624-186490778 | 0.6733 | 8.495 | 0.009519 |
| 276 | MAX.chr3.69591053-69591097 | 0.9518 | 21.05 | 0.00000792 |
| 277 | MAX.chr4.174430671-174430719 | 0.9441 | 13.81 | 5.443E−08 |
| 278 | MAX.chr4.174430751-174430776 | 0.6694 | 9.455 | 0.001239 |
| 279 | MAX.chr4.41869404-41869433 | 0.8639 | 8.957 | 7.459E−07 |
| 280 | MAX.chr4.8859707-8859944 | 0.9304 | 11.03 | 0.00001052 |
| 281 | MAX.chr4.8859995-8860062 | 1 | 15.92 | 6.853E−09 |
| 282 | MAX.chr4.8860076-8860122 | 0.725 | 7.894 | 0.0001833 |
| 283 | MAX.chr5.178957539-178957851 | 0.7267 | 9.425 | 0.0001272 |
| 284 | MAX.chr5.2038771-2038990 | 0.9 | 28.04 | 7.505E−07 |
| 285 | MAX.chr5.42951482-42951568 | 0.8983 | 8.985 | 7.898E−07 |
| 286 | MAX.chr5.42952182-42952292 | 1 | 12.51 | 7.848E−09 |
| 287 | MAX.chr6.10382190-10382225 | 0.9412 | 17.5 | 7.771E−10 |
| 288 | MAX.chr6.108440553-108440720 | 0.8866 | 13.62 | 0.00004107 |
| 289 | MAX.chr6.157557273-157557374 | 0.8583 | 9.341 | 0.00009311 |

TABLE 1B-continued

| DMR No. | Gene Annotation | Area Under Curve | Fold-Change | p-value |
|---|---|---|---|---|
| 290 | MAX.chr6.28175549-28175579 | 0.9 | 8.988 | 0.00002146 |
| 291 | MAX.chr6.42738979-42739055 | 0.7807 | 11.24 | 0.0006332 |
| 292 | MAX.chr7.127744282-127744490 | 0.65 | 11.98 | 0.0001731 |
| 293 | MAX.chr7.142494643-142495353 | 0.9433 | 45.64 | 0.0005619 |
| 294 | MAX.chr7.1706293-1706418 | 0.8485 | 5.619 | 0.0001293 |
| 295 | MAX.chr7.99595234-99595474 | 0.6667 | 8.374 | 0.0001195 |
| 296 | MAX.chr8.124173231-124173268 | 0.7722 | 4.552 | 0.001168 |
| 297 | MAX.chr8.142215938-142216298 | 0.9567 | 87.27 | 3.469E-07 |
| 298 | MAX.chr8.145103855-145103943 | 0.6882 | 6.976 | 0.007105 |
| 299 | MAX.chr8.145104058-145104455 | 0.9267 | 50.22 | 0.001557 |
| 300 | MAX.chr8.145105537-145105891 | 0.8777 | 20.95 | 0.003006 |
| 301 | MAX.chr8.145105977-145106067 | 0.9196 | 18.25 | 0.0001214 |
| 302 | MAX.chr8.6658405-6658443 | 0.6833 | 6.011 | 0.003327 |
| 303 | MAX.chr8.688047-688103 | 0.8817 | 28 | 0.001064 |
| 304 | MAX.chr9.113594-113689 | 0.8971 | 5.339 | 0.00004707 |
| 305 | MAX.chr9.129485515-129485818 | 0.9133 | 106 | 0.006038 |
| 306 | MDFI | 1 | 73.57 | 0.000004885 |
| 307 | MFSD2B | 0.7933 | 37.02 | 0.001475 |
| 308 | MGC16275 | 0.9333 | 10.26 | 0.00006057 |
| 309 | MPZ | 0.8417 | 23.23 | 0.0005555 |
| 310 | MSX2 | 0.7639 | 5.593 | 0.0001681 |
| 311 | MT1A_A | 0.7678 | 10.91 | 0.0000658 |
| 312 | MT1A_B | 0.9339 | 12.34 | 0.000001177 |
| 313 | MYO15B_A | 0.93 | 43.36 | 0.0001431 |
| 314 | MYO15B_B | 0.8433 | 17.27 | 0.003642 |
| 315 | MYO15B_C | 0.9 | 14.9 | 0.007671 |
| 316 | MYOZ3 | 0.7912 | 5.008 | 0.0001528 |
| 317 | NBPF3 | 0.6706 | 8.853 | 0.005487 |
| 318 | NCOR2 | 0.9955 | 38.93 | 2.476E-10 |
| 319 | NEFL | 0.8825 | 25.46 | 0.0006411 |
| 320 | NFATC1 | 0.82 | 8.974 | 0.0003065 |
| 321 | NFATC4 | 0.91 | 22.36 | 0.006938 |
| 322 | NFIC_A | 0.96 | 27.22 | 0.000488 |
| 323 | NFIC_B | 0.9367 | 84.11 | 0.00185 |
| 324 | NFIC_C | 0.6972 | 32.63 | 0.0001043 |
| 325 | NFIX | 0.8234 | 14.95 | 0.00007753 |
| 326 | NID2 | 0.9278 | 7.711 | 3.206E-07 |
| 327 | NKX2-3 | 0.8579 | 8.629 | 0.00000336 |
| 328 | NKX2-6 | 1 | 14.31 | 9.91E-11 |
| 329 | NR2F6 | 0.9417 | 67.65 | 0.0001251 |
| 330 | NRTN | 0.6997 | 89.44 | 0.002364 |
| 331 | NTN1 | 0.6676 | 21.88 | 0.0001142 |
| 332 | NTRK3_A | 0.8553 | 31.75 | 0.005009 |
| 333 | NTRK3_B | 0.9529 | 39.83 | 0.003353 |
| 334 | OBSCN | 0.7347 | 35.22 | 0.002406 |
| 335 | OLIG1 | 0.6767 | 6.84 | 0.003567 |
| 336 | OLIG2 | 0.9107 | 11.58 | 0.000001446 |
| 337 | OPLAH_A | 0.9917 | 15.82 | 0.000007607 |
| 338 | OPLAH_B | 0.9235 | 29.03 | 0.0001982 |
| 339 | OPRL1 | 0.8317 | 6.596 | 0.0004722 |
| 340 | OSR2 | 0.6176 | 5.538 | 0.003435 |
| 341 | OXT_A | 0.9233 | 17.05 | 0.000002882 |
| 342 | OXT_B | 0.9467 | 63.26 | 0.0002042 |
| 343 | PALLD | 0.9656 | 19.54 | 1.219E-10 |
| 344 | PALM3 | 0.88 | 168.5 | 0.006656 |
| 345 | PARP15 | 1 | 62.6 | 1.898E-08 |
| 346 | PAX6 | 0.8728 | 9.994 | 0.000000247 |
| 347 | PDE6B | 0.9118 | 19.01 | 0.00001524 |
| 348 | PDE10A | 1 | 45.15 | 0.000009912 |
| 349 | PDX1 | 0.9167 | 30.83 | 0.0000925 |
| 350 | PEAR1_A | 0.8786 | 6.704 | 0.00007155 |
| 351 | PIF1 | 0.9633 | 13.9 | 1.939E-09 |
| 352 | PIP5KL1 | 0.6933 | 6.343 | 0.008768 |
| 353 | PISD | 0.93 | 465.4 | 0.03728 |
| 354 | PLEKHA6 | 0.9393 | 21.27 | 0.000001155 |
| 355 | PLEKHO1 | 0.7567 | 4.877 | 0.008098 |
| 356 | PLXNC1 | 0.8162 | 7.564 | 0.0006475 |
| 357 | PNMAL2 | 0.6574 | 9.419 | 0.001336 |
| 358 | PPFIA4_A | 0.9054 | 22.96 | 0.000005626 |
| 359 | PPP1R16B | 1 | 16.73 | 9.679E-10 |
| 360 | PRDM14 | 0.9295 | 13.12 | 0.000002319 |
| 361 | PRKAG2 | 0.7722 | 31.49 | 0.00008639 |
| 362 | PRKAR1B_A | 0.8972 | 25.88 | 0.00003686 |
| 363 | PRKCB_A | 0.7706 | 8.209 | 0.0002441 |
| 364 | PRKCB_B | 0.9167 | 7.564 | 0.00003846 |
| 365 | PRKCB_C | 0.7508 | 8.802 | 0.0003597 |
| 366 | PRKCB_D | 0.8279 | 10.52 | 0.000001553 |

TABLE 1B-continued

| DMR No. | Gene Annotation | Area Under Curve | Fold-Change | p-value |
|---|---|---|---|---|
| 367 | PROCA1 | 0.8706 | 27.19 | 0.00001691 |
| 368 | PROKR2 | 0.7088 | 16.37 | 0.00005348 |
| 369 | PTGDR | 0.875 | 15.13 | 0.000001258 |
| 370 | PTP4A3__A | 0.6389 | 81100000 | 0.9931 |
| 371 | PTP4A3__B | 0.95 | 19.27 | 0.000007774 |
| 372 | PTPRS | 0.8556 | 15.35 | 0.000009913 |
| 373 | PTPRU | 0.8433 | 19.24 | 0.001639 |
| 374 | PYCARD | 0.9833 | 66.56 | 0.0002255 |
| 375 | RAI1__A | 0.87 | 114 | 0.000005652 |
| 376 | RAI1__B | 0.955 | 163.4 | 0.00001528 |
| 377 | RASGEF1A | 0.83 | 17.9 | 0.0001497 |
| 378 | RASSF1__A | 0.9833 | 41.85 | 0.000002522 |
| 379 | RASSF1__B | 0.9933 | 24.8 | 9.235E−09 |
| 380 | RBFOX3 | 0.7681 | 7.262 | 0.00104 |
| 381 | RET | 0.7838 | 9.604 | 0.0004724 |
| 382 | RFTN1__A | 0.8389 | 18.25 | 0.0002672 |
| 383 | RILPL2 | 0.9083 | 89.71 | 0.0009295 |
| 384 | RNF220 | 0.9364 | 7.609 | 7.141E−07 |
| 385 | RTN4RL2 | 0.7183 | 12.52 | 0.004958 |
| 386 | RUNX3 | 0.805 | 10.17 | 0.0007233 |
| 387 | SALL3 | 0.8309 | 27.66 | 0.0005659 |
| 388 | SCGB3A1 | 0.8042 | 14.23 | 0.00007877 |
| 389 | SEPTIN9 | 0.9933 | 87.79 | 0.0007871 |
| 390 | SFMBT2__A | 0.7353 | 17.61 | 0.00299 |
| 391 | SFMBT2__B | 0.7681 | 30.47 | 0.002173 |
| 392 | SFMBT2__C | 0.9133 | 36.08 | 0.00007163 |
| 393 | SH2B3 | 0.9868 | 17.79 | 0.00003501 |
| 394 | SH3PXD2A | 0.7603 | 12.73 | 0.006045 |
| 395 | SHH__A | 0.7933 | 86.22 | 0.0009818 |
| 396 | SHH__B | 0.725 | 17.6 | 0.004096 |
| 397 | SIM2__A | 0.9152 | 14.67 | 1.523E−07 |
| 398 | SKI | 1 | 79.27 | 1.098E−07 |
| 399 | SLC12A8 | 1 | 77.66 | 3.571E−08 |
| 400 | SLC25A47 | 0.9733 | 66.69 | 0.001407 |
| 401 | SLC4A11 | 0.8833 | 13.13 | 0.0001207 |
| 402 | SLC5A5__A | 0.8767 | 9.298 | 0.000003536 |
| 403 | SLC5A5__B | 0.7767 | 9.372 | 0.002392 |
| 404 | SLC8A3 | 0.9353 | 38.43 | 0.0001207 |
| 405 | SLFN12L | 0.8421 | 43.3 | 0.0001534 |
| 406 | SMTN | 0.91 | 16.65 | 0.00177 |
| 407 | SOBP__A | 0.9333 | 8.568 | 4.472E−08 |
| 408 | SP9 | 0.6676 | 3.771 | 0.0008535 |
| 409 | SPATA18 | 0.6833 | 11.52 | 0.0003341 |
| 410 | SPDYA | 0.8324 | 22.84 | 0.000003646 |
| 411 | SPEF1 | 0.81 | 44.2 | 0.001272 |
| 412 | SPOCK2__A | 0.9467 | 56.14 | 0.0001242 |
| 413 | SPOCK2__B | 0.9733 | 18.93 | 0.00001608 |
| 414 | SPON2__A | 0.8333 | 9.385 | 0.00001783 |
| 415 | SPON2__B | 0.8667 | 7.556 | 0.000009146 |
| 416 | SRC__A | 0.9933 | 364.7 | 0.002044 |
| 417 | SSBP4__A | 0.9433 | 12.18 | 2.734E−09 |
| 418 | SSBP4__B | 0.99 | 33.82 | 4.907E−10 |
| 419 | SSBP4__C | 0.9404 | 17.04 | 2.022E−08 |
| 420 | ST8SIA1 | 0.9917 | 34.46 | 2.652E−09 |
| 421 | STX16 | 0.8735 | 25.58 | 0.0002471 |
| 422 | TACC1 | 0.9583 | 30.34 | 0.00001213 |
| 423 | TACC2__A | 1 | 217.2 | 0.0003304 |
| 424 | TBKBP1 | 0.94 | 35.27 | 2.28E−10 |
| 425 | TBX20 | 0.93 | 28.72 | 0.00199 |
| 426 | TCF3 | 0.9267 | 18.76 | 0.000004029 |
| 427 | TEAD3 | 0.8633 | 11.71 | 0.00002807 |
| 428 | TET2 | 0.7778 | 5.054 | 0.0006353 |
| 429 | TGFB1 | 0.8917 | 17.59 | 0.0006773 |
| 430 | TJP2 | 0.9765 | 56.47 | 0.002008 |
| 431 | TMC4 | 0.6667 | 5.203 | 0.004701 |
| 432 | TMC6 | 0.89 | 8.028 | 0.0002984 |
| 433 | TMEFF2 | 0.7735 | 7.797 | 0.0001361 |
| 434 | TMEM101 | 0.93 | 51.4 | 0.00001231 |
| 435 | TMEM106A | 0.7417 | 14.14 | 0.0004017 |
| 436 | TNFRSF10C | 0.6647 | 7.404 | 0.001976 |
| 437 | TNFRSF8 | 0.678 | 14.86 | 0.002477 |
| 438 | TRIM15 | 0.9737 | 25.3 | 0.00002151 |
| 439 | TRIM71 | 0.6912 | 17.62 | 0.004034 |
| 440 | TRIM9__A | 0.7867 | 9.348 | 0.00001029 |
| 441 | TRIM9__B | 0.9412 | 7.746 | 0.000001165 |
| 442 | TRPV2 | 0.7983 | 5.552 | 0.001986 |
| 443 | TSC22D4 | 0.8667 | 45.25 | 0.0002631 |

TABLE 1B-continued

| DMR No. | Gene Annotation | Area Under Curve | Fold-Change | p-value |
|---|---|---|---|---|
| 444 | TSHZ3 | 1 | 330.4 | 0.002852 |
| 445 | TSPY26P | 0.72 | 13.24 | 0.005337 |
| 446 | TXNRD1 | 0.7779 | 29.56 | 0.00005732 |
| 447 | UBTF | 0.99 | 37.3 | 1.175E-07 |
| 448 | ULBP1 | 0.9567 | 21.94 | 0.000001494 |
| 449 | UST | 0.96 | 73.73 | 0.0009294 |
| 450 | VASP | 0.8167 | 25.26 | 0.007948 |
| 451 | VILL | 0.8324 | 26.28 | 0.003267 |
| 452 | VIM | 1 | 128.6 | 3.678E-07 |
| 453 | VIPR2__A | 1 | 49.5 | 0.000003125 |
| 454 | WNT7B | 0.83 | 113.3 | 0.0002042 |
| 455 | XKR6 | 0.7162 | 13.39 | 0.006601 |
| 456 | XYLT1 | 0.7765 | 5.564 | 0.000001447 |
| 457 | ZBED4 | 1 | 33.68 | 0.00003722 |
| 458 | ZEB2__A | 0.9386 | 59.23 | 0.004218 |
| 459 | ZEB2__B | 0.8833 | 17.62 | 0.0001426 |
| 460 | ZFP3 | 0.865 | 94.31 | 0.003443 |
| 461 | ZMIZ1__A | 1 | 43.45 | 2.878E-07 |
| 462 | ZMIZ1__B | 1 | 307.9 | 3.498E-09 |
| 463 | ZMIZ1__C | 1 | 297.4 | 2.396E-09 |
| 464 | ZNF132 | 0.8867 | 56.31 | 0.000001664 |
| 465 | ZNF382__A | 1 | 86.86 | 1.14E-09 |
| 466 | ZNF469__A | 0.9833 | 24.13 | 0.0001099 |
| 467 | ZNF469__B | 1 | 15.78 | 0.000000149 |
| 468 | ZNF703 | 0.98 | 66.04 | 0.005629 |
| 469 | ZNF781 | 0.7191 | 40.16 | 0.0009516 |
| 470 | ZSCAN12 | 0.7426 | 50.98 | 0.009365 |
| 471 | ZSCAN23 | 0.7309 | 26.36 | 0.0004899 |
| 472 | ATP6V1B1__A | 0.999 | 169.2 | 0.003 |
| 473 | ATP6V1B1__B | 0.984 | 116.5 | 0.002 |
| 474 | BANK1 | 0.813 | 10.77 | 0.048 |
| 475 | BCL2L11 | 0.979 | 63.01 | 0.003 |
| 476 | BZRAP1 | 0.994 | 77.62 | 0.00001416 |
| 477 | C17orf64__C | 0.983 | 101.6 | 0.009 |
| 478 | C19orf35__C | 0.951 | 40.84 | 0.007 |
| 479 | C2CD4D | 0.982 | 103.7 | 3E-04 |
| 480 | CCDC88C | 0.965 | 124.5 | 0.005 |
| 481 | TRIM9__C | 0.956 | 32.22 | 0.01 |
| 482 | CORO1A | 0.958 | 33.47 | 0.002 |
| 483 | DNMT3A__B | 0.958 | 44.81 | 0.004 |
| 484 | DNMT3A__C | 0.987 | 57.07 | 0.002 |
| 485 | FAM189B | 0.982 | 41.54 | 0.002 |
| 486 | FCHO1 | 0.979 | 54.92 | 0.002 |
| 487 | FXYD5 | 0.963 | 43.45 | 7E-04 |
| 488 | GDF6 | 1 | 80.2 | 0.003 |
| 489 | GMDS | 0.967 | 91.6 | 0.01 |
| 490 | IFFO1__A | 0.999 | 285.5 | 1E-03 |
| 491 | IFFO1__B | 0.998 | 164.8 | 1E-04 |
| 492 | INA__B | 0.969 | 38.89 | 0.004 |
| 493 | ITPKB__B | 0.978 | 207.9 | 0.00002857 |
| 494 | ITPKB__C | 0.981 | 97.94 | 0.006 |
| 495 | JAK3__B | 0.981 | 41.07 | 0.002 |
| 496 | KANK3 | 0.984 | 41.48 | 0.002 |
| 497 | KCNAB2 | 0.991 | 50.86 | 0.003 |
| 498 | LIMD2 | 0.992 | 153.6 | 6E-04 |
| 499 | MAML3__B | 0.991 | 39.57 | 0.002 |
| 500 | MAX.chr1.9689803-9690241 | 0.984 | 86.99 | 0.00001809 |
| 501 | MAX.chr10.101300125-101300155 | 0.962 | 30.08 | 0.002 |
| 502 | MAX.chr11.14926756-14927227 | 0.97 | 64.79 | 0.004 |
| 503 | MAX.chr12.30975740-30975961 | 0.966 | 71.51 | 0.004 |
| 504 | MAX.chr14.102172350-102172770 | 0.998 | 60.04 | 0.003 |
| 505 | MAX.chr16.85482307-85482494 | 1 | 110.5 | 0.001 |
| 506 | MAX.chr17.76254728-76254841 | 0.998 | 79.79 | 0.003 |
| 507 | MAX.chr20.56008090-56008227 | 0.973 | 62.96 | 8E-04 |
| 508 | MAX.chr4.174430662-174430790 | 0.963 | 90.75 | 0.009 |
| 509 | MAX.chr5.42993898-42994179 | 0.999 | 103.2 | 0.000006147 |
| 510 | MAX.chr6.1379890-1379965 | 0.964 | 42.04 | 0.002 |
| 511 | MAX.chr7.2569526-2569650 | 0.983 | 40.92 | 0.004 |
| 512 | MAX.chr8.124173112-124173541 | 0.966 | 54.57 | 0.003 |
| 513 | PPFIA4__B | 0.969 | 56.41 | 5E-04 |
| 514 | PPFIA4__C | 0.961 | 54.65 | 0.002 |
| 515 | PRKAR1B__B | 0.981 | 110.1 | 0.004 |
| 516 | PRKAR1B__C | 0.953 | 73.58 | 0.004 |
| 517 | PTGER4__A | 0.965 | 66.17 | 0.006 |
| 518 | PTGER4__B | 0.983 | 75.21 | 0.004 |
| 519 | PTPRCAP | 0.985 | 80.48 | 2E-04 |
| 520 | RASAL3 | 0.995 | 115.7 | 0.00001693 |

TABLE 1B-continued

| DMR No. | Gene Annotation | Area Under Curve | Fold-Change | p-value |
|---|---|---|---|---|
| 521 | RASSF1_C | 0.984 | 106.3 | 0.009 |
| 522 | RUNX1 | 0.987 | 152.2 | 0.007 |
| 523 | SLC29A4 | 0.96 | 45.59 | 0.001 |
| 524 | SLC35D3 | 0.961 | 56.18 | 0.003 |
| 525 | SOBP_B | 0.98 | 61.02 | 0.002 |

TABLE 1C

| DMR # | Name | 5'-3' Sequence (hg19) | SEQ ID NO. |
|---|---|---|---|
| 318 | NCOR2 | Forward: GAGGAGTTTTAATATTTTTATAGCGG | 1 |
| 318 | NCOR2 | Reverse: AACAAACTTCAATAAACCCGACGCA | 2 |
| 343 | PALLD | Forward: GGCGACGGCGAGGAGGAGTTTTAC | 3 |
| 343 | PALLD | Reverse: GCAACCCTTCGACGCTAAACCCG | 4 |
| 207 | MAX.chr1.147790358-147790381 | Forward: GATATGTTGTCGGGGTTCGTTACGA | 5 |
| 207 | MAX.chr1.147790358-147790381 | Reverse: CAAAATACCCGATAAACAATCGAA | 6 |
| 287 | MAX.chr6.10382190-10382225 | Forward: CGTTAGTCGTTTTTATTTTTAATTTATCGT | 7 |
| 287 | MAX.chr6.10382190-10382225 | Reverse: CTTCAAAAACTCCAACGCGTC | 8 |
| 354 | PLEKHA6 | Forward: GATTAGATTAGATTCGGAGTTTCGT | 9 |
| 354 | PLEKHA6 | Reverse: ACCAACTAAAATCCTCCTCCCCCGC | 10 |
| 384 | RNF220 | Forward: TAGTTTGGTTAAAGGGTGCGAATTCGA | 11 |
| 384 | RNF220 | Reverse: CGAAACTCTTCCGAACTAAATAATACACCCGCT | 12 |
| 81 | DNMT3A_A | Forward: TTTGTTGGGAGTTCGGGGTTTTATC | 13 |
| 81 | DNMT3A_A | Reverse: AACCTATCCGAAACCTCCCCGTT | 14 |
| 312 | MT1A_B | Forward: TTGCGTATAGGTTAGTTTAGGATCGT | 15 |
| 312 | MT1A_B | Reverse: CTTACACCCGCCCCGCTAAATTCG | 16 |
| 311 | MT1A_A | Forward: TCGTTGGTTATCGTACGTTTTTCGT | 17 |
| 311 | MT1A_A | Reverse: ACTAAACCTATCCCGAAATCCCGAT | 18 |
| 360 | PRDM14 | Forward: GGTTGTTTTTGTAGTGTTTATAGGACGG | 19 |
| 360 | PRDM14 | Reverse: AAAACAAAATATACTACCCGCCGAA | 20 |
| 25 | BCAT1 | Forward: GGGGAGGAGTTTTAATCGTTTCGT | 21 |
| 25 | BCAT1 | Reverse: AAACAACCGCTTCGATTTTAACGAC | 22 |
| 84 | DSCR6 | Forward: CGGTAGGGGAAGTTTAGTAGGTGAGCGT | 23 |
| 84 | DSCR6 | Reverse: GAACTAAAAACGTTTCCGTCGAACGCA | 24 |
| 398 | SKI | Forward: GGTAGTTAGGCGGTTATTACGGGTCGC | 25 |
| 398 | SKI | Reverse: AAAATCTACTCCCTCCCCGAACGCT | 26 |
| 61 | CDO1_A | Forward: CGCGCGTTTTATTGTTGGGTTGC | 27 |
| 61 | CDO1_A | Reverse: AACGAACTATTAAACTCCCTCGCC | 28 |
| 397 | SIM2_A | Forward: GTTAGTAGTTGTTGGGGCGGCGTTC | 29 |
| 397 | SIM2_A | Reverse: AACCCGATACCCCCATTACCGTACG | 30 |
| 185 | LIME1_B | Forward: CGCGTAGTAGTAGGGGTGAGTAGAGGGC | 31 |

TABLE 1C-continued

| DMR # | Name | 5'-3' Sequence (hg19) | SEQ ID NO. |
|---|---|---|---|
| 185 | LIME1_B | Reverse: GAATCTAACCCAAAAATTAACACGCGCT | 32 |
| 63 | CELF2_A | Forward: CGGGATCGGAGTTAGAATTTTTCGT | 33 |
| 63 | CELF2_A | Reverse: ACCTAAACGCCTAACGACCCCCG | 34 |
| 99 | FAIM2_A | Forward: TATTTCGGGGAGGGTTAAGGGCG | 35 |
| 99 | FAIM2_A | Reverse: GCTACGAATTCGCGAACCCGAA | 36 |
| 64 | CELF2_B | Forward: GGGTTGTTTAGAAAGTGATTTTTCGGGAGC | 37 |
| 64 | CELF2_B | Reverse: AAAACCGAAACAAAACGAAAACGCA | 38 |
| 204 | MAML3_A | Forward: TGTTTTTTTATTTTATTTTTAGTTTTTTCGT | 39 |
| 204 | MAML3_A | Reverse: AATTTCTCATTACCGACTTTTCTTCCAACCGAA | 40 |
| 329 | NR2F6 | Forward: GGCGCGTATTTGGTTTATGAAAGTTACGG | 41 |
| 329 | NR2F6 | Reverse: CAAACGACGCTACCCCTACACACGA | 42 |
| 447 | UBTF | Forward: GGCGTTAGTTTTTTATTTATTTTTAGGGGCGC | |
| 447 | UBTF | Reverse: CCAACCCATACTTCTACCCGCCGAC | 44 |
| 398 | SKI | Forward: ACGAAATATTTTTAATTGAGTTCGA | 45 |
| 398 | SKI | Reverse: AAAAAATACGAAACACAAAAACGAC | 46 |
| 131 | HIST1H2BE | Forward: TTGGCGTATTATAATAAGCGTTCGA | 47 |
| 131 | HIST1H2BE | Reverse: GAAAACAACAAACGCACGACCGTC | 48 |
| 164 | KCNA3_A | Forward: ACGTAGTTGAAGATTTTTGTTAGTTTTTCGA | 49 |
| 164 | KCNA3_A | Reverse: ACCTCATACGCCGCTTAAAATCGCC | 50 |
| 345 | PARP15 | Forward: TAGTAGGGTTGAGTTTGGGGTTCGT | 51 |
| 345 | PARP15 | Reverse: GTAAAATCTCTACGCCCGCTCGAA | 52 |
| 50 | CAPN2_A | Forward: CGTTCGAGTTGCGAAAGGGACGT | 53 |
| 50 | CAPN2_A | Reverse: GCACTCCTAAAATTCCGCGCGAA | 54 |
| 334 | OBSCN | Forward: GGTAAAATTTACGTTGTGTAGAATTAGGCGG | 55 |
| 334 | OBSCN | Reverse: ACGTAAAATCCACGCCGAAAACGC | 56 |
| 399 | SLC12A8 | Forward: TTATTTTTGGATTAGCGATCGACGA | 57 |
| 399 | SLC12A8 | Reverse: GCGCTAACTATTCTCGATTACGCC | 58 |
| 452 | VIM | Forward: CGTTTAGGTTATCGTTATTTTTCGT | 59 |
| 452 | VIM | Reverse: GAACCGCCGAACATCCTACGAT | 60 |
| 462 | ZMIZ1_B | Forward: GGGGGCGGGAGATATTCGAAGTTATTTATC | 61 |
| 462 | ZMIZ1_B | Reverse: AAACGCTATCGCCCGAAAAAACCG | 62 |
| 19 | ATP10A_B | Forward: TTTTGGGTAGGAAGGATAGTAGCGT | 63 |
| 19 | ATP10A_B | Reverse: CAAAAACGAACGACGACGAC | 64 |
| 463 | ZMIZ1_C | Forward: GCGAGTCGGGGTTTTTTGGAGAC | 65 |
| 463 | ZMIZ1_C | Reverse: CACCCACCCTACGTATACCCGCGT | 66 |
| 444 | TSHZ3 | Forward: GATTTGGCGCGGTTTAGCGC | 67 |
| 444 | TSHZ3 | Reverse: CCCTCTCGCACCCATTTAAAAAACCG | 68 |
| 226 | MAX.chr11.14926602-14926671 | Forward: TGAATGTTAATTAAGATTGCGTTCG | 69 |

TABLE 1C-continued

| DMR # | Name | 5'-3' Sequence (hg19) | SEQ ID NO. |
|---|---|---|---|
| 226 | MAX.chr11.14926602-14926671 | Reverse: AACACCCTCACGAAAAACCCGCG | 70 |
| 236 | MAX.chr14.105512178-105512224 | Forward: TTGTAGTTGTTGTTTTTTGGCGGTCGC | 71 |
| 236 | MAX.chr14.105512178-105512224 | Reverse: AAACCGAACGAATTTCGCTTTCCCG | 72 |
| 121 | GPRIN1_A | Forward: TGGCGGCGTCGTATATTTTTACGT | 73 |
| 121 | GPRIN1_A | Reverse: ACCGCTATAACGCCCCCGAA | 74 |
| 39 | C17orf46 | Forward: TAGTTAAAGAGTATATTGGAGGCGG | 75 |
| 39 | C17orf46 | Reverse: CTCTATCCTAAAAACGAAAAACGAA | 76 |
| 434 | TMEM101 | Forward: AGGGGTAGCGTGTGAGTAGTATCGA | 77 |
| 434 | TMEM101 | Reverse: TACCCTTTCCCAAAATAACGTCGAA | 78 |
| 123 | GYPC_A | Forward: GTTAGTTTTCGCGGTTTTTGTTCGG | 79 |
| 123 | GYPC_A | Reverse: CGCCGTACTATTAAAACTTCTCGTCGAC | 80 |
| 306 | MDFI | Forward: TTTTTGGTTGGGTTAAGTTCGGCGC | 81 |
| 306 | MDFI | Reverse: GCCTTCTCAATCGCCCCTCTACGAA | 82 |
| 423 | TACC2_A | Forward: TTAGTTTCGTTTTCGGAGTTCGCGA | 83 |
| 423 | TACC2_A | Reverse: CTCCTATATATAACACGATAATATCATCATCGCC | 84 |
| 7 | AGRN_B | Forward: TTTTTAGTTTTTTTCGTTTTCGCGG | 85 |
| 7 | AGRN_B | Reverse: ACGACTTCCTTTATCTCTACTCCCGCC | 86 |
| 96 | EPS8L2_E | Forward: CGGAAAATTAGTAATATTAGGGCGT | 87 |
| 96 | EPS8L2_E | Reverse: CGAACCCGACTCGTAAATAAACGAC | 88 |
| 297 | MAX.chr8.142215938-142216298 | Forward: GTCGTACGTATCGGGTGGACGA | 89 |
| 297 | MAX.chr8.142215938-142216298 | Reverse: CCCTAACTAACGCGAACCCG | 90 |
| 418 | SSBP4_B | Forward: GGAGGGGCGAATAGAGTTTTTTCG | 91 |
| 418 | SSBP4_B | Reverse: AAAACGACCCCTTCCTCTCTCGCC | 92 |
| 490 | IFFO1_A | Forward: TTTGGTTAGGAAGTAGCGGAATCGG | 93 |
| 490 | IFFO1_A | Reverse: GCAATAACCTAAACTCCAACATCAACGTA | 94 |
| 493 | ITPKB_B | Forward: ATAATTTTAAGGGGGAAACGTTCGT | 95 |
| 493 | ITPKB_B | Reverse: CCAATATAACCGACTTCTTAAACGCT | 96 |
| 491 | IFFO1_B | Forward: GATTAATTAGGCGGTTCGGTAGCGG | 97 |
| 491 | IFFO1_B | Reverse: CAATTAAAACCTATCATTAACTTCCCCTCGAC | 98 |
| 475 | BCL2L11 | Forward: GGTTGTAAGGGTTTTTGGTTTTCGACGC | 99 |
| 475 | BCL2L11 | Reverse: AACGAATTCATACGTCCCCCGAA | 100 |
| 488 | GDF6 | Forward: CGTTTCGTTAGTAGTTATCGATTTTCGT | 101 |
| 488 | GDF6 | Reverse: AAACGAACCCCCTCCTTCGCGT | 102 |
| 479 | C2CD4D | Forward: GTTTACGCGCGAGAGCGTGTTGC | 103 |
| 479 | C2CD4D | Reverse: GCCCGAACCCGACCTAATATTCGAT | 104 |
| 250 | MAX.chr19.2273768-2273823 | Forward: GGATGTTTGTGTTTTAATTTAATTTTTGAGTTC | 105 |
| 250 | MAX.chr19.2273768-2273823 | Reverse: AAATACTACTACCCCGAACGACGCT | 106 |
| 409 | SPATA18 | Forward: ACATATACACACATATCCTTCCTTCCCCAACGAT | 107 |

TABLE 1C-continued

| DMR # | Name | 5'-3' Sequence (hg19) | SEQ ID NO. |
|---|---|---|---|
| 409 | SPATA18 | Reverse: TTTTGTAAAGTTTTCGCGGTTGCGA | 108 |
| 370 | PTP4A3_A | Forward: TCGTCGGTTACGTTTTTTACGTGAC | 109 |
| 370 | PTP4A3_A | Reverse: CGAAACCGACTCCAAACGCT | 110 |
| 310 | MSX2 | Forward: GGGTGTCGAAGTCGGATTTTACGA | 111 |
| 310 | MSX2 | Reverse: AACCACAAAAAAACATTTCCTCCCCGC | 112 |
| 348 | PDE10A | Forward: GAGTTTCGGCGGTTTTTCGAAAGTAGC | 113 |
| 348 | PDE10A | Reverse: CCACGAACAACGACACTACGACGCT | 114 |
| 137 | HOXB3 | Forward: TGTTTTTTCGTTTTTGGTCGTCGGC | 115 |
| 137 | HOXB3 | Reverse: AACCCCAAATTCCCTCCATACGAA | 116 |
| 388 | SCGB3A1 | Forward: GGGAGGCGTTTAGGAATCGTCGC | 117 |
| 388 | SCGB3A1 | Reverse: CCTATATCCCGAAAACTCGCA | 118 |
| 111 | GATA2 | Forward: AGGAGTGTTTGAGTAGGGGTTTCGG | 119 |
| 111 | GATA2 | Reverse: TTTTTCCTCTACACCGAATTACGAA | 120 |
| 340 | OSR2 | Forward: TAGGGTTAGTAGGCGGTTTAGGCGC | 121 |
| 340 | OSR2 | Reverse: CGAACTCCAACTTTAAAAAATACCGCGTA | 122 |
| 255 | MAX.chr19.5828277-5828498 | Forward: GATTTATTTTCGGCGAGGGGTTCGC | 123 |
| 255 | MAX.chr19.5828277-5828498 | Reverse: CGCTTTCCCGATAAAAACGACGACGTA | 124 |
| 181 | LAPTM4B | Forward: AGTAGTAGTTGTTGGAGTAGAATCGCGT | 125 |
| 181 | LAPTM4B | Reverse: GCCCGAAACGATAAAAATAATCGCGC | 126 |
| 317 | NBPF3 | Forward: TTTTATTTTCGAGGTCGGAAATCGG | 127 |
| 317 | NBPF3 | Reverse: CAAATCAAAAACGCGAACGCTCTCG | 128 |
| 97 | ESPN | Forward: TTAGTTGCGGGAAGATAGTGATCGG | 129 |
| 97 | ESPN | Reverse: AACGCCTACCGAACAAATACCCGAA | 130 |
| 353 | PISD | Forward: TCGTGTTTACGTGGGGACGG | 131 |
| 353 | PISD | Reverse: CGCGAACAAAATTAAACGAATCGTA | 132 |
| 33 | BOLA1 | Forward: TAGACGTTAGGAGTGAGGGTCGGGGC | 133 |
| 33 | BOLA1 | Reverse: TAAAACGAATACGAAAATCGCGAAACGAA | 134 |
| 474 | BANK1 | Forward: TTTAGGTGGGTAGTCGCGTATTCGG | 135 |
| 474 | BANK1 | Reverse: CTAACGATAACCCGTAATCTCCGCA | 136 |

A subset of the DMRs was chosen for further development. The criteria were primarily the logistic-derived area under the ROC curve metric which provides a performance assessment of the discriminant potential of the region. An AUC of 0.85 was chosen as the cut-off. In addition, the methylation fold-change ratio (average cancer hypermethylation ratio/average control hypermethylation ratio) was calculated and a lower limit of 10 was employed for tissue vs tissue comparisons and 20 for the tissue vs buffy coat comparisons. P values were required to be less than 0.01. DMRs had to be listed in both the average and individual CpG selection processes. Quantitative methylation specific PCR (qMSP) primers were designed for candidate regions using MethPrimer (Li LC and Dahiya R. Bioinformatics 2002 November; 18(11):1427-31) and QC checked on 20 ng (6250 equivalents) of positive and negative genomic methylation controls. Multiple annealing temperatures were tested for optimal discrimination. Validation was performed in two stages of qMSP. The first consisted of re-testing the sequenced DNA samples. This was done to verify that the DMRs were truly discriminant and not the result of overfitting the extremely large next generation datasets. The second utilized a larger set of independent samples (Serous OC—36 samples; Clear Cell OC—21 samples; Mucinous OC—14 samples; Endometrioid OC—23 samples; Control Fallopian Tube Benign—29 samples; Control Buffy Coat—28 samples).

Tissues were identified as before, with expert clinical and pathological review. DNA purification was performed as previously described. The EZ-96 DNA Methylation kit (Zymo Research, Irvine Calif.) was used for the bisulfate conversion step. 10 ng of converted DNA (per marker) was amplified using SYBR Green detection on Roche 480 LightCyclers (Roche, Basel Switzerland). Serially diluted universal methylated genomic DNA (Zymo Research) was used as a quantitation standard. A CpG agnostic ACTB (β-actin) assay was used as an input reference and normalization control. Results were expressed as methylated copies (specific marker)/copies of ACTB.

Results were analyzed logistically for individual MDMs (methylated DNA marker) performance. For combinations of markers, two techniques were used. First, the rPart technique was applied to the entire MDM set and limited to combinations of 3 MDMs, upon which an rPart predicted probability of cancer was calculated. The second approach used random forest regression (rForest) which generated 500 individual rPart models that were fit to boot strap samples of the original data (roughly ⅔ of the data for training) and used to estimate the cross-validation error (⅓ of the data for testing) of the entire MDM panel and was repeated 500 times. to avoid spurious splits that either under- or overestimate the true cross-validation metrics. Results were then averaged across the 500 iterations.

Table 2A shows ten methylated regions that distinguished clear cell OC tissue from buffy coat control and control fallopian tube tissue (percentage methylation for control buffy coat, control fallopian tube tissue, and clear cell OC tissue) (AUC and p-value between % methylation clear cell tissue and % methylation control fallopian tube).

TABLE 2A

Ten methylated regions that distinguished clear cell OC tissue from buffy coat control, control fallopian tube tissue, clear cell ovarian cancer tissue.

| DMR# | Gene | % M Buffy Coat | % M Fallopian Tube | % M Clear Cell OC | AUC | Fold Change | pvalue |
|---|---|---|---|---|---|---|---|
| 423 | TACC2_A | 0.99% | 0.40% | 46.37% | 1 | 217 | 0.0003304 |
| 198 | LRRC41_A | 0.46% | 0.30% | 36.28% | 1 | 190 | 6.696E−06 |
| 94 | EPS8L2_C | 0.56% | 0.96% | 60.94% | 1 | 160 | 5.736E−06 |
| 182 | LBH | 0.40% | 0.25% | 28.17% | 1 | 158 | 0.0000823 |
| 185 | LIME1_B | 0.27% | 1.32% | 51.66% | 1 | 80 | 8.084E−07 |
| 306 | MDFI | 0.51% | 0.78% | 36.78% | 1 | 74 | 4.885E−06 |
| 99 | FAIM2_A | 0.59% | 1.58% | 42.93% | 1 | 47 | 2.702E−09 |
| 123 | GYPC_A | 0.37% | 1.52% | 41.92% | 1 | 47 | 1.207E−08 |
| 7 | AGRN_B | 0.73% | 2.39% | 51.24% | 1 | 43 | 6.792E−10 |
| 457 | ZBED4 | 0.70% | 1.13% | 27.85% | 1 | 34 | 3.722E−05 |

Table 2B shows ten methylated regions that distinguished endometrioid OC tissue from buffy coat control and control fallopian tube tissue (percentage methylation for control buffy coat, control fallopian tube tissue, and endometrioid OC tissue) (AUC and p-value between % methylation endometrioid tissue and % methylation control fallopian tube).

TABLE 2B

Ten methylated regions that distinguished endometrioid OC tissue from buffy coat control, control fallopian tube tissue, endometrioid ovarian cancer tissue.

| DMR# | Gene | % M Buffy Coat | % M Fallopian Tube | % M endometrioid OC | AUC | Fold Change | pvalue |
|---|---|---|---|---|---|---|---|
| 345 | PARP15 | 0.44% | 1.27% | 44.65% | 1 | 63 | 1.898E−08 |
| 121 | GPRIN1_A | 0.58% | 1.41% | 44.79% | 1 | 57 | 1.866E−07 |
| 123 | GYPC_A | 0.37% | 1.52% | 39.96% | 0.9912 | 43 | 7.342E−07 |
| 103 | FLJ34208 | 0.16% | 2.51% | 41.87% | 0.9912 | 28 | 3.514E−08 |
| 207 | MAX.chr1.147790358-147790381 | 0.62% | 4.41% | 48.42% | 0.9912 | 20 | 2.389E−08 |
| 99 | FAIM2_A | 0.59% | 1.58% | 42.27% | 0.9889 | 46 | 7.617E−07 |
| 393 | SH2B3 | 0.86% | 1.62% | 22.66% | 0.9868 | 18 | 3.501E−05 |
| 175 | KCNQ5 | 0.24% | 1.14% | 22.85% | 0.9853 | 26 | 0.0002584 |
| 150 | IRF4 | 0.17% | 1.57% | 28.91% | 0.9824 | 26 | 0.000017 |
| 25 | BCAT1 | 0.30% | 1.25% | 24.95% | 0.9722 | 26 | 0.0001114 |

Table 2C shows ten methylated regions that distinguished mucinous OC tissue from buffy coat control and control fallopian tube tissue (percentage methylation for control buffy coat, control fallopian tube tissue, and mucinous OC tissue) (AUC and p-value between % methylation mucinous tissue and % methylation control fallopian tube).

TABLE 2C

Ten methylated regions that distinguished mucinous OC tissue from buffy coat control, control fallopian tube tissue, and mucinous ovarian cancer tissue.

| DMR# | Gene | % M Buffy Coat | % M Fallopian Tube | M % mucinous OC | AUC | Fold Change | pvalue |
|---|---|---|---|---|---|---|---|
| 66 | CMTM3_A | 0.32% | 0.22% | 45.24% | 1 | 380 | 4.80E−06 |
| 20 | ATP10A_C | 0.35% | 0.27% | 47.77% | 1 | 341 | 7.31E−05 |
| 444 | TSHZ3 | 0.68% | 0.27% | 47.30% | 1 | 330 | 0.002852 |
| 462 | ZMIZ1_B | 0.19% | 0.23% | 41.58% | 1 | 308 | 3.50E−09 |
| 19 | ATP10A_B | 0.69% | 0.20% | 32.41% | 1 | 245 | 1.10E−09 |
| 87 | ELMO1_B | 0.11% | 0.16% | 24.45% | 1 | 204 | 8.38E−05 |
| 423 | TACC2_A | 0.99% | 0.40% | 44.62% | 1 | 202 | 3.82E−08 |
| 197 | LRRC4 | 0.37% | 0.21% | 26.81% | 1 | 177 | 0.0002576 |
| 452 | VIM | 0.11% | 0.27% | 25.61% | 1 | 129 | 3.68E−07 |
| 465 | ZNF382_A | 0.47% | 0.51% | 30.72% | 1 | 87 | 1.14E−09 |

Table 2D shows ten methylated regions that distinguished serous OC tissue from buffy coat control and control fallopian tube tissue (percentage methylation for control buffy coat, control fallopian tube tissue, and serous OC tissue) (AUC and p-value between % methylation serous tissue and % methylation control fallopian tube).

TABLE 2D

Ten methylated regions that distinguished serous OC tissue from buffy coat control, control fallopian tube tissue, ovarian cancer tissue.

| DMR# | Gene | % M Buffy Coat | % M Fallopian Tube | % M serous OC | AUC | Fold Change | pvalue |
|---|---|---|---|---|---|---|---|
| 207 | MAX.chr1.147790358-147790381 | 0.62% | 4.41% | 49.78% | 0.9917 | 22 | 5.145E−07 |
| 204 | MAML3 | 0.75% | 2.88% | 17.15% | 0.9583 | 7 | 1.176E−07 |
| 329 | NR2F6 | 0.23% | 0.73% | 33.21% | 0.9417 | 68 | 0.0001251 |
| 81 | DNMT3A_A | 0.44% | 0.90% | 21.39% | 0.9333 | 30 | 0.0003524 |
| 398 | SKI | 0.31% | 1.03% | 32.03% | 0.9284 | 45 | 6.022E−07 |
| 407 | SOBP | 0.56% | 4.19% | 28.61% | 0.925 | 9 | 3.089E−06 |
| 447 | UBTF | 0.49% | 1.57% | 39.00% | 0.8972 | 40 | 1.662E−07 |

TABLE 2D-continued

Ten methylated regions that distinguished serous OC tissue from buffy coat
control, control fallopian tube tissue, ovarian cancer tissue.

| DMR# | Gene | % M Buffy Coat | % M Fallopian Tube | % M serous OC | AUC | Fold Change | pvalue |
|---|---|---|---|---|---|---|---|
| 8 | AGRN_C | 0.46% | 0.74% | 12.44% | 0.8903 | 19 | 0.002814 |
| 232 | MAX.chr12.30975740-30975780 | 0.18% | 4.76% | 40.01% | 0.8861 | 13 | 2.012E-07 |
| 50 | CAPN2_A | 0.21% | 0.79% | 28.39% | 0.8806 | 50 | 0.004007 |

Table 3 shows the top ten methylated regions that distinguished OC tissue from buffy coat control (percentage methylation difference between OC and control buffy coat provided; percentage methylation difference between OC and control fallopian tube provided; AUC provided; fold-change difference provided; and p-value provided.

TABLE 3

| DMR# | Gene | % M Buffy Coat | % M Fallopian Tube | % M OC | AUC | Fold Change | pvalue |
|---|---|---|---|---|---|---|---|
| MAX.chr16.85482307-85482494 | 505 | 0.52% | 19.64% | 36.76% | 1 | 111 | 0.001246 |
| GDF6 | 488 | 0.52% | 17.12% | 29.59% | 1 | 80 | 0.002582 |
| IFFO1_A | 490 | 0.49% | 15.96% | 58.34% | 0.999 | 286 | 0.0009795 |
| ATP6V1B1_A | 472 | 0.60% | 21.70% | 50.68% | 0.9989 | 169 | 0.002853 |
| MAX.chr5.42993898-42994179 | 509 | 0.94% | 21.49% | 49.41% | 0.9989 | 103 | 0.000006147 |
| MAX.chr17.76254728-76254841 | 506 | 0.53% | 13.96% | 29.83% | 0.9979 | 80 | 0.003074 |
| MAX.chr14.102172350-102172770 | 504 | 0.46% | 14.88% | 21.82% | 0.9979 | 60 | 0.003098 |
| RASAL3 | 520 | 0.68% | 35.36% | 44.23% | 0.9954 | 116 | 0.00001693 |
| BZRAP1 | 476 | 0.72% | 25.52% | 36.09% | 0.9937 | 78 | 0.00001416 |
| LIMD2 | 498 | 0.45% | 12.86% | 40.78% | 0.9919 | 154 | 0.000554 |

Tables 4A-E are results from an initial tissue validation where upwards of 60 top DMRs were chosen from the sequencing data, and designed qMSP assays. These DMRs were run on OC tissue, clear cell OC tissue, endometrioid OC tissue, mucinous OC tissue, serous OC tissue, and control fallopian tube tissue. Next, a larger, independent tissue validation was performed where new untested cases and controls are tested (see, Table 5).

TABLE 4A

| DMR No. | Marker | AUC (all OC vs all benign tissue) | AUC (all OC vs buffy) |
|---|---|---|---|
| 318 | NCOR2 | 0.88377 | 0.99908 |
| 311 | MT1A_A | 0.88816 | 0.988 |
| 63 | CELF2_A | 0.89232 | 0.97599 |
| 164 | KCNA3_A | 0.87259 | 0.94598 |
| 463 | ZMIZ1_C | 0.55789 | 0.71191 |
| 306 | MDFI | 0.62719 | 0.77101 |
| 343 | PALLD | 0.93114 | 1 |
| 360 | PRDM14 | 0.91667 | 1 |
| 345 | PARP15 | 0.8057 | 0.91782 |
| 423 | TACC2_A | 0.68969 | 0.88458 |
| 207 | MAX.chr1.147790358-147790381 | 0.97675 | 1 |
| 25 | BCAT1 | 0.93991 | 0.98199 |
| 64 | CELF2_B | 0.84649 | 0.93629 |
| 50 | CAPN2_A | 0.79671 | 0.89612 |
| 226 | MAX.chr11.14926602-14926671 | 0.86886 | 0.97922 |
| 7 | AGRN_B | 0.77325 | 0.95199 |
| 287 | MAX.chr6.10382190-10382225 | 0.88158 | 0.97692 |

TABLE 4A-continued

| DMR No. | Marker | AUC (all OC vs all benign tissue) | AUC (all OC vs buffy) |
|---|---|---|---|
| 84 | DSCR6 | 0.86667 | 0.94183 |
| 204 | MAML3_A | 0.92412 | 0.94737 |
| 334 | OBSCN | 0.69561 | 0.90028 |
| 236 | MAX.chr14.105512178-105512224 | 0.78026 | 0.91782 |
| 96 | EPS8L2_E | 0.76404 | 0.84765 |
| 398 | SKI | 0.96579 | 1 |
| 329 | NR2F6 | 0.70614 | 0.91413 |
| 399 | SLC12A8 | 0.74386 | 0.90859 |
| 121 | GPRIN1_A | 0.87018 | 0.89751 |
| 297 | MAX.chr8.142215938-142216298 | 0.6557 | 0.8144 |
| 61 | CDO1_A | 0.86228 | 0.91043 |
| 81 | DNMT3A_A | 0.90132 | 0.98615 |
| 397 | SIM2_A | 0.88026 | 0.98615 |
| 398 | SKI | 0.95482 | 0.99815 |
| 462 | ZMIZ1_B | 0.60439 | 0.70083 |
| 434 | TMEM101 | 0.62939 | 0.84765 |
| 490 | IFFO1_A | 0.81404 | 1 |
| 312 | MT1A_B | 0.89825 | 0.99169 |
| 19 | ATP10A_B | 0.46009 | 0.64774 |
| 123 | GYPC_A | 0.77281 | 0.91136 |
| 491 | IFFO1_B | 0.80175 | 0.99354 |
| 348 | PDE10A | 0.58333 | 0.72946 |
| 475 | BCL2L11 | 0.86228 | 1 |
| 137 | HOXB3 | 0.46711 | 0.27239 |
| 353 | PISD | 0.63684 | 0.62512 |
| 488 | GDF6 | 0.82982 | 1 |
| 388 | SCGB3A1 | 0.47193 | 0.54663 |
| 33 | BOLA1 | 0.67544 | 0.65374 |
| 479 | C2CD4D | 0.92982 | 0.99123 |
| 111 | GATA2 | 0.59298 | 0.89104 |
| 474 | BANK1 | 0.63114 | 0.89935 |
| 250 | MAX.chr19.2273768-2273823 | 0.58596 | 0.85134 |
| 340 | OSR2 | 0.775 | 0.90397 |
| 370 | PTP4A3_A | 0.62522 | 0.7627 |
| 181 | LAPTM4B | 0.48289 | 0.49354 |
| 310 | MSX2 | 0.44781 | 0.5337 |
| 317 | NBPF3 | 0.4943 | 0.46491 |

TABLE 4B

| DMR No. | Marker | AUC (clear cell vs all benign tissue) |
|---|---|---|
| 318 | NCOR2 | 0.89333 |
| 311 | MT1A_A | 0.96833 |
| 63 | CELF2_A | 0.91833 |
| 164 | KCNA3_A | 0.9225 |
| 463 | ZMIZ1_C | 0.48167 |
| 306 | MDFI | 0.90333 |
| 343 | PALLD | 0.96333 |
| 360 | PRDM14 | 0.95333 |
| 345 | PARP15 | 0.965 |
| 423 | TACC2_A | 0.985 |
| 207 | MAX.chr1.147790358-147790381 | 0.97667 |
| 25 | BCAT1 | 0.93 |
| 64 | CELF2_B | 0.89667 |
| 50 | CAPN2_A | 0.85417 |
| 226 | MAX.chr11.14926602-14926671 | 0.96167 |
| 7 | AGRN_B | 0.94333 |
| 287 | MAX.chr6.10382190-10382225 | 0.9425 |
| 84 | DSCR6 | 1 |
| 204 | MAML3_A | 0.94583 |
| 334 | OBSCN | 0.84333 |
| 236 | MAX.chr14.105512178-105512224 | 0.91667 |
| 96 | EPS8L2_E | 0.99833 |
| 398 | SKI | 0.99833 |
| 329 | NR2F6 | 0.675 |
| 399 | SLC12A8 | 0.73 |
| 121 | GPRIN1_A | 0.99833 |
| 297 | MAX.chr8.142215938-142216298 | 0.97833 |
| 61 | CDO1_A | 1 |
| 81 | DNMT3A_A | 0.95667 |
| 397 | SIM2_A | 1 |
| 398 | SKI | 0.98667 |
| 462 | ZMIZ1_B | 0.49167 |
| 434 | TMEM101 | 0.88583 |
| 490 | IFFO1_A | 0.83 |
| 312 | MT1A_B | 0.995 |
| 19 | ATP10A_B | 0.58667 |
| 123 | GYPC_A | 0.98667 |
| 491 | IFFO1_B | 0.81333 |
| 348 | PDE10A | 0.66 |
| 475 | BCL2L11 | 0.94833 |
| 137 | HOXB3 | 0.39333 |
| 353 | PISD | 0.995 |
| 488 | GDF6 | 0.86333 |
| 388 | SCGB3A1 | 0.41833 |
| 33 | BOLA1 | 0.87833 |
| 479 | C2CD4D | 0.95833 |
| 111 | GATA2 | 0.50833 |
| 474 | BANK1 | 0.54667 |
| 250 | MAX.chr19.2273768-2273823 | 0.62667 |
| 340 | OSR2 | 0.83333 |
| 370 | PTP4A3_A | 0.74167 |
| 181 | LAPTM4B | 0.57333 |
| 310 | MSX2 | 0.34167 |
| 317 | NBPF3 | 0.44167 |

TABLE 4C

| DMR No. | Marker | AUC (endometrioid vs all benign tissue) |
|---|---|---|
| 318 | NCOR2 | 0.90278 |
| 311 | MT1A__A | 0.81111 |
| 63 | CELF2__A | 0.97639 |
| 164 | KCNA3__A | 0.84097 |
| 463 | ZMIZ1__C | 0.45139 |
| 306 | MDFI | 0.45278 |
| 343 | PALLD | 0.91667 |
| 360 | PRDM14 | 0.90278 |
| 345 | PARP15 | 0.89722 |
| 423 | TACC2__A | 0.65694 |
| 207 | MAX.chr1.147790358-147790381 | 0.9875 |
| 25 | BCAT1 | 0.98611 |
| 64 | CELF2__B | 0.89514 |
| 50 | CAPN2__A | 0.75556 |
| 226 | MAX.chr11.14926602-14926671 | 0.93889 |
| 7 | AGRN__B | 0.67639 |
| 287 | MAX.chr6.10382190-10382225 | 0.75903 |
| 84 | DSCR6 | 0.7875 |
| 204 | MAML3__A | 0.96042 |
| 334 | OBSCN | 0.49306 |
| 236 | MAX.chr14.105512178-105512224 | 0.84583 |
| 96 | EPS8L2__E | 0.725 |
| 398 | SKI | 0.95 |
| 329 | NR2F6 | 0.6875 |
| 399 | SLC12A8 | 0.66944 |
| 121 | GPRIN1__A | 0.99722 |
| 297 | MAX.chr8.142215938-142216298 | 0.58889 |
| 61 | CDO1__A | 0.81111 |
| 81 | DNMT3A__A | 0.88472 |
| 397 | SIM2__A | 0.88472 |
| 398 | SKI | 0.93472 |
| 462 | ZMIZ1__B | 0.57083 |
| 434 | TMEM101 | 0.86736 |
| 490 | IFFO1__A | 0.77917 |
| 312 | MT1A__B | 0.81667 |
| 19 | ATP10A__B | 0.39722 |
| 123 | GYPC__A | 0.78194 |
| 491 | IFFO1__B | 0.7625 |
| 348 | PDE10A | 0.64306 |
| 475 | BCL2L11 | 0.90972 |
| 137 | HOXB3 | 0.6375 |
| 353 | PISD | 0.49653 |
| 488 | GDF6 | 0.7375 |
| 388 | SCGB3A1 | 0.62361 |
| 33 | BOLA1 | 0.41667 |
| 479 | C2CD4D | 0.96528 |
| 111 | GATA2 | 0.53194 |
| 474 | BANK1 | 0.58472 |
| 250 | MAX.chr19.2273768-2273823 | 0.40833 |
| 340 | OSR2 | 0.73056 |
| 370 | PTP4A3__A | 0.58264 |
| 181 | LAPTM4B | 0.43611 |
| 310 | MSX2 | 0.30417 |
| 317 | NBPF3 | 0.42917 |

TABLE 4D

| DMR No. | Marker | AUC (mucinous vs all benign tissue) |
|---|---|---|
| 318 | NCOR2 | 0.925 |
| 311 | MT1A__A | 1 |
| 63 | CELF2__A | 0.71667 |
| 164 | KCNA3__A | 0.99583 |
| 463 | ZMIZ1__C | 1 |
| 306 | MDFI | 0.23333 |
| 343 | PALLD | 0.80833 |
| 360 | PRDM14 | 0.83333 |
| 345 | PARP15 | 0.42917 |
| 423 | TACC2__A | 1 |
| 207 | MAX.chr1.147790358-147790381 | 0.90417 |
| 25 | BCAT1 | 1 |
| 64 | CELF2__B | 0.6625 |
| 50 | CAPN2__A | 0.56667 |
| 226 | MAX.chr11.14926602-14926671 | 0.62083 |
| 7 | AGRN__B | 0.9125 |
| 287 | MAX.chr6.10382190-10382225 | 0.7875 |
| 84 | DSCR6 | 0.775 |
| 204 | MAML3__A | 0.88125 |
| 334 | OBSCN | 0.49167 |
| 236 | MAX.chr14.105512178-105512224 | 0.8625 |
| 96 | EPS8L2__E | 0.49583 |
| 398 | SKI | 0.95 |
| 329 | NR2F6 | 0.83333 |
| 399 | SLC12A8 | 0.97917 |
| 121 | GPRIN1__A | 0.5125 |
| 297 | MAX.chr8.142215938-142216298 | 0.57083 |
| 61 | CDO1__A | 0.8375 |
| 81 | DNMT3A__A | 0.89583 |
| 397 | SIM2__A | 0.8625 |
| 398 | SKI | 0.97917 |
| 462 | ZMIZ1__B | 1 |
| 434 | TMEM101 | 0.81875 |
| 490 | IFFO1__A | 0.47083 |
| 312 | MT1A__B | 0.87917 |
| 19 | ATP10A__B | 0.8375 |
| 123 | GYPC__A | 0.74167 |
| 491 | IFFO1__B | 0.54583 |
| 348 | PDE10A | 0.47083 |
| 475 | BCL2L11 | 0.99583 |
| 137 | HOXB3 | 0.80417 |
| 353 | PISD | 0.69375 |
| 488 | GDF6 | 0.62917 |
| 388 | SCGB3A1 | 0.72917 |
| 33 | BOLA1 | 0.5375 |
| 479 | C2CD4D | 0.725 |
| 111 | GATA2 | 0.9125 |
| 474 | BANK1 | 0.525 |
| 250 | MAX.chr19.2273768-2273823 | 0.52083 |
| 340 | OSR2 | 0.8375 |
| 370 | PTP4A3__A | 0.70417 |
| 181 | LAPTM4B | 0.36458 |
| 310 | MSX2 | 0.70417 |
| 317 | NBPF3 | 0.64167 |

TABLE 4E

| DMR No. | Marker | AUC (serous vs all benign tissue) |
|---|---|---|
| 318 | NCOR2 | 0.84306 |
| 311 | MT1A__A | 0.86111 |
| 63 | CELF2__A | 0.84514 |
| 164 | KCNA3__A | 0.82153 |
| 463 | ZMIZ1__C | 0.58056 |
| 306 | MDFI | 0.56875 |
| 343 | PALLD | 0.95972 |
| 360 | PRDM14 | 0.92778 |
| 345 | PARP15 | 0.70694 |
| 423 | TACC2__A | 0.37292 |
| 207 | MAX.chr1.147790358-147790381 | 0.99028 |
| 25 | BCAT1 | 0.88194 |
| 64 | CELF2__B | 0.81736 |
| 50 | CAPN2__A | 0.91111 |
| 226 | MAX.chr11.14926602-14926671 | 0.80417 |
| 7 | AGRN__B | 0.68194 |
| 287 | MAX.chr6.10382190-10382225 | 0.98472 |
| 84 | DSCR6 | 0.86528 |
| 204 | MAML3__A | 0.88403 |
| 334 | OBSCN | 0.8375 |
| 236 | MAX.chr14.105512178-105512224 | 0.81528 |
| 96 | EPS8L2__E | 0.69722 |
| 398 | SKI | 0.95972 |
| 329 | NR2F6 | 0.93056 |

TABLE 4E-continued

| DMR No. | Marker | AUC (serous vs all benign tissue) |
|---|---|---|
| 399 | SLC12A8 | 0.75139 |
| 121 | GPRIN1_A | 0.76389 |
| 297 | MAX.chr8.142215938-142216298 | 0.70694 |
| 61 | CDO1_A | 0.80694 |
| 81 | DNMT3A_A | 0.87361 |
| 397 | SIM2_A | 0.78194 |
| 398 | SKI | 0.94028 |
| 462 | ZMIZ1_B | 0.6 |
| 434 | TMEM101 | 0.32708 |
| 490 | IFFO1_A | 0.93056 |
| 312 | MT1A_B | 0.90556 |
| 19 | ATP10A_B | 0.56389 |
| 123 | GYPC_A | 0.59583 |
| 491 | IFFO1_B | 0.91667 |
| 348 | PDE10A | 0.50278 |
| 475 | BCL2L11 | 0.69861 |
| 137 | HOXB3 | 0.44861 |
| 353 | PISD | 0.58889 |
| 488 | GDF6 | 0.96111 |
| 388 | SCGB3A1 | 0.47361 |
| 33 | BOLA1 | 0.66944 |
| 479 | C2CD4D | 0.93889 |
| 111 | GATA2 | 0.37361 |
| 474 | BANK1 | 0.78333 |
| 250 | MAX.chr19.2273768-2273823 | 0.76528 |
| 340 | OSR2 | 0.75 |
| 370 | PTP4A3_A | 0.70972 |
| 181 | LAPTM4B | 0.475 |
| 310 | MSX2 | 0.73056 |
| 317 | NBPF3 | 0.50694 |

Table 5A shows area under the curve for various markers from Table 1 that distinguished serous OC tissue from benign ovarian tissue and buffy coat.

TABLE 5A

| DMR No. | Marker | tissue AUC | buffy AUC |
|---|---|---|---|
| 318 | NCOR2 | 0.90805 | 0.96329 |
| 312 | MT1A_B | 0.71169 | 0.94147 |
| 63 | CELF2_A | 0.70642 | 0.83333 |
| 164 | KCNA3_A | 0.78065 | 0.79663 |
| 343 | PALLD | 0.87931 | 0.93452 |
| 360 | PRDM14 | 0.85441 | 0.78671 |
| 345 | PARP15 | 0.77395 | 0.77579 |
| 423 | TACC2_A | 0.76054 | 0.70139 |
| 207 | MAX.chr1.147790358-147790381 | 0.91092 | 0.98413 |
| 25 | BCAT1 | 0.88697 | 0.85417 |
| 50 | CAPN2_A | 0.84674 | 0.89484 |
| 226 | MAX.chr11.14926602-14926671 | 0.7931 | 0.85516 |
| 7 | AGRN_B | 0.83238 | 0.93056 |
| 287 | MAX.chr6.10382190-10382225 | 0.92816 | 0.92063 |
| 84 | DSCR6 | 0.84195 | 0.78869 |
| 204 | MAML3_A | 0.81466 | 0.92758 |
| 236 | MAX.chr14.105512178-105512224 | 0.70259 | 0.84474 |
| 398 | SKI | 0.87452 | 0.99802 |
| 329 | NR2F6 | 0.86973 | 0.95437 |
| 399 | SLC12A8 | 0.79502 | 1 |
| 121 | GPRIN1_A | 0.65134 | 0.5129 |
| 61 | CDO1_A | 0.7318 | 0.71825 |
| 81 | DNMT3A_A | 0.67529 | 0.60863 |
| 397 | SIM2_A | 0.81609 | 0.90278 |
| 462 | ZMIZ1_B | 0.55077 | 0.46528 |
| 490 | IFFO1_A | 0.91954 | 1 |
| 312 | MT1A_B | 0.78161 | 0.97321 |
| 123 | GYPC_A | 0.62165 | 0.87599 |
| 475 | BCL2L11 | 0.64847 | 0.9375 |
| 488 | GDF6 | 0.93487 | 1 |
| 479 | C2CD4D | 0.91284 | 0.98413 |

TABLE 5A-continued

| DMR No. | Marker | tissue AUC | buffy AUC |
|---|---|---|---|
| 111 | GATA2 | 0.48755 | 0.39583 |
| 474 | BANK1 | 0.57375 | 0.94444 |

Table 5B shows area under the curve for various markers from Table 1 that distinguished clear cell OC tissue from benign ovarian tissue and buffy coat.

TABLE 5B

| DMR No. | Marker | tissue AUC | buffy AUC |
|---|---|---|---|
| 318 | NCOR2 | 0.99343 | 1 |
| 312 | MT1A_B | 0.99015 | 1 |
| 63 | CELF2_A | 0.94828 | 0.97279 |
| 164 | KCNA3_A | 0.89491 | 0.90136 |
| 343 | PALLD | 1 | 1 |
| 360 | PRDM14 | 0.99507 | 0.9966 |
| 345 | PARP15 | 1 | 1 |
| 423 | TACC2_A | 0.96388 | 0.95068 |
| 207 | MAX.chr1.147790358-147790381 | 1 | 1 |
| 25 | BCAT1 | 0.99343 | 0.9966 |
| 50 | CAPN2_A | 0.83251 | 0.90646 |
| 226 | MAX.chr11.14926602-14926671 | 0.95567 | 0.95493 |
| 7 | AGRN_B | 0.99507 | 0.9966 |
| 287 | MAX.chr6.10382190-10382225 | 1 | 1 |
| 84 | DSCR6 | 1 | 1 |
| 204 | MAML3_A | 0.96388 | 1 |
| 236 | MAX.chr14.105512178-105512224 | 0.79228 | 0.91241 |
| 398 | SKI | 0.96223 | 0.98639 |
| 329 | NR2F6 | 0.83333 | 0.91412 |
| 399 | SLC12A8 | 0.86535 | 1 |
| 121 | GPRIN1_A | 1 | 1 |
| 61 | CDO1_A | 1 | 1 |
| 81 | DNMT3A_A | 0.89491 | 0.87245 |
| 397 | SIM2_A | 1 | 1 |
| 462 | ZMIZ1_B | 0.54187 | 0.46429 |
| 490 | IFFO1_A | 0.95402 | 1 |
| 312 | MT1A_B | 1 | 1 |
| 123 | GYPC_A | 1 | 1 |
| 475 | BCL2L11 | 0.96059 | 1 |
| 488 | GDF6 | 0.95895 | 1 |
| 479 | C2CD4D | 1 | 1 |
| 111 | GATA2 | 0.42529 | 0.39116 |
| 474 | BANK1 | 0.77668 | 0.93367 |

Table 5C shows area under the curve for various markers from Table 1 that distinguished endometrioid OC tissue from benign ovarian tissue and buffy coat.

TABLE 5C

| DMR No. | Marker | tissue AUC | buffy AUC |
|---|---|---|---|
| 318 | NCOR2 | 0.94003 | 0.95807 |
| 312 | MT1A_B | 0.78711 | 0.93323 |
| 63 | CELF2_A | 0.85007 | 0.90683 |
| 164 | KCNA3_A | 0.8051 | 0.81832 |
| 343 | PALLD | 1 | 1 |
| 360 | PRDM14 | 0.90555 | 0.87267 |
| 345 | PARP15 | 0.86132 | 0.85714 |
| 423 | TACC2_A | 0.84558 | 0.79814 |
| 207 | MAX.chr1.147790358-147790381 | 0.997 | 1 |
| 25 | BCAT1 | 0.89805 | 0.88509 |
| 50 | CAPN2_A | 0.73013 | 0.79969 |
| 226 | MAX.chr11.14926602-14926671 | 0.92804 | 0.95807 |
| 7 | AGRN_B | 0.7099 | 0.78882 |
| 287 | MAX.chr6.10382190-10382225 | 0.86807 | 0.86491 |
| 84 | DSCR6 | 0.96252 | 0.91925 |

TABLE 5C-continued

| DMR No. | Marker | tissue AUC | buffy AUC |
|---|---|---|---|
| 204 | MAML3_A | 0.86057 | 0.94099 |
| 236 | MAX.chr14.105512178-105512224 | 0.85907 | 0.9441 |
| 398 | SKI | 0.73988 | 0.93944 |
| 329 | NR2F6 | 0.61694 | 0.76941 |
| 399 | SLC12A8 | 0.8021 | 1 |
| 121 | GPRIN1_A | 0.92054 | 0.87811 |
| 61 | CDO1_A | 0.93778 | 0.93634 |
| 81 | DNMT3A_A | 0.71514 | 0.64596 |
| 397 | SIM2_A | 0.93553 | 0.99845 |
| 462 | ZMIZ1_B | 0.53523 | 0.45497 |
| 490 | IFFO1_A | 0.90105 | 0.99845 |
| 312 | MT1A_B | 0.85607 | 0.92857 |
| 123 | GYPC_A | 0.89205 | 0.96661 |
| 475 | BCL2L11 | 0.81934 | 0.93012 |
| 488 | GDF6 | 0.61169 | 1 |
| 479 | C2CD4D | 0.997 | 1 |
| 111 | GATA2 | 0.33358 | 0.2764 |
| 474 | BANK1 | 0.30735 | 0.87422 |

Table 5D shows area under the curve for various markers from Table 1 that distinguished mucinous OC tissue from benign ovarian tissue and buffy coat.

TABLE 5D

| DMR No. | Marker | tissue AUC | buffy AUC |
|---|---|---|---|
| 318 | NCOR2 | 0.98768 | 1 |
| 312 | MT1A_B | 0.82759 | 1 |
| 63 | CELF2_A | 0.68596 | 0.80867 |
| 164 | KCNA3_A | 0.88177 | 0.88903 |
| 343 | PALLD | 0.91626 | 0.95663 |
| 360 | PRDM14 | 0.82759 | 0.75 |
| 345 | PARP15 | 0.77833 | 0.78061 |
| 423 | TACC2_A | 0.9803 | 0.96173 |
| 207 | MAX.chr1.147790358-147790381 | 0.87685 | 0.97194 |
| 25 | BCAT1 | 0.99754 | 0.9949 |
| 50 | CAPN2_A | 0.6601 | 0.77806 |
| 226 | MAX.chr11.14926602-14926671 | 0.85961 | 0.90689 |
| 7 | AGRN_B | 0.92118 | 0.95408 |
| 287 | MAX.chr6.10382190-10382225 | 0.86207 | 0.85969 |
| 84 | DSCR6 | 0.62808 | 0.55102 |
| 204 | MAML3_A | 0.85961 | 0.9898 |
| 236 | MAX.chr14.105512178-105512224 | 0.75739 | 0.67474 |
| 398 | SKI | 1 | 1 |
| 329 | NR2F6 | 0.47167 | 0.70281 |
| 399 | SLC12A8 | 0.90887 | 1 |
| 121 | GPRIN1_A | 0.63793 | 0.49617 |
| 61 | CDO1_A | 0.84975 | 0.85459 |
| 81 | DNMT3A_A | 0.78325 | 0.70536 |
| 397 | SIM2_A | 0.8399 | 0.96173 |
| 462 | ZMIZ1_B | 0.92365 | 0.90816 |
| 490 | IFFO1_A | 0.84729 | 1 |
| 312 | MT1A_B | 0.84606 | 0.93878 |
| 123 | GYPC_A | 0.76108 | 0.98469 |
| 475 | BCL2L11 | 0.94828 | 1 |
| 488 | GDF6 | 0.69458 | 1 |
| 479 | C2CD4D | 0.73153 | 1 |
| 111 | GATA2 | 0.85714 | 0.84184 |
| 474 | BANK1 | 0.4532 | 0.93367 |

Example II

This example describes identification of ovarian cancer tissue markers, clear cell ovarian cancer tissue markers, endometrioid ovarian cancer tissue markers, mucinous ovarian cancer tissue markers, and serous ovarian cancer tissue markers.

Candidate methylation markers for the detection of ovarian cancer, clear cell OC, endometrioid OC, mucinous OC, and serous OC were identified by RRBS of ovarian tissue samples, clear cell OC tissue samples, endometrioid OC tissue samples, mucinous OC tissue samples, serous OC tissue samples, and normal ovarian tissue samples. To identify methylated DNA markers, 149 samples per patient group (see Table 7) underwent an RRBS process followed by an alignment to a bisulfate converted human genome. CpG regions of high ratios of methylation in ovarian cancer, clear cell OC, endometrioid OC, mucinous OC, and serous OC relative to normal ovarian tissue and buffy coat were selected and mapped to their gene names

TABLE 7

| Sample type | Number | Stage I | Stage II | Stage III | Stage IV |
|---|---|---|---|---|---|
| Normal | 35 | NA | NA | NA | NA |
| Cancer | 57 | 25 | 8 | 19 | 5 |
| Cancer Subtype | | | | | |
| Clear Cell | 15 | 8 | 4 | 3 | 0 |
| Endometrioid | 18 | 12 | 3 | 3 | 0 |
| Mucinous | 6 | 4 | 1 | 0 | 1 |
| Serous | 18 | 1 | 0 | 13 | 4 |

After markers were selected by RRBS, a total of 49 methylation markers were identified and target enrichment long-probe quantitative amplified signal assays were designed and ordered (see, e.g., WO2017/075061 and U.S. patent application Ser. No. 15/841,006 for general techniques). Table 6A shows the marker chromosomal regions used for the 49 methylation markers. Table 6B shows primer information and probe information for the markers. FIG. 1 further provides marker chromosomal regions used for the 49 methylation markers and related primer and probe information.

TABLE 6A

| DMR No. | Gene Annotation | Chromosome No. | DMR Start-End Positions |
|---|---|---|---|
| 526 | AGRN_8794 | 1 | 968670-968849 |
| 527 | BCAT1_6015 | 12 | 25055940-25056138 |
| 528 | BHLHE23_8339 | 20 | 61638294-61638506 |
| 529 | ELMO1_9100 | 7 | 37488054-37488165 |
| 530 | EPS8L2_F | 11 | 726397-726519 |
| 531 | JAM3_B | 11 | 133938908-133939011 |
| 532 | KCNA3_7320 | 1 | 111217250-111217357 |
| 533 | KCNA3_7518 | 1 | 111217487-111217673 |
| 534 | MDFI_6321 | 6 | 41606064-41606357 |
| 545 | RASSF1_8293 | 3 | 50378182-50378372 |
| 536 | SFMBT2_2363 | 10 | 7451790-7452428 |
| 398 | SKI | 1 | 2222218-2222508 |
| 537 | SPOCK2_7433 | 10 | 73847355-73847446 |
| 538 | VIPR2_B | 7 | 158937203-158937476 |
| 539 | ZMIZ1_D | 8 | 81002589-81002797 |
| 540 | ZNF382_B | 19 | 37096085-37096209 |
| 541 | GYPC_3753 | 2 | 127413592-127413887 |
| 542 | GYPC_C | 2 | 127413898-127413988 |
| 543 | RFTN1_B | 3 | 16554329-16554496 |
| 345 | PARP15 | 3 | 122296692-122296851 |
| 119 | GP5 | 3 | 194118822-194118924 |
| 544 | GPRIN1_B | 5 | 176023887-176023974 |
| 545 | HCG4_0331 | 6 | 29760284-29760410 |
| 546 | HCG4_0556 | 6 | 29760436-29760577 |
| 547 | NKX2-6_4159 | 8 | 23564076-23564193 |
| 548 | C1QL3_B | 10 | 16562562-16562645 |

TABLE 6A-continued

| DMR No. | Gene Annotation | Chromosome No. | DMR Start-End Positions |
|---|---|---|---|
| 549 | FAIM2__B | 12 | 50297643-50297814 |
| 550 | LOC100131366 | 14 | 103655515-103655633 |
| 551 | NTN1 | 17 | 9143164-9143445 |
| 552 | ARL5C__1519 | 17 | 37321484-37321627 |
| 40 | C17orf64__A | 17 | 58498720-58498794 |
| 553 | OXT__C | 20 | 3052753-3052884 |
| 554 | PEAR1__B | 1 | 156863357-156863488 |
| 555 | ATP10A__E | 15 | 26108540-26108828 |
| 63 | CELF2__A | 10 | 11207221-11207812 |
| 556 | CAPN2__B | 1 | 223936858-223937009 |
| 84 | DSCR6 | 21 | 38378492-38378858 |
| 329 | NR2F6 | 19 | 17346347-17346780 |
| 61 | CDO1__A | 5 | 115152022-115152432 |
| 81 | DNMT3A__A | 2 | 25500046-25500305 |
| 557 | SIM2__B | 21 | 38076882-38077036 |
| 558 | CMTM3__B | 16 | 66638172-66638351 |
| 559 | SRC__B | 20 | 36013121-36013303 |
| 199 | LRRC41__B | 1 | 46769340-46769650 |
| 444 | TSHZ3 | 19 | 31839415-31840120 |
| 128 | HDGFRP3 | 15 | 83875827-83875946 |
| 560 | TACC2__B | 10 | 123922953-123923142 |
| 182 | LBH | 2 | 30453651-30453973 |

TABLE 6B

| Gene Annotation | Forward DMR Primer No. 5'-3' | SEQ ID NO: | Reverse Primer 5'-3' | SEQ ID NO: | Probe Sequence | SEQ ID NO: |
|---|---|---|---|---|---|---|
| AGRN_8794 | 526 GCGGTTTTTCGAGTTTTTTGCG | 137 | GAACGAATCCGCGCC | 138 | AGGCCACGGACGGCGATTTCGATTTATTTCG/3C6/ | 235 |
| BCAT1_6015 | 527 GCGGTGTGGTTAAGTTTCGG | 139 | CGCGACCCCAAATCGTA | 140 | CGCGCCGAGGGCGTACGGTTTATAGGGC/3C6/ | 236 |
| BHLHE23_8339 | 528 CGGGTTTTATTTTTTTTTCGTTTTCGTTTC | 141 | AACGAAATCCCACCGAACG | 142 | CGCGCCGAGGCGGTTTTAAGTCGCGGA/3C6/ | 237 |
| ELMO1_9100 | 529 GTAGAGCGTTTCGACGCG | 143 | TCGAACGAAAATAACCGCCG | 144 | AGGCCACGGACGGCGCTCGACAAAATAAAAAC/3C6/ | 238 |
| EPS8L2_F | 530 GTTTTTAGTTAGGCGCGGATTTC | 145 | AACCCGTAAACCAACCGC | 146 | CGCGCCGAGGCGTTCGGATTCGATTCGT/3C6/ | 239 |
| JAM3_B | 531 TGGTCGTTTTAGCGTTATGTCG | 147 | CGAAAACTACAAACCGCGC | 148 | AGGCCACGGACGCCGCGCTACCGCTA/3C6/ | 240 |
| KCNA3_7320 | 532 CGGTTATGTCGGGCGG | 149 | CAACGACGATACCCACACG | 150 | CGCGCCGAGGGCTAATAAACCACGACTACG/3C6/ | 241 |
| KCNA3_7518 | 533 TCGTTTTTTCGTCGTTTTCGTTTTC | 151 | CCCGTACGAAAACCCGA | 152 | AGGCCACGGACGCGAGTCGAGTTTATCGTTTG/3C6/ | 242 |

TABLE 6B-continued

| Gene Annotation | Forward DMR Primer No. 5'-3' | SEQ ID NO: | Reverse Primer 5'-3' | SEQ ID NO: | Probe Sequence | SEQ ID NO: |
|---|---|---|---|---|---|---|
| MDF1_6321 | 534 GTTCGT TATGCG CGTTTG TTTC | 153 | GAACACCC GAAAACCA ACGA | 154 | CGCGCC GAGG CGGGCG TTTTTGT TTAGG/ 3C6/ | 243 |
| RASSF1_8293 | 545 GTTTTG TGGTTT CGTTCG GTTC | 155 | CCGATTAA ACCCGTAC TTCGC | 156 | AGGCCA CGGACG CGCGTT TGTTAG CGTTTAA A/3C6/ | 244 |
| SFMBT2_2363 | 536 TTTCGT TTTTGT ATTTAT TTTAGC GACGT | 157 | ACGCGAAA AAAACGCG AAAACG | 158 | CGCGCC GAGG GCGAAA TAAATAA CAACGA CGA/3C6/ | 245 |
| SKI | 398 GTTAGG CGGTTA TTACGG GTC | 159 | GAAATCTA CTCCCTCC CCGA | 160 | AGGCCA CGGACG CGCGTT TTTTATT AGTTAGT CGTT/ 3C6/ | 246 |
| SPOCK2_7433 | 537 TATGTT GTTTTT TTTTCG TAAAGT TTACGG T | 161 | CCGACAAT AAAAATAA CATCGACT CG | 162 | CGCGCC GAGG GCGCGA TACCCT CTATTC/ 3C6/ | 247 |
| VIPR2_B | 538 TCGTTC GCGTTT TAGTAT TCGG | 163 | CGAAAAAA ACGCTCCT CCCG | 164 | AGGCCA CGGACG GCCGAT CTTCGC CTT/3C6/ | 248 |
| ZMIZ1_D | 539 GTTCGT TCGGTA GCGGC | 165 | ACCACTTC GCTACGAA AAAACG | 166 | CGCGCC GAGG GCGAAC GAATATA AATCGA AAAC/ 3C6/ | 249 |
| ZNF382_B | 540 TAGTCG TAATAG GGCGG TCG | 167 | CCGAAAC GACCCGTT AATCG | 168 | AGGCCA CGGACG GCCGCG CGATAC TAA/3C6/ | 250 |
| GYPC_3753 | 541 TGATTT AGGTGT CGTTTT TTTTCG TC | 169 | GAAAAAAA ATCGCGCT CCCG | 170 | AGGCCA CGGACG CGTCGA GGGTTA GGAGT/ 3C6/ | 251 |
| GYPC_C | 542 ATTTAT TGGAG GTCGC GGTTC | 171 | CCGAAACA CCAAAACG TCCG | 172 | CGCGCC GAGG GTAACC GTAACT CGACCC/ 3C6/ | 252 |

TABLE 6B-continued

| Gene Annotation | Forward DMR Primer No. 5'-3' | SEQ ID NO: | Reverse Primer 5'-3' | SEQ ID NO: | Probe Sequence | SEQ ID NO: |
|---|---|---|---|---|---|---|
| RFTN1_B | 543 GTGTTTTTGGTGGTTTCGGC | 173 | ATACTAAACGTATAAAAACAAACATACCGC | 174 | AGGCCACGGACGCGCGCTCCGAAAAAAC/3C6/ | 253 |
| PARP15 | 345 GGTTCGTAAGATTTAGTAGTTCGAGC | 175 | CGAAACAAAAAAATCAATATAATCGACGC | 176 | CGCGCCGAGGCGGGCGTAGAGATTTTACG/3C6/ | 254 |
| GPS | 119 TAGGACGTCGCGGTTTATTTC | 177 | CGCAATACTCGAAAAACGACG | 178 | AGGCCACGGACGGTAACGCGCATCTCCG/3C6/ | 255 |
| GPRIN1_B | 544 TCGCGTCGTCGTTCGT | 179 | GACGCCATCTAAAAACGCGA | 180 | CGCGCCGAGGTCGTTCGTGTCGGTTTC/3C6/ | 256 |
| HCG4_0331 | 545 GGCGACGTGGACGATAC | 181 | CTAAAACTCGTAACGTCGCTATCG | 182 | AGGCCACGGACGGAACCGCACGCACTA/3C6/ | 257 |
| HCG4_0556 | 546 GGTTTGTGAGTGATATCGGTCG | 183 | CGAACCCAAAAACTCGAAAAAACC | 184 | CGCGCCGAGGCCGAACGATCCGTAAAAAATATAA/3C6/ | 258 |
| NKX2-6_4159 | 547 GGGTTTAGTAGTATTTCGAAGGCG | 185 | GAAAAATTCAAAATACCGCTCCTCAC | 186 | AGGCCACGGACGCCCGAACCTCCTCGA/3C6/ | 259 |
| C1QL3_B | 548 GAAGGTTACGAGGTGTTTAAGTTCG | 187 | AACAAATAAACTTACCGATAATAAAATCGTAATAATTTC | 188 | CGCGCCGAGGGACGACGTGGTTATTAATTTCG/3C6/ | 260 |
| FAIM2_B | 549 TTGCGGAGGACGTTGC | 189 | GAAAAAAAACGATACGCCGCC | 190 | CGCGCCGAGGCGGATTCGCGAGTTCG/3C6/ | 261 |
| LOC100131366 | 550 TTTCGATTTCGTAGTTTCGCGG | 191 | CTCGCGAAACGTAACGAAAAC | 192 | AGGCCACGGACGGCGCGTTTTTTGAGGC/3C6/ | 262 |
| NTN1 | 551 CGTTCGTTTTCGTTCGGTTTC | 193 | ACCTAACGCCGAAACAACG | 194 | CGCGCCGAGGCGTTTTGCGTTCGTTC/3C6/ | 263 |

TABLE 6B-continued

| Gene Annotation | Forward DMR Primer No. 5'-3' | SEQ ID NO: | Reverse Primer 5'-3' | SEQ ID NO: | Probe Sequence | SEQ ID NO: |
|---|---|---|---|---|---|---|
| ARL5C_1519 | 552 GTTGTT TTTTTA TCGTTT CGGAGT G | 195 | CCTCTACC CACCGTAC CG | 196 | AGGCCA CGGACG GCGTCT ACTTCC CACC/ 3C6/ | 264 |
| C17orf64_A | 40 GTTTTC GGGTTA TTTTTAT TTGAAG TCG | 197 | TCCCCTAC CACCCAAC G | 198 | CGCGCC GAGG GACCAC CTCGAA CACAAA/ 3C6/ | 265 |
| OXT_C | 553 GGGTTT AATATT TGTTGC GCGG | 199 | CGAAGCG TTGCGTTG TTAG | 200 | AGGCCA CGGACG GACGAT ACCCAC GAAACA A/3C6/ | 266 |
| PEAR1_B | 554 TTGGCG AGGGTT CGAGT | 201 | CTAATCGC AAAACCGA AAAAAACG | 202 | CGCGCC GAGG GCCGAA AAACGA AAAACAA AAA/3C6/ | 267 |
| ATP10A_E | 555 GAGAG GAAATC GCGAA GCG | 203 | CCCCTAAA AAAACGCG CGA | 204 | AGGCCA CGGACG GCGAGA AAAGGC GTTTTC/ 3C6/ | 268 |
| CELF2_A | 63 GACGTT TATTTG GACGTT TGGC | 205 | ACCGAAAT CAAAACCC TCCG | 206 | CGCGCC GAGG CGATTTT CGTTTC GCGTT/ 3C6/ | 269 |
| CELF2_A | 63 GTTTCG CGACGT TTATTT GGAC | 207 | ACCGAAAT CAAAACCC TCCG | 208 | CGCGCC GAGG CGTTTG GCGATT TTCGTT/ 3C6/ | 270 |
| CAPN2_B | 556 GCGCG GAATTT TAGGAG TGC | 209 | CGCGACC CCACGATA ATC | 210 | AGGCCA CGGACG CGGGGT TCGAGT GTAAAT/ 3C6/ | 271 |
| DSCR6 | 84 GTTTTC GAGGG AGTGCG TTC | 211 | CGAAAAA AAAAACGA AACCCGC | 212 | CGCGCC GAGG CGACGG AAACGTT TTTAGTT C/3C6/ | 272 |
| NR2F6 | 329 GGTGTT GAAGAG TAGTCG CGT | 213 | CGACGCA AAAAACGA CGC | 214 | AGGCCA CGGACG TCGTTA GTTCGT ATACGTT GTC/3C6/ | 273 |
| CDO1_A | 61 CGAAAC GTAAGG ATGTCG TCG | 215 | AATTTATA TATACACC GCGTCTCC AAC | 216 | CGCGCC GAGG CGATCC CGAATC CACTAC/ 3C6/ | 274 |

TABLE 6B-continued

| Gene Annotation | Forward DMR Primer No.5'-3' | SEQ ID NO: | Reverse Primer 5'-3' | SEQ ID NO: | Probe Sequence | SEQ ID NO: |
|---|---|---|---|---|---|---|
| DNMT3A_A | 81TGTTTTGTTCGGTGAGGTTTCG | 217 | CAAACCGCCACCTAATCGC | 218 | AGGCCACGGACGCGAACAAACGCCCCC/3C6/ | 275 |
| SIM2_B | 557AAAGGGAGTTTTCGGGCG | 219 | ACCCGATACCCCCATTACC | 220 | CGCGCCGAGGCGTACGCAAACCTAAAAAATTC/3C6/ | 276 |
| CMTM3_B | 558GGTGGTTAAGAAAGTCGTAAGAAAATTTCG | 221 | TCTAAACAACAAAAACCCCGACC | 222 | AGGCCACGGACGCGTAATATCGACTCCGCAA/3C6/ | 277 |
| SRC_B | 559GGATGGTTTCGGTTGGGTTC | 223 | GCAAAACGCCAACAAAAAACG | 224 | AGGCCACGGACGCGCGTTAGGATGCGT/3C6/ | 278 |
| LRRC41_B | 199GGTCGAGGGAATTAGAGTTTTCG | 225 | AACCTAACCGCCAAAACAC | 226 | CGCGCCGAGGCGCACGAAACCCTCTTA/3C6/ | 279 |
| TSHZ3 | 444GGGATCGGTTCGTTTATTCGTTC | 227 | CCCGAAACATCTTCCGCG | 228 | AGGCCACGGACGCGCGTTTTTTGGTTCGG/3C6/ | 280 |
| HDGFRP3 | 128GATTCGTTTTCGAAAGTGGGC | 229 | TAAAACAAAAACTCCCGACCTCG | 230 | CGCGCCGAGGCGGAAGGATGGTCGTTTT/3C6/ | 281 |
| TACC2_B | 560GTTTTTGTGTGTGATACGATGATGTTATTATC | 231 | GTTTCCGAAACCCGCGA | 232 | AGGCCACGGACGCGTCGAGTAGTTTTAACGTTTG/3C6/ | 282 |
| LBH | 182TAGTTTTTCGTAAGTTAACGCGTTTC | 233 | CCCGCAACCTTACGATCAAC | 234 | CGCGCCGAGGCGTGGGTATTCGGTTTTC/3C6/ | 283 |

Sensitivities for each methylation marker were calculated at a 95% cutoff per subtype and listed in Tables 8A (ovarian cancer), 8B (clear cell OC), 8C (endometrioid OC), 8D (mucinous OC), and 8E (serous OC). Table 8A-E shows the ovarian cancer and sub-type tissue sensitivity at 95% specificity for the markers shown in Table 6A for OC, clear cell OC, endometrioid OC, mucinous, and serous OC.

TABLE 8A

| DMR No. | Marker | OC Sensitivity @95% specificity |
|---|---|---|
| 526 | AGRN_8794 | 49.1% |
| 527 | BCAT1_6015 | 80.7% |

TABLE 8A-continued

| DMR No. | Marker | OC Sensitivity @95% specificity |
|---|---|---|
| 529 | ELMO1_9100 | 24.6% |
| 528 | BHLHE23_8339 | 63.2% |
| 531 | JAM3_B | 26.3% |
| 530 | EPS8L2_F | 77.2% |
| 533 | KCNA3_7518 | 33.3% |
| 532 | KCNA3_7320 | 52.6% |
| 545 | RASSF1_8293 | 61.4% |
| 534 | MDFI_6321 | 70.2% |
| 398 | SKI | 89.5% |
| 536 | SFMBT2_2363 | 59.6% |
| 538 | VIPR_B | 56.1% |
| 537 | SPOCK2_7433 | 42.1% |
| 540 | ZNF382_B | 15.8% |
| 551 | NTN1 | 56.1% |
| 541 | GYPC_3753 | 63.2% |
| 542 | GYPC_C | 70.2% |
| 545 | HCG4_0331 | 43.9% |
| 546 | HCG4_0556 | 40.4% |
| 547 | NKX2-6_4159 | 77.2% |
| 548 | C1QL3_B | 64.9% |
| 550 | LOC100131366 | 71.9% |
| 549 | FAIM2_B | 71.9% |
| 555 | ATP10A_E | 45.6% |
| 544 | GPRIN1_B | 73.7% |
| 558 | CMTM3_B | 56.1% |
| 199 | LRRC41_B | 56.1% |
| 119 | GP5 | 61.4% |
| 345 | PARP15 | 70.2% |
| 552 | ARL5C_1519 | 64.9% |
| 539 | ZMIZ1_D | 38.6% |
| 553 | OXT_C | 68.4% |
| 40 | C17orf64_A | 45.6% |
| 557 | SRC_B | 66.7% |
| 128 | HDGFRP3 | 26.3% |
| 560 | TACC2_B | 68.4% |
| 543 | RFTN1_B | 33.3% |
| 554 | PEAR1_B | 73.7% |
| 444 | TSHZ3 | 70.2% |
| 182 | LBH | 63.2% |
| 556 | CAPN2_B | 68.4% |
| 557 | SIM2_B | 87.7% |
| 81 | DNMT3A_A | 82.5% |
| 61 | CDO1_A | 84.2% |
| 329 | NR2F6 | 61.4% |
| 84 | DSCR6 | 80.7% |
| 63 | CELF2_A | 70.2% |

TABLE 8B

| DMR No. | Marker | Clear cell OC sensitivity @95% spec. |
|---|---|---|
| 526 | AGRN_8794 | 100.0% |
| 527 | BCAT1_6015 | 73.3% |
| 529 | ELMO1_9100 | 6.7% |
| 528 | BHLHE23_8339 | 100.0% |
| 531 | JAM3_B | 53.3% |
| 530 | EPS8L2_F | 100.0% |
| 533 | KCNA3_7518 | 40.0% |
| 532 | KCNA3_7320 | 53.3% |
| 545 | RASSF1_8293 | 100.0% |
| 534 | MDFI_6321 | 100.0% |
| 398 | SKI | 100.0% |
| 536 | SFMBT2_2363 | 66.7% |
| 538 | VIPR_B | 66.7% |
| 537 | SPOCK2_7433 | 73.3% |
| 540 | ZNF382_B | 0.0% |
| 551 | NTN1 | 80.0% |
| 541 | GYPC_3753 | 93.3% |
| 542 | GYPC_C | 100.0% |
| 545 | HCG4_0331 | 46.7% |
| 546 | HCG4_0556 | 53.3% |
| 547 | NKX2-6_4159 | 100.0% |
| 548 | C1QL3_B | 93.3% |

TABLE 8B-continued

| DMR No. | Marker | Clear cell OC sensitivity @95% spec. |
|---|---|---|
| 550 | LOC100131366 | 100.0% |
| 549 | FAIM2_B | 100.0% |
| 555 | ATP10A_E | 20.0% |
| 544 | GPRIN1_B | 100.0% |
| 558 | CMTM3_B | 80.0% |
| 199 | LRRC41_B | 100.0% |
| 119 | GP5 | 93.3% |
| 345 | PARP15 | 93.3% |
| 552 | ARL5C_1519 | 93.3% |
| 539 | ZMIZ1_D | 46.7% |
| 553 | OXT_C | 93.3% |
| 40 | C17orf64_A | 46.7% |
| 557 | SRC_B | 86.7% |
| 128 | HDGFRP3 | 20.0% |
| 560 | TACC2_B | 100.0% |
| 543 | RFTN1_B | 40.0% |
| 554 | PEAR1_B | 93.3% |
| 444 | TSHZ3 | 93.3% |
| 182 | LBH | 100.0% |
| 556 | CAPN2_B | 73.3% |
| 557 | SIM2_B | 100.0% |
| 81 | DNMT3A_A | 86.7% |
| 61 | CDO1_A | 100.0% |
| 329 | NR2F6 | 60.0% |
| 84 | DSCR6 | 100.0% |
| 63 | CELF2_A | 73.3% |

TABLE 8C

| DMR No. | Marker | Endometrioid OC sensitivity @95% spec. |
|---|---|---|
| 526 | AGRN_8794 | 22.2% |
| 527 | BCAT1_6015 | 88.9% |
| 529 | ELMO1_9100 | 22.2% |
| 528 | BHLHE23_8339 | 77.8% |
| 531 | JAM3_B | 27.8% |
| 530 | EPS8L2_F | 83.3% |
| 533 | KCNA3_7518 | 44.4% |
| 532 | KCNA3_7320 | 55.6% |
| 545 | RASSF1_8293 | 72.2% |
| 534 | MDFI_6321 | 66.7% |
| 398 | SKI | 83.3% |
| 536 | SFMBT2_2363 | 55.6% |
| 538 | VIPR_B | 66.7% |
| 537 | SPOCK2_7433 | 55.6% |
| 540 | ZNF382_B | 11.1% |
| 551 | NTN1 | 61.1% |
| 541 | GYPC_3753 | 72.2% |
| 542 | GYPC_C | 77.8% |
| 545 | HCG4_0331 | 50.0% |
| 546 | HCG4_0556 | 55.6% |
| 547 | NKX2-6_4159 | 88.9% |
| 548 | C1QL3_B | 83.3% |
| 550 | LOC100131366 | 77.8% |
| 549 | FAIM2_B | 77.8% |
| 555 | ATP10A_E | 50.0% |
| 544 | GPRIN1_B | 100.0% |
| 558 | CMTM3_B | 55.6% |
| 199 | LRRC41_B | 38.9% |
| 119 | GP5 | 50.0% |
| 345 | PARP15 | 88.9% |
| 552 | ARL5C_1519 | 72.2% |
| 539 | ZMIZ1_D | 27.8% |
| 553 | OXT_C | 88.9% |
| 40 | C17orf64_A | 50.0% |
| 557 | SRC_B | 55.6% |
| 128 | HDGFRP3 | 22.2% |
| 560 | TACC2_B | 61.1% |
| 543 | RFTN1_B | 44.4% |
| 554 | PEAR1_B | 61.1% |
| 444 | TSHZ3 | 66.7% |
| 182 | LBH | 66.7% |
| 556 | CAPN2_B | 66.7% |

TABLE 8C-continued

| DMR No. | Marker | Endometrioid OC sensitivity @95% spec. |
|---|---|---|
| 557 | SIM2_B | 88.9% |
| 81 | DNMT3A_A | 83.3% |
| 61 | CDO1_A | 77.8% |
| 329 | NR2F6 | 55.6% |
| 84 | DSCR6 | 72.2% |
| 63 | CELF2_A | 94.4% |

TABLE 8D

| DMR No. | Marker | Mucinous OC sensitivity @95% spec. |
|---|---|---|
| 526 | AGRN_8794 | 16.7% |
| 527 | BCAT1_6015 | 100.0% |
| 529 | ELMO1_9100 | 83.3% |
| 528 | BHLHE23_8339 | 66.7% |
| 531 | JAM3_B | 16.7% |
| 530 | EPS8L2_F | 50.0% |
| 533 | KCNA3_7518 | 83.3% |
| 532 | KCNA3_7320 | 83.3% |
| 545 | RASSF1_8293 | 33.3% |
| 534 | MDFI_6321 | 100.0% |
| 398 | SKI | 83.3% |
| 536 | SFMBT2_2363 | 66.7% |
| 538 | VIPR_B | 100.0% |
| 537 | SPOCK2_7433 | 0.0% |
| 540 | ZNF382_B | 100.0% |
| 551 | NTN1 | 0.0% |
| 541 | GYPC_3753 | 33.3% |
| 542 | GYPC_C | 33.3% |
| 545 | HCG4_0331 | 16.7% |
| 546 | HCG4_0556 | 0.0% |
| 547 | NKX2-6_4159 | 66.7% |
| 548 | C1QL3_B | 66.7% |
| 550 | LOC100131366 | 33.3% |
| 549 | FAIM2_B | 50.0% |
| 555 | ATP10A_E | 100.0% |
| 544 | GPRIN1_B | 0.0% |
| 558 | CMTM3_B | 100.0% |
| 199 | LRRC41_B | 0.0% |
| 119 | GP5 | 50.0% |
| 345 | PARP15 | 33.3% |
| 552 | ARL5C_1519 | 33.3% |
| 539 | ZMIZ1_D | 100.0% |
| 553 | OXT_C | 0.0% |
| 40 | C17orf64_A | 0.0% |
| 557 | SRC_B | 83.3% |
| 128 | HDGFRP3 | 83.3% |
| 560 | TACC2_B | 100.0% |
| 543 | RFTN1_B | 16.7% |
| 554 | PEAR1_B | 33.3% |
| 444 | TSHZ3 | 83.3% |
| 182 | LBH | 100.0% |
| 556 | CAPN2_B | 16.7% |
| 557 | SIM2_B | 66.7% |
| 81 | DNMT3A_A | 83.3% |
| 61 | CDO1_A | 66.7% |
| 329 | NR2F6 | 0.0% |
| 84 | DSCR6 | 66.7% |
| 63 | CELF2_A | 16.7% |

TABLE 8E

| DMR No. | Marker | Serous OC sensitivity @95% spec. |
|---|---|---|
| 526 | AGRN_8794 | 44.4% |
| 527 | BCAT1_6015 | 72.2% |
| 529 | ELMO1_9100 | 22.2% |
| 528 | BHLHE23_8339 | 16.7% |
| 531 | JAM3_B | 5.6% |
| 530 | EPS8L2_F | 61.1% |
| 533 | KCNA3_7518 | 0.0% |
| 532 | KCNA3_7320 | 38.9% |
| 545 | RASSF1_8293 | 27.8% |
| 534 | MDFI_6321 | 38.9% |
| 398 | SKI | 88.9% |
| 536 | SFMBT2_2363 | 55.6% |
| 538 | VIPR_B | 22.2% |
| 537 | SPOCK2_7433 | 16.7% |
| 540 | ZNF382_B | 5.6% |
| 551 | NTN1 | 50.0% |
| 541 | GYPC_3753 | 38.9% |
| 542 | GYPC_C | 50.0% |
| 545 | HCG4_0331 | 44.4% |
| 546 | HCG4_0556 | 27.8% |
| 547 | NKX2-6_4159 | 50.0% |
| 548 | C1QL3_B | 22.2% |
| 550 | LOC100131366 | 55.6% |
| 549 | FAIM2_B | 50.0% |
| 555 | ATP10A_E | 44.4% |
| 544 | GPRIN1_B | 50.0% |
| 558 | CMTM3_B | 22.2% |
| 199 | LRRC41_B | 55.6% |
| 119 | GP5 | 50.0% |
| 345 | PARP15 | 44.4% |
| 552 | ARL5C_1519 | 44.4% |
| 539 | ZMIZ1_D | 22.2% |
| 553 | OXT_C | 50.0% |
| 40 | C17orf64_A | 55.6% |
| 557 | SRC_B | 55.6% |
| 128 | HDGFRP3 | 16.7% |
| 560 | TACC2_B | 38.9% |
| 543 | RFTN1_B | 22.2% |
| 554 | PEAR1_B | 83.3% |
| 444 | TSHZ3 | 50.0% |
| 182 | LBH | 16.7% |
| 556 | CAPN2_B | 83.3% |
| 557 | SIM2_B | 83.3% |
| 81 | DNMT3A_A | 77.8% |
| 61 | CDO1_A | 83.3% |
| 329 | NR2F6 | 88.9% |
| 84 | DSCR6 | 77.8% |
| 63 | CELF2_A | 61.1% |

Example III

This example describes the identification of plasma markers for detecting ovarian cancer (OC).

DNA methylation is an early event in carcinogenesis and can be detected in blood plasma samples from cancer patients. In DNA extracted from tissues, experiments (described in Examples I and II) first discovered, then validated discriminant methylated DNA marker (MDM) candidates for OC within tissue samples. Subsequent experiments independently tested plasma from women with and without OC and identified, validated, and demonstrated clinical feasibility for methylated DNA markers for plasma detection of OC.

For discovery, DNA from 67 frozen tissues (18 high grade serous (HGS), 18 endometrioid, 15 clear cell (CC), 6 mucinous OCs; 10 benign fallopian tube epithelium (FTE); and 19 buffy coats from cancer-free women underwent reduced representation bisulfate sequencing (RRBS) to identify MDMs associated with OC. Candidate MDM selection was based on receiver operating characteristic (ROC) discrimination, methylation fold change, and low background methylation among controls. Blinded biological validation was performed using MSP on DNA extracted from independent FFPE tissues from OCs (36 HGS, 22 endometrioid, 21 CC, and 14 mucinous) and 29 FTE. Top performing MDMs in tissue were tested using long-probe quantitative signal assays in independent pre-treatment plasma samples from women newly-diagnosed with OC and population-sampled healthy women. A random forest modeling analysis was performed to generate predictive probability of disease; results were 500-fold in silico cross-validated.

After RRBS discovery and biological validation, 33 MDMs showed marked methylation fold changes (10 to >1000) across all OC histologies vs FTE. The top 11 MDMs (GPRIN1, CDO1, SRC, SIM2, AGRN, FAIM42, CELF2, DSCR6, GYPC, CAPN2, BCAT1) were tested on plasma from 91 women with OC (76 (84%) HGS) and 91 without OC; the cross-validated 11-MDM panel highly discriminated OC from controls (95% specificity; 79% sensitivity, and AUC 0.91 (0.86-0.96)). Among HGS, the panel correctly identified 83%, including 5/6 stage I/II, and the majority of other subtypes (Table 9).

Whole methylome sequencing, stringent filtering criteria, and biological validation yielded outstanding candidate MDMs for OC that performed with promisingly high sensitivity and specificity in plasma.

TABLE 9

| OC histology | Serous | Clear cell | Endometrioid | Mucinous | Mixed |
|---|---|---|---|---|---|
| Sample Size | 76 | 4 | 8 | 2 | 1 |
| Sensitivity at 95% specificity % (95% CI) | 83% (73-90%) | 75% (19-99%) | 50% (16-84%) | 50% (13-99%) | 100% (3-100%) |

The following markers MDMs were additionally tested with 66 plasma samples from patient's with OC (e.g., 6 Stage I OC, 3 Stage II OC, 27 Stage III OC, 12 Stage IV OC, 18 ND) and compared with 237 control plasma from patients not having OC: ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GPS, DSCR6, SKI, SIM2_A, AGRN_8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333. Table 10 shows the sensitivity and specificity percentages for each marker for detecting OC.

TABLE 10

| Marker | Sensitivity | Specificity |
|---|---|---|
| ATP10A | 30 | 98 |
| EP8SL2 | 30 | 100 |
| CIQL3 | 30 | 95 |
| FAIM2 | 55 | 99 |
| CAPN2_B | 60 | 96 |
| LBH | 10 | 100 |
| CMTM3 | 10 | 100 |
| ZMIZ1_A | 15 | 100 |
| GPRIN2 | 50 | 94 |
| CDO1 | 70 | 95 |
| GP5_8905 | 30 | 95 |
| DSCR6 | 60 | 95 |
| SKI | 40 | 95 |
| SIM2_A | 75 | 95 |
| AGRN_8794 | 70 | 90 |
| BCAT1_6105 | 60 | 90 |
| KCNA3_7518 | 10 | 100 |
| KCNA3_7320 | 20 | 100 |
| LOC10013136 | 40 | 100 |
| GYPC_C | 63 | 95 |
| SRC_A | 32 | 98 |
| NR2F6 | 45 | 95 |
| TSHZ3 | 40 | 90 |
| CELF2 | 71 | 95 |
| TACC2 | 40 | 90 |
| VIPR | 47 | 93 |
| SPOCK2_7433 | 25 | 98 |

Subsequent experiments demonstrated clinical feasibility for identifying OC through detection of a combination of 1) increased cancer antigen 125 (CA-125) levels in comparison to normal non-cancerous levels, and 2) measured methylation level changes in comparison to normal non-cancerous methylation levels for the following markers: ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GPS, DSCR6, SKI, and SIM2_A.

Such markers MDMs were tested with 66 plasma samples from patient's with OC (e.g., 6 Stage I OC, 3 Stage II OC, 27 Stage III OC, 12 Stage IV OC, 18 ND) and compared with 237 control plasma from patients not having OC. The levels of CA-125 was also measured in the 66 plasma samples and 237 control plasma samples. Table 11 shows 90% specificity for detecting OC for the MDMs. Table 12 shows 90% specificity for detecting OC for CA-125. Table 13 shows 90% specificity for detecting OC for both the MDMs and CA-125.

TABLE 11

| | Tabulate | |
|---|---|---|
| | MDM Call@90% Spec. | |
| | Neg Row % | Pos Row % |
| Disease Type | | |
| Healthy Normal | 90.06% | 9.94% |
| Ovarian | 19.70% | 80.30% |
| Overall Stage | | |
| I | 16.67% | 83.33% |
| II | 0.00% | 100.00% |
| III | 11.11% | 88.89% |
| IV | 0.00% | 100.00% |
| ND | 50.00% | 50.00% |

TABLE 12

| | Tabulate | |
|---|---|---|
| | CA-125 Call@90% Spec. | |
| | Neg Row % | Pos Row % |
| Disease Type | | |
| Healthy Normal | 89.47% | 10.53% |
| Ovarian | 9.09% | 90.91% |
| Overall Stage | | |
| I | 0.00% | 100.00% |
| II | 0.00% | 100.00% |
| III | 3.70% | 96.30% |
| IV | 0.00% | 100.00% |
| ND | 27.78% | 72.22% |

TABLE 13

| | Tabulate | |
|---|---|---|
| | MDM + CA125 Call@90% Spec. | |
| | Neg Row % | Pos Row % |
| Disease Type | | |
| Healthy Normal | 90.06% | 9.94% |
| Ovarian | 7.58% | 92.42% |
| Overall Stage | | |
| I | 0.00% | 100.00% |
| II | 0.00% | 100.00% |
| III | 3.70% | 96.30% |
| IV | 0.00% | 100.00% |
| ND | 22.22% | 77.78% |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A method, comprising:
   treating genomic DNA from a biological sample from a human individual having or suspected of having an ovarian cancer with a reagent that modifies DNA in a methylation-specific manner;
   amplifying the treated genomic DNA using a set of primers for at least one of CAPN2 and/or SIM2; and
   determining a methylation level of at least one differentially methylated region (DMR) in CAPN2 and/or SIM2 using polymerase chain reaction, nucleic acid sequencing, mass spectrometry, methylation-specific nuclease, mass-based separation, or target capture.

2. The method of claim 1, wherein the biological sample comprises one or more of a plasma sample, a whole blood sample, a leukocyte sample, a serum sample, and an ovarian tissue sample.

3. The method of claim 1,
   wherein CAPN2 is selected from CAPN2_A and CAPN2_B; and
   wherein SIM2 is selected from SIM2_A and SIM2_B.

4. The method of claim 3, wherein the set of primers for CAPN2_A are capable of binding an amplicon bound by a sequence comprising SEQ ID NO: 53 and SEQ ID NO: 54; and/or wherein the set of primers for CAPN2_B are capable of binding an amplicon bound by a sequence comprising SEQ ID NO: 209 and SEQ ID NO: 210.

5. The method of claim 3, wherein the set of primers for SIM2_A are capable of binding an amplicon bound by a sequence comprising SEQ ID NO: 29 and SEQ ID NO: 30; and/or wherein the set of primers for SIM2_B are capable of binding an amplicon bound by a sequence comprising SEQ ID NO: 219 and SEQ ID NO: 220.

6. The method of claim 1, further comprising measuring a level of cancer antigen 125 (CA-125) in the biological sample.

7. The method of claim 1, wherein the genomic DNA is treated with a bisulfite reagent to produce bisulfite-treated genomic DNA.

8. The method of claim 1, wherein determining the methylation level of the at least one DMR in CAPN2 and/or SIM2 comprises using one or more methods selected from the group consisting of methylation-specific PCR, quantitative methylation-specific PCR, methylation-specific DNA restriction enzyme analysis, quantitative bisulfite pyrosequencing, flap endonuclease assay, PCR-flap assay, and bisulfite genomic sequencing PCR.

9. The method of claim 1, wherein amplifying the treated genomic DNA comprises:
   using primers specific for a CpG site in CAPN2, wherein the primers specifically bind at least a portion of a genetic region comprising chromosome 1 coordinates 223936858-223937009 or chromosome 1 coordinates 223936868-223937004; and/or
   using primers specific for a CpG site in SIM2, wherein the primers specifically bind at least a portion of a genetic region comprising chromosome 21 coordinates 38076882-38077036 or chromosome 21 coordinates 38076892-38077026.

10. The method of claim 1, wherein the method comprises using a set of primers for CAPN2 and a set of primers for SIM2, and determining a methylation level of at least one DMR in CAPN2 and SIM2.

11. The method of claim 1, wherein the method further comprises using a set of primers for FAIM2, and determining a methylation level of at least one DMR in FAIM2.

12. The method of claim 11, wherein FAIM2 is selected from FAIM2_A and FAIM2_B.

13. The method of claim 12, wherein the set of primers for FAIM2_A are capable of binding an amplicon bound by a sequence comprising SEQ ID NO: 35 and SEQ ID NO: 36; and/or wherein the set of primers for FAIM2_B are capable of binding an amplicon bound by a sequence comprising SEQ ID NO: 189 and SEQ ID NO: 190.

14. The method of claim 11, wherein amplifying the treated genomic DNA comprises using primers specific for a CpG site in FAIM2, wherein the primers specifically bind at least a portion of a genetic region comprising chromosome 12 coordinates 50297610-50297988 or chromosome 12 coordinates 50297643-50297814.

15. The method of claim 1, wherein the ovarian cancer is at least one of clear cell ovarian cancer, endometrioid ovarian cancer, mucinous ovarian cancer, and/or serous ovarian cancer.

16. The method of claim 1, wherein the at least one DMR is present in a coding region or a regulatory region of CAPN2 and/or SIM2.

17. The method of claim 11, wherein the at least one DMR is present in a coding region or a regulatory region of FAIM2.

* * * * *

UNITED STATES PATENT AND TRADEMARK OFFICE
CERTIFICATE OF CORRECTION

PATENT NO. : 11,702,704 B2
APPLICATION NO. : 17/085542
DATED : July 18, 2023
INVENTOR(S) : Taylor et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 245 days.

Signed and Sealed this
Twelfth Day of November, 2024

*Katherine Kelly Vidal*

Katherine Kelly Vidal
*Director of the United States Patent and Trademark Office*

SEQUENCE LISTING

```
<160> NUMBER OF SEQ ID NOS: 397

<210> SEQ ID NO 1
<211> LENGTH: 26
<212> TYPE: DNA
<213> ORGANISM: Artificial Sequence
<220> FEATURE:
<223> OTHER INFORMATION: synthetic

<400> SEQUENCE: 1
gaggagtttt aatattttta tagcgg                                           26

<210> SEQ ID NO 2
<211> LENGTH: 25
<212> TYPE: DNA
<213> ORGANISM: Artificial Sequence
<220> FEATURE:
<223> OTHER INFORMATION: synthetic

<400> SEQUENCE: 2
aacaaacttc aataaacccg acgca                                            25

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggcgacggcg aggaggagtt ttac                                             24
```

```
<210> SEQ ID NO 4
<211> LENGTH: 23
<212> TYPE: DNA
<213> ORGANISM: Artificial Sequence
<220> FEATURE:
<223> OTHER INFORMATION: synthetic

<400> SEQUENCE: 4
gcaacccttc gacgctaaac ccg                                         23

<210> SEQ ID NO 5
<211> LENGTH: 25
<212> TYPE: DNA
<213> ORGANISM: Artificial Sequence
<220> FEATURE:
<223> OTHER INFORMATION: synthetic

<400> SEQUENCE: 5
gatatgttgt cggggttcgt tacga                                       25

<210> SEQ ID NO 6
<211> LENGTH: 25
<212> TYPE: DNA
<213> ORGANISM: Artificial Sequence
<220> FEATURE:
<223> OTHER INFORMATION: synthetic

<400> SEQUENCE: 6
caaaataccc gataaaacaa tcgaa                                       25

<210> SEQ ID NO 7
<211> LENGTH: 30
<212> TYPE: DNA
<213> ORGANISM: Artificial Sequence
<220> FEATURE:
<223> OTHER INFORMATION: synthetic

<400> SEQUENCE: 7
cgttagtcgt ttttattttt aatttatcgt                                  30

<210> SEQ ID NO 8
<211> LENGTH: 21
<212> TYPE: DNA
<213> ORGANISM: Artificial Sequence
<220> FEATURE:
<223> OTHER INFORMATION: synthetic

<400> SEQUENCE: 8
cttcaaaaac tccaacgcgt c                                           21

<210> SEQ ID NO 9
<211> LENGTH: 25
<212> TYPE: DNA
<213> ORGANISM: Artificial Sequence
<220> FEATURE:
<223> OTHER INFORMATION: synthetic

<400> SEQUENCE: 9
gattagatta gattcggagt ttcgt                                       25

<210> SEQ ID NO 10
<211> LENGTH: 25
<212> TYPE: DNA
<213> ORGANISM: Artificial Sequence
<220> FEATURE:
<223> OTHER INFORMATION: synthetic
```

<400> SEQUENCE: 10
accaactaaa atcctcctcc cccgc                                              25

<210> SEQ ID NO 11
<211> LENGTH: 27
<212> TYPE: DNA
<213> ORGANISM: Artificial Sequence
<220> FEATURE:
<223> OTHER INFORMATION: synthetic

<400> SEQUENCE: 11
tagtttggtt aaagggtgcg aattcga                                            27

<210> SEQ ID NO 12
<211> LENGTH: 33
<212> TYPE: DNA
<213> ORGANISM: Artificial Sequence
<220> FEATURE:
<223> OTHER INFORMATION: synthetic

<400> SEQUENCE: 12
cgaaactctt ccgaactaaa taatacaccc gct                                     33

<210> SEQ ID NO 13
<211> LENGTH: 25
<212> TYPE: DNA
<213> ORGANISM: Artificial Sequence
<220> FEATURE:
<223> OTHER INFORMATION: synthetic

<400> SEQUENCE: 13
tttgttggga gttcggggtt ttatc                                              25

<210> SEQ ID NO 14
<211> LENGTH: 23
<212> TYPE: DNA
<213> ORGANISM: Artificial Sequence
<220> FEATURE:
<223> OTHER INFORMATION: synthetic

<400> SEQUENCE: 14
aacctatccg aaacctcccc gtt                                                23

<210> SEQ ID NO 15
<211> LENGTH: 26
<212> TYPE: DNA
<213> ORGANISM: Artificial Sequence
<220> FEATURE:
<223> OTHER INFORMATION: synthetic

<400> SEQUENCE: 15
ttgcgtatag gttagtttag gatcgt                                             26

<210> SEQ ID NO 16
<211> LENGTH: 24
<212> TYPE: DNA
<213> ORGANISM: Artificial Sequence
<220> FEATURE:
<223> OTHER INFORMATION: synthetic

<400> SEQUENCE: 16
cttacacccg ccccgctaaa ttcg                                               24

<210> SEQ ID NO 17

```
<211> LENGTH: 25
<212> TYPE: DNA
<213> ORGANISM: Artificial Sequence
<220> FEATURE:
<223> OTHER INFORMATION: synthetic

<400> SEQUENCE: 17
tcgttggtta tcgtacgttt ttcgt                                          25

<210> SEQ ID NO 18
<211> LENGTH: 25
<212> TYPE: DNA
<213> ORGANISM: Artificial Sequence
<220> FEATURE:
<223> OTHER INFORMATION: synthetic

<400> SEQUENCE: 18
actaaaccta tcccgaaatc ccgat                                          25

<210> SEQ ID NO 19
<211> LENGTH: 28
<212> TYPE: DNA
<213> ORGANISM: Artificial Sequence
<220> FEATURE:
<223> OTHER INFORMATION: synthetic

<400> SEQUENCE: 19
ggttgttttt gtagtgttta taggacgg                                       28

<210> SEQ ID NO 20
<211> LENGTH: 25
<212> TYPE: DNA
<213> ORGANISM: Artificial Sequence
<220> FEATURE:
<223> OTHER INFORMATION: synthetic

<400> SEQUENCE: 20
aaaacaaaat atactacccg ccgaa                                          25

<210> SEQ ID NO 21
<211> LENGTH: 25
<212> TYPE: DNA
<213> ORGANISM: Artificial Sequence
<220> FEATURE:
<223> OTHER INFORMATION: synthetic

<400> SEQUENCE: 21
ggggaggagt ttttaatcgt ttcgt                                          25

<210> SEQ ID NO 22
<211> LENGTH: 25
<212> TYPE: DNA
<213> ORGANISM: Artificial Sequence
<220> FEATURE:
<223> OTHER INFORMATION: synthetic

<400> SEQUENCE: 22
aaacaaccgc ttcgatttta acgac                                          25

<210> SEQ ID NO 23
<211> LENGTH: 28
<212> TYPE: DNA
<213> ORGANISM: Artificial Sequence
<220> FEATURE:
<223> OTHER INFORMATION: synthetic

<400> SEQUENCE: 23
``` cggtaggggga agtttagtag gtgagcgt                                    28

<210> SEQ ID NO 24
<211> LENGTH: 27
<212> TYPE: DNA
<213> ORGANISM: Artificial Sequence
<220> FEATURE:
<223> OTHER INFORMATION: synthetic

<400> SEQUENCE: 24
gaactaaaaa cgtttccgtc gaacgca                                      27

<210> SEQ ID NO 25
<211> LENGTH: 27
<212> TYPE: DNA
<213> ORGANISM: Artificial Sequence
<220> FEATURE:
<223> OTHER INFORMATION: synthetic

<400> SEQUENCE: 25
ggtagttagg cggttattac gggtcgc                                      27

<210> SEQ ID NO 26
<211> LENGTH: 25
<212> TYPE: DNA
<213> ORGANISM: Artificial Sequence
<220> FEATURE:
<223> OTHER INFORMATION: synthetic

<400> SEQUENCE: 26
aaaatctact ccctccccga acgct                                        25

<210> SEQ ID NO 27
<211> LENGTH: 23
<212> TYPE: DNA
<213> ORGANISM: Artificial Sequence
<220> FEATURE:
<223> OTHER INFORMATION: synthetic

<400> SEQUENCE: 27
cgcgcgtttt attgttgggt tgc                                          23

<210> SEQ ID NO 28
<211> LENGTH: 24
<212> TYPE: DNA
<213> ORGANISM: Artificial Sequence
<220> FEATURE:
<223> OTHER INFORMATION: synthetic

<400> SEQUENCE: 28
aacgaactat taaactccct cgcc                                         24

<210> SEQ ID NO 29
<211> LENGTH: 25
<212> TYPE: DNA
<213> ORGANISM: Artificial Sequence
<220> FEATURE:
<223> OTHER INFORMATION: synthetic

<400> SEQUENCE: 29
gttagtagtt gttggggcgg cgttc                                        25

<210> SEQ ID NO 30
<211> LENGTH: 25
<212> TYPE: DNA

```
<213> ORGANISM: Artificial Sequence
<220> FEATURE:
<223> OTHER INFORMATION: synthetic

<400> SEQUENCE: 30 aaccgatac cccattacc gtacg                                    25

<210> SEQ ID NO 31
<211> LENGTH: 28
<212> TYPE: DNA
<213> ORGANISM: Artificial Sequence
<220> FEATURE:
<223> OTHER INFORMATION: synthetic

<400> SEQUENCE: 31
cgcgtagtag tagggtgag tagagggc                                28

<210> SEQ ID NO 32
<211> LENGTH: 28
<212> TYPE: DNA
<213> ORGANISM: Artificial Sequence
<220> FEATURE:
<223> OTHER INFORMATION: synthetic

<400> SEQUENCE: 32
gaatctaacc caaaaattaa cacgcgct                               28

<210> SEQ ID NO 33
<211> LENGTH: 25
<212> TYPE: DNA
<213> ORGANISM: Artificial Sequence
<220> FEATURE:
<223> OTHER INFORMATION: synthetic

<400> SEQUENCE: 33
cgggatcgga gttagaattt ttcgt                                  25

<210> SEQ ID NO 34
<211> LENGTH: 23
<212> TYPE: DNA
<213> ORGANISM: Artificial Sequence
<220> FEATURE:
<223> OTHER INFORMATION: synthetic

<400> SEQUENCE: 34
acctaaacgc ctaacgaccc ccg                                    23

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
tatttcgggg gagggttaag ggcg                                   24

<210> SEQ ID NO 36
<211> LENGTH: 22
<212> TYPE: DNA
<213> ORGANISM: Artificial Sequence
<220> FEATURE:
<223> OTHER INFORMATION: synthetic

<400> SEQUENCE: 36
gctacgaatt cgcgaacccg aa                                     22
```

<210> SEQ ID NO 37
<211> LENGTH: 30
<212> TYPE: DNA
<213> ORGANISM: Artificial Sequence
<220> FEATURE:
<223> OTHER INFORMATION: synthetic

<400> SEQUENCE: 37
gggttgttta gaaagtgatt tttcgggagc                                    30

<210> SEQ ID NO 38
<211> LENGTH: 25
<212> TYPE: DNA
<213> ORGANISM: Artificial Sequence
<220> FEATURE:
<223> OTHER INFORMATION: synthetic

<400> SEQUENCE: 38
aaaaccgaaa caaaacgaaa acgca                                         25

<210> SEQ ID NO 39
<211> LENGTH: 31
<212> TYPE: DNA
<213> ORGANISM: Artificial Sequence
<220> FEATURE:
<223> OTHER INFORMATION: synthetic

<400> SEQUENCE: 39
tgttttttta ttttattttt agttttttcg t                                  31

<210> SEQ ID NO 40
<211> LENGTH: 33
<212> TYPE: DNA
<213> ORGANISM: Artificial Sequence
<220> FEATURE:
<223> OTHER INFORMATION: synthetic

<400> SEQUENCE: 40
aatttctcat taccgactttt tcttccaacc gaa                               33

<210> SEQ ID NO 41
<211> LENGTH: 29
<212> TYPE: DNA
<213> ORGANISM: Artificial Sequence
<220> FEATURE:
<223> OTHER INFORMATION: synthetic

<400> SEQUENCE: 41
ggcgcgtatt tggtttatga aagttacgg                                     29

<210> SEQ ID NO 42
<211> LENGTH: 25
<212> TYPE: DNA
<213> ORGANISM: Artificial Sequence
<220> FEATURE:
<223> OTHER INFORMATION: synthetic

<400> SEQUENCE: 42
caaacgacgc taccccctaca cacga                                        25

<210> SEQ ID NO 43
<211> LENGTH: 33
<212> TYPE: DNA
<213> ORGANISM: Artificial Sequence
<220> FEATURE:

<223> OTHER INFORMATION: synthetic

<400> SEQUENCE: 43
ggcgttagtt ttttatttat ttttaggggg cgc                33

<210> SEQ ID NO 44
<211> LENGTH: 25
<212> TYPE: DNA
<213> ORGANISM: Artificial Sequence
<220> FEATURE:
<223> OTHER INFORMATION: synthetic

<400> SEQUENCE: 44
ccaacccata cttctacccg ccgac                25

<210> SEQ ID NO 45
<211> LENGTH: 25
<212> TYPE: DNA
<213> ORGANISM: Artificial Sequence
<220> FEATURE:
<223> OTHER INFORMATION: synthetic

<400> SEQUENCE: 45
acgaaatatt tttaattgag ttcga                25

<210> SEQ ID NO 46
<211> LENGTH: 25
<212> TYPE: DNA
<213> ORGANISM: Artificial Sequence
<220> FEATURE:
<223> OTHER INFORMATION: synthetic

<400> SEQUENCE: 46
aaaaaatacg aaacacaaaa acgac                25

<210> SEQ ID NO 47
<211> LENGTH: 25
<212> TYPE: DNA
<213> ORGANISM: Artificial Sequence
<220> FEATURE:
<223> OTHER INFORMATION: synthetic

<400> SEQUENCE: 47
ttggcgtatt ataataagcg ttcga                25

<210> SEQ ID NO 48
<211> LENGTH: 25
<212> TYPE: DNA
<213> ORGANISM: Artificial Sequence
<220> FEATURE:
<223> OTHER INFORMATION: synthetic

<400> SEQUENCE: 48
gaaaaacaac aaacgcacga ccgtc                25

<210> SEQ ID NO 49
<211> LENGTH: 32
<212> TYPE: DNA
<213> ORGANISM: Artificial Sequence
<220> FEATURE:
<223> OTHER INFORMATION: synthetic

<400> SEQUENCE: 49
acgtagttga agatttttg ttagtttttc ga                32

```
<210> SEQ ID NO 50
<211> LENGTH: 25
<212> TYPE: DNA
<213> ORGANISM: Artificial Sequence
<220> FEATURE:
<223> OTHER INFORMATION: synthetic

<400> SEQUENCE: 50
acctcatacg ccgcttaaaa tcgcc                                          25

<210> SEQ ID NO 51
<211> LENGTH: 25
<212> TYPE: DNA
<213> ORGANISM: Artificial Sequence
<220> FEATURE:
<223> OTHER INFORMATION: synthetic

<400> SEQUENCE: 51
tagtagggtt gagtttgggg ttcgt                                          25

<210> SEQ ID NO 52
<211> LENGTH: 24
<212> TYPE: DNA
<213> ORGANISM: Artificial Sequence
<220> FEATURE:
<223> OTHER INFORMATION: synthetic

<400> SEQUENCE: 52
gtaaaatctc tacgcccgct cgaa                                           24

<210> SEQ ID NO 53
<211> LENGTH: 23
<212> TYPE: DNA
<213> ORGANISM: Artificial Sequence
<220> FEATURE:
<223> OTHER INFORMATION: synthetic

<400> SEQUENCE: 53
cgttcgagtt gcgaaaggga cgt                                            23

<210> SEQ ID NO 54
<211> LENGTH: 23
<212> TYPE: DNA
<213> ORGANISM: Artificial Sequence
<220> FEATURE:
<223> OTHER INFORMATION: synthetic

<400> SEQUENCE: 54
gcactcctaa aattccgcgc gaa                                            23

<210> SEQ ID NO 55
<211> LENGTH: 31
<212> TYPE: DNA
<213> ORGANISM: Artificial Sequence
<220> FEATURE:
<223> OTHER INFORMATION: synthetic

<400> SEQUENCE: 55
ggtaaaattt acgttgtgta gaattaggcg g                                   31

<210> SEQ ID NO 56
<211> LENGTH: 25
<212> TYPE: DNA
<213> ORGANISM: Artificial Sequence
<220> FEATURE:
<223> OTHER INFORMATION: synthetic
```

```
<400> SEQUENCE: 56
acgtaaaaat ccacgccgaa aacgc                                         25

<210> SEQ ID NO 57
<211> LENGTH: 25
<212> TYPE: DNA
<213> ORGANISM: Artificial Sequence
<220> FEATURE:
<223> OTHER INFORMATION: synthetic

<400> SEQUENCE: 57 ttattttgg attagcgatc gacga                                          25

<210> SEQ ID NO 58
<211> LENGTH: 24
<212> TYPE: DNA
<213> ORGANISM: Artificial Sequence
<220> FEATURE:
<223> OTHER INFORMATION: synthetic

<400> SEQUENCE: 58
gcgctaacta ttctcgatta cgcc                                          24

<210> SEQ ID NO 59
<211> LENGTH: 25
<212> TYPE: DNA
<213> ORGANISM: Artificial Sequence
<220> FEATURE:
<223> OTHER INFORMATION: synthetic

<400> SEQUENCE: 59
cgtttaggtt atcgttattt ttcgt                                         25

<210> SEQ ID NO 60
<211> LENGTH: 22
<212> TYPE: DNA
<213> ORGANISM: Artificial Sequence
<220> FEATURE:
<223> OTHER INFORMATION: synthetic

<400> SEQUENCE: 60
gaaccgccga acatcctacg at                                            22

<210> SEQ ID NO 61
<211> LENGTH: 30
<212> TYPE: DNA
<213> ORGANISM: Artificial Sequence
<220> FEATURE:
<223> OTHER INFORMATION: synthetic

<400> SEQUENCE: 61
gggggcggga gatattcgaa gttatttatc                                    30

<210> SEQ ID NO 62
<211> LENGTH: 24
<212> TYPE: DNA
<213> ORGANISM: Artificial Sequence
<220> FEATURE:
<223> OTHER INFORMATION: synthetic

<400> SEQUENCE: 62
aaacgctatc gcccgaaaaa accg                                          24

<210> SEQ ID NO 63
<211> LENGTH: 25
```

```
<212> TYPE: DNA
<213> ORGANISM: Artificial Sequence
<220> FEATURE:
<223> OTHER INFORMATION: synthetic

<400> SEQUENCE: 63
ttttgggtag gaaggatagt agcgt                                              25

<210> SEQ ID NO 64
<211> LENGTH: 20
<212> TYPE: DNA
<213> ORGANISM: Artificial Sequence
<220> FEATURE:
<223> OTHER INFORMATION: synthetic

<400> SEQUENCE: 64
caaaaacgaa cgacgacgac                                                    20

<210> SEQ ID NO 65
<211> LENGTH: 23
<212> TYPE: DNA
<213> ORGANISM: Artificial Sequence
<220> FEATURE:
<223> OTHER INFORMATION: synthetic

<400> SEQUENCE: 65
gcgagtcggg gtttttt gga gac                                               23

<210> SEQ ID NO 66
<211> LENGTH: 24
<212> TYPE: DNA
<213> ORGANISM: Artificial Sequence
<220> FEATURE:
<223> OTHER INFORMATION: synthetic

<400> SEQUENCE: 66
cacccaccct acgtataccc gcgt                                               24

<210> SEQ ID NO 67
<211> LENGTH: 20
<212> TYPE: DNA
<213> ORGANISM: Artificial Sequence
<220> FEATURE:
<223> OTHER INFORMATION: synthetic

<400> SEQUENCE: 67
gatttggcgc ggtttagcgc                                                    20

<210> SEQ ID NO 68
<211> LENGTH: 26
<212> TYPE: DNA
<213> ORGANISM: Artificial Sequence
<220> FEATURE:
<223> OTHER INFORMATION: synthetic

<400> SEQUENCE: 68
ccctctcgca cccatttaaa aaaccg                                             26

<210> SEQ ID NO 69
<211> LENGTH: 25
<212> TYPE: DNA
<213> ORGANISM: Artificial Sequence
<220> FEATURE:
<223> OTHER INFORMATION: synthetic

<400> SEQUENCE: 69
```
tgaatgttaa ttaagattgc gttcg    25

<210> SEQ ID NO 70
<211> LENGTH: 23
<212> TYPE: DNA
<213> ORGANISM: Artificial Sequence
<220> FEATURE:
<223> OTHER INFORMATION: synthetic

<400> SEQUENCE: 70
aacaccctca cgaaaaaccc gcg    23

<210> SEQ ID NO 71
<211> LENGTH: 27
<212> TYPE: DNA
<213> ORGANISM: Artificial Sequence
<220> FEATURE:
<223> OTHER INFORMATION: synthetic

<400> SEQUENCE: 71
ttgtagttgt tgtttttggg cggtcgc    27

<210> SEQ ID NO 72
<211> LENGTH: 25
<212> TYPE: DNA
<213> ORGANISM: Artificial Sequence
<220> FEATURE:
<223> OTHER INFORMATION: synthetic

<400> SEQUENCE: 72
aaaccgaacg aatttcgctt tcccg    25

<210> SEQ ID NO 73
<211> LENGTH: 25
<212> TYPE: DNA
<213> ORGANISM: Artificial Sequence
<220> FEATURE:
<223> OTHER INFORMATION: synthetic

<400> SEQUENCE: 73
tggcggcgtc gtatattttt tacgt    25

<210> SEQ ID NO 74
<211> LENGTH: 20
<212> TYPE: DNA
<213> ORGANISM: Artificial Sequence
<220> FEATURE:
<223> OTHER INFORMATION: synthetic

<400> SEQUENCE: 74
accgctataa cgcccccgaa    20

<210> SEQ ID NO 75
<211> LENGTH: 25
<212> TYPE: DNA
<213> ORGANISM: Artificial Sequence
<220> FEATURE:
<223> OTHER INFORMATION: synthetic

<400> SEQUENCE: 75
tagttaaaga gtatattgga ggcgg    25

<210> SEQ ID NO 76
<211> LENGTH: 25
<212> TYPE: DNA
<213> ORGANISM: Artificial Sequence

```
<220> FEATURE:
<223> OTHER INFORMATION: synthetic

<400> SEQUENCE: 76
ctctatccta aaacgaaaa acgaa                                            25

<210> SEQ ID NO 77
<211> LENGTH: 25
<212> TYPE: DNA
<213> ORGANISM: Artificial Sequence
<220> FEATURE:
<223> OTHER INFORMATION: synthetic

<400> SEQUENCE: 77
aggggtagcg tgtgagtagt atcga                                           25

<210> SEQ ID NO 78
<211> LENGTH: 25
<212> TYPE: DNA
<213> ORGANISM: Artificial Sequence
<220> FEATURE:
<223> OTHER INFORMATION: synthetic

<400> SEQUENCE: 78 tacctttcc caaataacg tcgaa                                             25

<210> SEQ ID NO 79
<211> LENGTH: 25
<212> TYPE: DNA
<213> ORGANISM: Artificial Sequence
<220> FEATURE:
<223> OTHER INFORMATION: synthetic

<400> SEQUENCE: 79
gttagttttc gcggttttg ttcgg                                            25

<210> SEQ ID NO 80
<211> LENGTH: 28
<212> TYPE: DNA
<213> ORGANISM: Artificial Sequence
<220> FEATURE:
<223> OTHER INFORMATION: synthetic

<400> SEQUENCE: 80
cgccgtacta ttaaaacttc tcgtcgac                                        28

<210> SEQ ID NO 81
<211> LENGTH: 25
<212> TYPE: DNA
<213> ORGANISM: Artificial Sequence
<220> FEATURE:
<223> OTHER INFORMATION: synthetic

<400> SEQUENCE: 81
tttttggttg ggttaagttc ggcgc                                           25

<210> SEQ ID NO 82
<211> LENGTH: 25
<212> TYPE: DNA
<213> ORGANISM: Artificial Sequence
<220> FEATURE:
<223> OTHER INFORMATION: synthetic

<400> SEQUENCE: 82
gccttctcaa tcgcccctct acgaa                                           25
```

<210> SEQ ID NO 83
<211> LENGTH: 25
<212> TYPE: DNA
<213> ORGANISM: Artificial Sequence
<220> FEATURE:
<223> OTHER INFORMATION: synthetic

<400> SEQUENCE: 83
ttagtttcgt tttcggagtt cgcga    25

<210> SEQ ID NO 84
<211> LENGTH: 34
<212> TYPE: DNA
<213> ORGANISM: Artificial Sequence
<220> FEATURE:
<223> OTHER INFORMATION: synthetic

<400> SEQUENCE: 84
ctcctatata taacacgata atatcatcat cgcc    34

<210> SEQ ID NO 85
<211> LENGTH: 25
<212> TYPE: DNA
<213> ORGANISM: Artificial Sequence
<220> FEATURE:
<223> OTHER INFORMATION: synthetic

<400> SEQUENCE: 85
tttttagttt tttcgtttt cgcgg    25

<210> SEQ ID NO 86
<211> LENGTH: 27
<212> TYPE: DNA
<213> ORGANISM: Artificial Sequence
<220> FEATURE:
<223> OTHER INFORMATION: synthetic

<400> SEQUENCE: 86
acgacttcct ttatctctac tcccgcc    27

<210> SEQ ID NO 87
<211> LENGTH: 25
<212> TYPE: DNA
<213> ORGANISM: Artificial Sequence
<220> FEATURE:
<223> OTHER INFORMATION: synthetic

<400> SEQUENCE: 87
cggaaaatta gtaatattag ggcgt    25

<210> SEQ ID NO 88
<211> LENGTH: 25
<212> TYPE: DNA
<213> ORGANISM: Artificial Sequence
<220> FEATURE:
<223> OTHER INFORMATION: synthetic

<400> SEQUENCE: 88
cgaacccgac tcgtaaataa acgac    25

<210> SEQ ID NO 89
<211> LENGTH: 22
<212> TYPE: DNA
<213> ORGANISM: Artificial Sequence
<220> FEATURE:
<223> OTHER INFORMATION: synthetic

```
<400> SEQUENCE: 89
gtcgtacgta tcgggtggac ga                                          22

<210> SEQ ID NO 90
<211> LENGTH: 20
<212> TYPE: DNA
<213> ORGANISM: Artificial Sequence
<220> FEATURE:
<223> OTHER INFORMATION: synthetic

<400> SEQUENCE: 90
ccctaactaa cgcgaacccg                                             20

<210> SEQ ID NO 91
<211> LENGTH: 25
<212> TYPE: DNA
<213> ORGANISM: Artificial Sequence
<220> FEATURE:
<223> OTHER INFORMATION: synthetic

<400> SEQUENCE: 91
ggaggggcga atagagtttt tttcg                                       25

<210> SEQ ID NO 92
<211> LENGTH: 24
<212> TYPE: DNA
<213> ORGANISM: Artificial Sequence
<220> FEATURE:
<223> OTHER INFORMATION: synthetic

<400> SEQUENCE: 92
aaaacgaccc cttcctctct cgcc                                        24

<210> SEQ ID NO 93
<211> LENGTH: 25
<212> TYPE: DNA
<213> ORGANISM: Artificial Sequence
<220> FEATURE:
<223> OTHER INFORMATION: synthetic

<400> SEQUENCE: 93
tttggttagg aagtagcgga atcgg                                       25

<210> SEQ ID NO 94
<211> LENGTH: 29
<212> TYPE: DNA
<213> ORGANISM: Artificial Sequence
<220> FEATURE:
<223> OTHER INFORMATION: synthetic

<400> SEQUENCE: 94
gcaataacct aaactccaac atcaacgta                                   29

<210> SEQ ID NO 95
<211> LENGTH: 25
<212> TYPE: DNA
<213> ORGANISM: Artificial Sequence
<220> FEATURE:
<223> OTHER INFORMATION: synthetic

<400> SEQUENCE: 95
ataattttaa gggggaaacg ttcgt                                       25

<210> SEQ ID NO 96
```

```
<210> SEQ ID NO 96
<211> LENGTH: 26
<212> TYPE: DNA
<213> ORGANISM: Artificial Sequence
<220> FEATURE:
<223> OTHER INFORMATION: synthetic

<400> SEQUENCE: 96
ccaatataac cgacttctta aacgct                                          26

<210> SEQ ID NO 97
<211> LENGTH: 25
<212> TYPE: DNA
<213> ORGANISM: Artificial Sequence
<220> FEATURE:
<223> OTHER INFORMATION: synthetic

<400> SEQUENCE: 97
gattaattag gcggttcggt agcgg                                           25

<210> SEQ ID NO 98
<211> LENGTH: 32
<212> TYPE: DNA
<213> ORGANISM: Artificial Sequence
<220> FEATURE:
<223> OTHER INFORMATION: synthetic

<400> SEQUENCE: 98
caattaaaac ctatcattaa cttcccctcg ac                                   32

<210> SEQ ID NO 99
<211> LENGTH: 28
<212> TYPE: DNA
<213> ORGANISM: Artificial Sequence
<220> FEATURE:
<223> OTHER INFORMATION: synthetic

<400> SEQUENCE: 99
ggttgtaagg gtttttggtt ttcgacgc                                        28

<210> SEQ ID NO 100
<211> LENGTH: 23
<212> TYPE: DNA
<213> ORGANISM: Artificial Sequence
<220> FEATURE:
<223> OTHER INFORMATION: synthetic

<400> SEQUENCE: 100
aacgaattca tacgtccccc gaa                                             23

<210> SEQ ID NO 101
<211> LENGTH: 28
<212> TYPE: DNA
<213> ORGANISM: Artificial Sequence
<220> FEATURE:
<223> OTHER INFORMATION: synthetic

<400> SEQUENCE: 101
cgtttcgtta gtagttatcg attttcgt                                        28

<210> SEQ ID NO 102
<211> LENGTH: 22
<212> TYPE: DNA
<213> ORGANISM: Artificial Sequence
<220> FEATURE:
<223> OTHER INFORMATION: synthetic

<400> SEQUENCE: 102
```
aaacgaaccc cctccttcgc gt                                          22

<210> SEQ ID NO 103
<211> LENGTH: 23
<212> TYPE: DNA
<213> ORGANISM: Artificial Sequence
<220> FEATURE:
<223> OTHER INFORMATION: synthetic

<400> SEQUENCE: 103
gtttacgcgc gagagcgtgt tgc                                         23

<210> SEQ ID NO 104
<211> LENGTH: 25
<212> TYPE: DNA
<213> ORGANISM: Artificial Sequence
<220> FEATURE:
<223> OTHER INFORMATION: synthetic

<400> SEQUENCE: 104
gcccgaaccc gacctaatat tcgat                                       25

<210> SEQ ID NO 105
<211> LENGTH: 34
<212> TYPE: DNA
<213> ORGANISM: Artificial Sequence
<220> FEATURE:
<223> OTHER INFORMATION: synthetic

<400> SEQUENCE: 105
ggatgtttgt gtttttaatt taatttttga gttc                             34

<210> SEQ ID NO 106
<211> LENGTH: 25
<212> TYPE: DNA
<213> ORGANISM: Artificial Sequence
<220> FEATURE:
<223> OTHER INFORMATION: synthetic

<400> SEQUENCE: 106
aaatactact accccgaacg acgct                                       25

<210> SEQ ID NO 107
<211> LENGTH: 34
<212> TYPE: DNA
<213> ORGANISM: Artificial Sequence
<220> FEATURE:
<223> OTHER INFORMATION: synthetic

<400> SEQUENCE: 107
acatatacac acatatcctt ccttccccaa cgat                             34

<210> SEQ ID NO 108
<211> LENGTH: 25
<212> TYPE: DNA
<213> ORGANISM: Artificial Sequence
<220> FEATURE:
<223> OTHER INFORMATION: synthetic

<400> SEQUENCE: 108
ttttgtaaag ttttcgcggt tgcga                                       25

<210> SEQ ID NO 109
<211> LENGTH: 25
<212> TYPE: DNA

<213> ORGANISM: Artificial Sequence
<220> FEATURE:
<223> OTHER INFORMATION: synthetic

<400> SEQUENCE: 109
tcgtcggtta cgttttttac gtgac                                  25

<210> SEQ ID NO 110
<211> LENGTH: 20
<212> TYPE: DNA
<213> ORGANISM: Artificial Sequence
<220> FEATURE:
<223> OTHER INFORMATION: synthetic

<400> SEQUENCE: 110
cgaaaccgac tccaaacgct                                        20

<210> SEQ ID NO 111
<211> LENGTH: 24
<212> TYPE: DNA
<213> ORGANISM: Artificial Sequence
<220> FEATURE:
<223> OTHER INFORMATION: synthetic

<400> SEQUENCE: 111
gggtgtcgaa gtcggatttt acga                                   24

<210> SEQ ID NO 112
<211> LENGTH: 27
<212> TYPE: DNA
<213> ORGANISM: Artificial Sequence
<220> FEATURE:
<223> OTHER INFORMATION: synthetic

<400> SEQUENCE: 112
aaccacaaaa aaacatttcc tccccgc                                27

<210> SEQ ID NO 113
<211> LENGTH: 27
<212> TYPE: DNA
<213> ORGANISM: Artificial Sequence
<220> FEATURE:
<223> OTHER INFORMATION: synthetic

<400> SEQUENCE: 113
gagtttcggc ggttttcga aagtagc                                 27

<210> SEQ ID NO 114
<211> LENGTH: 25
<212> TYPE: DNA
<213> ORGANISM: Artificial Sequence
<220> FEATURE:
<223> OTHER INFORMATION: synthetic

<400> SEQUENCE: 114
ccacgaacaa cgacactacg acgct                                  25

<210> SEQ ID NO 115
<211> LENGTH: 25
<212> TYPE: DNA
<213> ORGANISM: Artificial Sequence
<220> FEATURE:
<223> OTHER INFORMATION: synthetic

<400> SEQUENCE: 115 tgtttttcg ttttggtcg tcggc                                    25

<210> SEQ ID NO 116
<211> LENGTH: 24
<212> TYPE: DNA
<213> ORGANISM: Artificial Sequence
<220> FEATURE:
<223> OTHER INFORMATION: synthetic

<400> SEQUENCE: 116
aaccccaaat tccctccata cgaa                                          24

<210> SEQ ID NO 117
<211> LENGTH: 23
<212> TYPE: DNA
<213> ORGANISM: Artificial Sequence
<220> FEATURE:
<223> OTHER INFORMATION: synthetic

<400> SEQUENCE: 117
gggaggcgtt taggaatcgt cgc                                           23

<210> SEQ ID NO 118
<211> LENGTH: 21
<212> TYPE: DNA
<213> ORGANISM: Artificial Sequence
<220> FEATURE:
<223> OTHER INFORMATION: synthetic

<400> SEQUENCE: 118
cctatatccc gaaaactcgc a                                             21

<210> SEQ ID NO 119
<211> LENGTH: 25
<212> TYPE: DNA
<213> ORGANISM: Artificial Sequence
<220> FEATURE:
<223> OTHER INFORMATION: synthetic

<400> SEQUENCE: 119
aggagtgttt gagtaggggt ttcgg                                         25

<210> SEQ ID NO 120
<211> LENGTH: 25
<212> TYPE: DNA
<213> ORGANISM: Artificial Sequence
<220> FEATURE:
<223> OTHER INFORMATION: synthetic

<400> SEQUENCE: 120
tttttcctct acaccgaatt acgaa                                         25

<210> SEQ ID NO 121
<211> LENGTH: 25
<212> TYPE: DNA
<213> ORGANISM: Artificial Sequence
<220> FEATURE:
<223> OTHER INFORMATION: synthetic

<400> SEQUENCE: 121
tagggttagt aggcggttta ggcgc                                         25

<210> SEQ ID NO 122
<211> LENGTH: 29
<212> TYPE: DNA
<213> ORGANISM: Artificial Sequence
<220> FEATURE:

<223> OTHER INFORMATION: synthetic

<400> SEQUENCE: 122
cgaactccaa ctttaaaaaa taccgcgta                                      29

<210> SEQ ID NO 123
<211> LENGTH: 25
<212> TYPE: DNA
<213> ORGANISM: Artificial Sequence
<220> FEATURE:
<223> OTHER INFORMATION: synthetic

<400> SEQUENCE: 123
gatttatttt cggcgagggg ttcgc                                          25

<210> SEQ ID NO 124
<211> LENGTH: 27
<212> TYPE: DNA
<213> ORGANISM: Artificial Sequence
<220> FEATURE:
<223> OTHER INFORMATION: synthetic

<400> SEQUENCE: 124
cgctttcccg ataaaaacga cgacgta                                        27

<210> SEQ ID NO 125
<211> LENGTH: 28
<212> TYPE: DNA
<213> ORGANISM: Artificial Sequence
<220> FEATURE:
<223> OTHER INFORMATION: synthetic

<400> SEQUENCE: 125
agtagtagtt gttggagtag aatcgcgt                                       28

<210> SEQ ID NO 126
<211> LENGTH: 26
<212> TYPE: DNA
<213> ORGANISM: Artificial Sequence
<220> FEATURE:
<223> OTHER INFORMATION: synthetic

<400> SEQUENCE: 126
gcccgaaacg ataaaaataa tcgcgc                                         26

<210> SEQ ID NO 127
<211> LENGTH: 25
<212> TYPE: DNA
<213> ORGANISM: Artificial Sequence
<220> FEATURE:
<223> OTHER INFORMATION: synthetic

<400> SEQUENCE: 127
ttttattttc gaggtcggaa atcgg                                          25

<210> SEQ ID NO 128
<211> LENGTH: 25
<212> TYPE: DNA
<213> ORGANISM: Artificial Sequence
<220> FEATURE:
<223> OTHER INFORMATION: synthetic

<400> SEQUENCE: 128
caaatcaaaa acgcgaacgc tctcg                                          25

```
<210> SEQ ID NO 129
<211> LENGTH: 25
<212> TYPE: DNA
<213> ORGANISM: Artificial Sequence
<220> FEATURE:
<223> OTHER INFORMATION: synthetic

<400> SEQUENCE: 129
ttagttgcgg gaagatagtg atcgg                                              25

<210> SEQ ID NO 130
<211> LENGTH: 25
<212> TYPE: DNA
<213> ORGANISM: Artificial Sequence
<220> FEATURE:
<223> OTHER INFORMATION: synthetic

<400> SEQUENCE: 130
aacgcctacc gaacaaatac ccgaa                                              25

<210> SEQ ID NO 131
<211> LENGTH: 20
<212> TYPE: DNA
<213> ORGANISM: Artificial Sequence
<220> FEATURE:
<223> OTHER INFORMATION: synthetic

<400> SEQUENCE: 131
tcgtgtttac gtggggacgg                                                    20

<210> SEQ ID NO 132
<211> LENGTH: 25
<212> TYPE: DNA
<213> ORGANISM: Artificial Sequence
<220> FEATURE:
<223> OTHER INFORMATION: synthetic

<400> SEQUENCE: 132
cgcgaacaaa attaaacgaa tcgta                                              25

<210> SEQ ID NO 133
<211> LENGTH: 26
<212> TYPE: DNA
<213> ORGANISM: Artificial Sequence
<220> FEATURE:
<223> OTHER INFORMATION: synthetic

<400> SEQUENCE: 133
tagacgttag gagtgagggt cggggc                                             26

<210> SEQ ID NO 134
<211> LENGTH: 29
<212> TYPE: DNA
<213> ORGANISM: Artificial Sequence
<220> FEATURE:
<223> OTHER INFORMATION: synthetic

<400> SEQUENCE: 134
taaaacgaat acgaaaatcg cgaaacgaa                                          29

<210> SEQ ID NO 135
<211> LENGTH: 25
<212> TYPE: DNA
<213> ORGANISM: Artificial Sequence
<220> FEATURE:
<223> OTHER INFORMATION: synthetic
```

<400> SEQUENCE: 135
tttaggtggg tagtcgcgta ttcgg                                         25

<210> SEQ ID NO 136
<211> LENGTH: 25
<212> TYPE: DNA
<213> ORGANISM: Artificial Sequence
<220> FEATURE:
<223> OTHER INFORMATION: synthetic

<400> SEQUENCE: 136
ctaacgataa cccgtaatct ccgca                                         25

<210> SEQ ID NO 137
<211> LENGTH: 22
<212> TYPE: DNA
<213> ORGANISM: Artificial Sequence
<220> FEATURE:
<223> OTHER INFORMATION: synthetic

<400> SEQUENCE: 137
gcggtttttc gagttttttg cg                                            22

<210> SEQ ID NO 138
<211> LENGTH: 15
<212> TYPE: DNA
<213> ORGANISM: Artificial Sequence
<220> FEATURE:
<223> OTHER INFORMATION: synthetic

<400> SEQUENCE: 138
gaacgaatcc gcgcc                                                    15

<210> SEQ ID NO 139
<211> LENGTH: 20
<212> TYPE: DNA
<213> ORGANISM: Artificial Sequence
<220> FEATURE:
<223> OTHER INFORMATION: synthetic

<400> SEQUENCE: 139
gcggtgtggt taagtttcgg                                               20

<210> SEQ ID NO 140
<211> LENGTH: 17
<212> TYPE: DNA
<213> ORGANISM: Artificial Sequence
<220> FEATURE:
<223> OTHER INFORMATION: synthetic

<400> SEQUENCE: 140
cgcgacccca aatcgta                                                  17

<210> SEQ ID NO 141
<211> LENGTH: 30
<212> TYPE: DNA
<213> ORGANISM: Artificial Sequence
<220> FEATURE:
<223> OTHER INFORMATION: synthetic

<400> SEQUENCE: 141
cgggttttat tttttttcg ttttcgtttc                                     30

<210> SEQ ID NO 142
<211> LENGTH: 19

```
<212> TYPE: DNA
<213> ORGANISM: Artificial Sequence
<220> FEATURE:
<223> OTHER INFORMATION: synthetic

<400> SEQUENCE: 142
aacgaaatcc caccgaacg                                                  19

<210> SEQ ID NO 143
<211> LENGTH: 18
<212> TYPE: DNA
<213> ORGANISM: Artificial Sequence
<220> FEATURE:
<223> OTHER INFORMATION: synthetic

<400> SEQUENCE: 143
gtagagcgtt tcgacgcg                                                   18

<210> SEQ ID NO 144
<211> LENGTH: 20
<212> TYPE: DNA
<213> ORGANISM: Artificial Sequence
<220> FEATURE:
<223> OTHER INFORMATION: synthetic

<400> SEQUENCE: 144
tcgaacgaaa ataaccgccg                                                 20

<210> SEQ ID NO 145
<211> LENGTH: 23
<212> TYPE: DNA
<213> ORGANISM: Artificial Sequence
<220> FEATURE:
<223> OTHER INFORMATION: synthetic

<400> SEQUENCE: 145
gtttttagtt aggcgcggat ttc                                             23

<210> SEQ ID NO 146
<211> LENGTH: 18
<212> TYPE: DNA
<213> ORGANISM: Artificial Sequence
<220> FEATURE:
<223> OTHER INFORMATION: synthetic

<400> SEQUENCE: 146
aacccgtaaa ccaaccgc                                                   18

<210> SEQ ID NO 147
<211> LENGTH: 22
<212> TYPE: DNA
<213> ORGANISM: Artificial Sequence
<220> FEATURE:
<223> OTHER INFORMATION: synthetic

<400> SEQUENCE: 147
tggtcgtttt agcgttatgt cg                                              22

<210> SEQ ID NO 148
<211> LENGTH: 19
<212> TYPE: DNA
<213> ORGANISM: Artificial Sequence
<220> FEATURE:
<223> OTHER INFORMATION: synthetic

<400> SEQUENCE: 148
```

```
cgaaaactac aaaccgcgc                                              19

<210> SEQ ID NO 149
<211> LENGTH: 16
<212> TYPE: DNA
<213> ORGANISM: Artificial Sequence
<220> FEATURE:
<223> OTHER INFORMATION: synthetic

<400> SEQUENCE: 149
cggttatgtc gggcgg                                                 16

<210> SEQ ID NO 150
<211> LENGTH: 19
<212> TYPE: DNA
<213> ORGANISM: Artificial Sequence
<220> FEATURE:
<223> OTHER INFORMATION: synthetic

<400> SEQUENCE: 150
caacgacgat acccacacg                                              19

<210> SEQ ID NO 151
<211> LENGTH: 25
<212> TYPE: DNA
<213> ORGANISM: Artificial Sequence
<220> FEATURE:
<223> OTHER INFORMATION: synthetic

<400> SEQUENCE: 151 tcgtttttc gtcgttttcg ttttc                                        25

<210> SEQ ID NO 152
<211> LENGTH: 17
<212> TYPE: DNA
<213> ORGANISM: Artificial Sequence
<220> FEATURE:
<223> OTHER INFORMATION: synthetic

<400> SEQUENCE: 152
cccgtacgaa aacccga                                                17

<210> SEQ ID NO 153
<211> LENGTH: 22
<212> TYPE: DNA
<213> ORGANISM: Artificial Sequence
<220> FEATURE:
<223> OTHER INFORMATION: synthetic

<400> SEQUENCE: 153
gttcgttatg cgcgtttgtt tc                                          22

<210> SEQ ID NO 154
<211> LENGTH: 20
<212> TYPE: DNA
<213> ORGANISM: Artificial Sequence
<220> FEATURE:
<223> OTHER INFORMATION: synthetic

<400> SEQUENCE: 154
gaacacccga aaaccaacga                                             20

<210> SEQ ID NO 155
<211> LENGTH: 22
<212> TYPE: DNA
<213> ORGANISM: Artificial Sequence
```

<220> FEATURE:
<223> OTHER INFORMATION: synthetic

<400> SEQUENCE: 155
gttttgtggt ttcgttcggt tc                                    22

<210> SEQ ID NO 156
<211> LENGTH: 21
<212> TYPE: DNA
<213> ORGANISM: Artificial Sequence
<220> FEATURE:
<223> OTHER INFORMATION: synthetic

<400> SEQUENCE: 156
ccgattaaac ccgtacttcg c                                     21

<210> SEQ ID NO 157
<211> LENGTH: 29
<212> TYPE: DNA
<213> ORGANISM: Artificial Sequence
<220> FEATURE:
<223> OTHER INFORMATION: synthetic

<400> SEQUENCE: 157
tttcgttttt gtatttattt tagcgacgt                             29

<210> SEQ ID NO 158
<211> LENGTH: 22
<212> TYPE: DNA
<213> ORGANISM: Artificial Sequence
<220> FEATURE:
<223> OTHER INFORMATION: synthetic

<400> SEQUENCE: 158
acgcgaaaaa aacgcgaaaa cg                                    22

<210> SEQ ID NO 159
<211> LENGTH: 21
<212> TYPE: DNA
<213> ORGANISM: Artificial Sequence
<220> FEATURE:
<223> OTHER INFORMATION: synthetic

<400> SEQUENCE: 159
gttaggcggt tattacgggt c                                     21

<210> SEQ ID NO 160
<211> LENGTH: 20
<212> TYPE: DNA
<213> ORGANISM: Artificial Sequence
<220> FEATURE:
<223> OTHER INFORMATION: synthetic

<400> SEQUENCE: 160
gaaatctact ccctccccga                                       20

<210> SEQ ID NO 161
<211> LENGTH: 31
<212> TYPE: DNA
<213> ORGANISM: Artificial Sequence
<220> FEATURE:
<223> OTHER INFORMATION: synthetic

<400> SEQUENCE: 161
tatgttgttt tttttcgta agtttacgg t                            31

<210> SEQ ID NO 162
<211> LENGTH: 26
<212> TYPE: DNA
<213> ORGANISM: Artificial Sequence
<220> FEATURE:
<223> OTHER INFORMATION: synthetic

<400> SEQUENCE: 162
ccgacaataa aaataacatc gactcg                                    26

<210> SEQ ID NO 163
<211> LENGTH: 22
<212> TYPE: DNA
<213> ORGANISM: Artificial Sequence
<220> FEATURE:
<223> OTHER INFORMATION: synthetic

<400> SEQUENCE: 163
tcgttcgcgt tttagtattc gg                                        22

<210> SEQ ID NO 164
<211> LENGTH: 20
<212> TYPE: DNA
<213> ORGANISM: Artificial Sequence
<220> FEATURE:
<223> OTHER INFORMATION: synthetic

<400> SEQUENCE: 164
cgaaaaaaac gctcctcccg                                           20

<210> SEQ ID NO 165
<211> LENGTH: 17
<212> TYPE: DNA
<213> ORGANISM: Artificial Sequence
<220> FEATURE:
<223> OTHER INFORMATION: synthetic

<400> SEQUENCE: 165
gttcgttcgg tagcggc                                              17

<210> SEQ ID NO 166
<211> LENGTH: 22
<212> TYPE: DNA
<213> ORGANISM: Artificial Sequence
<220> FEATURE:
<223> OTHER INFORMATION: synthetic

<400> SEQUENCE: 166
accacttcgc tacgaaaaaa cg                                        22

<210> SEQ ID NO 167
<211> LENGTH: 20
<212> TYPE: DNA
<213> ORGANISM: Artificial Sequence
<220> FEATURE:
<223> OTHER INFORMATION: synthetic

<400> SEQUENCE: 167
tagtcgtaat agggcggtcg                                           20

<210> SEQ ID NO 168
<211> LENGTH: 20
<212> TYPE: DNA
<213> ORGANISM: Artificial Sequence
<220> FEATURE:
<223> OTHER INFORMATION: synthetic

<400> SEQUENCE: 168
ccgaaacgac ccgttaatcg                                              20

<210> SEQ ID NO 169
<211> LENGTH: 26
<212> TYPE: DNA
<213> ORGANISM: Artificial Sequence
<220> FEATURE:
<223> OTHER INFORMATION: synthetic

<400> SEQUENCE: 169
tgatttaggt gtcgtttttt ttcgtc                                       26

<210> SEQ ID NO 170
<211> LENGTH: 20
<212> TYPE: DNA
<213> ORGANISM: Artificial Sequence
<220> FEATURE:
<223> OTHER INFORMATION: synthetic

<400> SEQUENCE: 170
gaaaaaaaat cgcgctcccg                                              20

<210> SEQ ID NO 171
<211> LENGTH: 21
<212> TYPE: DNA
<213> ORGANISM: Artificial Sequence
<220> FEATURE:
<223> OTHER INFORMATION: synthetic

<400> SEQUENCE: 171
atttattgga ggtcgcggtt c                                            21

<210> SEQ ID NO 172
<211> LENGTH: 20
<212> TYPE: DNA
<213> ORGANISM: Artificial Sequence
<220> FEATURE:
<223> OTHER INFORMATION: synthetic

<400> SEQUENCE: 172
ccgaaacacc aaaacgtccg                                              20

<210> SEQ ID NO 173
<211> LENGTH: 20
<212> TYPE: DNA
<213> ORGANISM: Artificial Sequence
<220> FEATURE:
<223> OTHER INFORMATION: synthetic

<400> SEQUENCE: 173
gtgtttttgg tggtttcggc                                              20

<210> SEQ ID NO 174
<211> LENGTH: 30
<212> TYPE: DNA
<213> ORGANISM: Artificial Sequence
<220> FEATURE:
<223> OTHER INFORMATION: synthetic

<400> SEQUENCE: 174
atactaaacg tataaaaaca aacataccgc                                   30

<210> SEQ ID NO 175

```
<211> LENGTH: 26
<212> TYPE: DNA
<213> ORGANISM: Artificial Sequence
<220> FEATURE:
<223> OTHER INFORMATION: synthetic

<400> SEQUENCE: 175
ggttcgtaag atttagtagt tcgagc                                          26

<210> SEQ ID NO 176
<211> LENGTH: 29
<212> TYPE: DNA
<213> ORGANISM: Artificial Sequence
<220> FEATURE:
<223> OTHER INFORMATION: synthetic

<400> SEQUENCE: 176
cgaaacaaaa aaatcaatat aatcgacgc                                       29

<210> SEQ ID NO 177
<211> LENGTH: 21
<212> TYPE: DNA
<213> ORGANISM: Artificial Sequence
<220> FEATURE:
<223> OTHER INFORMATION: synthetic

<400> SEQUENCE: 177
taggacgtcg cggtttattt c                                               21

<210> SEQ ID NO 178
<211> LENGTH: 21
<212> TYPE: DNA
<213> ORGANISM: Artificial Sequence
<220> FEATURE:
<223> OTHER INFORMATION: synthetic

<400> SEQUENCE: 178
cgcaatactc gaaaaacgac g                                               21

<210> SEQ ID NO 179
<211> LENGTH: 16
<212> TYPE: DNA
<213> ORGANISM: Artificial Sequence
<220> FEATURE:
<223> OTHER INFORMATION: synthetic

<400> SEQUENCE: 179
tcgcgtcgtc gttcgt                                                     16

<210> SEQ ID NO 180
<211> LENGTH: 20
<212> TYPE: DNA
<213> ORGANISM: Artificial Sequence
<220> FEATURE:
<223> OTHER INFORMATION: synthetic

<400> SEQUENCE: 180
gacgccatct aaaaacgcga                                                 20

<210> SEQ ID NO 181
<211> LENGTH: 17
<212> TYPE: DNA
<213> ORGANISM: Artificial Sequence
<220> FEATURE:
<223> OTHER INFORMATION: synthetic

<400> SEQUENCE: 181
```
ggcgacgtgg acgatac                                                    17

<210> SEQ ID NO 182
<211> LENGTH: 24
<212> TYPE: DNA
<213> ORGANISM: Artificial Sequence
<220> FEATURE:
<223> OTHER INFORMATION: synthetic

<400> SEQUENCE: 182
ctaaaactcg taacgtcgct atcg                                            24

<210> SEQ ID NO 183
<211> LENGTH: 22
<212> TYPE: DNA
<213> ORGANISM: Artificial Sequence
<220> FEATURE:
<223> OTHER INFORMATION: synthetic

<400> SEQUENCE: 183
ggtttgtgag tgatatcggt cg                                              22

<210> SEQ ID NO 184
<211> LENGTH: 24
<212> TYPE: DNA
<213> ORGANISM: Artificial Sequence
<220> FEATURE:
<223> OTHER INFORMATION: synthetic

<400> SEQUENCE: 184
cgaacccaaa aactcgaaaa aacc                                            24

<210> SEQ ID NO 185
<211> LENGTH: 24
<212> TYPE: DNA
<213> ORGANISM: Artificial Sequence
<220> FEATURE:
<223> OTHER INFORMATION: synthetic

<400> SEQUENCE: 185
gggtttagta gtatttcgaa ggcg                                            24

<210> SEQ ID NO 186
<211> LENGTH: 26
<212> TYPE: DNA
<213> ORGANISM: Artificial Sequence
<220> FEATURE:
<223> OTHER INFORMATION: synthetic

<400> SEQUENCE: 186
gaaaaattca aaataccgct cctcac                                          26

<210> SEQ ID NO 187
<211> LENGTH: 25
<212> TYPE: DNA
<213> ORGANISM: Artificial Sequence
<220> FEATURE:
<223> OTHER INFORMATION: synthetic

<400> SEQUENCE: 187
gaaggttacg aggtgtttaa gttcg                                           25

<210> SEQ ID NO 188
<211> LENGTH: 39
<212> TYPE: DNA

```
<213> ORGANISM: Artificial Sequence
<220> FEATURE:
<223> OTHER INFORMATION: synthetic

<400> SEQUENCE: 188
aacaaataaa cttaccgata ataaaatcgt aataatttc                    39

<210> SEQ ID NO 189
<211> LENGTH: 16
<212> TYPE: DNA
<213> ORGANISM: Artificial Sequence
<220> FEATURE:
<223> OTHER INFORMATION: synthetic

<400> SEQUENCE: 189
ttgcggagga cgttgc                                             16

<210> SEQ ID NO 190
<211> LENGTH: 21
<212> TYPE: DNA
<213> ORGANISM: Artificial Sequence
<220> FEATURE:
<223> OTHER INFORMATION: synthetic

<400> SEQUENCE: 190 gaaaaaaac gatacgccgc c                                        21

<210> SEQ ID NO 191
<211> LENGTH: 22
<212> TYPE: DNA
<213> ORGANISM: Artificial Sequence
<220> FEATURE:
<223> OTHER INFORMATION: synthetic

<400> SEQUENCE: 191
tttcgatttc gtagtttcgc gg                                      22

<210> SEQ ID NO 192
<211> LENGTH: 21
<212> TYPE: DNA
<213> ORGANISM: Artificial Sequence
<220> FEATURE:
<223> OTHER INFORMATION: synthetic

<400> SEQUENCE: 192
ctcgcgaaac gtaacgaaaa c                                       21

<210> SEQ ID NO 193
<211> LENGTH: 21
<212> TYPE: DNA
<213> ORGANISM: Artificial Sequence
<220> FEATURE:
<223> OTHER INFORMATION: synthetic

<400> SEQUENCE: 193
cgttcgtttt cgttcggttt c                                       21

<210> SEQ ID NO 194
<211> LENGTH: 19
<212> TYPE: DNA
<213> ORGANISM: Artificial Sequence
<220> FEATURE:
<223> OTHER INFORMATION: synthetic

<400> SEQUENCE: 194
acctaacgcc gaaacaacg                                          19
```

<210> SEQ ID NO 195
<211> LENGTH: 26
<212> TYPE: DNA
<213> ORGANISM: Artificial Sequence
<220> FEATURE:
<223> OTHER INFORMATION: synthetic

<400> SEQUENCE: 195 gttgttttttt ttatcgtttc ggagtg                                26

<210> SEQ ID NO 196
<211> LENGTH: 18
<212> TYPE: DNA
<213> ORGANISM: Artificial Sequence
<220> FEATURE:
<223> OTHER INFORMATION: synthetic

<400> SEQUENCE: 196
cctctaccca ccgtaccg                                          18

<210> SEQ ID NO 197
<211> LENGTH: 28
<212> TYPE: DNA
<213> ORGANISM: Artificial Sequence
<220> FEATURE:
<223> OTHER INFORMATION: synthetic

<400> SEQUENCE: 197
gttttcgggt tatttttatt tgaagtcg                               28

<210> SEQ ID NO 198
<211> LENGTH: 17
<212> TYPE: DNA
<213> ORGANISM: Artificial Sequence
<220> FEATURE:
<223> OTHER INFORMATION: synthetic

<400> SEQUENCE: 198 tccctacca cccaacg                                            17

<210> SEQ ID NO 199
<211> LENGTH: 22
<212> TYPE: DNA
<213> ORGANISM: Artificial Sequence
<220> FEATURE:
<223> OTHER INFORMATION: synthetic

<400> SEQUENCE: 199
gggtttaata tttgttgcgc gg                                     22

<210> SEQ ID NO 200
<211> LENGTH: 19
<212> TYPE: DNA
<213> ORGANISM: Artificial Sequence
<220> FEATURE:
<223> OTHER INFORMATION: synthetic

<400> SEQUENCE: 200
cgaagcgttg cgttgttag                                         19

<210> SEQ ID NO 201
<211> LENGTH: 17
<212> TYPE: DNA
<213> ORGANISM: Artificial Sequence
<220> FEATURE:

<223> OTHER INFORMATION: synthetic

<400> SEQUENCE: 201
ttggcgaggg ttcgagt                                          17

<210> SEQ ID NO 202
<211> LENGTH: 24
<212> TYPE: DNA
<213> ORGANISM: Artificial Sequence
<220> FEATURE:
<223> OTHER INFORMATION: synthetic

<400> SEQUENCE: 202
ctaatcgcaa aaccgaaaaa aacg                                  24

<210> SEQ ID NO 203
<211> LENGTH: 19
<212> TYPE: DNA
<213> ORGANISM: Artificial Sequence
<220> FEATURE:
<223> OTHER INFORMATION: synthetic

<400> SEQUENCE: 203
gagaggaaat cgcgaagcg                                        19

<210> SEQ ID NO 204
<211> LENGTH: 19
<212> TYPE: DNA
<213> ORGANISM: Artificial Sequence
<220> FEATURE:
<223> OTHER INFORMATION: synthetic

<400> SEQUENCE: 204
cccctaaaaa aacgcgcga                                        19

<210> SEQ ID NO 205
<211> LENGTH: 22
<212> TYPE: DNA
<213> ORGANISM: Artificial Sequence
<220> FEATURE:
<223> OTHER INFORMATION: synthetic

<400> SEQUENCE: 205
gacgtttatt tggacgtttg gc                                    22

<210> SEQ ID NO 206
<211> LENGTH: 20
<212> TYPE: DNA
<213> ORGANISM: Artificial Sequence
<220> FEATURE:
<223> OTHER INFORMATION: synthetic

<400> SEQUENCE: 206
accgaaatca aaaccctccg                                       20

<210> SEQ ID NO 207
<211> LENGTH: 22
<212> TYPE: DNA
<213> ORGANISM: Artificial Sequence
<220> FEATURE:
<223> OTHER INFORMATION: synthetic

<400> SEQUENCE: 207
gtttcgcgac gtttatttgg ac                                    22

<210> SEQ ID NO 208
<211> LENGTH: 20
<212> TYPE: DNA
<213> ORGANISM: Artificial Sequence
<220> FEATURE:
<223> OTHER INFORMATION: synthetic

<400> SEQUENCE: 208
accgaaatca aaaccctccg                                               20

<210> SEQ ID NO 209
<211> LENGTH: 20
<212> TYPE: DNA
<213> ORGANISM: Artificial Sequence
<220> FEATURE:
<223> OTHER INFORMATION: synthetic

<400> SEQUENCE: 209
gcgcggaatt ttaggagtgc                                               20

<210> SEQ ID NO 210
<211> LENGTH: 18
<212> TYPE: DNA
<213> ORGANISM: Artificial Sequence
<220> FEATURE:
<223> OTHER INFORMATION: synthetic

<400> SEQUENCE: 210
cgcgacccca cgataatc                                                 18

<210> SEQ ID NO 211
<211> LENGTH: 20
<212> TYPE: DNA
<213> ORGANISM: Artificial Sequence
<220> FEATURE:
<223> OTHER INFORMATION: synthetic

<400> SEQUENCE: 211
gttttcgagg gagtgcgttc                                               20

<210> SEQ ID NO 212
<211> LENGTH: 23
<212> TYPE: DNA
<213> ORGANISM: Artificial Sequence
<220> FEATURE:
<223> OTHER INFORMATION: synthetic

<400> SEQUENCE: 212
cgaaaaaaaa aaacgaaacc cgc                                           23

<210> SEQ ID NO 213
<211> LENGTH: 21
<212> TYPE: DNA
<213> ORGANISM: Artificial Sequence
<220> FEATURE:
<223> OTHER INFORMATION: synthetic

<400> SEQUENCE: 213
ggtgttgaag agtagtcgcg t                                             21

<210> SEQ ID NO 214
<211> LENGTH: 18
<212> TYPE: DNA
<213> ORGANISM: Artificial Sequence
<220> FEATURE:
<223> OTHER INFORMATION: synthetic

<400> SEQUENCE: 214
cgacgcaaaa aacgacgc                                               18

<210> SEQ ID NO 215
<211> LENGTH: 21
<212> TYPE: DNA
<213> ORGANISM: Artificial Sequence
<220> FEATURE:
<223> OTHER INFORMATION: synthetic

<400> SEQUENCE: 215
cgaaacgtaa ggatgtcgtc g                                           21

<210> SEQ ID NO 216
<211> LENGTH: 27
<212> TYPE: DNA
<213> ORGANISM: Artificial Sequence
<220> FEATURE:
<223> OTHER INFORMATION: synthetic

<400> SEQUENCE: 216
aatttatata tacaccgcgt ctccaac                                     27

<210> SEQ ID NO 217
<211> LENGTH: 22
<212> TYPE: DNA
<213> ORGANISM: Artificial Sequence
<220> FEATURE:
<223> OTHER INFORMATION: synthetic

<400> SEQUENCE: 217
tgttttgttc ggtgaggttt cg                                          22

<210> SEQ ID NO 218
<211> LENGTH: 19
<212> TYPE: DNA
<213> ORGANISM: Artificial Sequence
<220> FEATURE:
<223> OTHER INFORMATION: synthetic

<400> SEQUENCE: 218
caaaccgcca cctaatcgc                                              19

<210> SEQ ID NO 219
<211> LENGTH: 18
<212> TYPE: DNA
<213> ORGANISM: Artificial Sequence
<220> FEATURE:
<223> OTHER INFORMATION: synthetic

<400> SEQUENCE: 219
aaagggagtt ttcgggcg                                               18

<210> SEQ ID NO 220
<211> LENGTH: 19
<212> TYPE: DNA
<213> ORGANISM: Artificial Sequence
<220> FEATURE:
<223> OTHER INFORMATION: synthetic

<400> SEQUENCE: 220
acccgatacc cccattacc                                              19

<210> SEQ ID NO 221
<211> LENGTH: 30

```
<212> TYPE: DNA
<213> ORGANISM: Artificial Sequence
<220> FEATURE:
<223> OTHER INFORMATION: synthetic

<400> SEQUENCE: 221
ggtggttaag aaagtcgtaa gaaaatttcg                                   30

<210> SEQ ID NO 222
<211> LENGTH: 23
<212> TYPE: DNA
<213> ORGANISM: Artificial Sequence
<220> FEATURE:
<223> OTHER INFORMATION: synthetic

<400> SEQUENCE: 222
tctaaacaac aaaaaccccg acc                                          23

<210> SEQ ID NO 223
<211> LENGTH: 20
<212> TYPE: DNA
<213> ORGANISM: Artificial Sequence
<220> FEATURE:
<223> OTHER INFORMATION: synthetic

<400> SEQUENCE: 223
ggatggtttc ggttgggttc                                              20

<210> SEQ ID NO 224
<211> LENGTH: 21
<212> TYPE: DNA
<213> ORGANISM: Artificial Sequence
<220> FEATURE:
<223> OTHER INFORMATION: synthetic

<400> SEQUENCE: 224
gcaaaacgcc aacaaaaaac g                                            21

<210> SEQ ID NO 225
<211> LENGTH: 23
<212> TYPE: DNA
<213> ORGANISM: Artificial Sequence
<220> FEATURE:
<223> OTHER INFORMATION: synthetic

<400> SEQUENCE: 225
ggtcgaggga attagagttt tcg                                          23

<210> SEQ ID NO 226
<211> LENGTH: 20
<212> TYPE: DNA
<213> ORGANISM: Artificial Sequence
<220> FEATURE:
<223> OTHER INFORMATION: synthetic

<400> SEQUENCE: 226
aacctaaccc gccaaaacac                                              20

<210> SEQ ID NO 227
<211> LENGTH: 23
<212> TYPE: DNA
<213> ORGANISM: Artificial Sequence
<220> FEATURE:
<223> OTHER INFORMATION: synthetic

<400> SEQUENCE: 227
```
gggatcggtt cgtttattcg ttc                                        23

<210> SEQ ID NO 228
<211> LENGTH: 18
<212> TYPE: DNA
<213> ORGANISM: Artificial Sequence
<220> FEATURE:
<223> OTHER INFORMATION: synthetic

<400> SEQUENCE: 228
cccgaaacat cttccgcg                                              18

<210> SEQ ID NO 229
<211> LENGTH: 21
<212> TYPE: DNA
<213> ORGANISM: Artificial Sequence
<220> FEATURE:
<223> OTHER INFORMATION: synthetic

<400> SEQUENCE: 229
gattcgtttt cgaaagtggg c                                          21

<210> SEQ ID NO 230
<211> LENGTH: 23
<212> TYPE: DNA
<213> ORGANISM: Artificial Sequence
<220> FEATURE:
<223> OTHER INFORMATION: synthetic

<400> SEQUENCE: 230
taaaacaaaa actcccgacc tcg                                        23

<210> SEQ ID NO 231
<211> LENGTH: 32
<212> TYPE: DNA
<213> ORGANISM: Artificial Sequence
<220> FEATURE:
<223> OTHER INFORMATION: synthetic

<400> SEQUENCE: 231
gtttttgtgt gtgatacgat gatgttatta tc                              32

<210> SEQ ID NO 232
<211> LENGTH: 17
<212> TYPE: DNA
<213> ORGANISM: Artificial Sequence
<220> FEATURE:
<223> OTHER INFORMATION: synthetic

<400> SEQUENCE: 232
gtttccgaaa cccgcga                                               17

<210> SEQ ID NO 233
<211> LENGTH: 26
<212> TYPE: DNA
<213> ORGANISM: Artificial Sequence
<220> FEATURE:
<223> OTHER INFORMATION: synthetic

<400> SEQUENCE: 233 tagttttcg taagttaacg cgtttc                                      26

<210> SEQ ID NO 234
<211> LENGTH: 20
<212> TYPE: DNA
<213> ORGANISM: Artificial Sequence

```
<220> FEATURE:
<223> OTHER INFORMATION: synthetic

<400> SEQUENCE: 234
cccgcaacct tacgatcaac                                                   20

<210> SEQ ID NO 235
<211> LENGTH: 33
<212> TYPE: DNA
<213> ORGANISM: Artificial Sequence
<220> FEATURE:
<223> OTHER INFORMATION: synthetic

<400> SEQUENCE: 235
aggccacgga cgggcgattt cgatttattt tcg                                    33

<210> SEQ ID NO 236
<211> LENGTH: 28
<212> TYPE: DNA
<213> ORGANISM: Artificial Sequence
<220> FEATURE:
<223> OTHER INFORMATION: synthetic

<400> SEQUENCE: 236
cgcgccgagg gcgtacggtt tatagggc                                          28

<210> SEQ ID NO 237
<211> LENGTH: 27
<212> TYPE: DNA
<213> ORGANISM: Artificial Sequence
<220> FEATURE:
<223> OTHER INFORMATION: synthetic

<400> SEQUENCE: 237
cgcgccgagg cggttttaag tcgcgga                                           27

<210> SEQ ID NO 238
<211> LENGTH: 32
<212> TYPE: DNA
<213> ORGANISM: Artificial Sequence
<220> FEATURE:
<223> OTHER INFORMATION: synthetic

<400> SEQUENCE: 238
aggccacgga cggcgctcga caaaataaaa ac                                     32

<210> SEQ ID NO 239
<211> LENGTH: 28
<212> TYPE: DNA
<213> ORGANISM: Artificial Sequence
<220> FEATURE:
<223> OTHER INFORMATION: synthetic

<400> SEQUENCE: 239
cgcgccgagg cgttcggatt cgattcgt                                          28

<210> SEQ ID NO 240
<211> LENGTH: 26
<212> TYPE: DNA
<213> ORGANISM: Artificial Sequence
<220> FEATURE:
<223> OTHER INFORMATION: synthetic

<400> SEQUENCE: 240
aggccacgga cgccgcgcta ccgcta                                            26
```

```
<210> SEQ ID NO 241
<211> LENGTH: 30
<212> TYPE: DNA
<213> ORGANISM: Artificial Sequence
<220> FEATURE:
<223> OTHER INFORMATION: synthetic

<400> SEQUENCE: 241
cgcgccgagg gctaataaac cacgactacg                                     30

<210> SEQ ID NO 242
<211> LENGTH: 32
<212> TYPE: DNA
<213> ORGANISM: Artificial Sequence
<220> FEATURE:
<223> OTHER INFORMATION: synthetic

<400> SEQUENCE: 242
aggccacgga cgcgagtcga gtttatcgtt tg                                  32

<210> SEQ ID NO 243
<211> LENGTH: 28
<212> TYPE: DNA
<213> ORGANISM: Artificial Sequence
<220> FEATURE:
<223> OTHER INFORMATION: synthetic

<400> SEQUENCE: 243
cgcgccgagg cgggcgtttt tgtttagg                                       28

<210> SEQ ID NO 244
<211> LENGTH: 32
<212> TYPE: DNA
<213> ORGANISM: Artificial Sequence
<220> FEATURE:
<223> OTHER INFORMATION: synthetic

<400> SEQUENCE: 244
aggccacgga cgcgcgtttg ttagcgttta aa                                  32

<210> SEQ ID NO 245
<211> LENGTH: 32
<212> TYPE: DNA
<213> ORGANISM: Artificial Sequence
<220> FEATURE:
<223> OTHER INFORMATION: synthetic

<400> SEQUENCE: 245
cgcgccgagg gcgaaataaa taacaacgac ga                                  32

<210> SEQ ID NO 246
<211> LENGTH: 36
<212> TYPE: DNA
<213> ORGANISM: Artificial Sequence
<220> FEATURE:
<223> OTHER INFORMATION: synthetic

<400> SEQUENCE: 246
aggccacgga cgcgcgtttt ttattagtta gtcgtt                              36

<210> SEQ ID NO 247
<211> LENGTH: 28
<212> TYPE: DNA
<213> ORGANISM: Artificial Sequence
<220> FEATURE:
<223> OTHER INFORMATION: synthetic
```

```
<400> SEQUENCE: 247
cgcgccgagg gcgcgatacc ctctattc                                      28

<210> SEQ ID NO 248
<211> LENGTH: 27
<212> TYPE: DNA
<213> ORGANISM: Artificial Sequence
<220> FEATURE:
<223> OTHER INFORMATION: synthetic

<400> SEQUENCE: 248
aggccacgga cggccgatct tcgcctt                                       27

<210> SEQ ID NO 249
<211> LENGTH: 33
<212> TYPE: DNA
<213> ORGANISM: Artificial Sequence
<220> FEATURE:
<223> OTHER INFORMATION: synthetic

<400> SEQUENCE: 249
cgcgccgagg gcgaacgaat ataaatcgaa aac                                33

<210> SEQ ID NO 250
<211> LENGTH: 27
<212> TYPE: DNA
<213> ORGANISM: Artificial Sequence
<220> FEATURE:
<223> OTHER INFORMATION: synthetic

<400> SEQUENCE: 250
aggccacgga cggccgcgcg atactaa                                       27

<210> SEQ ID NO 251
<211> LENGTH: 29
<212> TYPE: DNA
<213> ORGANISM: Artificial Sequence
<220> FEATURE:
<223> OTHER INFORMATION: synthetic

<400> SEQUENCE: 251
aggccacgga cgcgtcgagg gttaggagt                                     29

<210> SEQ ID NO 252
<211> LENGTH: 28
<212> TYPE: DNA
<213> ORGANISM: Artificial Sequence
<220> FEATURE:
<223> OTHER INFORMATION: synthetic

<400> SEQUENCE: 252
cgcgccgagg gtaaccgtaa ctcgaccc                                      28

<210> SEQ ID NO 253
<211> LENGTH: 28
<212> TYPE: DNA
<213> ORGANISM: Artificial Sequence
<220> FEATURE:
<223> OTHER INFORMATION: synthetic

<400> SEQUENCE: 253
aggccacgga cgcgcgctcc gaaaaaac                                      28

<210> SEQ ID NO 254
```

```
<211> LENGTH: 29
<212> TYPE: DNA
<213> ORGANISM: Artificial Sequence
<220> FEATURE:
<223> OTHER INFORMATION: synthetic

<400> SEQUENCE: 254
cgcgccgagg cgggcgtaga gattttacg                                    29

<210> SEQ ID NO 255
<211> LENGTH: 28
<212> TYPE: DNA
<213> ORGANISM: Artificial Sequence
<220> FEATURE:
<223> OTHER INFORMATION: synthetic

<400> SEQUENCE: 255
aggccacgga cggtaacgcg catctccg                                     28

<210> SEQ ID NO 256
<211> LENGTH: 27
<212> TYPE: DNA
<213> ORGANISM: Artificial Sequence
<220> FEATURE:
<223> OTHER INFORMATION: synthetic

<400> SEQUENCE: 256
cgcgccgagg tcgttcgtgt cggtttc                                      27

<210> SEQ ID NO 257
<211> LENGTH: 27
<212> TYPE: DNA
<213> ORGANISM: Artificial Sequence
<220> FEATURE:
<223> OTHER INFORMATION: synthetic

<400> SEQUENCE: 257
aggccacgga cggaaccgca cgcacta                                      27

<210> SEQ ID NO 258
<211> LENGTH: 34
<212> TYPE: DNA
<213> ORGANISM: Artificial Sequence
<220> FEATURE:
<223> OTHER INFORMATION: synthetic

<400> SEQUENCE: 258
cgcgccgagg ccgaacgatc cgtaaaaaat ataa                              34

<210> SEQ ID NO 259
<211> LENGTH: 27
<212> TYPE: DNA
<213> ORGANISM: Artificial Sequence
<220> FEATURE:
<223> OTHER INFORMATION: synthetic

<400> SEQUENCE: 259
aggccacgga cgcccgaacc tcctcga                                      27

<210> SEQ ID NO 260
<211> LENGTH: 32
<212> TYPE: DNA
<213> ORGANISM: Artificial Sequence
<220> FEATURE:
<223> OTHER INFORMATION: synthetic

<400> SEQUENCE: 260
```

```
cgcgccgagg gacgacgtgg ttattaattt cg                               32
```

<210> SEQ ID NO 261
<211> LENGTH: 26
<212> TYPE: DNA
<213> ORGANISM: Artificial Sequence
<220> FEATURE:
<223> OTHER INFORMATION: synthetic

<400> SEQUENCE: 261

```
cgcgccgagg cggattcgcg agttcg                                     26
```

<210> SEQ ID NO 262
<211> LENGTH: 28
<212> TYPE: DNA
<213> ORGANISM: Artificial Sequence
<220> FEATURE:
<223> OTHER INFORMATION: synthetic

<400> SEQUENCE: 262

```
aggccacgga cggcgcgttt tttgaggc                                   28
```

<210> SEQ ID NO 263
<211> LENGTH: 27
<212> TYPE: DNA
<213> ORGANISM: Artificial Sequence
<220> FEATURE:
<223> OTHER INFORMATION: synthetic

<400> SEQUENCE: 263

```
cgcgccgagg cgttttggcg ttcgttc                                    27
```

<210> SEQ ID NO 264
<211> LENGTH: 28
<212> TYPE: DNA
<213> ORGANISM: Artificial Sequence
<220> FEATURE:
<223> OTHER INFORMATION: synthetic

<400> SEQUENCE: 264

```
aggccacgga cggcgtctac ttcccacc                                   28
```

<210> SEQ ID NO 265
<211> LENGTH: 28
<212> TYPE: DNA
<213> ORGANISM: Artificial Sequence
<220> FEATURE:
<223> OTHER INFORMATION: synthetic

<400> SEQUENCE: 265

```
cgcgccgagg gaccacctcg aacacaaa                                   28
```

<210> SEQ ID NO 266
<211> LENGTH: 31
<212> TYPE: DNA
<213> ORGANISM: Artificial Sequence
<220> FEATURE:
<223> OTHER INFORMATION: synthetic

<400> SEQUENCE: 266

```
aggccacgga cggacgatac ccacgaaaca a                               31
```

<210> SEQ ID NO 267
<211> LENGTH: 32
<212> TYPE: DNA

```
<213> ORGANISM: Artificial Sequence
<220> FEATURE:
<223> OTHER INFORMATION: synthetic

<400> SEQUENCE: 267
cgcgccgagg gccgaaaaac gaaaaacaaa aa                                32

<210> SEQ ID NO 268
<211> LENGTH: 30
<212> TYPE: DNA
<213> ORGANISM: Artificial Sequence
<220> FEATURE:
<223> OTHER INFORMATION: synthetic

<400> SEQUENCE: 268
aggccacgga cggcgagaaa aggcgttttc                                   30

<210> SEQ ID NO 269
<211> LENGTH: 28
<212> TYPE: DNA
<213> ORGANISM: Artificial Sequence
<220> FEATURE:
<223> OTHER INFORMATION: synthetic

<400> SEQUENCE: 269
cgcgccgagg cgattttcgt ttcgcgtt                                     28

<210> SEQ ID NO 270
<211> LENGTH: 28
<212> TYPE: DNA
<213> ORGANISM: Artificial Sequence
<220> FEATURE:
<223> OTHER INFORMATION: synthetic

<400> SEQUENCE: 270
cgcgccgagg cgtttggcga ttttcgtt                                     28

<210> SEQ ID NO 271
<211> LENGTH: 30
<212> TYPE: DNA
<213> ORGANISM: Artificial Sequence
<220> FEATURE:
<223> OTHER INFORMATION: synthetic

<400> SEQUENCE: 271
aggccacgga cgcggggttc gagtgtaaat                                   30

<210> SEQ ID NO 272
<211> LENGTH: 31
<212> TYPE: DNA
<213> ORGANISM: Artificial Sequence
<220> FEATURE:
<223> OTHER INFORMATION: synthetic

<400> SEQUENCE: 272
cgcgccgagg cgacggaaac gtttttagtt c                                 31

<210> SEQ ID NO 273
<211> LENGTH: 34
<212> TYPE: DNA
<213> ORGANISM: Artificial Sequence
<220> FEATURE:
<223> OTHER INFORMATION: synthetic

<400> SEQUENCE: 273
aggccacgga cgtcgttagt tcgtatacgt tgtc                              34
```

<210> SEQ ID NO 274
<211> LENGTH: 28
<212> TYPE: DNA
<213> ORGANISM: Artificial Sequence
<220> FEATURE:
<223> OTHER INFORMATION: synthetic

<400> SEQUENCE: 274
cgcgccgagg cgatcccgaa tccactac                                      28

<210> SEQ ID NO 275
<211> LENGTH: 27
<212> TYPE: DNA
<213> ORGANISM: Artificial Sequence
<220> FEATURE:
<223> OTHER INFORMATION: synthetic

<400> SEQUENCE: 275
aggccacgga cgcgaacaaa cgccccc                                       27

<210> SEQ ID NO 276
<211> LENGTH: 32
<212> TYPE: DNA
<213> ORGANISM: Artificial Sequence
<220> FEATURE:
<223> OTHER INFORMATION: synthetic

<400> SEQUENCE: 276
cgcgccgagg cgtacgcaaa cctaaaaaat tc                                 32

<210> SEQ ID NO 277
<211> LENGTH: 31
<212> TYPE: DNA
<213> ORGANISM: Artificial Sequence
<220> FEATURE:
<223> OTHER INFORMATION: synthetic

<400> SEQUENCE: 277
aggccacgga cgcgtaatat cgactccgca a                                  31

<210> SEQ ID NO 278
<211> LENGTH: 27
<212> TYPE: DNA
<213> ORGANISM: Artificial Sequence
<220> FEATURE:
<223> OTHER INFORMATION: synthetic

<400> SEQUENCE: 278
aggccacgga cgcgcgttag gatgcgt                                       27

<210> SEQ ID NO 279
<211> LENGTH: 27
<212> TYPE: DNA
<213> ORGANISM: Artificial Sequence
<220> FEATURE:
<223> OTHER INFORMATION: synthetic

<400> SEQUENCE: 279
cgcgccgagg cgcacgaaac cctctta                                       27

<210> SEQ ID NO 280
<211> LENGTH: 29
<212> TYPE: DNA
<213> ORGANISM: Artificial Sequence
<220> FEATURE:

<223> OTHER INFORMATION: synthetic

<400> SEQUENCE: 280
aggccacgga cgcgcgtttt ttggttcgg                                29

<210> SEQ ID NO 281
<211> LENGTH: 28
<212> TYPE: DNA
<213> ORGANISM: Artificial Sequence
<220> FEATURE:
<223> OTHER INFORMATION: synthetic

<400> SEQUENCE: 281
cgcgccgagg cggaaggatg gtcgtttt                                 28

<210> SEQ ID NO 282
<211> LENGTH: 34
<212> TYPE: DNA
<213> ORGANISM: Artificial Sequence
<220> FEATURE:
<223> OTHER INFORMATION: synthetic

<400> SEQUENCE: 282
aggccacgga cgcgtcgagt agttttaacg tttg                          34

<210> SEQ ID NO 283
<211> LENGTH: 29
<212> TYPE: DNA
<213> ORGANISM: Artificial Sequence
<220> FEATURE:
<223> OTHER INFORMATION: synthetic

<400> SEQUENCE: 283
cgcgccgagg cgtgggtatt cggttttcc                                29

<210> SEQ ID NO 284
<211> LENGTH: 180
<212> TYPE: DNA
<213> ORGANISM: Homo sapiens

<400> SEQUENCE: 284
gcgccgcacc tggggccctc ccccacctac gccccgccag ggcggggccg cgggcgcaga     60
cactcgcggg cacacgcacg acgacgcgca cacgcggtcg cacgcggccc ccgagcccc    120 ctgcggcgac tccgattcac ccccgcgggt gcggggcgcg acccgcccg gcccagctcc    180

<210> SEQ ID NO 285
<211> LENGTH: 180
<212> TYPE: DNA
<213> ORGANISM: Artificial Sequence
<220> FEATURE:
<223> OTHER INFORMATION: synthetic

<400> SEQUENCE: 285
gcgtcgtatt tggggttttt ttttatttac gtttcgttag ggcggggtcg cgggcgtaga     60
tattcgcggg tatacgtacg acgacgcgta tacgcggtcg tacgcggttt ttcgagtttt    120
ttgcggcgat ttcgatttat tttcgcgggt gcggggcgcg gattcgttcg gtttagtttt    180

<210> SEQ ID NO 286
<211> LENGTH: 199
<212> TYPE: DNA
<213> ORGANISM: Homo sapiens

<400> SEQUENCE: 286

```
gcggggctgc agagagcggc agtggcacgg agcgcgcggc tggaagcgaa agcaggcggt    60
gtggccaagc cccggcgcac ggcccatagg gcgctgggta ccacgacctg ggccgcgcg    120 ccagggccag gcgcagggta cgacgcaacc cctccagcat cccttgggga ggagcctcca   180
accgtctcgt cccagtctg                                                199
```

<210> SEQ ID NO 287
<211> LENGTH: 199
<212> TYPE: DNA
<213> ORGANISM: Artificial Sequence
<220> FEATURE:
<223> OTHER INFORMATION: synthetic

<400> SEQUENCE: 287

```
gcggggttgt agagagcggt agtggtacgg agcgcgcggt tggaagcgaa agtaggcggt    60
gtggttaagt ttcggcgtac ggtttatagg gcgttgggta ttacgatttg ggtcgcgcg    120 ttagggttag gcgtagggta cgacgtaatt tttttagtat tttttgggga ggagttttta   180
atcgtttcgt tttagtttg                                                199
```

<210> SEQ ID NO 288
<211> LENGTH: 213
<212> TYPE: DNA
<213> ORGANISM: Homo sapiens

<400> SEQUENCE: 288

```
gcgacgcgca gggggcgggc tctacctccc cctcgccccc gcttcggttt taagccgcgg    60
aggcgcccgg tgggacctcg ctgctgtcca atcagggggg accgggtgag ctcctcttcc   120
tggagccggg ctccaccagc gccgcaggct cacaggccgg gggtgggggc tctggaccga   180
ggggcggcgc ggggcggcgc ggggcggcgc gcg                                213
```

<210> SEQ ID NO 289
<211> LENGTH: 213
<212> TYPE: DNA
<213> ORGANISM: Artificial Sequence
<220> FEATURE:
<223> OTHER INFORMATION: synthetic

<400> SEQUENCE: 289

```
gcgacgcgta gggggcgggt tttatttttt tttcgttttc gtttcggttt taagtcgcgg    60
aggcgttcgg tgggatttcg ttgttgttta attagggggg atcgggtgag tttttttttt   120
tggagtcggg ttttattagc gtcgtaggtt tataggtcgg gggtgggggt tttggatcga   180
ggggcggcgc ggggcggcgc ggggcggcgc gcg                                213
```

<210> SEQ ID NO 290
<211> LENGTH: 112
<212> TYPE: DNA
<213> ORGANISM: Homo sapiens

<400> SEQUENCE: 290

```
aactgcagag cgccccgacg cgcccgcagc cctcaccctg ccgagcgcgg cggccacccc    60
cgcccgagcc gcggcgcccc cagggaggaa acaaaagtgt ctccgcggcg cc           112
```

<210> SEQ ID NO 291
<211> LENGTH: 112
<212> TYPE: DNA
<213> ORGANISM: Artificial Sequence
<220> FEATURE:

<223> OTHER INFORMATION: synthetic

<400> SEQUENCE: 291
aattgtagag cgtttcgacg cgttcgtagt ttttattttg tcgagcgcgg cggttatttt    60
cgttcgagtc gcggcgtttt tagggaggaa ataaaagtgt tttcgcggcg tt            112

<210> SEQ ID NO 292
<211> LENGTH: 123
<212> TYPE: DNA
<213> ORGANISM: Homo sapiens

<400> SEQUENCE: 292
gcccgggccc cagctcatcc cccgcccccg ctcaccgcgg gctgaaggcc ttggcttcca    60
gccaggcgcg gacctcgtcc ggacccgact cgtaggtgag cggctggctc acgggctggc    120
tgc                                                                 123

<210> SEQ ID NO 293
<211> LENGTH: 123
<212> TYPE: DNA
<213> ORGANISM: Artificial Sequence
<220> FEATURE:
<223> OTHER INFORMATION: synthetic

<400> SEQUENCE: 293
gttcgggttt tagtttatttt ttcgttttcg tttatcgcgg gttgaaggtt ttggttttta   60
gttaggcgcg gatttcgttc ggattcgatt cgtaggtgag cggttggttt acgggttggt    120
tgt                                                                 123

<210> SEQ ID NO 294
<211> LENGTH: 104
<212> TYPE: DNA
<213> ORGANISM: Homo sapiens

<400> SEQUENCE: 294
gagccggagt cgcggtggcc gcctcagcgc catgtcgagg gttgctgagg ggccagcggc    60
agcgcggcgc ggcttgtagt ccccgcgcgc atgcgcccag cctg                    104

<210> SEQ ID NO 295
<211> LENGTH: 104
<212> TYPE: DNA
<213> ORGANISM: Artificial Sequence
<220> FEATURE:
<223> OTHER INFORMATION: synthetic

<400> SEQUENCE: 295
gagtcggagt cgcggtggtc gttttagcgt tatgtcgagg gttgttgagg ggttagcggt    60
agcgcggcgc ggtttgtagt tttcgcgcgt atgcgtttag tttg                    104

<210> SEQ ID NO 296
<211> LENGTH: 108
<212> TYPE: DNA
<213> ORGANISM: Homo sapiens

<400> SEQUENCE: 296
aggtggtccc cgggcaccac ggtcatgtcg ggcggcagct cgcggcctgc ggcgggctcc    60
gcgtagccgt ggttcaccag cgtgtgggca ccgccgctgc tcgctggg                108

<210> SEQ ID NO 297
<211> LENGTH: 108

```
<212> TYPE: DNA
<213> ORGANISM: Artificial Sequence
<220> FEATURE:
<223> OTHER INFORMATION: synthetic

<400> SEQUENCE: 297
aggtggtttt cgggtattac ggttatgtcg ggcggtagtt cgcggtttgc ggcgggtttc    60
gcgtagtcgt ggtttattag cgtgtgggta tcgtcgttgt tcgttggg              108

<210> SEQ ID NO 298
<211> LENGTH: 199
<212> TYPE: DNA
<213> ORGANISM: Homo sapiens

<400> SEQUENCE: 298
ctccccgccc tttcgccgcc tccgccccg agccgagccc accgcctgtt gcagccaaag    60
ccgcgatgct ctgtctgggt ctggcgcggt cagccgggct cccgcacggg gacgcctcct   120
ccctccttct cgcgctctcc gcccctccc ctgcggggcg cgcgcccgcc tccgcgtccc   180
cttaggattc ccgcccacc                                                199

<210> SEQ ID NO 299
<211> LENGTH: 199
<212> TYPE: DNA
<213> ORGANISM: Artificial Sequence
<220> FEATURE:
<223> OTHER INFORMATION: synthetic

<400> SEQUENCE: 299
tttttcgttt tttcgtcgtt ttcgttttcg agtcgagttt atcgtttgtt gtagttaaag    60
tcgcgatgtt ttgtttgggt ttggcgcggt tagtcgggtt ttcgtacggg gacgtttttt   120
tttttttttt cgcgtttttc gttttttttt ttgcggggcg cgcgttcgtt ttcgcgtttt   180
tttaggattt tcgtttatt                                                199

<210> SEQ ID NO 300
<211> LENGTH: 294
<212> TYPE: DNA
<213> ORGANISM: Homo sapiens

<400> SEQUENCE: 300
gatccccgcg cggggcccgc catgcgcgcc tgctccgggc gcccctgccc aggtcccgct    60
ggctcccggg tgctcgcctg gcgccccttc ccctctcact cgctgctttc tcccatttcg   120
gcgccagctc acgccgttcg ccccttcctt cttccttctc tccctccagc cccctcgct   180 cctcccctac tcgcctctcc cctccctct tccctggccc accctctccc cgccccctcc   240
tcgccttctc agtcgcccct ctgcgggtcc cctcccccgc gccgggcttg gccc        294

<210> SEQ ID NO 301
<211> LENGTH: 294
<212> TYPE: DNA
<213> ORGANISM: Artificial Sequence
<220> FEATURE:
<223> OTHER INFORMATION: synthetic

<400> SEQUENCE: 301
gattttcgcg cggggttcgt tatgcgcgtt tgtttcgggc gttttgtttt aggtttcgtt    60
ggttttcggg tgttcgtttg gcgtttttt tttttttatt cgttgttttt tttatttcg   120 gcgttagttt acgtcgttcg tttttttttt tttttttttt tttttttagt tttttcgtt   180
```

```
ttttttttat tcgttttttt ttttttttttt tttttggttt attttttttt cgttttttt      240 tcgttttttt agtcgttttt ttgcgggttt ttttttttcgc gtcgggtttg gttt           294
```

<210> SEQ ID NO 302
<211> LENGTH: 169
<212> TYPE: DNA
<213> ORGANISM: Artificial Sequence
<220> FEATURE:
<223> OTHER INFORMATION: synthetic

<400> SEQUENCE: 302

```
gattttcgcg cggggttcgt tatgcgcgtt tgtttcgggc gttttgttt aggtttcgtt        60 ggttttcggg tgttcgtttg gcgttttttt tttttttatt cgttgtttt ttttatttcg      120 gcgttagttt acgtcgttcg tttttttttt tttttttttt tttttttag                 169
```

<210> SEQ ID NO 303
<211> LENGTH: 211
<212> TYPE: DNA
<213> ORGANISM: Homo sapiens

<400> SEQUENCE: 303

```
tttccattgc gcggctctcc tcagctcctt cccgccgccc agtctggatc ctggggagg        60 cgctgaagtc ggggcccgcc ctgtggcccc gcccggcccg gcttgctag cgcccaaagc      120 cagcgaagca cgggcccaac cgggccatgt cgggggagcc tgagctcatt gagctgcggg     180
agctggcacc cgctgggcgc gctgggaagg g                                    211
```

<210> SEQ ID NO 304
<211> LENGTH: 211
<212> TYPE: DNA
<213> ORGANISM: Artificial Sequence
<220> FEATURE:
<223> OTHER INFORMATION: synthetic

<400> SEQUENCE: 304

```
tttttattgc gcggttttttt ttagttttttt ttcgtcgttt agtttggatt ttgggggagg    60
cgttgaagtc ggggttcgtt ttgtggtttc gttcggttcg cgtttgttag cgtttaaagt    120
tagcgaagta cgggtttaat cgggttatgt cgggggagtt tgagtttatt gagttgcggg   180
agttggtatt cgttgggcgc gttgggaagg g                                  211
```

<210> SEQ ID NO 305
<211> LENGTH: 651
<212> TYPE: DNA
<213> ORGANISM: Homo sapiens

<400> SEQUENCE: 305

```
gccgcccacc ttcctcgttt ctgcactcat tttagcgacg cagccgccgc tgctacctac     60
cccgcgctcc cgcgtctcct ccgcgctggg gtctcccctt tcttttggtt tgggtgggag   120
aaaaagatgg tgaggacggg gaatcggaga ccggcatggg ggtaaaaatc gtgcagacat   180
tcggaatcgc tcccttggaa acatttgcct gagcaactga aataaaattg gcagtagtag   240
ttttggagcg tgctccagcg aggatggtct ttttgttcat tattttctct ttaaagtaat   300
atcctgtcac ttagggggctt tccggttgtc tcctcttatt cgaccccctt tcaaaattgc   360
tgacttgagc tggttctgga gtttattttt taatatgcgt gcgtgggtat gtgtatgtgt   420
gtgtatgttt tgcagaaatc cgccaaaatg caactgtagg aactgcgaga tgtatttatt   480
gattttgacc aggggcggtg ggaagggggct ggagggagct gggggatcct ggagggtggg   540
```
aagtggctga ttctcggtgg ccggacactc atccagagcc tgatccgtac tcgtgttttc    600
ttggaagcgc cacaactgcg gggaaggagt ctttagaaac cgtgccagtt t    651

<210> SEQ ID NO 306
<211> LENGTH: 651
<212> TYPE: DNA
<213> ORGANISM: Artificial Sequence
<220> FEATURE:
<223> OTHER INFORMATION: synthetic

<400> SEQUENCE: 306
gtcgtttatt ttttcgtttt ttgtatttat tttagcgacg tagtcgtcgt tgttatttat    60
ttcgcgtttt cgcgtttttt tcgcgttggg gttttttttt tttttggtt tgggtgggag    120 aaaaagatgg tgaggacggg gaatcggaga tcggtatggg ggtaaaaatc gtgtagatat    180
tcggaatcgt ttttttggaa atatttgttt gagtaattga ataaaattg gtagtagtag    240 ttttggagcg tgttttagcg aggatggttt ttttgtttat tatttttttt ttaaagtaat    300
attttgttat ttaggggttt ttcggttgtt ttttttatt cgattttttt ttaaaattgt    360
tgatttgagt tggttttgga gtttatttt taatatgcgt gcgtgggtat gtgtatgtgt    420
gtgtatgttt tgtagaaatt cgttaaaatg taattgtagg aattgcgaga tgtatttatt    480
gattttgatt aggggcggtg ggaaggggtt ggagggagtt ggggggatttt ggagggtggg    540 aagtggttga ttttcggtgg tcggatattt atttagagtt tgattcgtat tcgtgttttt    600
ttggaagcgt tataattgcg gggaaggagt ttttagaaat cgtgttagtt t    651

<210> SEQ ID NO 307
<211> LENGTH: 94
<212> TYPE: DNA
<213> ORGANISM: Artificial Sequence
<220> FEATURE:
<223> OTHER INFORMATION: synthetic

<400> SEQUENCE: 307
gtcgtttatt ttttcgtttt ttgtatttat tttagcgacg tagtcgtcgt tgttatttat    60
ttcgcgtttt cgcgtttttt tcgcgttggg gttt    94

<210> SEQ ID NO 308
<211> LENGTH: 112
<212> TYPE: DNA
<213> ORGANISM: Artificial Sequence
<220> FEATURE:
<223> OTHER INFORMATION: synthetic

<400> SEQUENCE: 308
gaagtggctg attctcggtg gccggacact catccagagc tgatccgta ctcgtgtttt    60 cttggaagcg ccacaactgc ggggaaggag tctttagaaa ccgtgccagt tt    112

<210> SEQ ID NO 309
<211> LENGTH: 17
<212> TYPE: DNA
<213> ORGANISM: Artificial Sequence
<220> FEATURE:
<223> OTHER INFORMATION: synthetic

<400> SEQUENCE: 309
ctgattctcg gtggccg    17

<210> SEQ ID NO 310

<211> LENGTH: 20
<212> TYPE: DNA
<213> ORGANISM: Artificial Sequence
<220> FEATURE:
<223> OTHER INFORMATION: synthetic

<400> SEQUENCE: 310
ggcgcttcca agaaaacacg                                                    20

<210> SEQ ID NO 311
<211> LENGTH: 29
<212> TYPE: DNA
<213> ORGANISM: Artificial Sequence
<220> FEATURE:
<223> OTHER INFORMATION: synthetic

<400> SEQUENCE: 311
aggccacgga cgcgagtacg gatcaggct                                          29

<210> SEQ ID NO 312
<211> LENGTH: 311
<212> TYPE: DNA
<213> ORGANISM: Homo sapiens

<400> SEQUENCE: 312
cctgtaaagc cggggatggc aggacgcatt gtcaccccct cctgccgctc ttacgaaaca        60
ctcttaattg agtccgattc ttggtgaatc agccttccaa gaaccgcgac cgcagcatcc       120
tgtgccgctt ctgtgttccg cattttctc tttctgcagc gtttcctctc attctggatg       180
gaaaggcctg tttgtctccc tcaatctttg gcgagggtgg caggcagcca ggcggccatt      240
acgggccgcg cctcccacca gccagtcgct ggcaggagcg tccggggagg gagcagaccc      300
cgttcaccct c                                                            311

<210> SEQ ID NO 313
<211> LENGTH: 311
<212> TYPE: DNA
<213> ORGANISM: Artificial Sequence
<220> FEATURE:
<223> OTHER INFORMATION: synthetic

<400> SEQUENCE: 313
tttgtaaagt cggggatggt aggacgtatt gttatttttt tttgtcgttt ttacgaaata        60
tttttaattg agttcgattt ttggtgaatt agttttttaa gaatcgcgat cgtagtattt       120
tgtgtcgttt ttgtgtttcg tattttttt ttttgtagc gttttttttt attttggatg        180
gaaaggtttg tttgttttt ttaattttg gcgagggtgg taggtagtta ggcggttatt        240
acgggtcgcg tttttatta gttagtcgtt ggtaggagcg ttcggggagg gagtagattt       300
cgtttatttt t                                                            311

<210> SEQ ID NO 314
<211> LENGTH: 92
<212> TYPE: DNA
<213> ORGANISM: Artificial Sequence
<220> FEATURE:
<223> OTHER INFORMATION: synthetic

<400> SEQUENCE: 314
gtaggtagtt aggcggttat tacgggtcgc gtttttatt agttagtcgt tggtaggagc        60
gttcggggag ggagtagatt tcgtttattt tt                                      92

```
<210> SEQ ID NO 315
<211> LENGTH: 112
<212> TYPE: DNA
<213> ORGANISM: Homo sapiens

<400> SEQUENCE: 315
cccagagccc cggtcacact cccgtcccat gctgtccccc tcccgcaaag cccacggtgg    60
gaacagaggg caccgcgcga gccgatgcca ccctcactgc cggccccacc ca           112

<210> SEQ ID NO 316
<211> LENGTH: 112
<212> TYPE: DNA
<213> ORGANISM: Artificial Sequence
<220> FEATURE:
<223> OTHER INFORMATION: synthetic

<400> SEQUENCE: 316
tttagagttt cggttatatt ttcgttttat gttgtttttt tttcgtaaag tttacggtgg    60
gaatagaggg tatcgcgcga gtcgatgtta tttttattgt cggttttatt ta           112

<210> SEQ ID NO 317
<211> LENGTH: 287
<212> TYPE: DNA
<213> ORGANISM: Homo sapiens

<400> SEQUENCE: 317
cctcccaacc cgagtcccgc aacccggcgg gaccggagct cagcgcttca cgctctccgg    60
gaggaagctc cggaccccgg gcgaccccgc tccctctccc ggaccccgcc cgcgctccag   120
cacccgggag gaaggcgaag accggcggga ggagcgctct tctcggaagg ggagaaccgg   180
gtccgaggcg ccgtggggcg ggggtcgcgg gcgcactcac gggggcgagc agccagcagg   240
tcagcagcgc gggaggcagc agcgtccgca tcccgagctc agcgtgc                 287

<210> SEQ ID NO 318
<211> LENGTH: 287
<212> TYPE: DNA
<213> ORGANISM: Artificial Sequence
<220> FEATURE:
<223> OTHER INFORMATION: synthetic

<400> SEQUENCE: 318 tttttttaatt cgagtttcgt aattcggcgg gatcggagtt tagcgtttta cgttttttcgg   60 gaggaagttt cggatttcgg gcgatttcgt ttttttttttc ggatttcgtt cgcgttttag  120
tattcgggag gaaggcgaag atcggcggga ggagcgtttt tttcggaagg ggagaatcgg   180
gttcgaggcg tcgtggggcg ggggtcgcgg gcgtatttac gggggcgagt agttagtagg   240
ttagtagcgc gggaggtagt agcgttcgta tttcgagttt agcgtgt                 287

<210> SEQ ID NO 319
<211> LENGTH: 215
<212> TYPE: DNA
<213> ORGANISM: Homo sapiens

<400> SEQUENCE: 319
gtcgggtcgt gcgttcgctc ggcagcggcg tgcaccagca ccaccctgc gtgcaagttt    60 gaaatgtgag ctgcctccga ttcatactcg ctcgcgctcc ctcgcagcga agtggctggg  120
ctgacggtct gcgcgcgcga gtgagtgcgg cggcgggct gggggggcggg gtgcggacgg  180 cgaggctcgc ggggcgggga gggcgcgcgc gagcc                              215
```

```
<210> SEQ ID NO 320
<211> LENGTH: 215
<212> TYPE: DNA
<213> ORGANISM: Artificial Sequence
<220> FEATURE:
<223> OTHER INFORMATION: synthetic

<400> SEQUENCE: 320
gtcgggtcgt gcgttcgttc ggtagcggcg tgtattagta ttattttgc gtgtaagttt      60 gaaatgtgag ttgttttcga tttatattcg ttcgcgtttt ttcgtagcga agtggttggg     120
ttgacggttt gcgcgcgcga gtgagtgcgg cggcgggtt ggggggcggg gtgcggacgg      180
cgaggttcgc ggggcgggga gggcgcgcgc gagtt                               215

<210> SEQ ID NO 321
<211> LENGTH: 140
<212> TYPE: DNA
<213> ORGANISM: Homo sapiens

<400> SEQUENCE: 321
tggcagaagc gtagtgccag ccgcaatagg gcggccgtgg gtgcaaacgg aggggagcgc      60
cggcagctag caccgcgcgg cgactaacgg gccgccccgg agactcctgg gagctcaggc     120
ccacgcgcga gtgcgcaggc                                                140

<210> SEQ ID NO 322
<211> LENGTH: 140
<212> TYPE: DNA
<213> ORGANISM: Artificial Sequence
<220> FEATURE:
<223> OTHER INFORMATION: synthetic

<400> SEQUENCE: 322
tggtagaagc gtagtgttag tcgtaatagg gcggtcgtgg gtgtaaacgg aggggagcgt      60
cggtagttag tatcgcgcgg cgattaacgg gtcgtttcgg agattttgg gagtttaggt      120 ttacgcgcga gtgcgtaggt                                                140

<210> SEQ ID NO 323
<211> LENGTH: 316
<212> TYPE: DNA
<213> ORGANISM: Homo sapiens

<400> SEQUENCE: 323
agaagtgggc gggtgtgtgt ttaaaaaaaa aaaggggt ggaaacccca ccagccaagt       60
ctgcagaaaa aaaataaatg aagtctgcct atctccgggc cagagcccct ccctcggcc      120 cgcgcgggag gagtgtgacc caggtgccgc ttcctctcgc cgccgagggt caggagcccg     180
ggagcgcgac cctccccggg cccggcctgg cccggcctgg ccagtccccg cggtctctgc     240
ccgggctgac gcccaggaat gtggtcgacg agaagcccca acagcacggc gtggcctctc     300
agcctcggtg agtacc                                                    316

<210> SEQ ID NO 324
<211> LENGTH: 316
<212> TYPE: DNA
<213> ORGANISM: Artificial Sequence
<220> FEATURE:
<223> OTHER INFORMATION: synthetic

<400> SEQUENCE: 324
agaagtgggc gggtgtgtgt ttaaaaaaaa aaaggggt ggaaatttta ttagttaagt       60
```

```
ttgtagaaaa aaaataaatg aagtttgttt attttcgggt tagagttttt tttttcggtt    120
cgcgcgggag gagtgtgatt taggtgtcgt ttttttttcgt cgtcgagggt taggagttcg    180
ggagcgcgat ttttttttcgg ttcggtttgg ttcggtttgg ttagtttttcg cggttttttgt    240 tcggggttgac gtttaggaat gtggtcgacg agaagtttta atagtacggc gtggtttttt    300
agtttcggtg agtatt                                                      316

<210> SEQ ID NO 325
<211> LENGTH: 77
<212> TYPE: DNA
<213> ORGANISM: Artificial Sequence
<220> FEATURE:
<223> OTHER INFORMATION: synthetic

<400> SEQUENCE: 325
ggagtgtgat ttaggtgtcg ttttttttcg tcgtcgaggg ttaggagttc gggagcgcga     60 tttttttttcg gttcggt                                                    77

<210> SEQ ID NO 326
<211> LENGTH: 105
<212> TYPE: DNA
<213> ORGANISM: Homo sapiens

<400> SEQUENCE: 326
ggtgagtacc cgccgtgggg aagggtcctg ggacccact ggaggccgcg gcccgcagca     60
gccaggggcc gagccacggc cacggacgcc ctggtgtccc ggtcc                     105

<210> SEQ ID NO 327
<211> LENGTH: 105
<212> TYPE: DNA
<213> ORGANISM: Artificial Sequence
<220> FEATURE:
<223> OTHER INFORMATION: synthetic

<400> SEQUENCE: 327
ggtgagtatt cgtcgtgggg aagggttttg gggatttatt ggaggtcgcg gttcgtagta     60 gttagggggtc gagttacggt tacgacgtt ttggtgtttc ggttt                     105

<210> SEQ ID NO 328
<211> LENGTH: 184
<212> TYPE: DNA
<213> ORGANISM: Homo sapiens

<400> SEQUENCE: 328
ggggactctc ggcacccgcg tccctgtgct tctggtggtt ccggcgcttc ctcggagcgc     60
gcggcatgtc tgctcctaca cgtccagcac ctctgtcccc agagcaaacc cacctcccag   120
ggcacacgca gaggggcagt caggcaccgc ctccacccctg ccccacccag gccgcgcgca   180
cccc                                                                  184

<210> SEQ ID NO 329
<211> LENGTH: 184
<212> TYPE: DNA
<213> ORGANISM: Artificial Sequence
<220> FEATURE:
<223> OTHER INFORMATION: synthetic

<400> SEQUENCE: 329
ggggattttc ggtattcgcg tttttgtgtt tttggtggtt tcggcgtttt ttcggagcgc     60
```

```
gcggtatgtt tgtttttata cgtttagtat ttttgttttt agagtaaatt tattttttag    120
ggtatacgta gaggggtagt taggtatcgt ttttattttg ttttatttag gtcgcgcgta    180
tttt                                                                 184

<210> SEQ ID NO 330
<211> LENGTH: 180
<212> TYPE: DNA
<213> ORGANISM: Homo sapiens

<400> SEQUENCE: 330
ctcttcctcc cggagtatgg tgaggagcgc gggggacggg tgcgggaagg ggacagcagg     60
gctgagcctg gggcccgcaa gacccagcag cccgagcggg cgcagagacc ccacgccacg    120
cacaaccctc tcttctaggg ggcgccgact acactgactt ccctgttccg gaagaggggg    180

<210> SEQ ID NO 331
<211> LENGTH: 180
<212> TYPE: DNA
<213> ORGANISM: Artificial Sequence
<220> FEATURE:
<223> OTHER INFORMATION: synthetic

<400> SEQUENCE: 331
tttttttttt cggagtatgg tgaggagcgc gggggacggg tgcgggaagg ggatagtagg     60
gttgagtttg gggttcgtaa gattagtag ttcgagcggg cgtagagatt ttacgttacg     120
tataattttt tttttaggg ggcgtcgatt atattgattt ttttgtttcg gaagaggggg    180

<210> SEQ ID NO 332
<211> LENGTH: 123
<212> TYPE: DNA
<213> ORGANISM: Homo sapiens

<400> SEQUENCE: 332
ctctgcagga cgccgcggcc cattccgaag agcaggatgt gcgtgaggtt ggtgggcagg     60
cctagcgcgg agatgcgcgc cacgtcgccc cccgagcact gcgcggcgtc ccggaagaca    120
cac                                                                  123

<210> SEQ ID NO 333
<211> LENGTH: 123
<212> TYPE: DNA
<213> ORGANISM: Artificial Sequence
<220> FEATURE:
<223> OTHER INFORMATION: synthetic

<400> SEQUENCE: 333
ttttgtagga cgtcgcggtt tatttcgaag agtaggatgt gcgtgaggtt ggtgggtagg     60
tttagcgcgg agatgcgcgt tacgtcgttt ttcgagtatt gcgcggcgtt tcggaagata    120
tat                                                                  123

<210> SEQ ID NO 334
<211> LENGTH: 101
<212> TYPE: DNA
<213> ORGANISM: Homo sapiens

<400> SEQUENCE: 334
gccaaggggc gccgcgccg ccgccgccg cccgtgccgg ccccggccgt tcgggctcgg       60
tgcgcaccgc gcccccagat ggcgccgcca agcgtccgcc c                        101
```

```
<210> SEQ ID NO 335
<211> LENGTH: 101
<212> TYPE: DNA
<213> ORGANISM: Artificial Sequence
<220> FEATURE:
<223> OTHER INFORMATION: synthetic

<400> SEQUENCE: 335
gttaaggggc gttcgcgtcg tcgttcgtcg ttcgtgtcgg tttcggtcgt tcgggttcgg      60
tgcgtatcgc gtttttagat ggcgtcgtta agcgttcgtt t                        101

<210> SEQ ID NO 336
<211> LENGTH: 147
<212> TYPE: DNA
<213> ORGANISM: Homo sapiens

<400> SEQUENCE: 336
gcttcctctc cgtgggcgac gtggacgaca cgcagtgcgt gcggctcgac agcgacgcca      60
cgagtcccag gatggagccg cgggcgccgt ggatggagca ggaggggccg gaatattggg     120
aagaggagac agggaccgcc aaggcca                                        147

<210> SEQ ID NO 337
<211> LENGTH: 147
<212> TYPE: DNA
<213> ORGANISM: Artificial Sequence
<220> FEATURE:
<223> OTHER INFORMATION: synthetic

<400> SEQUENCE: 337
gttttttttt cgtgggcgac gtggacgata cgtagtgcgt gcggttcgat agcgacgtta      60
cgagttttag gatggagtcg cgggcgtcgt ggatggagta ggaggggtcg gaatattggg     120
aagaggagat agggatcgtt aaggtta                                        147

<210> SEQ ID NO 338
<211> LENGTH: 153
<212> TYPE: DNA
<213> ORGANISM: Homo sapiens

<400> SEQUENCE: 338
cagttttacc gagtgaacct gcggaccctg agcggctact acaaccagag tgaggcctgt      60
gagtgacacc ggccgggggc gcaggtcact accectccac atcccccacg daccgcccgg     120
gtctccccga gtctctgggt ccgagatcca cgc                                 153

<210> SEQ ID NO 339
<211> LENGTH: 153
<212> TYPE: DNA
<213> ORGANISM: Artificial Sequence
<220> FEATURE:
<223> OTHER INFORMATION: synthetic

<400> SEQUENCE: 339
tagttttatc gagtgaattt gcggattttg agcggttatt ataattagag tgaggtttgt      60
gagtgatatc ggtcgggggc gtaggttatt atttttttat attttttacg gatcgttcgg     120
gttttttcga gttttgggt tcgagattta cgt                                  153

<210> SEQ ID NO 340
<211> LENGTH: 138
<212> TYPE: DNA
<213> ORGANISM: Homo sapiens
```

-continued

```
<400> SEQUENCE: 340
tgtccttgac cgagaagggg gtggaggtga cggggctcag cagcatcccg aaggcggatg    60
gggcggggcc gaggaggtcc gggtgaggag cggcaccctg aacttcccgt cttgtcgctg   120
caggccccgc agacagac                                                 138

<210> SEQ ID NO 341
<211> LENGTH: 138
<212> TYPE: DNA
<213> ORGANISM: Artificial Sequence
<220> FEATURE:
<223> OTHER INFORMATION: synthetic

<400> SEQUENCE: 341
tgtttttgat cgagaagggg gtggaggtga cggggtttag tagtatttcg aaggcggatg    60
gggcggggtc gaggaggttc gggtgaggag cggtattttg aattttttcgt tttgtcgttg  120 taggtttcgt agatagat                                                 138

<210> SEQ ID NO 342
<211> LENGTH: 104
<212> TYPE: DNA
<213> ORGANISM: Homo sapiens

<400> SEQUENCE: 342
atgaaggcta cgaggtgctc aagttcgacg acgtggtcac caacctcgga aaccactacg    60
accccaccac cggcaagttc acctgctcca tcccgggcat ctac                    104

<210> SEQ ID NO 343
<211> LENGTH: 104
<212> TYPE: DNA
<213> ORGANISM: Artificial Sequence
<220> FEATURE:
<223> OTHER INFORMATION: synthetic

<400> SEQUENCE: 343
atgaaggtta cgaggtgttt aagttcgacg acgtggttat taatttcgga aattattacg    60
attttattat cggtaagttt atttgttttta tttcgggtat ttat                   104

<210> SEQ ID NO 344
<211> LENGTH: 185
<212> TYPE: DNA
<213> ORGANISM: Homo sapiens

<400> SEQUENCE: 344
agcctgcctg cgtctcttcc ttcctccgcg tgggttctag caacatccac tgcagccggg    60
ccaggcgagc cggcgcgtac catcggcgcg ggggaggag agggccgggc ctggaagat    120 gctgcggagg acgctgcgga ttcgcgagcc cggggtaagg cggcggcgca ccgcccctc   180 ccgcc                                                               185

<210> SEQ ID NO 345
<211> LENGTH: 185
<212> TYPE: DNA
<213> ORGANISM: Artificial Sequence
<220> FEATURE:
<223> OTHER INFORMATION: synthetic

<400> SEQUENCE: 345
agtttgtttg cgttttttttt ttttttcgcg tgggttttag taatatttat tgtagtcggg   60
ttaggcgagt cggcgcgtat tatcggcgcg gggggaggag agggtcgggt ttgggaagat  120
```

```
gttgcggagg acgttgcgga ttcgcgagtt cggggtaagg cggcggcgta tcgttttttt    180
tcgtt                                                                185

<210> SEQ ID NO 346
<211> LENGTH: 132
<212> TYPE: DNA
<213> ORGANISM: Homo sapiens

<400> SEQUENCE: 346 gggggcggg gctggggaga gggtggcccc tgcacactag tcccctcccc tcgacccgc      60 agccccgcgg cgcgtttcct gaggcgcccc cgccacgtcc cgcgagtctc tgccaagttc    120
ccgcgcgggt gc                                                        132

<210> SEQ ID NO 347
<211> LENGTH: 132
<212> TYPE: DNA
<213> ORGANISM: Artificial Sequence
<220> FEATURE:
<223> OTHER INFORMATION: synthetic

<400> SEQUENCE: 347 gggggcggg gttggggaga gggtggtttt tgtatattag ttttttttttt tcgatttcgt    60 agtttcgcgg cgcgtttttt gaggcgtttt cgttacgttt cgcgagtttt tgttaagttt    120
tcgcgcgggt gt                                                        132

<210> SEQ ID NO 348
<211> LENGTH: 302
<212> TYPE: DNA
<213> ORGANISM: Homo sapiens

<400> SEQUENCE: 348 ggggagggc cgccgagggt cccgccccc gcgccgtgcg gccccgcccc ctccctcccc      60
ccacctggga aagccctcgc gggccaagtc cgcggcggcc gggccaaggc gcccgctctc    120
gctcggcccc gccctggcgc ccgcccgccc gcccgcccgc tgcctcggcg ctaggccttc    180
ttgcacttgc ccttcttctc acgctgctgg aacttgcgca gccgccgcgc ccacgtgtcc    240
cgccactgga tcaccaggct gcttttatcg gccacgatgc cgctctggtc cggagagtcc    300
tc                                                                   302

<210> SEQ ID NO 349
<211> LENGTH: 302
<212> TYPE: DNA
<213> ORGANISM: Artificial Sequence
<220> FEATURE:
<223> OTHER INFORMATION: synthetic

<400> SEQUENCE: 349 ggggagggt cgtcgagggt ttcgtttttc gcgtcgtgcg gtttcgtttt tttttttttt    60
ttatttggga aagttttcgc gggttaagtt cgcggcggtc gggttaaggc gttcgttttc    120
gttcggtttc gttttggcgt tcgttcgttc gttcgttcgt tgtttcggcg ttaggttttt    180
ttgtatttgt ttttttttttt acgttgttgg aatttgcgta gtcgtcgcgt ttacgtgttt    240
cgttattgga ttattaggtt gtttttatcg gttacgatgt cgttttggtt cggagagttt    300
tt                                                                   302

<210> SEQ ID NO 350
```

```
<211> LENGTH: 82
<212> TYPE: DNA
<213> ORGANISM: Artificial Sequence
<220> FEATURE:
<223> OTHER INFORMATION: synthetic

<400> SEQUENCE: 350
gttaaggcgt tcgttttcgt tcggtttcgt tttggcgttc gttcgttcgt tcgttcgttg    60
tttcggcgtt aggttttttt gt                                             82

<210> SEQ ID NO 351
<211> LENGTH: 158
<212> TYPE: DNA
<213> ORGANISM: Homo sapiens

<400> SEQUENCE: 351
gccccgggcc tttcagacac ttttctggaa tgtgaaggga ggtgggggct cagctgtctt    60
ttccaccgtc ccggagtggg gcaggtgtcg gagctgggtg ggaagcagac gcggtacggt   120
gggcagaggt cccagcctg cggggagcgc tatctcct                            158

<210> SEQ ID NO 352
<211> LENGTH: 158
<212> TYPE: DNA
<213> ORGANISM: Artificial Sequence
<220> FEATURE:
<223> OTHER INFORMATION: synthetic

<400> SEQUENCE: 352
gtttcgggtt ttttagatat ttttttggaa tgtgaaggga ggtgggggtt tagttgtttt    60
ttttatcgtt tcggagtggg gtaggtgtcg gagttgggtg ggaagtagac gcggtacggt   120
gggtagaggt tttagtttg cggggagcgt tatttttt                            158

<210> SEQ ID NO 353
<211> LENGTH: 86
<212> TYPE: DNA
<213> ORGANISM: Homo sapiens

<400> SEQUENCE: 353
gggcctccgg gctacccta cttgaagccg ctatgcccct ctcctgtgcc cgaggtggcc    60
gctgggtggc aggggaggcc cgggcc                                         86

<210> SEQ ID NO 354
<211> LENGTH: 86
<212> TYPE: DNA
<213> ORGANISM: Artificial Sequence
<220> FEATURE:
<223> OTHER INFORMATION: synthetic

<400> SEQUENCE: 354
gggttttcgg gttatttta tttgaagtcg ttatgttttt ttttgtgtt cgaggtggtc    60 gttgggtggt aggggaggtt cgggtt                                         86

<210> SEQ ID NO 355
<211> LENGTH: 149
<212> TYPE: DNA
<213> ORGANISM: Homo sapiens

<400> SEQUENCE: 355
gggcaaaggc cgctgcttcg ggcccaatat ctgctgcgcg gaagagctgg gctgcttcgt    60
gggcaccgcc gaagcgctgc gctgccagga ggagaactac ctgccgtcgc cctgccagtc   120
```
cggccagaag gcgtgcggga gcgggggcc                                    149

<210> SEQ ID NO 356
<211> LENGTH: 149
<212> TYPE: DNA
<213> ORGANISM: Artificial Sequence
<220> FEATURE:
<223> OTHER INFORMATION: synthetic

<400> SEQUENCE: 356
gggtaaaggt cgttgtttcg ggtttaatat ttgttgcgcg aaagagttgg gttgtttcgt    60
gggtatcgtc gaagcgttgc gttgttagga ggagaattat ttgtcgtcgt tttgttagtt   120
cggttagaag gcgtgcggga gcgggggtt                                    149

<210> SEQ ID NO 357
<211> LENGTH: 146
<212> TYPE: DNA
<213> ORGANISM: Homo sapiens

<400> SEQUENCE: 357
tttccctccc gggcgcctgg atctcccctc ccccggctcc tgtttccttg tcaaaacttc    60
ctgccttggc gagggcccga gttcccaccc ccttcctgcc ccccgcccct cggcgcccct   120
cccggccctg cgatcagcag cgtccc                                       146

<210> SEQ ID NO 358
<211> LENGTH: 146
<212> TYPE: DNA
<213> ORGANISM: Artificial Sequence
<220> FEATURE:
<223> OTHER INFORMATION: synthetic

<400> SEQUENCE: 358
tttttttttc gggcgtttgg atttttttttt tttcggtttt tgttttttttg ttaaaatttt   60 ttgttttggc gagggttcga gtttttatttt tttttttgtt tttcgttttt cggcgttttt   120
ttcggttttg cgattagtag cgtttt                                       146

<210> SEQ ID NO 359
<211> LENGTH: 289
<212> TYPE: DNA
<213> ORGANISM: Homo sapiens

<400> SEQUENCE: 359
cggtggccac ggccccgccc tcgttccgcg cccggactgg gccacgccgg atagcgggaa    60
acaaaaaaag cccgagctgg aaacttcaga gaggtttagt ttcgtttccc agaagcatca   120
gttcggtccc aaaacgctgc aaacgcgcgc tgcctgcagt aggagagagg aaaccgcgaa   180
gcgcgagaaa aggcgccccc gtccccaagc agcccgcgcg cccttccagg ggccagacct   240
gctccatcct ggacggcgaa acgacctcgg gagaccccgg ttaggacct               289

<210> SEQ ID NO 360
<211> LENGTH: 289
<212> TYPE: DNA
<213> ORGANISM: Artificial Sequence
<220> FEATURE:
<223> OTHER INFORMATION: synthetic

<400> SEQUENCE: 360
cggtggttac ggtttcgttt tcgtttcgcg ttcggattgg gttacgtcgg atagcgggaa    60

```
ataaaaaaag ttcgagttgg aaattttaga gaggtttagt ttcgtttttt agaagtatta    120
gttcggtttt aaaacgttgt aaacgcgcgt tgtttgtagt aggagagagg aaatcgcgaa    180
gcgcgagaaa aggcgttttc gttttaagt agttcgcgcg ttttttagg ggttagattt      240 gttttatttt ggacggcgaa acgatttcgg gagatttcgg ttaggattt                289
```

<210> SEQ ID NO 361
<211> LENGTH: 608
<212> TYPE: DNA
<213> ORGANISM: Homo sapiens

<400> SEQUENCE: 361

```
gggggtgcgg ggaggagtcg ggagcagccc ctggagcaca ggggccgcca gcaccggctg    60
cttccagccc tcctgcctac ccgcccttcc tcctgcaggc tgggggctcg acagcccca    120 gtgccccgcg acgcccacct ggacgcctgg cgaccccgc cccgcgctct gtacctttac    180
tctgcggagg gttctgactc cggtcccgga ggacgttgat ctggtagacg gctccgtaag   240
gctcaaaaag ttctttcagc tccttttccg accatgaccg gggatctgt ccgacaaaca    300 tcttaatggc atctgggtct ggttggtctg agtgatccaa agctccgttc atcttgttgg    360
ctgtgccgtt actgtcaaaa acggaaccgg gagccagagt tagggcggca cgatgaggga   420
caggaagaaa aaatagtggg ggtgggggag cggggaggcg gaaggaggag gaagaagagc   480
agtggcaaag tgcctaatga gtcgtagaaa tttgatgaac taaacaaag cggaggcacc    540 atgagttgct cctcggcggc ggcgaggctc tcactgcgtg ctgctgtcga gcagagccgg   600
gggagcac                                                            608
```

<210> SEQ ID NO 362
<211> LENGTH: 608
<212> TYPE: DNA
<213> ORGANISM: Artificial Sequence
<220> FEATURE:
<223> OTHER INFORMATION: synthetic

<400> SEQUENCE: 362

```
gggggtgcgg ggaggagtcg ggagtagttt ttggagtata ggggtcgtta gtatcggttg    60 ttttttagttt ttttgtttat tcgtttttt ttttgtaggt tgggggttcg gatagtttta   120
gtgtttcgcg acgttattt ggacgtttgg cgattttcgt ttcgcgtttt gtatttttat    180
tttgcggagg gttttgattt cggtttcgga ggacgttgat ttggtagacg gtttcgtaag   240
gtttaaaaag tttttttagt ttttttttcg attatgatcg gggatttgt tcgataaata    300 ttttaatggt atttgggttt ggttggtttg agtgatttaa agtttcgttt attttgttgg    360
ttgtgtcgtt attgttaaaa acggaatcgg gagttagagt tagggcggta cgatgaggga   420
taggaagaaa aaatagtggg ggtggggag cggggaggcg gaaggaggag gaagaagagt    480
agtggtaaag tgtttaatga gtcgtagaaa tttgatgaat aaaataaag cggaggtatt    540 atgagttgtt tttcggcggc ggcgaggttt ttattgcgtg ttgttgtcga gtagagtcgg   600
gggagtat                                                            608
```

<210> SEQ ID NO 363
<211> LENGTH: 96
<212> TYPE: DNA
<213> ORGANISM: Artificial Sequence
<220> FEATURE:
<223> OTHER INFORMATION: synthetic

<400> SEQUENCE: 363
gttttagtgt tcgcgacgt ttatttggac gtttggcgat tttcgtttcg cgttttgtat    60 ttttatttg cggagggttt tgatttcggt ttcgga    96

<210> SEQ ID NO 364
<211> LENGTH: 152
<212> TYPE: DNA
<213> ORGANISM: Homo sapiens

<400> SEQUENCE: 364
gcacccggcg cccgagctgc gaaagggacg cccttctcct cccgcgcgga acttcaggag    60
tgcggggccc gagtgtaaac tggaccaccg tggggccgcg cgggcccctg ggcatcacca    120
caaactgtgc ctgtggccat cgtgtcagga ca    152

<210> SEQ ID NO 365
<211> LENGTH: 152
<212> TYPE: DNA
<213> ORGANISM: Artificial Sequence
<220> FEATURE:
<223> OTHER INFORMATION: synthetic

<400> SEQUENCE: 365
gtattcggcg ttcgagttgc gaaagggacg ttttttttt ttcgcgcgga attttaggag    60
tgcggggttc gagtgtaaat tggattatcg tggggtcgcg cgggttttg ggtattatta    120 taaattgtgt ttgtggttat cgtgttagga ta    152

<210> SEQ ID NO 366
<211> LENGTH: 384
<212> TYPE: DNA
<213> ORGANISM: Homo sapiens

<400> SEQUENCE: 366
ggagaagccg ggactcctca catcccacat ccggcagggg aagcccagca ggtgagcgca    60
ggtcccccca gtccccgagg gagtgcgccc gacggaaacg cccctagccc gcgggcctcg    120
ctttcctctc ccgggttcct gggtcacttc ccgctgtctc cagcccgagc tcgtggcccc    180
aatccctggt acctccatcc tctggtcacc ccttctctgg tgccccctcc ccgactttc    240 tttgtcccgt ccccacccct gcccgggcct gccggacccc cctccttgac acccggcgcc    300
acctccttga gcttttctcg tctcctcccc atccccggct ccctggtccc ctcccggaac    360
ttctctggtc ccctccgctc ctcc    384

<210> SEQ ID NO 367
<211> LENGTH: 384
<212> TYPE: DNA
<213> ORGANISM: Artificial Sequence
<220> FEATURE:
<223> OTHER INFORMATION: synthetic

<400> SEQUENCE: 367
ggagaagtcg ggatttttta tattttatat tcggtagggg aagtttagta ggtgagcgta    60
ggttttttta gttttcgagg gagtgcgttc gacggaaacg ttttagttc gcgggtttcg    120 ttttttttt tcgggttttt gggttatttt tcgttgtttt tagttcgagt tcgtggtttt    180 aattttggt atttttattt tttggttatt ttttttggt gtttttttt tcgattttt    240 tttgtttcgt tttattttt gttcgggttt gtcggatttt ttttttgat attcggcgtt    300 atttttttga gttttttcg tttttttttt attttcggtt ttttggtttt ttttcggaat    360

```
tttttttggtt ttttcgtttt tttt                                          384
```

<210> SEQ ID NO 368
<211> LENGTH: 75
<212> TYPE: DNA
<213> ORGANISM: Artificial Sequence
<220> FEATURE:
<223> OTHER INFORMATION: synthetic

<400> SEQUENCE: 368

```
gttttttag ttttcgaggg agtgcgttcg acggaaacgt ttttagttcg cgggtttcgt     60
tttttttttt cgggt                                                     75
```

<210> SEQ ID NO 369
<211> LENGTH: 447
<212> TYPE: DNA
<213> ORGANISM: Homo sapiens

<400> SEQUENCE: 369

```
cagccatact cggccgagtc gacctgcagg cggcccagct tgtccacctg ctcctggaag    60
gcgcgcacct ggtccatgaa agccacggcg cgctcggcgg ccataggcgc ggcgtggagg   120
ccggcggcgg ccagtagcgg cgccgtgtgc aggggcagcg ccgcctgcgc cgcgttcagc   180
acgaagagct cgctccagct caggcgcagc agcgccacct ggtcggccac cggcagctcg   240
gggaagaagg gcgcgtggcg cgcccactcc acggtgctga agagcagccg cgccgccagc   300
tcgcacacgt tgtcgatgcc cagcaccgcg cccgccgcgc cgcccctgc gccgaagcgt    360 ccggccgccg cagggtaggg ctcagcgcgc agcagctgcg cgatcagttc ggacaccggc   420
tgccccggga agaggtctcc gccgctc                                      447
```

<210> SEQ ID NO 370
<211> LENGTH: 447
<212> TYPE: DNA
<213> ORGANISM: Artificial Sequence
<220> FEATURE:
<223> OTHER INFORMATION: synthetic

<400> SEQUENCE: 370

```
tagttatatt cggtcgagtc gatttgtagg cggtttagtt tgtttatttg tttttggaag    60
gcgcgtattt ggtttatgaa agttacggcg cgttcggcgg ttataggcgc ggcgtggagg   120
tcggcggcgg ttagtagcgg cgtcgtgtgt aggggtagcg tcgtttgcgt cgcgtttagt   180
acgaagagtt cgttttagtt taggcgtagt agcgttattt ggtcggttat cggtagttcg   240
gggaagaagg gcgcgtggcg cgtttatttt acggtgttga agagtagtcg cgtcgttagt   300
tcgtatacgt tgtcgatgtt tagtatcgcg ttcgtcgcgt cgttttttgc gtcgaagcgt   360
tcggtcgtcg tagggtaggg tttagcgcgt agtagttgcg cgattagttc ggatatcggt   420
tgtttcggga agaggttttc gtcgttt                                      447
```

<210> SEQ ID NO 371
<211> LENGTH: 98
<212> TYPE: DNA
<213> ORGANISM: Artificial Sequence
<220> FEATURE:
<223> OTHER INFORMATION: synthetic

<400> SEQUENCE: 371

```
gtttatttta cggtgttgaa gagtagtcgc gtcgttagtt cgtatacgtt gtcgatgttt    60
agtatcgcgt tcgtcgcgtc gttttttgcg tcgaagcg                            98
```

<210> SEQ ID NO 372
<211> LENGTH: 416
<212> TYPE: DNA
<213> ORGANISM: Homo sapiens

<400> SEQUENCE: 372

```
gccggcaaag agctggtgca ggatgcggat cagatcagcc agggtccgtg gcttcagcac      60
ttcggtctgt tccatctcgt ggggagctgg ctgcgcgcgc gtctcactgc tgggctgcgg     120
tggaggagct gagcgagcca aggagctggg ggcgagggag cctaacagcc cgctagaccg     180
ctaagcagac acacacgcac aaacccagca ttagagtgcc gaaacgtaag gatgtcgtcg     240
cagagacagc aagagaccca cccccaggcc cctggcagcg cagtggatcc gggatcgctg     300
gagacgcggt gcacacacaa atcaggttca gatctgtggg gttcatcctc ccgggcccct     360
tttaagcgct tggagtcact aggaatgtac caacggccct cggagggagg acgagg         416
```

<210> SEQ ID NO 373
<211> LENGTH: 416
<212> TYPE: DNA
<213> ORGANISM: Artificial Sequence
<220> FEATURE:
<223> OTHER INFORMATION: synthetic

<400> SEQUENCE: 373

```
gtcggtaaag agttggtgta ggatgcggat tagattagtt agggttcgtg gttttagtat      60
ttcggttttgt tttatttcgt ggggagttgg ttgcgcgcgc gttttattgt tgggttgcgg    120
tggaggagtt gagcgagtta aggagttggg ggcgagggag tttaatagtt cgttagatcg     180
ttaagtagat atatacgtat aaatttagta ttagagtgtc gaaacgtaag gatgtcgtcg     240
tagagatagt aagagattta tttttaggtt tttggtagcg tagtggattc gggatcgttg     300
gagacgcggt gtatatataa attaggttta gatttgtggg gtttattttt tcgggttttt     360
tttaagcgtt tggagttatt aggaatgtat taacggtttt cggagggagg acgagg         416
```

<210> SEQ ID NO 374
<211> LENGTH: 119
<212> TYPE: DNA
<213> ORGANISM: Artificial Sequence
<220> FEATURE:
<223> OTHER INFORMATION: synthetic

<400> SEQUENCE: 374

```
gagtgtcgaa acgtaaggat gtcgtcgtag agatagtaag agatttattt ttaggttttt      60
ggtagcgtag tggattcggg atcgttggag acgcggtgta tatataaatt aggtttaga     119
```

<210> SEQ ID NO 375
<211> LENGTH: 267
<212> TYPE: DNA
<213> ORGANISM: Homo sapiens

<400> SEQUENCE: 375

```
gcactcgcca gcgctttgtt cgtgaccggc cttttaaggg ctgtctcacc catcttgtct      60
ggctctgcct ccctgttttcc tttccgtcct ctctcccacc acagccagct ccccactttt    120
ttcgcgggggg ccccctccag cctgtccggg gcctccccgt tcccaggcca gggcttcccc   180
ctcctcccag acctcgttgc tctgcccggt gaggccccgg gctcccagca gggggcgcct    240
gctcgcgatc aggtggcggc ctgggggg                                       267
```

<210> SEQ ID NO 376
<211> LENGTH: 267
<212> TYPE: DNA
<213> ORGANISM: Artificial Sequence
<220> FEATURE:
<223> OTHER INFORMATION: synthetic

<400> SEQUENCE: 376

```
gtattcgtta gcgttttgtt cgtgatcggt tttttaaggg ttgttttatt tattttgttt      60
ggttttgttt ttttgttttt ttttcgtttt tttttttatt atagttagtt tttattttt     120
ttcgcggggg ttttttttag tttgttcggg gttttttcgt ttttaggtta gggtttttt     180
tttttttag atttcgttgt tttgttcggt gaggtttcgg gttttagta gggggcgttt      240
gttcgcgatt aggtggcggt ttggggg                                         267
```

<210> SEQ ID NO 377
<211> LENGTH: 78
<212> TYPE: DNA
<213> ORGANISM: Artificial Sequence
<220> FEATURE:
<223> OTHER INFORMATION: synthetic

<400> SEQUENCE: 377

```
gatttcgttg ttttgttcgg tgaggtttcg ggttttagt aggggcgtt tgttcgcgat       60
taggtggcgg tttggggg                                                    78
```

<210> SEQ ID NO 378
<211> LENGTH: 155
<212> TYPE: DNA
<213> ORGANISM: Homo sapiens

<400> SEQUENCE: 378

```
gaggggacct ggatccctga accccggggc ggaaagggag cctccgggcg gctgtgggtg     60
ccgcgctcct cggagccagc agctgctggg gcggcgtccg aactccccag gtctgcgcac    120
ggcaatgggg gcaccgggcc ttctgtctgt cctca                                155
```

<210> SEQ ID NO 379
<211> LENGTH: 155
<212> TYPE: DNA
<213> ORGANISM: Artificial Sequence
<220> FEATURE:
<223> OTHER INFORMATION: synthetic

<400> SEQUENCE: 379

```
gaggggattt ggattttga atttcggggc ggaaagggag ttttcgggcg gttgtgggtg      60
tcgcgttttt cggagttagt agttgttggg gcggcgttcg aatttttag gtttgcgtac    120
ggtaatgggg gtatcgggtt ttttgtttgt tttta                                155
```

<210> SEQ ID NO 380
<211> LENGTH: 79
<212> TYPE: DNA
<213> ORGANISM: Artificial Sequence
<220> FEATURE:
<223> OTHER INFORMATION: synthetic

<400> SEQUENCE: 380

```
gaattcgggt ttagcgcggg ttttcgcgg tagtggtcgt agttcgggaa gttcggggc       60
gcggtgtttt cgtgaattc                                                   79
```

```
<210> SEQ ID NO 381
<211> LENGTH: 160
<212> TYPE: DNA
<213> ORGANISM: Homo sapiens

<400> SEQUENCE: 381
cggggacagg aggggtggcc aagaaagtcg caagaaaact ccggccccca agaaaaagag      60
agggcatggg ttgcggagcc gacatcacgg ccggggtctt tgctgtttag acgcctgggt     120
tcccggatcc cagacacgcg cacgggcagg aagttagacc                          160

<210> SEQ ID NO 382
<211> LENGTH: 160
<212> TYPE: DNA
<213> ORGANISM: Artificial Sequence
<220> FEATURE:
<223> OTHER INFORMATION: synthetic

<400> SEQUENCE: 382
cggggatagg aggggtggtt aagaaagtcg taagaaaatt tcggtttttta agaaaaagag     60 agggtatggg ttgcggagtc gatattacgg tcggggtttt tgttgtttag acgtttgggt    120
tttcggattt tagatacgcg tacgggtagg aagttagatt                          160

<210> SEQ ID NO 383
<211> LENGTH: 163
<212> TYPE: DNA
<213> ORGANISM: Homo sapiens

<400> SEQUENCE: 383
gttgcctggg tccgcccaga gatgagtcgg gacgcgcggc ccacgtgcgg cggaggggca      60
gctgggtcgc tcggggaacg gggcaccgga tggccccggt tgggcccgcg ccaggatgcg    120
cccctgcgcc ctctgctggc gctctgcggt caccgcagcc ccg                      163

<210> SEQ ID NO 384
<211> LENGTH: 163
<212> TYPE: DNA
<213> ORGANISM: Artificial Sequence
<220> FEATURE:
<223> OTHER INFORMATION: synthetic

<400> SEQUENCE: 384
gttgtttggg ttcgttttaga gatgagtcgg gacgcgcggt ttacgtgcgg cggaggggta     60
gttgggtcgt tcggggaacg gggtatcgga tggtttcggt tgggttcgcg ttaggatgcg    120
tttttgcgtt ttttgttggc gttttgcggt tatcgtagtt tcg                      163

<210> SEQ ID NO 385
<211> LENGTH: 311
<212> TYPE: DNA
<213> ORGANISM: Homo sapiens

<400> SEQUENCE: 385
cggacgaatt ctggggaaag gtcgagggaa ctagagctcc cgactatgca aaccctagag      60
ggtaaactgg gggctaagag ggccccgtgc gtgttttggc gggctaggtc ctgggcttca    120
gggcagagaa gagggccgag tggatcgcct tgccttacct cctcaggatc tccggattcg    180
gtaagcatct tttgctcgtc ctccagtccc atgtctggct acggttctag attcaacacg    240
agcagcaaca gcggcaccta acccagttca ggatcaagaa ggacttgtaa gggtcactca    300
gcggaaatcc g                                                         311
```

<210> SEQ ID NO 386
<211> LENGTH: 311
<212> TYPE: DNA
<213> ORGANISM: Artificial Sequence
<220> FEATURE:
<223> OTHER INFORMATION: synthetic

<400> SEQUENCE: 386

```
cggacgaatt tgggaaaag gtcgagggaa ttagagtttt cgattatgta aattttagag      60
ggtaaattgg gggttaagag ggtttcgtgc gtgttttggc gggttaggtt ttgggtttta     120
gggtagagaa gagggtcgag tggatcgttt tgttttattt ttttaggatt ttcggattcg     180
gtaagtattt tttgttcgtt ttttagtttt atgtttggtt acggttttag atttaatacg     240
agtagtaata gcggtattta atttagttta ggattaagaa ggatttgtaa gggttattta     300
gcggaaattc g                                                          311
```

<210> SEQ ID NO 387
<211> LENGTH: 154
<212> TYPE: DNA
<213> ORGANISM: Artificial Sequence
<220> FEATURE:
<223> OTHER INFORMATION: synthetic

<400> SEQUENCE: 387

```
cggacgaatt tgggaaaag gtcgagggaa ttagagtttt cgattatgta aattttagag      60
ggtaaattgg gggttaagag ggtttcgtgc gtgttttggc gggttaggtt ttgggtttta     120
gggtagagaa gagggtcgag tggatcgttt tgtt                                 154
```

<210> SEQ ID NO 388
<211> LENGTH: 706
<212> TYPE: DNA
<213> ORGANISM: Homo sapiens

<400> SEQUENCE: 388

```
cgtcccagaa ctaagtgcta tgcggagatg agggtgggag cagcagtaca aggagggggt      60
gggggcgagg aaacacaaac aggggagaag gaaacgccag catctaacat ggacttgaca     120
gtcatctgac aatacccaga ccctgtgcgc tccgggttcc accgctgtgc ccagtttggg     180
cccaagaaat gaggaatcaa tcgtgttagt actaaggtgg ccgaggggac cggctcgctc     240
actcgttcgc gctccctggc tcggcggaca ccaggcagtc ccccggcggt cggccgctcg     300
gaggacgcgg aagatgtccc ggggaactca ggtgaccccg cccgccaccc acagaaagag     360
ccaggccggg gttgcttccc attccctctg cagccggaga gctgaggagg tagggacctg     420
gcgcggctca gcgcgctccg cgagcggctc cccaaatggg tgcgagaggg aagagggcag     480
agcgcggcgg ggcgtccggg gggcgcccgg tacccgaggc gggcgcacgc acccaaacag     540
gagagcggcg cccggagtta ctcagtgcgg cagaagagc ggggcgagga gcgggtcgc      600
gcccgctgga ggcgcggggc gagcggagga agaggaggag gagagcagaa ggaagggaa     660
gcggctcgta cctgctgcgc gccggggcgc ctgctgcttc ctcctc                    706
```

<210> SEQ ID NO 389
<211> LENGTH: 706
<212> TYPE: DNA
<213> ORGANISM: Artificial Sequence
<220> FEATURE:
<223> OTHER INFORMATION: synthetic

<400> SEQUENCE: 389

```
cgtttagaa ttaagtgtta tgcggagatg agggtgggag tagtagtata aggaggggt      60 ggggcgagg aaatataaat aggggagaag gaaacgttag tatttaatat ggatttgata     120
gttatttgat aatatttaga ttttgtgcgt ttcgggtttt atcgttgtgt ttagtttggg    180
tttaagaaat gaggaattaa tcgtgttagt attaaggtgg tcgagggat cggttcgttt     240 attcgttcgc gttttttggt tcggcggata ttaggtagtt tttcggcggt cggtcgttcg    300
gaggacgcgg aagatgtttc ggggaattta ggtgatttcg ttcgttattt atagaaagag    360
ttaggtcggg gttgttttt attttttttg tagtcggaga gttgaggagg tagggatttg     420
gcgcggttta gcgcgtttcg cgagcggttt tttaaatggg tgcgagaggg aagagggtag    480
agcgcggcgg ggcgttcggg gggcgttcgg tattcgaggc gggcgtacgt atttaaatag    540
gagagcggcg ttcggagtta tttagtgcgg gtagaagagc ggggcgagga gcggggtcgc    600
gttcgttgga ggcgcgggc gagcggagga agaggaggag gagagtagaa ggaagggaa      660 gcggttcgta tttgttgcgc gtcgggcgt tgttgttt tttttt                      706

<210> SEQ ID NO 390
<211> LENGTH: 154
<212> TYPE: DNA
<213> ORGANISM: Artificial Sequence
<220> FEATURE:
<223> OTHER INFORMATION: synthetic

<400> SEQUENCE: 390
gaattaatcg tgttagtatt aaggtggtcg aggggatcgg ttcgtttatt cgttcgcgtt    60 tttggttcg gcggatatta ggtagttttt cggcggtcg tcgttcggag gacgcggaag     120
atgtttcggg gaatttaggt gatttcgttc gtta                                154

<210> SEQ ID NO 391
<211> LENGTH: 120
<212> TYPE: DNA
<213> ORGANISM: Homo sapiens

<400> SEQUENCE: 391
cgtcgggcct gcgggggccg gacccgcctt cgaaagtggg cggaaggatg gccgccctgg    60
cggagtgcgg gcgaggccgg gagcccttgc ctcagccccg gcccggtctt cttcgtgccg   120

<210> SEQ ID NO 392
<211> LENGTH: 120
<212> TYPE: DNA
<213> ORGANISM: Artificial Sequence
<220> FEATURE:
<223> OTHER INFORMATION: synthetic

<400> SEQUENCE: 392
cgtcgggttt gcggggtcg gattcgtttt cgaaagtggg cggaaggatg gtcgttttgg    60
cggagtgcgg gcgaggtcgg gagttttgt tttagtttcg gttcggtttt tttcgtgtcg   120

<210> SEQ ID NO 393
<211> LENGTH: 190
<212> TYPE: DNA
<213> ORGANISM: Homo sapiens

<400> SEQUENCE: 393
cggtgtggtc cgaaaggctc ttctcttaaa ccccccggca gccggctcct gtgtgtgaca    60
cgatgatgtc atcatcgccg agcagcccca acgcctgcat cttcacaaag ctccatcgcg   120
```

```
ggctccggaa acggggctgg gggtggggag gcgaagaccc tccctctgcc ccggcccctc    180
ccgcctcgcc                                                          190
```

<210> SEQ ID NO 394
<211> LENGTH: 190
<212> TYPE: DNA
<213> ORGANISM: Artificial Sequence
<220> FEATURE:
<223> OTHER INFORMATION: synthetic

<400> SEQUENCE: 394

```
cggtgtggtt cgaaaggttt tttttttaaa ttttcggta gtcggttttt gtgtgtgata    60
cgatgatgtt attatcgtcg agtagtttta acgtttgtat ttttataaag ttttatcgcg    120
ggtttcggaa acggggttgg gggtggggag gcgaagattt tttttttgtt tcggtttttt    180
tcgtttcgtt                                                          190
```

<210> SEQ ID NO 395
<211> LENGTH: 323
<212> TYPE: DNA
<213> ORGANISM: Homo sapiens

<400> SEQUENCE: 395

```
cgggcgtatg tgtgtctcca atggaaaaat cctacccagg acgacaccac atccttgctc    60
ccacaaataa aaccttccac ggaactcagg gctgcagacc agcccttcgc aagccaacgc    120
gccccgtggg cactcggtcc cccggctccg cgtctctgcc accttcccac cgcttcttct    180
ttaaccatgc tcttgtttcc cctcgctgat cgcaaggctg cgggcgagga ttccagagag    240
aggcctagta tggggaacaa acgcttcaga ggggtccgag gtgggctggg gacagccagt    300
ggatgggaag gagggcgctg gcg                                           323
```

<210> SEQ ID NO 396
<211> LENGTH: 323
<212> TYPE: DNA
<213> ORGANISM: Artificial Sequence
<220> FEATURE:
<223> OTHER INFORMATION: synthetic

<400> SEQUENCE: 396

```
cgggcgtatg tgtgttttta atggaaaaat tttatttagg acgatattat attttgttt    60 ttataaataa aattttttac ggaatttagg gttgtagatt agttttcgt aagttaacgc    120 gtttcgtggg tattcggttt ttcggtttcg cgttttttgtt atttttttat cgttttttt    180 ttaattatgt ttttgttttt tttcgttgat cgtaaggttg cgggcgagga ttttagagag    240
aggtttagta tggggaataa acgttttaga ggggttcgag gtgggttggg gatagttagt    300
ggatgggaag gagggcgttg gcg                                           323
```

```
<210> SEQ ID NO 397
<211> LENGTH: 177
<212> TYPE: DNA
<213> ORGANISM: Artificial Sequence
<220> FEATURE:
<223> OTHER INFORMATION: synthetic

<400> SEQUENCE: 397
tacggaattt agggttgtag attagttttt cgtaagttaa cgcgtttcgt gggtattcgg      60
tttttcggtt tcgcgttttt gttatttttt tatcgttttt tttttaatta tgttttgtt     120 tttttcgtt gatcgtaagg ttgcgggcga ggattttaga gagaggttta gtatggg        177
```